(12) United States Patent
Tamarkin et al.

(10) Patent No.: US 10,398,641 B2
(45) Date of Patent: Sep. 3, 2019

(54) COMPOSITIONS AND METHODS FOR TREATING ROSACEA AND ACNE

(71) Applicant: Foamix Pharmaceuticals Ltd., Rehovot (IL)

(72) Inventors: Dov Tamarkin, Ness Ziona (IL); Meir Eini, Ness Ziona (IL); Yohan Hazot, Rehovot (IL); Mitchell Shirvan, Kfar Saba (IL); Tal Hetzroni Kedem, Rehovot (IL); Rita Keynan, Rehovot (IL)

(73) Assignee: Foamix Pharmaceuticals Ltd., Rehovot (IL)

( * ) Notice: Subject to any disclaimer, the term of this patent is extended or adjusted under 35 U.S.C. 154(b) by 0 days.

(21) Appl. No.: 15/699,692

(22) Filed: Sep. 8, 2017

(65) Prior Publication Data

US 2018/0064638 A1 Mar. 8, 2018

Related U.S. Application Data

(60) Provisional application No. 62/550,158, filed on Aug. 25, 2017, provisional application No. 62/444,960, filed on Jan. 11, 2017, provisional application No. 62/393,545, filed on Sep. 12, 2016, provisional application No. 62/385,189, filed on Sep. 8, 2016.

(51) Int. Cl.

| | | |
|---|---|---|
| *A61K 9/00* | (2006.01) | |
| *A61K 9/12* | (2006.01) | |
| *A61K 31/65* | (2006.01) | |
| *A61K 47/06* | (2006.01) | |
| *A61K 47/10* | (2017.01) | |
| *A61K 47/12* | (2006.01) | |
| *A61K 47/24* | (2006.01) | |
| *A61K 47/44* | (2017.01) | |
| *A61K 47/46* | (2006.01) | |

(52) U.S. Cl.
CPC ............ *A61K 9/0014* (2013.01); *A61K 9/122* (2013.01); *A61K 31/65* (2013.01); *A61K 47/06* (2013.01); *A61K 47/10* (2013.01); *A61K 47/12* (2013.01); *A61K 47/24* (2013.01); *A61K 47/44* (2013.01); *A61K 47/46* (2013.01)

(58) Field of Classification Search
CPC ...... A61K 9/0014; A61K 9/122; A61K 47/06; A61K 47/10; A61K 47/12; A61K 47/24; A61K 47/44; A61K 47/46; A61K 31/65
See application file for complete search history.

(56) References Cited

U.S. PATENT DOCUMENTS

| | | |
|---|---|---|
| 1,159,250 A | 11/1915 | Moulton |
| 1,666,684 A | 4/1928 | Carstens |
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,334,147 A | 8/1967 | Brunelle et al. |
| 3,342,845 A | 9/1967 | Sayigh et al. |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |

(Continued)

FOREIGN PATENT DOCUMENTS

| | | |
|---|---|---|
| AU | 198780257 A | 9/1986 |
| AU | 782515 B2 | 12/2005 |

(Continued)

OTHER PUBLICATIONS

Beuchat (Feb. 1983) "Influence of Water Activity on Growth, Metabolic Activities and Survival of Yeasts and Molds" *J Food Prot*, 46(2):135-141.
Fontana (Apr. 1999) "Pharmaceutical Applications for Water Activity" *Pharmaceutical Online* [online]. Retrieved from https://www.pharmaceuticalonline.com/doc/pharmaceutical-applications-for-water-activit-..., on Jan. 17, 2018 (4 pages).
Sarpotdar, P.P. et al. (Jan. 1986) "Effect of Polyethylene Glycol 400 on the Penetration of Drugs Through Human Cadaver Skin In Vitro" *J Pharma Sci*, 75(1):26-28.
"Everything but the Olive." The Olive Oil Source 1998-2016 [online]. Retrieved from the Internet: http://www.oliveoilsource.com/pageA chemical-characteristics.

(Continued)

*Primary Examiner* — Umamaheswari Ramachandran
(74) *Attorney, Agent, or Firm* — Finnegan, Henderson, Farabow, Garrett & Dunner, LLP

(57) ABSTRACT

Provided are compositions and methods for treating rosacea and acne. Specifically, a gel or foam composition having a tetracycline antibiotic and uses thereof for treating rosacea and acne are provided.

4 Claims, 6 Drawing Sheets

(56) References Cited

U.S. PATENT DOCUMENTS

| | | |
|---|---|---|
| 3,383,280 A | 5/1968 | Kuehns |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,824,303 A | 7/1974 | Lanzet et al. |
| 3,841,525 A | 10/1974 | Siegel |
| 3,849,569 A | 11/1974 | Mead |
| 3,849,580 A | 11/1974 | Weinstein et al. |
| 3,865,275 A | 2/1975 | De Nunzio |
| 3,866,800 A | 2/1975 | Schmitt |
| 3,878,118 A | 4/1975 | Watson |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,912,667 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,953,591 A | 4/1976 | Snyder |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,052,513 A | 10/1977 | Kaplan |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,278,206 A | 7/1981 | Prussin |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,338,211 A | 7/1982 | Stiros |
| 4,352,808 A | 10/1982 | Rane et al. |
| 4,363,806 A | 12/1982 | Bergström et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,607,101 A | 8/1986 | Bernstein |
| 4,612,193 A | 9/1986 | Gordon et al. |
| 4,627,973 A | 12/1986 | Moran et al. |
| 4,628,063 A | 12/1986 | Haines et al. |
| 4,661,340 A | 4/1987 | Nagy née Kricsfalussy et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,849,211 A | 7/1989 | Schrauzer |
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,876,083 A | 10/1989 | Grollier et al. |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |
| 4,954,487 A | 9/1990 | Cooper et al. |
| 4,956,049 A | 9/1990 | Bernheim et al. |

(56) References Cited

U.S. PATENT DOCUMENTS

| | | |
|---|---|---|
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,530 A | 6/1993 | Janchitraponvej et al. |
| 5,221,534 A | 6/1993 | DesLauriers et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,305 A | 2/1995 | Repinec et al. |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,705,472 A | 1/1998 | Hayes et al. |
| 5,716,611 A | 2/1998 | Oshlack et al. |
| 5,716,621 A | 2/1998 | Bello |
| 5,719,122 A | 2/1998 | Chiodini et al. |

(56) References Cited

U.S. PATENT DOCUMENTS

| | | |
|---|---|---|
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,854,246 A | 12/1998 | Francois et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,939,376 A | 8/1999 | Durbut et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,017,912 A | 1/2000 | Bussell |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,060,041 A | 5/2000 | Candau et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,310 A | 7/2000 | Heinkel |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,133,327 A | 10/2000 | Kimura et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,662 B1 | 1/2001 | Lanzendörfer et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,241,971 B1 | 6/2001 | Fox et al. |
| 6,251,369 B1 | 6/2001 | Stoltz |
| 6,258,374 B1 | 7/2001 | Friess et al. |
| 6,261,544 B1 | 7/2001 | Coury et al. |
| 6,264,964 B1 | 7/2001 | Mohammadi |
| 6,270,781 B1 | 8/2001 | Gehlsen |
| 6,271,295 B1 | 8/2001 | Powell et al. |
| 6,274,150 B1 | 8/2001 | Simonnet et al. |
| 6,283,336 B1 | 9/2001 | Dwyer et al. |
| 6,284,802 B1 | 9/2001 | Bissett et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,352,727 B1 | 3/2002 | Takahashi |
| 6,355,230 B2 | 3/2002 | Gers-Barlag et al. |
| 6,358,541 B1 | 3/2002 | Goodman |
| 6,358,924 B1 | 3/2002 | Hoffmann |

(56) References Cited

U.S. PATENT DOCUMENTS

| | | |
|---|---|---|
| 6,364,854 B1 | 4/2002 | Ferrer et al. |
| 6,372,234 B1 | 4/2002 | Deckers et al. |
| 6,375,936 B1 | 4/2002 | Allard et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,423,329 B1 | 7/2002 | Sine et al. |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,433,068 B1 | 8/2002 | Morrison et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,060 B1 | 11/2002 | Jones et al. |
| 6,479,532 B1 | 11/2002 | Kamimura et al. |
| 6,482,810 B1 | 11/2002 | Brem et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,551,604 B1 | 4/2003 | Beck et al. |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,607,716 B1 | 8/2003 | Smith et al. |
| 6,610,315 B2 | 8/2003 | Scholz et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,706,290 B1 | 3/2004 | Kajander et al. |
| 6,709,663 B2 | 3/2004 | Espinoza |
| 6,723,309 B1 | 4/2004 | Deane |
| 6,730,288 B1 | 5/2004 | Abram |
| 6,736,860 B2 | 5/2004 | Patel et al. |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,841,547 B2 | 1/2005 | Brown et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |
| 6,914,057 B1 | 7/2005 | Ryan et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,986,883 B2 | 1/2006 | Pellico |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Meketa |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,842,791 B2 | 11/2010 | Britten et al. |
| 7,960,416 B2 | 6/2011 | Sato et al. |
| 8,114,385 B2 | 2/2012 | Tamarkin et al. |
| 8,119,106 B2 | 2/2012 | Tamarkin et al. |
| 8,119,109 B2 | 2/2012 | Tamarkin et al. |
| 8,119,150 B2 | 2/2012 | Tamarkin et al. |
| 8,158,109 B2 | 4/2012 | Abram et al. |
| 8,192,749 B2 | 6/2012 | Ashley |
| 8,211,874 B2 | 7/2012 | Theobald et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,374 B2 | 7/2013 | Tamarkin et al. |
| 8,486,375 B2 | 7/2013 | Tamarkin et al. |
| 8,486,376 B2 | 7/2013 | Friedman et al. |
| 8,512,718 B2 | 8/2013 | Eini et al. |
| 8,518,376 B2 | 8/2013 | Tamarkin et al. |
| 8,518,378 B2 | 8/2013 | Tamarkin et al. |
| 8,592,380 B2 | 11/2013 | Trumbore et al. |
| 8,617,100 B2 | 12/2013 | Eini et al. |
| 8,618,081 B2 | 12/2013 | Tamarkin et al. |
| 8,623,330 B2 | 1/2014 | Gurge et al. |
| 8,636,982 B2 | 1/2014 | Tamarkin et al. |
| 8,652,443 B2 | 2/2014 | Varanasi et al. |
| 8,703,105 B2 | 4/2014 | Tamarkin et al. |
| 8,709,385 B2 | 4/2014 | Tamarkin et al. |
| 8,722,021 B2 | 5/2014 | Friedman et al. |
| 8,735,377 B1 | 5/2014 | Sipos |
| 8,741,265 B2 | 6/2014 | Tamarkin et al. |
| 8,778,365 B1 | 7/2014 | Hardas et al. |
| 8,784,780 B2 | 7/2014 | Gurge et al. |
| 8,795,635 B2 | 8/2014 | Tamarkin et al. |
| 8,795,693 B2 | 8/2014 | Tamarkin et al. |

(56) References Cited

U.S. PATENT DOCUMENTS

| | | |
|---|---|---|
| 8,840,869 B2 | 9/2014 | Friedman et al. |
| 8,846,039 B2 | 9/2014 | Chung et al. |
| 8,865,139 B1 | 10/2014 | Tamarkin et al. |
| 8,871,184 B2 | 10/2014 | Tamarkin et al. |
| 8,895,536 B2 | 11/2014 | Bannister et al. |
| 8,900,553 B2 | 12/2014 | Tamarkin et al. |
| 8,900,554 B2 | 12/2014 | Tamarkin et al. |
| 8,945,516 B2 | 2/2015 | Tamarkin et al. |
| 8,992,896 B2 | 3/2015 | Tamarkin et al. |
| 9,050,253 B2 | 6/2015 | Tamarkin et al. |
| 9,072,667 B2 | 7/2015 | Tamarkin et al. |
| 9,101,662 B2 | 8/2015 | Tamarkin et al. |
| 9,161,916 B2 | 10/2015 | Tamarkin et al. |
| 9,167,813 B2 | 10/2015 | Tamarkin et al. |
| 9,192,558 B2 | 11/2015 | Chen et al. |
| 9,211,259 B2 | 12/2015 | Friedman et al. |
| 9,265,725 B2 | 2/2016 | Tamarkin et al. |
| 9,265,740 B2 | 2/2016 | Johnston et al. |
| 9,271,930 B2 | 3/2016 | At |
| 9,320,705 B2 | 4/2016 | Tamarkin et al. |
| 9,439,857 B2 | 9/2016 | Tamarkin et al. |
| 9,474,720 B2 | 10/2016 | Yamamoto |
| 9,492,412 B2 | 11/2016 | Tamarkin et al. |
| 9,539,208 B2 | 1/2017 | Tamarkin et al. |
| 9,539,266 B2 | 1/2017 | Mansouri |
| 9,549,898 B2 | 1/2017 | Tamarkin et al. |
| 9,572,775 B2 | 2/2017 | Tamarkin et al. |
| 9,592,246 B2 | 3/2017 | Salman et al. |
| 9,622,947 B2 | 4/2017 | Tamarkin et al. |
| 9,636,405 B2 | 5/2017 | Tamarkin et al. |
| 9,662,298 B2 | 5/2017 | Tamarkin et al. |
| 9,668,972 B2 | 6/2017 | Tamarkin et al. |
| 9,675,700 B2 | 6/2017 | Tamarkin et al. |
| 9,682,021 B2 | 6/2017 | Tamarkin et al. |
| 9,713,643 B2 | 7/2017 | Friedman et al. |
| 9,795,564 B2 | 10/2017 | Tamarkin et al. |
| 9,849,142 B2 | 12/2017 | Tamarkin et al. |
| 9,884,017 B2 | 2/2018 | Tamarkin et al. |
| 9,931,328 B2 | 4/2018 | Kandavilli et al. |
| 10,086,080 B2 | 10/2018 | Tamarkin et al. |
| 10,137,200 B2 | 11/2018 | Tamarkin et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0033838 A1 | 10/2001 | Farmer |
| 2001/0036450 A1 | 11/2001 | Verite et al. |
| 2001/0054574 A1 | 12/2001 | Navarro |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0031478 A1 | 3/2002 | Keller et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Halswanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0182234 A1 | 12/2002 | Riedel et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0013692 A1 | 1/2003 | Gullans et al. |
| 2003/0017181 A1 | 1/2003 | Rood et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0077301 A1 | 4/2003 | Maibach et al. |
| 2003/0078172 A1 | 4/2003 | Guiramand et al. |
| 2003/0082120 A1 | 5/2003 | Milstein |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0118527 A1 | 6/2003 | Jager et al. |
| 2003/0129259 A1 | 7/2003 | Mahalingam et al. |
| 2003/0130247 A1 | 7/2003 | Gans et al. |
| 2003/0148949 A1 | 8/2003 | Podolsky |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0185861 A1 | 10/2003 | Hori et al. |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215418 A1 | 11/2003 | Asmus et al. |
| 2003/0215472 A1 | 11/2003 | Bonda et al. |
| 2003/0235597 A1 | 12/2003 | Withiam et al. |
| 2004/0002550 A1 | 1/2004 | Mecurio |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0106688 A1 | 6/2004 | Koike et al. |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0198706 A1 | 10/2004 | Carrara |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0258627 A1 | 12/2004 | Riedel et al. |
| 2004/0258628 A1 | 12/2004 | Riedel et al. |
| 2004/0258643 A1 | 12/2004 | Yaqub et al. |
| 2005/0002976 A1 | 1/2005 | Wu |
| 2005/0013853 A1 | 1/2005 | Gil-Ad et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0075407 A1 | 4/2005 | Tamarkin et al. |
| 2005/0079139 A1 | 4/2005 | Jacques et al. |
| 2005/0079228 A1 | 4/2005 | Jaiswal et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |

(56) References Cited

U.S. PATENT DOCUMENTS

| | | |
|---|---|---|
| 2005/0148552 A1 | 7/2005 | Ryan et al. |
| 2005/0153943 A1 | 7/2005 | Ashley |
| 2005/0164993 A1 | 7/2005 | Ashley |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Meketa |
| 2006/0057168 A1 | 3/2006 | Larm et al. |
| 2006/0099151 A1 | 5/2006 | Neubourg |
| 2006/0108377 A1 | 5/2006 | Glynn et al. |
| 2006/0110415 A1 | 5/2006 | Gupta |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0015739 A1 | 1/2007 | Walker et al. |
| 2007/0017696 A1 | 1/2007 | Lin et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0111956 A1 | 5/2007 | Matsushima et al. |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0141086 A1 | 6/2007 | Ohara et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0166274 A1 | 7/2007 | Mazur et al. |
| 2007/0224143 A1 | 9/2007 | Konis |
| 2007/0237724 A1 | 10/2007 | Abram et al. |
| 2007/0264317 A1 | 11/2007 | Yosha et al. |
| 2007/0271235 A1 | 11/2007 | Frank et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0050317 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0311167 A1 | 12/2008 | Oronsky et al. |
| 2008/0317679 A1 | 12/2008 | Tamarkin et al. |
| 2009/0017147 A1 | 1/2009 | Lintner et al. |
| 2009/0053290 A1 | 2/2009 | Sand et al. |
| 2009/0061001 A1 | 3/2009 | Hougaz |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0214628 A1 | 8/2009 | De Rijk |
| 2009/0291917 A1 | 11/2009 | Akama et al. |
| 2010/0111879 A1 | 5/2010 | Tamarkin et al. |
| 2010/0221194 A1 | 9/2010 | Loupenok |
| 2010/0247449 A1 | 9/2010 | Graupe et al. |
| 2010/0286417 A1 | 11/2010 | Mendes et al. |
| 2011/0002969 A1 | 1/2011 | Serraima et al. |
| 2011/0097279 A1 | 4/2011 | Tamarkin et al. |
| 2011/0207765 A1 | 8/2011 | Van Den Bussche et al. |
| 2011/0262542 A1 | 10/2011 | Ashley |
| 2012/0064136 A1 | 3/2012 | Baker, Jr. et al. |
| 2012/0082632 A1 | 4/2012 | Phillips et al. |
| 2012/0087872 A1 | 4/2012 | Tamarkin et al. |
| 2012/0128598 A1 | 5/2012 | Trumbore et al. |
| 2012/0141384 A1 | 6/2012 | Tamarkin |
| 2012/0148503 A1 | 6/2012 | Tamarkin et al. |
| 2012/0156144 A1 | 6/2012 | Tamarkin et al. |
| 2012/0164087 A1 | 6/2012 | Carter |
| 2012/0181201 A1 | 7/2012 | Heggie |
| 2012/0237453 A1 | 9/2012 | Tamarkin et al. |
| 2013/0011342 A1 | 1/2013 | Tamarkin et al. |
| 2013/0053353 A1 | 2/2013 | Tamarkin et al. |
| 2013/0115173 A1 | 5/2013 | Trumbore et al. |
| 2013/0161351 A1 | 6/2013 | Eini et al. |
| 2013/0164225 A1 | 6/2013 | Tamarkin et al. |
| 2013/0189195 A1 | 7/2013 | Tamarkin et al. |
| 2013/0189196 A1 | 7/2013 | Tamarkin et al. |
| 2013/0225536 A1 | 8/2013 | Tamarkin et al. |

(56) References Cited

U.S. PATENT DOCUMENTS

| | | |
|---|---|---|
| 2013/0251644 A1 | 9/2013 | Majhi et al. |
| 2013/0261565 A1 | 10/2013 | Wong et al. |
| 2013/0295022 A1 | 11/2013 | Friedman et al. |
| 2013/0296387 A1 | 11/2013 | Saad |
| 2014/0066524 A1 | 3/2014 | Tamarkin et al. |
| 2014/0086848 A1 | 3/2014 | Tamarkin et al. |
| 2014/0121188 A1 | 5/2014 | Tamarkin et al. |
| 2014/0140937 A1 | 5/2014 | Gurge et al. |
| 2014/0182585 A1 | 7/2014 | Tamarkin et al. |
| 2014/0186269 A1 | 7/2014 | Tamarkin et al. |
| 2014/0221320 A1 | 8/2014 | Joks et al. |
| 2014/0228355 A1 | 8/2014 | Kortagere et al. |
| 2014/0242016 A1 | 8/2014 | Binks et al. |
| 2015/0025060 A1 | 1/2015 | Tamarkin et al. |
| 2015/0098907 A1 | 4/2015 | Tamarkin et al. |
| 2015/0141381 A1 | 5/2015 | Levy et al. |
| 2015/0157586 A1 | 6/2015 | Tamarkin et al. |
| 2015/0164922 A1 | 6/2015 | Tamarkin et al. |
| 2015/0174144 A1 | 6/2015 | Bowser et al. |
| 2015/0196570 A1 | 7/2015 | Tamarkin et al. |
| 2015/0209296 A1 | 7/2015 | Yamamoto |
| 2015/0374625 A1 | 12/2015 | Tamarkin et al. |
| 2016/0101184 A1 | 4/2016 | Tamarkin et al. |
| 2016/0128944 A1 | 5/2016 | Chawrai et al. |
| 2016/0158261 A1 | 6/2016 | Friedman et al. |
| 2016/0213757 A1 | 7/2016 | Edelson et al. |
| 2016/0279152 A1 | 9/2016 | Chen et al. |
| 2016/0287615 A1 | 10/2016 | Chan et al. |
| 2016/0354473 A1 | 12/2016 | Tamarkin et al. |
| 2016/0361252 A1 | 12/2016 | Franke |
| 2016/0361320 A1 | 12/2016 | Zhao et al. |
| 2017/0014517 A1 | 1/2017 | Tamarkin |
| 2017/0049712 A1 | 2/2017 | Bhalani et al. |
| 2017/0119665 A1 | 5/2017 | Tamarkin et al. |
| 2017/0157175 A1 | 6/2017 | Tamarkin et al. |
| 2017/0172857 A1 | 6/2017 | Tamarkin et al. |
| 2017/0181970 A1 | 6/2017 | Tamarkin et al. |
| 2017/0216334 A1 | 8/2017 | Tamarkin et al. |
| 2017/0231909 A1 | 8/2017 | Tamarkin et al. |
| 2017/0274084 A1 | 9/2017 | Friedman et al. |
| 2017/0340743 A1 | 11/2017 | Tamarkin et al. |
| 2017/0348418 A1 | 12/2017 | Tamarkin et al. |
| 2017/0354597 A1 | 12/2017 | Tamarkin et al. |
| 2018/0000734 A1 | 1/2018 | Tamarkin et al. |
| 2018/0147218 A1 | 5/2018 | Tamarkin et al. |
| 2018/0153804 A1 | 6/2018 | Tamarkin et al. |
| 2018/0214558 A1 | 8/2018 | Tamarkin et al. |
| 2018/0235984 A1 | 8/2018 | Eini et al. |

FOREIGN PATENT DOCUMENTS

| | | |
|---|---|---|
| CA | 2114537 A1 | 2/1993 |
| CA | 2154438 A1 | 1/1996 |
| CA | 2422244 A1 | 9/2003 |
| CA | 2502986 A1 | 5/2004 |
| CA | 2534372 A1 | 10/2005 |
| CH | 639913 A5 | 12/1983 |
| DE | 1 882 100 U | 11/1963 |
| DE | 1926796 A1 | 3/1970 |
| DE | 2 608 226 A1 | 9/1977 |
| DE | 4140474 A1 | 6/1993 |
| DE | 10009233 A1 | 8/2000 |
| DE | 10138495 A1 | 2/2003 |
| DE | 102004016710 A1 | 10/2005 |
| EP | 0 052 404 A2 | 5/1982 |
| EP | 0 156 507 A1 | 10/1985 |
| EP | 0 186 453 A2 | 7/1986 |
| EP | 0 213 827 A2 | 3/1987 |
| EP | 0 214 865 A2 | 3/1987 |
| EP | 0 270 316 A2 | 6/1988 |
| EP | 0 297 436 A2 | 1/1989 |
| EP | 0 336 812 A2 | 10/1989 |
| EP | 0 414 920 A1 | 3/1991 |
| EP | 0 211 550 B1 | 4/1991 |
| EP | 0 216 856 B1 | 7/1991 |
| EP | 0 454 102 A2 | 10/1991 |
| EP | 0 326 196 B2 | 3/1992 |
| EP | 0 484 530 A1 | 5/1992 |
| EP | 0 485 299 A1 | 5/1992 |
| EP | 0 488 089 A1 | 6/1992 |
| EP | 0 528 190 A1 | 2/1993 |
| EP | 0 552 612 A2 | 7/1993 |
| EP | 0 569 773 A2 | 11/1993 |
| EP | 0 404 376 B1 | 3/1994 |
| EP | 0 598 412 A2 | 5/1994 |
| EP | 0 391 124 B1 | 6/1995 |
| EP | 0 662 431 A2 | 7/1995 |
| EP | 0 535 327 B1 | 10/1996 |
| EP | 0 738 516 A1 | 10/1996 |
| EP | 0 757 959 A1 | 2/1997 |
| EP | 0 824 911 A2 | 2/1998 |
| EP | 0 829 259 A1 | 3/1998 |
| EP | 0 676 198 B1 | 10/1998 |
| EP | 0 979 654 A1 | 2/2000 |
| EP | 0 993 827 A1 | 4/2000 |
| EP | 1 025 836 A1 | 8/2000 |
| EP | 1 055 425 A2 | 11/2000 |
| EP | 0 506 197 B2 | 7/2001 |
| EP | 1 215 258 A2 | 6/2002 |
| EP | 1 287 813 A1 | 3/2003 |
| EP | 1 308 169 A1 | 5/2003 |
| EP | 1 375 386 A1 | 1/2004 |
| EP | 0 504 301 B1 | 3/2004 |
| EP | 1 428 521 A2 | 6/2004 |
| EP | 1 438 946 A1 | 7/2004 |
| EP | 1 189 579 B1 | 9/2004 |
| EP | 1 475 381 A1 | 11/2004 |
| EP | 1 500 385 A1 | 1/2005 |
| EP | 1 537 916 A1 | 6/2005 |
| EP | 1 600 185 A1 | 11/2005 |
| EP | 0 928 608 B1 | 3/2006 |
| EP | 1 653 932 A1 | 5/2006 |
| EP | 1 734 927 A1 | 12/2006 |
| EP | 1 758 547 A1 | 3/2007 |
| EP | 1 483 001 B1 | 11/2007 |
| EP | 1 584 324 B1 | 11/2007 |
| EP | 1 889 609 A2 | 2/2008 |
| EP | 1 902 706 A1 | 3/2008 |
| EP | 2 129 383 A1 | 12/2009 |
| EP | 2 422 768 A2 | 2/2012 |
| EP | 2 494 959 A1 | 9/2012 |
| FR | 2 456 522 A1 | 12/1980 |
| FR | 2 591 331 A1 | 6/1987 |
| FR | 2 640 942 A2 | 6/1990 |
| FR | 2 736 824 A1 | 1/1997 |
| FR | 2 774 595 A1 | 8/1999 |
| FR | 2 789 371 A1 | 8/2000 |
| FR | 2 793 479 A1 | 11/2000 |
| FR | 2 814 959 A1 | 4/2002 |
| FR | 2 833 246 A1 | 6/2003 |
| FR | 2 840 903 A1 | 12/2003 |
| FR | 2 843 373 A1 | 2/2004 |
| FR | 2 845 672 A1 | 4/2004 |
| FR | 2 848 998 A1 | 6/2004 |
| FR | 2 860 976 | 4/2005 |
| FR | 2 915 891 A1 | 11/2008 |
| GB | 808 104 A | 1/1959 |
| GB | 808 105 A | 1/1959 |
| GB | 922 930 A | 4/1963 |
| GB | 933 486 A | 8/1963 |
| GB | 998 490 A | 7/1965 |
| GB | 1 026 831 A | 4/1966 |
| GB | 1 033 299 A | 6/1966 |
| GB | 1 081 949 A | 9/1967 |
| GB | 1 121 358 A | 7/1968 |
| GB | 1 162 684 A | 8/1969 |
| GB | 1 170 152 A | 11/1969 |
| GB | 1 201 918 A | 8/1970 |
| GB | 1 347 950 A | 2/1974 |
| GB | 1 351 761 A | 5/1974 |
| GB | 1 351 762 A | 5/1974 |
| GB | 1 353 381 A | 5/1974 |
| GB | 1 376 649 A | 12/1974 |
| GB | 1 397 285 A | 6/1975 |

(56) References Cited

FOREIGN PATENT DOCUMENTS

| | | |
|---|---|---|
| GB | 1 408 036 A | 10/1975 |
| GB | 1 457 671 A | 12/1976 |
| GB | 1 489 672 A | 10/1977 |
| GB | 2 004 746 A | 4/1979 |
| GB | 1 561 423 A | 2/1980 |
| GB | 2 114 580 A | 8/1983 |
| GB | 2 166 651 A | 5/1986 |
| GB | 2 153 686 B | 7/1987 |
| GB | 2 172 298 B | 11/1988 |
| GB | 2 206 099 A | 12/1988 |
| GB | 2 337 461 A | 11/1999 |
| GB | 2 367 809 A | 4/2002 |
| GB | 2 406 330 A | 3/2005 |
| GB | 2 406 791 B | 2/2008 |
| GB | 2 474 930 A | 5/2011 |
| IL | 49491 A | 9/1979 |
| IL | 152 486 A | 5/2003 |
| JP | 55-069682 A | 5/1980 |
| JP | 56-039815 A | 4/1981 |
| JP | 57-044429 A | 3/1982 |
| JP | 60-001113 A | 1/1985 |
| JP | 61-275395 A | 12/1986 |
| JP | 62-241701 A | 10/1987 |
| JP | 63-119420 A | 5/1988 |
| JP | 01-100111 A | 4/1989 |
| JP | 01-156906 A | 6/1989 |
| JP | 02-184614 A | 7/1990 |
| JP | 02-255890 A | 10/1990 |
| JP | 03-050289 A | 3/1991 |
| JP | 04-51958 A | 2/1992 |
| JP | 04-282311 A | 10/1992 |
| JP | 04-312521 A | 11/1992 |
| JP | 05-070340 A | 3/1993 |
| JP | 05-213734 A | 8/1993 |
| JP | 06-100414 A | 4/1994 |
| JP | 06-263630 A | 9/1994 |
| JP | 06-329532 A | 11/1994 |
| JP | 07-215835 A | 8/1995 |
| JP | 08-040899 A | 2/1996 |
| JP | 08-501529 A | 2/1996 |
| JP | 08-119831 A | 5/1996 |
| JP | 08-165218 A | 6/1996 |
| JP | 08-277209 A | 10/1996 |
| JP | 09-84855 A | 3/1997 |
| JP | 09-099553 A | 4/1997 |
| JP | 09-110636 A | 4/1997 |
| JP | 10-114619 A | 5/1998 |
| JP | 10-332456 A | 12/1998 |
| JP | 11-501045 A | 1/1999 |
| JP | 11-250543 A | 9/1999 |
| JP | 2000-017174 A | 1/2000 |
| JP | 2000-080017 A | 3/2000 |
| JP | 2000-128734 A | 5/2000 |
| JP | 2000-191429 A | 7/2000 |
| JP | 2000-239140 A | 9/2000 |
| JP | 2000-351726 A | 12/2000 |
| JP | 2000-354623 A | 12/2000 |
| JP | 2001-002526 A | 1/2001 |
| JP | 2001-019606 A | 1/2001 |
| JP | 2001-072963 A | 3/2001 |
| JP | 2002-012513 A | 1/2002 |
| JP | 2002-047136 A | 2/2002 |
| JP | 2002-524490 A | 8/2002 |
| JP | 2002-302419 A | 10/2002 |
| JP | 2003-012511 A | 1/2003 |
| JP | 2003-055146 A | 2/2003 |
| JP | 2004-047136 A | 2/2004 |
| JP | 2004-250435 A | 9/2004 |
| JP | 2004-348277 A | 12/2004 |
| JP | 2005-314323 A | 11/2005 |
| JP | 2005-350378 A | 12/2005 |
| JP | 2006-008574 A | 1/2006 |
| JP | 2006-036317 A | 2/2006 |
| JP | 2006-103799 A | 4/2006 |
| JP | 2006-525145 A | 11/2006 |
| JP | 2007-131539 A2 | 5/2007 |
| JP | 2007-155667 A | 6/2007 |
| JP | 2007-326996 A | 12/2007 |
| KR | 0143232 A | 7/1998 |
| KR | 2001-003063 A | 1/2001 |
| NZ | 520014 A | 5/2005 |
| NZ | 540166 A | 6/2007 |
| RU | 2277501 C2 | 6/2006 |
| UA | 66796 C2 | 7/2001 |
| WO | WO 82/001821 A1 | 6/1982 |
| WO | WO 86/05389 A1 | 9/1986 |
| WO | WO 88/01502 A1 | 3/1988 |
| WO | WO 88/01863 A1 | 3/1988 |
| WO | WO 88/08316 A1 | 11/1988 |
| WO | WO 89/06537 A1 | 7/1989 |
| WO | WO 90/05774 A1 | 5/1990 |
| WO | WO 91/11991 A1 | 8/1991 |
| WO | WO 92/00077 A1 | 1/1992 |
| WO | WO 92/005142 A1 | 4/1992 |
| WO | WO 92/05763 A1 | 4/1992 |
| WO | WO 92/11839 A1 | 7/1992 |
| WO | WO 92/13602 A1 | 8/1992 |
| WO | WO 93/025189 A1 | 12/1993 |
| WO | WO 94/006440 A1 | 3/1994 |
| WO | WO 96/03115 A1 | 2/1996 |
| WO | WO 96/19921 A1 | 7/1996 |
| WO | WO 96/24325 A1 | 8/1996 |
| WO | WO 96/26711 A1 | 9/1996 |
| WO | WO 96/27376 A1 | 9/1996 |
| WO | WO 96/39119 A1 | 12/1996 |
| WO | WO 97/03638 A1 | 2/1997 |
| WO | WO 97/39745 A1 | 10/1997 |
| WO | WO 98/17282 A1 | 4/1998 |
| WO | WO 98/18472 A1 | 5/1998 |
| WO | WO 98/19654 A1 | 5/1998 |
| WO | WO 98/21955 A1 | 5/1998 |
| WO | WO 98/23291 A1 | 6/1998 |
| WO | WO 98/31339 A1 | 7/1998 |
| WO | WO 98/36733 A2 | 8/1998 |
| WO | WO 98/52536 A1 | 11/1998 |
| WO | WO 99/08649 A2 | 2/1999 |
| WO | WO 99/20250 A1 | 4/1999 |
| WO | WO 99/37282 A2 | 7/1999 |
| WO | WO 99/53923 A1 | 10/1999 |
| WO | WO 2000/09082 A1 | 2/2000 |
| WO | WO 2000/15193 A1 | 3/2000 |
| WO | WO 2000/23051 A1 | 4/2000 |
| WO | WO 2000/33825 A2 | 6/2000 |
| WO | WO 2000/38731 A1 | 7/2000 |
| WO | WO 2000/61076 A1 | 10/2000 |
| WO | WO 2000/62776 A1 | 10/2000 |
| WO | WO 2000/72805 A1 | 12/2000 |
| WO | WO 2000/76461 A2 | 12/2000 |
| WO | WO 2001/01949 A1 | 1/2001 |
| WO | WO 2001/05366 A1 | 1/2001 |
| WO | WO 2001/08681 A1 | 2/2001 |
| WO | WO 2001/10961 A1 | 2/2001 |
| WO | WO 2001/53198 A1 | 7/2001 |
| WO | WO 2001/54212 A1 | 7/2001 |
| WO | WO 2001/54679 A2 | 8/2001 |
| WO | WO 2001/62209 A2 | 8/2001 |
| WO | WO 2001/70242 A2 | 9/2001 |
| WO | WO 2001/76579 A1 | 10/2001 |
| WO | WO 2001/82880 A3 | 11/2001 |
| WO | WO 2001/82890 A1 | 11/2001 |
| WO | WO 2001/85102 A2 | 11/2001 |
| WO | WO 2001/85128 A1 | 11/2001 |
| WO | WO 2001/95728 A1 | 12/2001 |
| WO | WO 2002/00820 A1 | 1/2002 |
| WO | WO 2002/07685 A2 | 1/2002 |
| WO | WO 2002/15860 A1 | 2/2002 |
| WO | WO 2002/15873 A2 | 2/2002 |
| WO | WO 2002/24161 A1 | 3/2002 |
| WO | WO 2002/28435 A1 | 4/2002 |
| WO | WO 2002/41847 A1 | 5/2002 |
| WO | WO 2002/43490 A1 | 6/2002 |
| WO | WO 2002/062324 A2 | 8/2002 |
| WO | WO 2002/078667 A1 | 10/2002 |
| WO | WO 2002/087519 A2 | 11/2002 |

(56) References Cited

FOREIGN PATENT DOCUMENTS

| | | |
|---|---|---|
| WO | WO 2003/000223 A1 | 1/2003 |
| WO | WO 2003/002082 A1 | 1/2003 |
| WO | WO 2003/005985 A1 | 1/2003 |
| WO | WO 2003/013984 A1 | 2/2003 |
| WO | WO 2003/015699 A2 | 2/2003 |
| WO | WO 2003/051294 A2 | 6/2003 |
| WO | WO 2003/053292 A1 | 7/2003 |
| WO | WO 2003/055445 A2 | 7/2003 |
| WO | WO 2003/055454 A1 | 7/2003 |
| WO | WO 2003/070301 A1 | 8/2003 |
| WO | WO 2003/071995 A1 | 9/2003 |
| WO | WO 2003/075851 A2 | 9/2003 |
| WO | WO 2003/092641 A1 | 11/2003 |
| WO | WO 2003/094873 A1 | 11/2003 |
| WO | WO 2003/097002 A1 | 11/2003 |
| WO | WO 2004/017962 A2 | 3/2004 |
| WO | WO 2004/037197 A2 | 5/2004 |
| WO | WO 2004/037225 A2 | 5/2004 |
| WO | WO 2004/003284 A1 | 8/2004 |
| WO | WO 2004/064769 A2 | 8/2004 |
| WO | WO 2004/064833 A1 | 8/2004 |
| WO | WO 2004/071479 A1 | 8/2004 |
| WO | WO 2004/078158 A2 | 9/2004 |
| WO | WO 2004/078896 A1 | 9/2004 |
| WO | WO 2004/093895 A1 | 11/2004 |
| WO | WO 2004/112780 A1 | 12/2004 |
| WO | WO 2005/009416 A1 | 2/2005 |
| WO | WO 2005/011567 A2 | 2/2005 |
| WO | WO 2005/018530 A2 | 3/2005 |
| WO | WO 2005/032522 A1 | 4/2005 |
| WO | WO 2005/044219 A1 | 5/2005 |
| WO | WO 2005/063224 A1 | 7/2005 |
| WO | WO 2005/065652 A1 | 7/2005 |
| WO | WO 2005/076697 A2 | 8/2005 |
| WO | WO 2005/097068 A1 | 10/2005 |
| WO | WO 2005/102282 A1 | 11/2005 |
| WO | WO 2005/102539 A1 | 11/2005 |
| WO | WO 2005/117813 A1 | 12/2005 |
| WO | WO 2006/003481 A2 | 1/2006 |
| WO | WO 2006/010589 A2 | 2/2006 |
| WO | WO 2006/011046 A2 | 2/2006 |
| WO | WO 2006/020682 A1 | 2/2006 |
| WO | WO 2006/028339 A1 | 3/2006 |
| WO | WO 2006/031271 A2 | 3/2006 |
| WO | WO 2006/045170 A2 | 5/2006 |
| WO | WO 2006/079632 A1 | 8/2006 |
| WO | WO 2006/081327 A2 | 8/2006 |
| WO | WO 2006/091229 A2 | 8/2006 |
| WO | WO 2006/100485 A1 | 9/2006 |
| WO | WO 2006/120682 A2 | 11/2006 |
| WO | WO 2006/121610 A2 | 11/2006 |
| WO | WO 2006/122158 A2 | 11/2006 |
| WO | WO 2006/129161 A2 | 12/2006 |
| WO | WO 2006/131784 A1 | 12/2006 |
| WO | WO 2007/007208 A2 | 1/2007 |
| WO | WO 2007/010494 A1 | 1/2007 |
| WO | WO 2007/012977 A2 | 2/2007 |
| WO | WO 2007/023396 A2 | 3/2007 |
| WO | WO 2007/031621 A2 | 3/2007 |
| WO | WO 2007/039825 A2 | 4/2007 |
| WO | WO 2007/050543 A2 | 5/2007 |
| WO | WO 2007/054818 A2 | 5/2007 |
| WO | WO 2007/072216 A2 | 6/2007 |
| WO | WO 2007/082698 A1 | 7/2007 |
| WO | WO 2007/085902 A2 | 8/2007 |
| WO | WO 2007/099396 A2 | 9/2007 |
| WO | WO 2007/111962 A2 | 10/2007 |
| WO | WO 2008/008397 A2 | 1/2008 |
| WO | WO 2008/010963 A2 | 1/2008 |
| WO | WO 2008/038147 A2 | 4/2008 |
| WO | WO 2008/041045 A1 | 4/2008 |
| WO | WO 2008/075207 A2 | 6/2008 |
| WO | WO 2008/087148 A2 | 7/2008 |
| WO | WO 2008/104734 A1 | 9/2008 |
| WO | WO 2008/110872 A2 | 9/2008 |
| WO | WO 2008/152444 A2 | 12/2008 |
| WO | WO 2009/007785 A2 | 1/2009 |
| WO | WO 2009/069006 A2 | 6/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/090558 A2 | 7/2009 |
| WO | WO 2009/098595 A2 | 8/2009 |
| WO | WO 2011/006026 A1 | 1/2011 |
| WO | WO 2011/013008 A2 | 2/2011 |
| WO | WO 2011/013009 A2 | 2/2011 |
| WO | WO 2011/026094 A2 | 3/2011 |
| WO | WO 2011/039637 A2 | 4/2011 |
| WO | WO 2011/039638 A2 | 4/2011 |
| WO | WO 2011/064631 A1 | 6/2011 |
| WO | WO 2011/106026 A1 | 9/2011 |
| WO | WO 2011/138678 A2 | 11/2011 |
| WO | WO 2013/136192 A2 | 9/2013 |
| WO | WO 2014/134394 A1 | 9/2014 |
| WO | WO 2014/134427 A1 | 9/2014 |
| WO | WO 2014/151347 A1 | 9/2014 |
| WO | WO 2014/201541 A1 | 12/2014 |
| WO | WO 2015/075640 A1 | 5/2015 |
| WO | WO 2015/114320 A1 | 8/2015 |
| WO | WO 2015/153864 A2 | 10/2015 |
| WO | WO 2017/029647 A1 | 2/2017 |
| WO | WO 2017/030555 A1 | 2/2017 |

OTHER PUBLICATIONS

"Suppositories?" CareCure Community, SCI Forum [online]. http://sci.rutgers.edu/forum/showthread.php?4176-Suppositories. Published: Apr. 16, 2002, 3 pages.

1058. Benzalkonium Chloride; 2350. Citric Acid; 6143. Methyl Salicylate. The Merck Index: An Encyclopedia of Chemicals, Drugs, and Biologicals. 13th Edition, 2001, pp. 181, 405-406, 1090-1091, 1556.

242. Allantoin, The Merck Index: An Encyclopedia of Chemicals, Drugs, and Biologicals. 10th edition, Merck & Co., Inc., 1983, p. 39.

Abdullah, G.Z. et al. (Jan. 2013) "Carbopol 934, 940 and Ultrez 10 as viscosity modifiers of palm olein esters based nano-scaled emulsion containing ibuprofen" Pak J Pharm Sci, 26(1):75-83.

Abrams et al., "Ciclopirox gel treatment of scalp seborrheic dermatitis," in: Shuster, S. (ed.) Hydroxy-Piridones as Antifungal Agents with Special Emphasis on Onychomycosis. Springer, Berlin, Heidelberg; 1999, Chapter 8, pp. 45-50.

Adachi, "Storage and Oxidative Stability of O/W/ Nanoemulsions," Foods Food Ingredients J. Jpn., 2004, 209(11), 1 page (Abstract).

Adisen et al., "Topical tetracycline in the treatment of acne vulgaris," J Drugs Dermatol., Oct. 2008, 7(10):953-955.

Alcohol SDA 40B, 200 Proof. Material Safety Data Sheets [online]. Retrieved from the Internet: http://www.pharmco-prod.com/pages/MSDS/SDA.sub.--40B.sub.--200.pdf, on Dec. 9, 2008. MSDS 044, Revision 2.1, Revision Date Dec. 2005, 2 pages.

Alcohol, Wikipedia, the free encyclopedia [online]. Last modified on Apr. 23, 2014. Retrieved on May 17, 2014, http://en.wikipedia.org/wiki/Alcohol, 17 pages.

Aldara™ (imiquimod) Cream. Highlights of Prescribing Information, Graceway Pharmaceuticals, LLC, Mar. 2007, 29 pages.

Allantoin, Römpp Online, retrieved on Sep. 23, 2015, https://roempp.thieme.de/roempp4.0/do/data/RD-O 1-01552, 5 pages.

Al-Mughrabi et al., "Effectiveness of Essential Oils and Their Combinations with Aluminum Starch Octenylsuccinate on Potato Storage Pathogens," TEOP, 2013, 16(1):23-31.

Ambrose et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, Sep. 1991, 35(9):1799-1803.

Aminobenzoic Acid, Knovel, 2006, retrieved on Apr. 18, 2012, http://www.knovel.com/web/portal/knovel_content?p_p_id=EXT_KNOVEL_CONTENT . . . , 2 pages.

(56) References Cited

OTHER PUBLICATIONS

Anton et al., "Water-in-oil nano-emulsion formation by the phase inversion temperature method: a novel and general concept, a new template for nanoencapsulation," Proceedings of the 33rd Annual Meeting and Exposition of the Controlled Release Society, Jul. 2006, Vienna, Austria, 2 pages.
Arct et al., "Common cosmetic hydrophilic ingredients as penetration modifiers of flavonoids," International Journal of Cosmetic Science, Dec. 2002, 24(6):357-366 (Abstract Only).
Arisan, Kozmetic ve Kisisel Bakim Urunleri Grubu, retrieved on Dec. 10, 2008, http://www.arisankimya.com/kozmetik.htm, 8 pages.
Arquad HTL8-MS, AkzoNobel Functional Applications, retrieved on Mar. 18, 2013, Retrieved from the Internet: <URL: http://sc.akzonobel.com/en/fa/Pages/product-detail.aspx?prodID=8764>, 1 page.
Aslam et al. (2015) "Emerging drugs for the treatment of acne" *Expert Opin Emerging Drugs*, 20:91-101.
Atopic Dermatitis/Eczema, ibabydoc.com, Copyright 2000, retrieved on Jan. 30, 2010, http://www.ibabydoc.com/online/diseaseeczema.asp 6 pages.
Ausburger and Shangraw, "Bubble size analysis of high consistency aerosol foams and its relationship to foam rheology; Effects fo Container Emptying, Propellant Type, and Time," J. Pharma Sci, Apr. 1968, 57(4):624-631.
Austria, et al., "Stability of vitamin C derivatives in solution and topical formulations", Journal of Pharmaceutical and Biomedical Analysis, 1997, 15:795-801.
Barry and Badal, "Stability of minocycline, doxycycline, and tetracycline stored in agar plates and microdilution trays," Current Microbiology, 1978, 1:33-36.
Barry and Woodford, "Comparative bio-availability and activity of proprietary topical corticosteroid preparations: vasoconstrictor assays on thirty-one ointments," British J. Dermatology, 1975, 93:563-571.
Baskaran et al., "Poloxamer-188 improves capillary blood flow and tissue viability in a cutaneous burn wound," J. Surg. Res., 2001, 101(1):56-61.
Beauty Banter, "Interesting list of comedogenic ingredients!!!!!!!!!!!" QVC blog, Interesting list of comedogenic ingredients, 2014, 1-14.
Bell-Syer et al., "A systematic review of oral treatments for fungal infections of the skin of the feet," J. Dermatology. Treat., 2001, 12:69-74.
Ben-Et and Tatarsky "Application of NMR for the Determination of HLB Values of Nonionic Surfactants," Journal of the American Oil Chemists Society, Mar. 20, 1972, 49:499-500.
Bernstein and Harrison, "Effects of the Immunomodulating Agent R837 on Acute and Latent Herpes Simplex Virus Type 2 Infections," Antimicrobial Agents and Chemotherapy, Sep. 1989, 33(9):1511-1515.
Blaney and Cook, "Topical use of tetracycline in the treatment of acne," Arch Dermatol, Jul. 1976, 112:971-973.
Blute et al., "Phase behaviour of alkyl glycerol ether surfactants", Physikalische Chemie/Physical Chemistry Tenside Surf. Det., 1998, 35(3):207-212.
Boehm et al., "Synthesis of high specific activity [.sup.3 H]-9-cis-retinoic acid and its application for identifying retinoids with unusual binding properties," J. Med. Chem., 1994, 37:408-414.
Brenes, et al., "Stability of Copigmented Anthocyanins and Ascorbic Acid in a Grape Juice Model System", J. Agric Food Chem, 2005, 53(1):49-56 (Abstract Only).
Brisaert, M. et al. (1996) "Investigation on the chemical stability of erythromycin in solutions using an optimization system" *Pharm World Sci*, 18(5):182-186.
BRONOPOL, 2-Bromo-2-Nuro-1,3-Propanediol, Chemical land, Jul. 17, 2006, retrieved on Jun. 4, 2011, http://chemicalland21.com/specialtychem/perchem/BRONOPOL.html, 4 pages.
Brown et al., "Structural dependence of flavonoid interactions with Cu2+ ions: implications for their antioxidant properties," Biochem. J., 1998, 330:1173-1178.

Buck and Guth, "Treatment of Vaginal Intraepithelial Neoplasia (Primarily Low Grade) with Imiquimod 5% Cream", Journal of Lower Genital Tract Disease, 2003, 7(3):290-293.
Bucks et al., "Bioavailability of Topically Administered Steroids: A "Mass Balance" Technique," J. Investigative Dermatology, 1988, 91(1):29-33.
Bunker and Dowd, "Alterations in Scalp Blood Flow after the Epicutaneous Application of 3% Minoxidil and 0.1% Hexyl Nicotinate in Alopecia," British Society for Investigative Dermatology, Sep. 1986, 117(5):668-669.
Burn Patients Need Vitamin D Supplements, NUTRAingredients.com, Jan. 23, 2004, retrieved on May 5, 2010, http://www.nutraingredients.com/Research/Burn-patients-need-vitamin-D-supplements, 1page.
Burton and Marshall, "Hypertrichosis due to minoxidil," British J. Dermatology, 1979, 101:593-595.
C12-15 Alkyl Benzoate, Paula's Choice Skincare, retrieved on Oct. 24, 2010, http://ww.cosmeticscop.com/cosmetic-ingredient-dictionary/definition/259/c12-15-alkyl-benzoate.aspx, 1 page.
Campos and Silva, "Ascorbic Acid and Its Derivatives in Cosmetic Formulations", Cosmetics and Toiletries, 2000, 115(6):59-62 (Abstract Only).
Can Tuberous Sclerosis Be Prevented?, Sharecare, 2002, retrieved on Aug. 29, 2013, <URL: http://www.sharecare.com/health/autosomal-dominant-genetic-disorders/can-tuberous-sclerosis-be-prevented;jsessionid=850579B60520A907DE75930E061E60E6>, 2 pages.
Canavan et al. (2016) "Optimizing Non-Antibiotic Treatments for Patients with Acne: A Review" *Dermatol Ther*, 6:555-578.
Carapeti et al., "Topical diltiazem and bethanechol decrease anal sphincter pressure and heal anal fissures without side effects," Dis Colon Rectum, 2000, 43(10):1359-1362.
Carbowax 1000MSDS, Material Safety Data Sheet for Polyethylene glycol 1000 MSDS, last updated Nov. 6, 2008, retrieved on Dec. 13, 2008, http://www.sciencelab.com/xMSDS-Polyethylene.sub.-glycol.sub.-1000-9926-622, 6 pages.
Carelli et al., "Effect of Vehicles on Yohimbine Permeation Across Excised Hairless Mouse Skin", Pharm Acta Helv, Aug. 1978, 73(3):127-134 (Abstract Only).
Causes of Psoriasis, retrieved on Sep. 9, 2010, http://www.quickcare.org/skin/causes-of0psoriasis.html, 3 pages.
Cetearyl Alcohol, Natural Wellbeing, Copyright 2001-2012, retrieved on Apr. 10, 2014, http://www.naturalwellbeing.com/learning-center/Cetearyl_Alcohol, 3 pages.
Chebil et al., "Solubility of Flavonoids in Organic Solvents," J. Chem. Eng. Data, 2007, 52(5):1552-1556 (Abstract Only).
Chemical Characteristics, The Olive Oil Source, © 1998-2015, retrieved on Jun. 12, 2015, http://www.oliveoilsource.com/page/chemical-characteristics, 10 pages.
Cheshire and Freeman, "Disorders of Sweating," Semin Neurol, 2003, 23(4):399-406.
Chevrant-Breton et al., "Etude du Traitement Capillaire <<Bioscalin>> dans les Alopecies Diffuses de la Femme", Gazette Medicale, 1986, 93(17):75-79 (English Abstract).
Chiang et al., "Bioavailability Assessment of Topical Delivery Systems: In Vitro Delivery of Minoxidil from Prototypical Semi-Solid Formulations", Int. J. Pharm, 1989, 49(2):109-114 (Abstract Only).
Chinnian et al., "Photostability Profiles of Minoxidil Solutions", PDA J. Pharm Sci Technol., Mar.-Apr. 1996, 50(2):94-98 (English Abstract).
Chollet et al., "Development of a Topically Active Imiquimod Formulation", Pharmaceutical Development and Technology, 1999, 4(1):35-43.
Chollet et al., "The Effect of Temperatures on the Solubility of Imiquimod in Isostearic Acid", Abstract 3031, Pharmaceutical Research, Nov. 1997, 14(11 Supplemental):S475.
Chrysos et al., "Effect of nifedipine on rectoanal motility," Dis Colon Rectum, Feb. 1996, 39(2):212-216.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.
Cloez-Tayarani et al., "Differential effect of serotonin on cytokine production in lipopolysaccharide-stimulated human peripheral blood

(56) References Cited

OTHER PUBLICATIONS mononuclear cells: involvement of 5-hydroxytryptamine2A receptors," Int. Immunol., 2003, 15:233-240.
Coal Tars and Coal-Tar Pitches, *Report on Carcinogens, Twelfth Edition*, 2011, 3 pages.
Coatzee et al., "Acceptability and feasibility of Micralax® applicators and of methyl cellulose gel placebo for large-scale clinical trials of vaginal microbicides," AIDS, 2001, 15:1837-1842.
Coconut Oil, Wikipedia, the free encyclopedia, retrieved on Jul. 3, 2015, https://en.wikipedia.org/wiki/Coconut_oil, 8 pages.
Codex Standard for Olive Oils and Olive Pomace Oils Codex STAN 33-1981, Adopted in 1981, recently amended 2013, 8 pages.
Cole and Gazewood, "Diagnosis and Treatment of Impetigo," American Family Physical Website, 2007, http://www.aafp.org/afp, 6 pages.
Colloidal Silica, W.R. Grace & Co. Enriching Lives, Everywhere™, 2011, retrieved on Jun. 4, 2011, http://www.grace.com/engineeredmaterials/materialsciences/colloidalsilica/default.aspx, 4 pages.
Communication of a Notice of Opposition in European Application No. 03772600.7, dated Jan. 13, 2015, 36 pages.
Cook and Mortenson, "Nifedipine for treatment of anal fissures," Dis Colon Rectum, 2000, 43(3):430-431.
Craig, D.Q.M. et al. (Jul. 1994) "An investigation into the structure and properties of Carbopol 934 gels using dielectric spectroscopy and oscillatory rheometry" *J Controlled Rel*, 30(3):213-223 (Abstract).
Cremophor A Grades, BASF The Chemical Company, Jan. 2008, 6 pages.
Croda Crop Care, Arlacel 165, 2011, retrieved on Aug. 3, 2015, http://www.crodapersonalcare.com/home.aspx?view=dtl&d=content&s=157&r=401&p=2578&productName=&inciname=&application=&subapplication=&productfunction=&consumerbenefit=&prodID=1926, 2 pages.
Croda Product Care Europe, Cetomacrogol 1000, 2011, retrieved on Aug. 3, 2015, http://www.crodapersonalcare.com/home.aspx?view=dtl&d=content&s=157&r=273&p=1859&productName=&inciname=&chemicaltype=&application=&subapplication=&productfunction=&consumerbenefit=&prodID=27, 1 page.
Crohn's Disease, Merck Manual Home Edition, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
Cunha, "Minocycline versus Doxycycline in the treatment of Lyme Neuroborreliosis," Clin. Infect. Diseases, 2000, 30: 237-238.
Dacarbazine, Chemical Book, 2010, retrieved on Oct. 18, 2013, <URL: http://www.chemicalbook.com/ChemicalProductProperty_EN_CB7710656.htm>, 2 pages.
Dalby et al., "Determination of Drug Solubility in Aerosol Propellants," Pharmaceutical Research, 1991, 8(9):1206-1209.
Dawber and Rundegren, "Hypertrichosis in Females Applying Minoxidil Topical Solution and in Normal Controls", JEADV, 2003, 17:271-275.
Denatonium Benzoate, retrieved Dec. 9, 2008, http://www.newdruginfo.com/pharmaceopeia/usp28/v28230/usp28nf23s0_m-22790.htm, 2 pages.
Dentinger, et al., "Stability of Nifedipine in an Extemporaneously Compounded Oral Solution", American Journal of Health-System Pharmacy, 2003, 60(10):1019-1022 (English Abstract).
Derivative, Merriam Webster Online Dictionary, retrieved on Jul. 5, 2008, http://www.merriam-webster.com/cgi-bin/dictionary?book=dictionary&va=derivative, 1 page.
Devos and Miller, "Antisense Oligonucleotides: Treating neurodegeneration at the Level of RNA," Neurotherapeutics, 2013, 10:486-497.
Diethyltoluamide, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.
Disorder, American Heritage Dictionary of the English Language, 2007, retrieved on Oct. 9, 2010, http://www.credoreference.com/entry/hmdictenglang/disorder, 1 page.
Draelos, "Antiperspirants and the Hyperhidrosis Patients," Dermatologic Therapy, 2001, 14:220-224.
Drug Index—Dacarbazine, BC Cancer Agency, Jun. 2004, retrieved on Oct. 18, 2013, <URL:http://www.bccancer.bc.ca/HPI/DrugDatabase/DrugIndexPro/Dacarbazine.htm>, 6 pages.
Drugfuture, Chemical Index Database, "Sorbitan Esters" Monograph [online]. Retrieved from: http://www.drugfuture.com/chemdata/sorbitan-esters.html, on Jul. 1, 2016, 2 pages.
Durian et al., "Scaling behavior in shaving cream," The American Physical Society, Dec. 1991, 44(12):R7902-7905.
Durmortier et al., "A review of poloxamer 407 pharmaceutical and pharmacological characteristics," Pharmaceutical Res., Dec. 2006, 23(12):2709-2728.
E7023 Ethanol 200 Proof (Absolute), Sigma-Aldrich Co., © 2008, retrieved on Dec. 9, 2008, http://www.sigmaaldrich.com/catalog/ProductDetail.do?N4=E7023SIAL&N5=SEAR-CH.sub.--CONCAT.sub.--PNOBRAND.sub.--KEY&F=SPEC, 2 pages.
Ebadi et al., "Healing effect of topical nifedipine on skin wounds of diabetic rats," DARU, 2003, 11(1):19-22.
Edens et al., "Storage Stability and Safety of Active Vitamin C in a New Dual-Chamber Dispenser", Journal of Applied Cosmetology, 1999, 17(4):136-143 (English Abstract).
Edirisinghe et al., "Effect of fatty acids on endothelium-dependent relaxation in the rabbit aorta", Clin Sci, Aug. 2006, 111(2): 145-51.
Edwards, "Imiquimod in Clinical Practice," J. Am Acad Dermatol., Jul. 2000 43(1, Pt 2):S12-S17 (English Abstract).
Effendy and Maibach "Surfactants and Experimental Irritant Contact Dermatitis." Contact Dermatol., 1995, 33:217-225.
Elias and Ghadially, "The aged epidermal permeability barrier," Clinical Geriatric Medicine, Feb. 2002, 103-120.
Ellis et al., "The Treatment of Psoriasis with Liquor Carbonis Detergens," J. Invest Dermatology, 1948, 10:455-459.
Emulsifiers With HLB Values, The Herbarie, retrieved on Aug. 5, 2009, http://www.theherbarie.com/files/resources-center/formulating/Emulsifiers-.sub.--HLB.sub.--Values.pdf, 3 pages.
Esposito et al., "Nanosystems for Skin Hydration: A Comparative Study," International Journal of Cosmetic Science, 2007, 29: 39-47.
Established ("Approved") Excipients, Encyclopedia of Pharmaceutical Technology, Second Edition, © 2002, vol. 3, 2146-2147.
Ethylene Oxide Derivatives: An Essence of Every Industry, retrieved on Jul. 12, 2011, http://www.emulsifiers.in/ethylene_oxide_derivatives2.htm, 3 pages.
European Patent Application No. 03772600.7 (Patent No. 1556009): Communication of a Notice of Opposition, dated Sep. 23, 2015, 42 pages.
European Patent Application No. 03772600.7 (Patent No. 1556009): Communication of a Notice of Opposition. dated Sep. 24, 2015, 30 pages.
European Patent Application No. 03772600.7 (Patent No. 1556009): Reply of the Patent Proprietor to the Notices of Opposition, dated May 9, 2016, 134 pages.
European Patent Application No. 03772600.7 (Patent No. 1556009): Summons to Attend Oral Proceedings, dated Jun. 30, 2016, 19 pages.
European Patent Application No. 03772600.7 (Patent No. 1556009): Interlocutory Decision in Opposition Proceedings, dated Feb. 3, 2017, 54 pages.
European Patent Application No. 03772600.7 (Patent No. 1556009): Minutes of Oral Proceedings, dated Feb. 3, 2017, 6 pages.
Excessive Sweating, Merck Manual Home Edition, Oct. 2007, retrieved on Apr. 14, 2011, www.merckmanuals.com/home/print/sec18/ch206/ch206c.html, 2 pages.
Fantin et al., "Critical influence of resistance to streptogramin B-type antibiotics on activity of RP 59500 (Quinupristin-dalfopristin) in experimental endocarditis due to *Staphylococcus aureus*," Antimicrob Agents and Chemothery, Feb. 1995, 39:400-405.
Farahmand et al., "Formulation and Evaluation of a Vitamin C Multiple Emulsion", Pharmaceutical Development and Technology, May 2006, 11(2):255-261 (English Abstract).
Flick, Cosmetic and Toiletry Formulations, 2nd Edition, Copyright 1996, vol. 5, 251-309.

(56) References Cited

OTHER PUBLICATIONS

Floyd, "Silicone Surfactants: Applicants in the Personal Care Industry," Silicone Surfactants, 1999, Chapter 7, 181-207.
Fluhr et al., "Glycerol accelerates recovery of barrier function in vivo," Acta Derm. Venereol, 1999, 79:418-421.
Foamix Pharmaceuticals Ltd. (May 1, 2017) "Foamix Pharmaceuticals Announces Plans for Additional Phase 3 Trial for FMX101 in Moderate to Severe Acne," Press Release [online]. Retrieved from: http://www.foamix.co.il/news.asp?nodeID=564&itemID=204, on Jun. 12, 2017, 5 pages.
Foamix Pharmaceuticals, Statement: Use of Luviquat FC 370, Approved by Yohan Hazot, May 3, 2016, 3 pages.
Fontana, "Water Activity: Why It is Important for Food Safety," International Conference on Food Safety, Nov. 16-18, 1998, 177-185.
Frankel, A.J. et al. (2010) "Coal Tar 2% Foam in Combination with a Superpotent Corticosteroid Foam for Plaque Psoriasis. Case Report and Clinical Implications" *J Clin Aesthet Dermatol*, 3(10):42-45.
Fully-Refined Paraffin Wax (FRP Wax), Industrial Raw Materials LLC, Feb. 21, 2008, retrieved on Aug. 22, 2013, <http://irmwax.com/Wax/Paraffin/fully_refined.asp> 1 page.
Gallarate et al., "On the Stability of Ascorbic Acid in Emulsified Systems for Topical and Cosmetic Use", International Journal of Pharmaceutics, 1999, 188:233-241.
Galligan et al., "Adhesive Polyurethane Liners for Anterior Restorations," J. Dent. Res., Jul.-Aug. 1968, 629-632.
Garti et al. "Sucrose Esters microemulsions," J. Molec. Liquids, 1999, 80:253-296.
Gas Gangrene, Merck Manual Home Edition, 2008, retrieved on Jan. 16, 2013, <http://www.merckmanuals.com/home/infections/bacterial_infections/gas_gangrene.html?qt=gasgangrene&alt=sh>1 page.
Gelbard et al. "Primary Pediatric Hyperhidrosis: A Review of Current Treatment Options," Pediatric Dermatology, 2008, 25(6):591-598.
Gels, UNC: The Pharmaceutics and Compounding Laboratory, retrieved on Aug. 25, 2014, http://pharmlabs.unc.edu/labs/gels/agents/htm, 4 pages.
Ghica, M.V. et al. (2011) "Design and optimization of some collagen-minocycline based hydrogels potentially applicable for the treatment of cutaneous wound infections" *Pharmazie*, 66:853-861.
Gill et al., "Adverse Drug Reactions in a Paediatric Intensive Care Unit," Acta Paediatric, 1995, 84:438-441.
Gladkikh, "Ascorbic Acid and Methods of Increasing its Stability in Drugs", Translated from Khimiko-Farmatsevticheskii Zhurnal, 1970, 4(12):37-42.
Glaser and Ballard, "Hyperhidrosis: A Comprehensive and Practical Approach to Patient Management," Expert Rev. Dermatol., Oct. 2006, 1(6):773-775.
Google Search Strategy for Minocycline Solubility, retrieved on Aug. 15, 2013, <http://www.googl.com/search?rls=com.microsoft%3Aen-us%3AIE-SearchBox&q-melocycline+solubility>, 1 page.
Graves et al., "Structure of Concentrated Nanoemulsions," The Journal of Chemical Physics, Apr. 1, 2005, 122:134703, 6 pages.
Griffin, "Calculation of HLB Values of Non-Ionic Surfactants," Journal of the Society of Cosmetic Chemists, May 14, 1954, 249-256.
Groveman et al., "Lack of Efficacy of Polysorbate 60 in the Treatment of Male Pattern Baldness", Arch Intern Med, 1985, 145:1454-1458.
Gschnait et al., "Topical Indomethacin Protects from UVB and UVA Irradiation," Arch. Dermatol. Res., 1984, 276:131-132.
Hakan et al., "The protective effect of fish oil enema in acetic acid and ethanol induced colitis," The Turkish Journal of Gastroenterology, 2000, 11(2):155-161.
Hall, "Diaper Area Hemangiomas: A Unique Set of Concerns," retrieved on Dec. 1, 2008, http://members.tripod.com/.about.Michelle.sub.--G/diaper.html, 8 pages.
Hallstar® GMS SE/AS, retrieved on Jun. 4, 2011, http://www.hallstar.com/pis.php?product=1H022, 1 page.

Hammer et al., "Anti-Microbial Activity of Essential Oils and other Plant extracts," J. Applied Microbiology, 1999, 86:985-990.
Hargreaves, "Chemical Formulation, An Overview of Surfactant-Based Preparations Used in Everyday Life", The Royal Society of Chemistry, 2003, 114-115.
Harrison et al., "Effects of cytokines and R-837, a cytokine inducer, on UV-irradiation augmented recurrent genital herpes in guinea pigs", Antiviral Res., 1991, 15(4):315-322.
Harrison et al., "Modification of Immunological Responses and Clinical Disease During Topical R-837 Treatment of Genital HSV-2 Infection," Antiviral Research, 1988, 10:209-224.
Harrison et al., "Pharmacokinetics and Safety of Imiquimod 5% Cream in the Treatment of Actinic Keratoses of the Face, Scalp, or Hands and Arms", Arch. Dermatol. Res., Jun. 2004, 296(1):6-11 (English Abstract).
Harrison et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, Sep. 1994, 38(9):2059-2064.
Harry, "Skin Penetration," The British Journal of Dermatology and Syphilis, 1941, 53:65-82.
Hashim et al., "Tinea versicolor and visceral leishmaniasis," Int J Dermatol., Apr. 1994; 33(4):258-259 (Abstract).
haute.de, "Substance (INCI-Designation): Triethanolamine" [online]. Retrieved on Sep. 14, 2015, http://www.haut.de/service/inci/anzeige&id=I6384&query=Triethanolamine&funktio . . . ; German with English translation, 3 pages.
Haw, "The HLB System: A Time Saving Guide to Surfactant Selection," Presentation to the Midwest Chapter of the Society of Cosmetic Chemists, Mar. 9, 2004, 39 pages.
Healy, "Gelled Emollient Systems for Controlled Fragrance Release and Enhanced Product Performance," Cosmetics and toiletries, 2002, 117(2): 47-54.
Heart Failure, The Merck Manual, 2008, retrieved Oct. 9, 2010, http://www.merck.com/mmhe/sec03/ch025/ch025a.html, 12 pages.
Helmenstine, "Surfactant Definition—Chemistry Glossary Definition of Surfactant," About.com Chemistry, retrieved on Mar. 5, 2012, http://chemistry.about.com/od/chemistryglossary/g/surfactant.htm, 1 page.
Hepburn, "Cutaneous leishmaniasis," Clin Exp Dermatol, Jul. 2000, 25(5):363-370 (Abstract).
HLB Systems, Pharmcal.tripod.com, retrieved on Sep. 17, 2010, http://pharmcal.tripod.com/ch17.htm, 3 pages.
HLB-Numbers, Sigma Aldrich, 2009, retrieved on Feb. 2, 2009, http://www.sigmaaldrich.com/materials-science/micro-and-nanoelectronics/l- ithography-nanopatterning/hlb-numbers.html, 3 pages.
How to Have a Healthy Libido in Mid-Life and Beyond, GreenWillowTree.com, Jan. 2001, retrieved on Jul. 28, 2012, http://www.greenwillowtree.com/Page.bok?file=libido.html, 5 pages.
Hubbe, Colloidal Silica, Mini-Encyclopedia of Papermaking Wet-End Chemistry: Additives and Ingredients, their Composition, Functions, Strategies for Use, Feb. 1, 2001, retrieved on Jun. 4, 2011, http://www4.ncsu.edu/~hubbe/CSIL.htm, 2 pages.
Human Immunodeficiency Virus Infection, Merck Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh >, 11 pages.
Hwang et al., "Isolation and identification of mosquito repellents in *Artemisia vulgaris*," J. Chem. Ecol., 1985, 11: 1297-1306.
ICI Americas Inc., "Meaning of HLB Advantages and Limitations" Chapter 1 in *The HLB System. A Time-Saving Guide to Emulsifier Selection.* Wilmington, Delaware: 1980; pp. 1-4.
Ikuta et al., "Scanning Electron Microscopic Observation of Oil/Wax/Water/Surfactant System", Journal of SCCJ, 2004, 34(4):280-291 (English Abstract).
Indomethacin, Aug. 15, 2009, retrived on Jun. 3, 2011, http://it03.net/com/oxymatrine/down/1249534834.pdf, 3 pages.
Innocenzi et al., "An Open-Label Tolerability and Effacy Study of an Aluminum Sesquichlorhydrate Topical Foam in Axillary and Palmar Primary Hyperhidrosis," Dermatologic Therapy, 2008, 21:S27-S30.

(56) References Cited

OTHER PUBLICATIONS

Izquierdo et al. "Formation and Stability of Nano-Emulsions Prepared Using the Phase Inversion Temperature Method," Langmuir, 2002, 18(1):26-30 (Abstract).
Jan, "Troubled Times: Detergent Foam," retrieved on Feb. 9, 2012, http://zetatalk.com/health/theal17c.htm, 2 pages.
Joseph, "Understanding foams & foaming," University of Minnesota, May 1997, http://www.aem.umn.edu/people/faculty/joseph/archive/docs/understandingfoams.pdf, 8 pages.
Kalkan et al., "The Measurement of Sweat Intensity Using a New Technique," Tr. J. of Medical Sciences, 1998, 28:515-517.
Kanamoto et al., "Pharmacokinetics of two rectal dosage forms of ketoprofen in patients after anal surgery," J Pharmacobiodyn., Mar. 1988, 11(3):141-145.
Kang et al., "Enhancement of the Stability and Skin Penetration of Vitamin C by Polyphenol", Immune Netw., Dec. 2004, 4(4):250-254 (English Abstract).
Kanicky, J.R. and D.O. Shah (2002) "Effect of Degree, Type, and Position of Unsaturation on the $pK_a$ of Long-Chain Fatty Acids" *J Colloid and Interface Science*, 256:201-207.
Karasu et al., "Practice Guideline for the Treatment of Patients with Major Depressive Disorder," Second Edition, Apr. 2000, 78 pages.
Kathon™ CG, Rohm and Haas Personal Care, Jun. 2006, 9 pages.
Kaur et al., "Formulation Development of Self Nanoemulsifying Drug Delivery System (SNEDDS) of Celecoxib for Improvement of Oral Bioavailability," Pharmacophore, 2013, 4(4):120-133.
Kim, "Stability of Minoxidil in Aqueous Solution", Yakhak Hoechi, 1986, 30(5):228-231 (English Abstract).
Kinnunen and Hannuksela, "Skin reactions to hexylene glycol," Contact Dermatitis, Sep. 1989, 21(3):154-158.
Kircik, L.H. and S. Kumar (Aug. 2010) "Scalp Psoriasis" *J Drugs Dermatol*, 9(8 Suppl):s101-s137.
Kleber et al., "Practice Guideline for the Treatment of Patients with Substance Use Disorders," Aug. 2006, 276 pages.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Knight et al., "Topical diltiazem ointment in the treatment of chronic anal fissure," Br. J. Surg., 2001, 88(4):553-556.
Koerber, "Humectants and Water Activity," Water Activity News, 2000, 8 pages.
Kreuter, "Nanoparticles and microparticles for drug and vaccine delivery," J. Anat., 1996, 189:503-505.
Kucharekova et al., "Effect of a lipid-rich emollient containing ceramide 3 in experimentally induced skin barrier dysfunction," Contact Dermatitis, Jun. 2002, 46:331-338.
Kumar et al., "Application of Broad Spectrum Antiseptic Povidone Iodine as Powerful Action: A Review," Journal of Pharmaceutical Science and Technology, 2009, 1(2):48-58.
Kwak et al. "Study of Complete Transparent Nano-Emulsions which Contain Oils." IFSCC Conference, Seoul Korea, Sep. 2003, 3 pages.
Laboratory 6—Characteristics of Surfactants and Emulsions, retrieved on Jan. 29, 2010, http://web.archive.org/web/20000106225413/http://pharmacy.wilkes.edu/kibbeweb/lab7.html, 5 pages.
Lautenschlager, "A Closer Look on Natural Agents: Facts and Future Aspects," Kosmetic Konzept Kosmetische Praxis, 2006, 5:8-10.
Le Vine et al., "Components of the Goeckerman Regimen," Journal of Investigative Dermatology, 1979, 73:170-173.
Lebwohl and Ali, "Treatment of psoriasis. Part 1. Topical therapy and phototherapy," J. Am Acad Dermatol, Oct. 2001, 487-498.
Lebwohl et al., "A randomized, double-blind, placebo-controlled study of clobestasol propionate 0.05% foam in the treatment of nonscalp psoriasis," International Journal of Dermatology, 2002, 41(5): 269-274.
Lee et al., "Historical review of melanoma treatment and outcomes," Clinics in Dermatology, 2013, 31: 141-147.
Lee et al., "The Stabilization of L-Ascorbic Acid in Aqueous Solution and Water-in-Oil-in-Water Double Emulsion by Controlling pH and Electrolyte Concentration," J. Cosmet. Sci., Jan./Feb. 2004, 55:1-12.
Leive et al., "Tetracyclines of various hydrophobicities as a probe for permeability of *Escherichia coli* outer membrane," Antimicrobial Agents and Chemotherapy, 1984, 25:539-544.
Leunapon-F, Leuna-Tenside, Screenshot, retrieved on Sep. 18, 2015, http://www.leuna-tenside.de/2006_7_14_3143/2006_8_7 5750/2006_8_7 241/cas-68439-49-6, 1 page.
Leung and Robinson, "Bioadhesive Drug Delivery," American Chemical Society, 1991, Chapter 23, 350-366.
Li et al., "Solubility Behavior of Imiquimod in Alkanoic Acids", Pharmaceutical Research, Abstract 3029, Nov. 1997,14(11):S475, 2 pages.
Licking Vaginal Dryness Without a Prescription, retrieved on Dec. 14, 2008, http://www.estronaut.com/a/vag.sub.--dryness.htm, 3 pages.
Lin et al., "Ferulic acid stabilizes a solution of vitamins c and e and doubles its photoprotection of skin," J Invest Dermatol, 2005, 125:826-832.
Lippacher et al., "Liquid and Semisolid SLN Dispersions for Topical Application: Rheological Characterization," European Journal of Pharmaceutics and Biopharmaceutics, 2004, 58:561-567.
Livingstone and Hubel, "Segregation of form, color, movement, and depth: Anatomy, physiology, and perception," Science, May 1988, 240:740-749.
Lupke and Kemper, "The HET-CAM Test: An Alternative to the Draize Eye Test," FD Chem. Toxic., 1986, 24:495-196.
Lupo, "Antioxidants and Vitamins in Cosmetics", Clinics in Dermatology, 2001, 19:467-473.
Luviquat Polymer Grades, BASF The Chemical Company, May 2012, 32 pages.
Mailer, "Chemistry and quality of olive oil," NSW Dept. of Primary Industries, Aug. 2006, Primefact 227, 1-4.
Martindale: The Complete Drug Reference, 33rd Edition, Jun. 2002, Pharmaceutical Press, pp. 1073 and 1473.
Martindale: The Complete Drug Reference, Thirty-third edition, Bath Press, London, 2002, 1073 and 1473.
Martindale: The Extra Pharmacopoeia, Twenty-eighth edition, The Pharmaceutical Press, London, 1982, 862-864.
Material Safety Data Sheet, Luvitol EHO, Caelo, Nov. 28, 2013, 4 pages.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Safety Data Sheet, Dimethyl Ether, Airgas, May 14, 2015, 12 pages.
Material Safety Data Sheet, Hydroxyethyl Cellulose, Sigma-Aldrich, Jan. 14, 2004, http://terpconnect.umd.edu/-choi/MSDS/Sigma-Aldrich/HYDROXYETHYL%20CELLULOSE, 5 pages.
Material Safety Data Sheet, Hydroxyethyl Cellulose, Sigma-Aldrich, Jan. 2004, 5 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Material Safety Data Sheet, N-Butane, Airgas, May 7, 2015, 13 pages.
Material Safety Data Sheet, Nitrous Oxide, Airgas, Feb. 11, 2016, 11 pages.
Material Safety Data Sheet, Propane, Airgas, Oct. 20, 2015, 12 pages.
Material Safety Data Sheet, Science Lab.com, Polyethylene Glycol 200, MSDS, Nov. 6, 2008, 6 pages.
Material Safety Data Sheet, USP, Progesterone, Apr. 26, 2006, 5 pages.
Mead, "Electrostatic Mechanisms Underlie Neomycin Block of the Cardiac Ryanodine Receptor Channel (RyR2)," Biophysical Journal, 2004, (87): 3814-3825.
Messenger et al., "Minoxidil: Mechanisms of Action on Hair Growth", British Journal of Dermatology, 2004, 150:186-194.

(56) References Cited

OTHER PUBLICATIONS

Metronidazole (Veterinary—Systemic), The United States Pharmacopeial Convention, 2007, retrieved on Sep. 10, 2009, www.usp.org/pdf/EN/veterinary/metronidazole.pdf, 4 pages.

Metz et al., "A Phase I Study of Topical Tempol for the Prevention of Alopecia Induced by Whole Brain Radiotherapy," Clinical Cancer Research, Oct. 2004, 10:6411-6417.

Meucci et al., "Ascorbic Acid Stability in Aqueous Solutions", Acta Vitaminol Enzymol, 1985, 7(3-4):147-153 (English Abstact).

Milton, D.T. et al. (2006) "A Phase I/II Study of Weekly High-Dose Erlotinib in Previously Treated Patients With Nonsmall Cell Lung Cancer" *Cancer,* 107:1034-1041.

Mineral Oil USP, U.S. Department of Health & Human Services, Chemical Abstracts Service Registry No. 8012-95-1, 2011, 7 pages.

Minocycline (DB01017), Drug Bank, Feb. 8, 2013, retrieved on Aug. 15, 2013, <http://www.drugbank.ca/drugs/DB01017>, 10 pages.

Minocycline, Wikipedia, the free encyclopedia, retrieved on Oct. 21, 2011, http://en.wikipedia.org/wiki/Minocycline, 7 pages.

MMP Inc., International Development and Manufacturing, "Formulating specialties," retrieved on Feb. 2, 2010, http://mmpinc.com, 3 pages.

Molan, "World Wide Wounds: Honey as a topical antibacterial agent for treatment of infected wounds," Dec. 2001, retrieved May 7, 2008, http://www.worldwidewounds.com/2001/november/Molan/honey-as-topical-agent.html, 13 pages.

*Molins PLC v. Textron Inc.,* 48 F.3d 1172, 33 USPQ2d 1823 (Fed. Cir. 1995), 19 pages.

Morgan et al., "Enhanced Skin Permeation of Sex Hormones with Novel Topical Spray Vehicles," Journal of Pharmaceutical Sciences, Oct. 1998, 87(10):1213-1218.

Mousse, Merriam-Webster Online Dictionary, retrieved on Dec. 8, 2008, http://www.merriam-webster.com/dictionary/mousse, 2 pages.

Musial, W. and A. Kubis (2004) "Carbopols as factors buffering triethanolamine interacting with artificial skin sebum" *Polim Med,* 34(4):17-30 (Abstract).

Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.

Neutrogena Clinical SPF 30 Facial Lifting Wrinkle Treatment, Apr. 28, 2010, retrieved on Sep. 11, 2010, http://www.cosmetoscope.com/2010/04/neutrogea-clinical-with-johnson-johnsons-cytomimic-techology/, 5 pages.

Neves et al., "Rheological Properties of Vaginal Hydrophilic Polymer Gels," *Current Drug Delivery,* 2009, 6:83-92.

New Nanomaterials to Deliver Anticancer Drugs to Cells Developed, Science Daily, Jun. 2007, retrieved on Oct. 14, 2013, <URL: http://www.sciencedaily.com/releases/2007/06/070607112931.htm>, 3 pages.

Nietz, "Molecular orientation at surfaces of solids," J. Phys. Chem., 1928, 32(2): 255-269.

Niram Chemicals, Chemical products—Cetostearyl Alcohol, Cetyl Alcohol, Stearyl Alcohol and Polyethylene Glycol Importer & Supplier, retrieved on Jul. 17, 2012, http://www.indiamart.com/niramchemicals/chemicals.html, 7 pages.

Novartis "Lamisil®" Product Information, T2001-29 [online]. Retrieved from: http://www.fda.gov/downloads/Drugs/DrugSafety/PostmarketDrugSafetyInformationforPatientsandProviders/ucm052213.pdf; Published: Apr. 2001, 8 pages.

Oh et al., "Antimicrobial activity of ethanol, glycerol monolaurate or lactic acid against *Listeria moncylogenes,*" Int. J. Food Microbiology, 1993, 20:239-246.

Olsen et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, Nov. 2007, 57:767-774.

OM-Cinnamate, MakingCosmetics.com, retrieved on Sep. 26, 2009, http://www.makingcosmetics.com/sunscreens/OM-Cinnamate-p102.html, 1 page.

Omega-9 Fatty Acids (Oleic Acid), Orthomolecular.org, Dec. 2004, retrieved on Aug. 15, 2014, http://orthomolecular.org/nutrients/omega9.html, 1 page.

Optimization of Nano-Emulsions Production by Microfluidization, European Food Research and Technology. Sep. 2007, 22:5-6 (English Abstract).

Oranje et al., "Topical retapamulin ointment, 1%, versus sodium fusidate ointment, 2%, for impetigo: a randomized, observer-blinded, noninferiority study," Dermatology, 2007, 215(4):331-340.

Osborne and Henke, "Skin Penetration Enhancers Cited in the Technical Literature," Pharm. Technology, Nov. 1997, 21(11):58-86.

Padhi et al., "Phospho-olivines as positive-electrode materials for rechargeable lithium batteries," J. Electrochemical Soc., Apr. 1997, 144(4): 1188-1194.

Padi and Kulkarni, "Minocycline prevents the development of neuropathic pain, but not acute pain: possible anti-inflammatory and antioxidant mechanisms," Eur J. Pharmacol, 2008, 601:79-87.

Pakpayat et al., "Formulation of Ascorbic Acid Microemulsions with Alkyl Polyglycosides", European Journal of Pharmaceutics and Biopharmaceutics, 2009, 72:444-452.

Palamaras and Kyriakis, "Calcium antagonists in dermatology: a review of the evidence and research-based studies," Derm. Online Journal, 2005, 11(2):8.

Passi et al., "Lipophilic antioxidants in human sebum and aging," Free Radical Research, 2002,36(4):471-477.

Pharmaceutical Benefits Advisory Committee (PBAC) of Australia. PBAC *Public Summary Document—Nov. 2014 Meeting* (5 pages).

Pendergrass et al., "The shape and dimension of the human vagina as seen in three-dimensional vinyl polysiloxane casts," Gynecol Obstet. Invest., 1996, 42(3):178-82 (Abstract).

Penreco, "Intelligent Gel Technology Product Specifications," Rev. Jun. 2016 (2 pages).

Permethrin (Insecticide), Wildpro, retrieved on Jun. 4, 2015, http://wildpro.twycrosszoo.org/S/00Chem/ChComplex/perm.htm, 5 pages.

Perotti et al., "Topical Nifedipine With Lidocaine Ointment vs. Active Control for Treatment of Chronic Anal Fissure," Dis Colon Rectum, 2002, 45(11):1468-1475.

Polystyrene, Wikipedia the free encyclopedia, retrieved Apr. 21, 2014, http://web.archive.org/web/20060312210423/http://en.wikipedia.org/wiki/Polystyrene, 4 pages.

PPG-40-PEG-60 Lanolin Oil, Environmental Working Group, 2010, retrieved on May 19, 2010, http://www.cosmeticsdatabase.com/ingredient/722972/PPG-40-PEG-60_Lanolin_Oil/?ingred06=722972., 3 pages.

Prevent, The American Heritage Dictionary of the English Language, 2007, retrieved on Oct. 9, 2010, http://www.credoreference.com/entry/hmdictenglang/prevent, 1 page.

Product Data Sheet for Meclocycline, bioaustralis fine chemicals, Jun. 28, 2013, 1 page.

Promius™ Pharma LLC (2012) *Scytera*™ (*coal tar*) *Foam, 2%.* Product Information Sheet, 1 page.

Prud'Homme et al., Foams: theory, measurements and applications, Marcel Dekker, Inc., 1996, 327-328.

Purcell, "Natural Jojoba Oil Versus Dryness and Free Radicals," Cosmetics and Toiletries Manufacture Worldwide, 1988, 4 pages.

Purdy et al., "Transfusion-transmitted malaria: unpreventable by current donor exclusion guidelines?" Transfusion, Mar. 2004, 44:464.

Raschke et al., "Topical Activity of Ascorbic Acid: From In Vitro Optimization to In Vivo Efficacy", Skin Pharmacology and Physiology, Jul./Aug. 2004, 17(4):200-206 (Abstract).

Ravet et al., "Electroactivity of natural and sythetic triphylite," J. Power Sources, 2001, 97-98: 503-507.

Raymond, "Iodine as an Aerial Disinfectant," J. Hygiene, May 1946, 44(5):359-361.

Reaction Rate, Wikipedia, the free encyclopedia, retrieved on Dec. 18, 2011, en.wikipedia.org/wiki/Reaction_rate, 6 pages.

Receptacle, Merriam Webster, retrieved on Jul. 12, 2011, http://www.merriam-webster.com/dictionary/receptacle, 1 page.

Refina, "Viscosity Guide for Paints, Petroleum & Food Products," accessed Mar. 4, 2015, http://www.refina.co.uk/webpdfs/info_docs/Viscosity_guide_chart.pdf, 2 pages.

(56) References Cited

OTHER PUBLICATIONS

Regulation (EC) No. 2003/2003 of the European Parliament and of the Council, Official Journal of the European Union, Oct. 13, 2003, 2 pages.
Repa et al. "All-trans-retinol is a ligand for the retinoic acid receptors," Proc. Natl. Acad Sci, USA, Aug. 1993, 90: 7293-7297.
Reregistration Eligibility Decision for Pyrethrins, EPA, Jun. 7, 2006, 108 pages.
Richwald, "Imiquimod", Drugs Today, 1999, 35(7):497 (Abstract).
Rieger and Rhien, "Emulsifier Selection/HLB," Surfactants in Cosmetics, 129, 1997.
Rohstoffinformationen, Hoffmann Mineral, 2008, 8 pages (with English translation).
Rosacea, Clinuvel Pharmaceuticals, 2010, retrieved on Sep. 9, 2010, http://clinuvel.com/skin-conditions/common-skin-conditions/rosacea#h0-6-prevention, 5 pages.
Rowe et al., "Glyceryl Monooleate," Handbook of Pharmaceutical Excipients, 2011, 10 pages, retrieved on Dec. 19, 2011, http://www.medicinescomplete.com/mc/excipients/current/1001938996.htm?q=glyceryl%20monooleate&t=search&ss=text&p=1# hit.
Rowe et al., "Octyldodecanol," Handbook of Pharmaceutical Excipients, 2011, 9 pages, retrieved on Dec. 19, 2011, URL:http://www.medicinescomplete.com/mc/excipients/current/1001942450.htm?q=octyldodecanol&t=search&ss=text&p=1# hit.
Rowe et al., "Sucrose Palmitate," Handbook of Pharmaceutical Excipients, 2011, 11 pages, retrieved on Dec. 19, 2011, URL:http://www.medicinescomplete.com/mc/excipients/current/EXP-TD-c46-mn0001.htm?q=sucrose%20stearate&t=search&ss=text&p=1# hit.
Rowe et al., "Sucrose Stearate," Handbook of Pharmaceutical Excipients, 2011, 11 pages, retrieved on Dec. 19, 2011, URL:http://www.medicinescomplete.com/mc/excipients/current/EXP-TD-cII-mnOOOI-mnOOOI.htm?q=sucrose%20stearate&t=search&ss=text&p=3# hit.
RSES (Oil in Refrigerator Systems, Service Application Manual, 2009).
Rutledge, "Some corrections to the record on insect repellents and attractants," J. Am. Mosquito Control Assoc, Dec. 1988, 4(4): 414-425.
Sakai et al., "Characterization of the physical properties of the stratum corneum by a new tactile sensor," Skin Research and Technology, Aug. 2000, 6:128-134.
Sanders et al., "Stabilization of Aerosol Emulsions and Foams," J. Soc. Cosmet. Chem., 1970, 21:377-391.
Savin et al., "Tinea versicolor treated with terbinafine 1% solution," Int J. Dermatol, Nov. 1999; 38(11): 863-865.
Schaefer, "Silicone Surfactants," Tenside Surf. Det., 1990, 27(3): 154-158.
Schmidt, "Malassezia furfur: a fungus belonging to the physiological skin flora and its relevance in skin disorders," Cutis, Jan. 1997, 59(1):21-24 (Abstract).
Schmolka, "A review of block polymer surfactants," Journal of the American Oil Chemists Society, Mar. 1977, 54: 110-116.
Schott, "Rheology," Remington's Pharmaceutical Sciences, 17th Edition, 1985, 330-345.
Schutze, "Iodine and Sodium Hypochlorite as Wound Disinfectants," The British Medical Journal, 1915, 921-922.
Sciarra, "Aerosol Technology," *Kirk-Othmer Encyclopedia of Chemical Technology,* Jul. 2012, 20 pages.
Scientific Discussion for the Approval of Aldara, EMEA, 2005, 10 pages.
Scott, "A Practical Guide to Equipment Selection and Operating Techniques," Pharmaceutical Dosage Forms: Disperse Systems, vol. 3, Copyright 1998, 291-362.
Scully et al., "Cancers of the oral mucosa treatment and management," Medscape Drugs, Diseases and Procedures, Apr. 20, 2012, retrieved on Oct. 12, 2013, <http://emedicine.medscape.com/article/1075729-treatment>, 10 pages.
Seborrheic Dermatitis, retrieved on Sep. 9, 2010, http://www.cumc.columbia.edu/student/health/pdf/R-S/Seborrhea%20Dermatitis.pdf, 2 pages.

Security Datasheet, Luvitol EHO, Cetearyloctanoat, Nov. 27, 2013, 10 pages.
Sehgal, "Ciclopirox: a new topical pyrodonium antimycotic agent: A double-blind study in superficial dermatomycoses," *British Journal of Dermatology,* 1976, 95:83-88.
Sharp, "Oil," Dictionary of Chemistry, Copyright 1990, 286.
Shear et al., "Pharmacoeconomic analysis of topical treatments for tinea infections," Pharmacoeconomics, Mar. 1995, 7(3):251-267.
Shear, Vocabulary.com, retrieved on Aug. 23, 2013, <URL: https://www.vocabulary.com/dictionary/shear>, 3 pages.
Sheer, Vocabulary.com, retrieved on Aug. 23, 2013, https://www.vocabulary.com/dictionary/sheer, 3 pages.
Shemer, A. et al. (2016) "Topical minocycline foam for moderate to severe acne vulgaris: Phase 2 randomized double-blind, vehicle-controlled study results" *J Am Acad Dermatol,* 74(6):1251-1252.
Sheu et al., "Effect of Tocopheryl Polyethylene Glycol Succinate on the Percutaneous Penetration of Minoxidil from Water/Ethanol/Polyethylene Glycol 400 Solutions," Drug Dev. Ind. Pharm., Jun. 2006, 32(5):595-607 (Abstract).
Shim et al., "Transdermal Delivery of Mixnoxidil with Block Copolymer Nanoparticles," J. Control Release, Jul. 2004, 97(3):477-484 (Abstract).
Shrestha et al., "Forming properties of monoglycerol fatty acid esters in nonpolar oil systems," *Langmuir,* 2006, 22: 8337-8345.
Sigma-Aldrich. http://www.sigmaaldrich.com/catalog/product/sial/p1754?lang=en® ion=. Published:Mar. 5, 2014.
Sigma Aldrich, "Surfactants Classified by HLB Numbers" 2017 [online]. Retrieved from the Internet: www.sigmaaldrich.com/materials-science/material-science-products.html?TablePage=22686648, on Jul. 8, 2017 (3 pages).
Silicone, Oxford Dictionaries Online, retrieved on Apr. 19, 2011, http://www.oxforddictionaries.com/definition/silicone?view=uk, 1 page.
Simoni et al., "Retinoic acid and analogs as potent inducers of differentiation and apoptosis. New promising chemopreventive and chemotherapeutic agents in oncology," Pure Appl Chem., 2001, 73(9):1437-1444.
Simovic et al., "The influence of Processing Variables on Performance of O/W Emulsion Gels Based on Polymeric Emulsifier (Pemulen® TR-2NF)," International Journal of Cosmetic Science, Dec. 2001, 21(2)119-125 (Abstract).
Smith, "Hydroxy acids and skin again," Soap Cosmetics Chemical Specialties, Sep. 1993, 69(9):54-59.
Smith, "Sore Nipples," Breastfeeding Mom's Sore Nipples / Breastfeeding Basics, retrieved on Feb. 8, 2012, http://breastfeedingbasics.com/articles/sore-nipples, 9 pages.
Softemul-165: Product Data Sheet, Mohini Organics PVT LTD, retrieved Apr. 10, 2014, http://www.mohiniorganics.com/Softemul165.html#, 1 page.
Solans et al., "Overview of basic aspects of microemulsions," Industrial Applications of Microemulsions, New York, 1997, 1-17.
Solodyn® (Minocycline HCI, USP) Prescribing Information; revised Jun. 2016, 2 pages.
Sonneville-Aubrun et al., "Nanoemulsions: A New Vehicle for Skincare Products," Advances in Colloid and Interface Science, 2004, 108-109:145-149.
Spa Collections, AG & Co. Essential oil workshop, retrieved on Jan. 31, 2010, http://www.agworkshop.com/p3.asp, 1 page.
Squillante et al., "Codiffusion of propylene glycol and dimethyl isosorbide in hairless mouse skin," European J. Pharm. Biopharm., 1998, 46:265-271.
Squire and Goode, "A randomized, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat., Jun. 2002, 13(2):51-60 (Abstract).
Sreenivasa et al., "Preparation and Evaluation of Minoxidil Gels for Topical Application in Alopecia," Indian Journal of Pharmaceutical Sciences, 2006, 68(4):432-436.
Sreenivasan, B. et al. (1956)"Studies on Castor Oil. I. Fatty Acid Composition of Castor Oil" *J Am Oil Chem Soc,* 33:61-66.

(56) References Cited

OTHER PUBLICATIONS

Stehle et al., "Uptake of minoxidil from a new foam formulation devoid of propylene glycol to hamster ear hair follicles," J. Invest. Dermatol., 2005, 124(4): A101 (Abstract).
Sugisaka et al., "The Physicochemical Properties of Imiquimod, The First Imidazoquinoline Immune Response Modifier", Pharmaceutical Research, Nov. 1997, 14(11):S475, Abstract 3030.
*Sun Pharmaceutical Industries Ltd.* v. *Eli Lilly and Co.*, 611 F.3d 1381, 95 USPQ2d 1797 (Fed. Cir. 2010),7 pages.
Sung, J.H. et al. (2010) "Gel characterisation and in vivo evaluation of minocycline-loaded wound dressing with enhanced wound healing using polyvinyl alcohol and chitosan" *Intl J Pharmaceut*, 392:232-240.
Surfactant, Wikipedia, the free encyclopedia, retrieved on Oct. 24, 2010, http://en.wikipedia.org/wiki/Surfactant, 7 pages.
Tadros, "Surfactants in Nano-Emulsions." Applied Surfactants: Principles and Applications, 2005, 285-308.
Tamarkin, D. (2013) "Foam: A Unique Delivery Vehicle for Topically Applied Formulations" in: *Formulating Topical Applications—a Practical Guide*. Dayan N, Ed., Carol Stream, IL: CT Books, Chapter 9, pp. 233-260.
Tan et al., "Effect of Carbopol and PolyvinYlpyrrolidone on the Mechanical, Rheological, and Release Properties of Bioadhesive Polyethylene Glycol Gels," AAPS PharmSciTech, 2000; 1(3) Article 24, 10 pages.
Tanhehco, "Potassium Channel Modulators as Anti-Inflammatory Agents", Expert Opinion on Therapeutic Patents, Jul. 2001, 11(7):1137-1145 (Abstract).
Tarumoto et al., "Studies on toxicity of hydrocortisone 17-butyrate 21-propionate-1. Acute toxicity of hydrocortisone 17-butyrate 21-propionate and its analogues in mice, rats and dogs (author's transl)," J Toxicol Sci., Jul. 1981, 6:1-16 (Abstract).
Tata et al., "Penetration of Minoxidil from Ethanol Propylene Glycol Solutions: Effect of Application Volume on Occlusion," Journal of Pharmaceutical Sciences, Jun. 1995, 84(6):688-691.
Tata et al., "Relative Influence of Ethanol and Propylene Glycol Cosolvents on Deposition of Minoxidil into the Skin," Journal of Pharmaceutical Sciences, Jul. 1994, 83(10):1508-1510.
Tavss et al., "Anionic detergent-induced skin irritation and anionic detergent-induced pH rise of bovine serum albumin," *J. Soc. Cosmet. Chem.*, Jul./Aug. 1988, 39:267-272.
TCI America, Safety Data Sheet; Product Name: Squalane. Product Code: H0096 [online]. Retrieved from: https://www.spectrumchemical.com/MSDS/TCI-H0096.pdf. Revised: Oct. 6, 2014, 5 pages.
Tea Tree Oil, LookChem, Chemical Abstract No. 68647-73-4, 2012, 2 pages.
The HLB System—A Time-Saving Guide to Emulsifier Selection, ICI Americas Inc., Mar. 1980, 1-22.
The United States Pharmacopeia: The National Formulary, USP23/NF18, US Pharmacopoeia, Jan. 1995, p. 10-14.
Third Party Submission in Published Patent Application, U.S. Appl. No. 12/014,088, filed Feb. 4, 2009, 4 pages.
Thorgeirsdottir et al., "Antimicrobial activity of monocaprin: a monoglyceride with potential use as a denture disinfectant," Acta Odontologica Scandinavica, Feb. 2006, 64:21-26 (Abstract only).
Tirumala et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
Tjulandin, S. et al. (2013) "Phase I, dose-finding study of AZD8931, an inhibitor of EGFR (erbB1), HER2 (erbB2) and HER3 (erbB3) signaling, in patients with advanced solid tumors" *Invest New Drugs*, 32(1):145-153.
Todd et al., "Volatile Silicone Fluids for Cosmetic Formulations," Cosmetics and Toiletries, Jan. 1976, 91:27-32.
Torma et al., "Biologic activities of retinoic acid and 3,4-Didehydroretinoic acid in human keratinocytes are similar and correlate with receptor affinities and transactivation properties," J. Invest. Dermatology, 1994, 102: 49-54.

Torres-Rodriguez, "New topical antifungal drugs," Arch Med Res., Winter 1993, 24(4): 371-375 (Abstract).
Toxicology and Carcinogenesis Studies of T-Butyl Alcohol (CAS No. 75-65-0) in F344/N Rats and B6C3F1 Mice (Drinking Water Studies), May 1995, retrieved on Dec. 9, 2008, http://ntp.niehs.nih.gob/?objectid-=0709F73D-A849-80CA-5FB784E866B576D1, 4 pages.
Trofatter, "Imiqimod in clinical practice", European Journal of Dermatology, Oct./Nov. 1998, 8(7 Supp.):17-19 (Abstract).
Tsai et al., "Drug and Vehicle Deposition from Topical Applications: Use of In Vitro Mass Balance Technique with Minoxidil Solutions", J. Pharm. Sci., Aug. 1992, 81(8):736-743 (Abstract).
Tsai et al., "Effect of Minoxidil Concentration on the Deposition of Drug and Vehicle into the Skin," International Journal of Pharmaceutics, 1993, 96(1-3):111-117 (Abstract).
Tsai et al., "Influence of Application Time and Formulation Reapplication on the Delivery of Minoxidil through Hairless Mouse Skin as Measured in Franz Diffusion Cells," Skin Pharmacol., 1994, 7:270-277.
Tyring, "Immune-Response Modifiers: A New Paradigm in the Treatment of Human Papillomavirus," Current Therapeutic Research, Sep. 2000, 61(9):584-596 (Abstract).
Tzen et al. "Surface Structure and Properties of Plant Seed Oil Bodies," Department of Botany and Plant Sciences, University of California, Riverside, California 92521, Apr. 15, 1992, 9 pages.
Tzen et al., "Lipids, proteins and structure of seed oil bodies from diverse species," Plant Physiol., 1993, 101:267-276.
U.S. Final Office Action for U.S. Appl. No. 11/430,437, Tamarkin et al., dated Dec. 16, 2008, 24 pages.
U.S. Office Action for U.S. Appl. No. 11/430,437, Tamarkin et al., dated May 9, 2008, 27 pages.
U.S. Office Action from U.S. Appl. No. 11/430,599, dated Jul. 28, 2008, 59 pages.
Uner et al., "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel," Pharmazie, 2005, 60:751-755.
United States Standards for Grades of Olive Oil and Olive-Pomace Oil, United States Dept. of Agriculture, Oct. 25, 2010, 21 pages.
Valenta, "Effects of Penetration Enhancers on the In-vitro Percutaneous Absorption of Progesterone," J. Pharm. Pharmacol., 1997, 49: 955-959.
Van Cutsem et al., "The anti-inflammatory effects of ketoconazole," J. Am. Acad. Dermatol., Aug. 1991, 25(2):257-261.
Van Slyke, "On the measurement of buffer values and on the relationship of buffer value to the dissociation constant of the buffer and the concentration and reaction of the buffer solution," J. Biol. Chem., 1922, 52:525-570.
Vera et al., "Scattering optics of Foam," Applied Optics, Aug. 20, 2001, 40(24):4210-4214.
Veron et al., "Stability of Minoxidil Topical Formulations", Ciencia Pharmaceutica, 1992, 2(6):411-414 (Abstract).
View of NCT01171326 on Dec. 7, 2010, ClinicalTrials.gov archive, Dec. 7, 2010, retrieved on Sep. 9, 2013, http://clinicaltrials.gov/archive/NCT01171326/2010_12_07, 4 pages.
View of NCT01362010 on Jun. 9, 2011, ClinicalTrials.gov archive, Jun. 9, 2011, retrieved on Sep. 9, 2013, < http://clinicaltrials.gov/archive/NCT01362010/2011_06_09>, 3 pages.
Wang and Chen, "Preparation and surface active properties of biodegradable dextrin derivative surfactants," Colloids and Surfaces A: Physicochemical and Engineering Aspects, 2006, 281(1-3):190-193.
Water Jel Technologies, "Material Safety Data Sheet for Neomycin Antibiotic Ointment," Dec. 1, 2004, 7 pages.
WebMD (2014) "Psoriasis Health Center" [online]. Retrieved Apr. 13, 2015; retrieved from the Internet: http://www.webmd.com/skin-problems-and-treatments/psoriasis/psoriasis-symptoms, 3 pages.
WebMD (2014) "Understanding Rosacea—the Basics" [online]. Retrieved Apr. 13, 2015; retrieved from the Internet: http://www.webmd.com/skin-problems-and-treatments/understanding-rosacea-basics (5 pages).
WebMD (2017) "User Reviews & Ratings—Scytera topical" [online]. Retrieved Mar. 1, 2017; retrieved from the Internet: http://www.

(56) References Cited

OTHER PUBLICATIONS webmd.com/drugs/drugreview-151502-Scytera+topical.aspx?drugid=151502&drugname=Scytera+topical&sortby=3 (2 pages).

Weindl et al., "Hyaluronic acid in the treatment and prevention of skin diseases: molecular biological, pharmaceutical and clinical aspects," Skin Pharmacology and Physiology, 2004, 17: 207-213.

Wenninger et al., "International Cosmetic Ingredient Dictionary and Handbook," The Cosmetic, Toiletry, and Fragrance Association, Washington, DC., 1997, vol. 1, 4 pages.

Wermuth, "Similarity in drugs: reflections on analogue design," Drug Discovery Today, Apr. 2006, 11(7/8):348-354.

What is CP Serum, Skin Biology, retrieved on Dec. 1, 2008, http://web.archive.org/web/20030810230608/http://www.skinbio.com/cpserum.-html, 21 pages.

What is TSC?, Tuberous Sclerosis Alliance, Jan. 1, 2005, retrieved on Feb. 6, 2014, http://www.tsalliance.org.pages.aspx?content=2, 3 pages.

Williams et al., "Acne vulgaris," Lancet, 2012, 379:361-372.

Williams et al., "Scale up of an olive/water cream containing 40% diethylene glycol monoethyl ether," Dev. Ind. Pharm., 2000, 26(1):71-77.

Williams et al., "Urea analogues in propylene glycol as penetration enhancers in human skin," International Journal of Pharmaceutics, 1989, 36, 43-50.

Wormser et al., "Protective effect of povidone-iodine ointment against skin lesions induced by sulphur and nitrogen mustards and by non-mustard vesicants," Arch. Toxicol., 1997, 71, 165-170.

Wormser, "Early topical treatment with providone-iodine ointment reduces, and sometimes prevents, skin damage following heat stimulus," Letter to the Editor, Burns, 1998, 24:383.

Wrightson, W.R. et al. (1998) "Analysis of minocycline by high-performance liquid chromatography in tissue and serum" *J Chromatography B,* 706:358-361.

Wu et al., "Interaction of Fatty Acid Monolayers with Cobalt Nanoparticles," NANO Letters, 2004, 4(2): 383-386.

Yamada et al., "Candesartan, an angiotensin II receptor antagonist, suppresses pancreatic inflammation and fibrosis in rats," J. Pharmacol. Exp. Ther., 2003, 307(1)17-23.

Zeichner, J.A. (2010) "Use of Topical Coal Tar Foam for the Treatment of Psoriasis in Difficult-to-treat Areas" *J Clin Aesthet Dermatol,* 3(9):37-40.

Zinc Oxide, Knovel, 2006, retrieved on Apr. 18, 2012, http://www.knovel.com/web/portal/knovel_content?p_p_id=EXT_KNOVEL_CONTENT . . . , 2 pages.

Ziolkowsky, "Moderne Aerosolschaume in der Kosmetik (Modern Aerosol Foams in Chemical and Marketing Aspects)" Seifen-Ole-Fette-Wachse, Aug. 1986, 112(13): 427-429 (with English translation).

Kolb, "Emulsifiers, emollients and solubilizers for personal care", pp. 1-9, accessed Jun. 20, 2018.

Versagel® M Series, Mineral Oil Moisturizing Gels. Product Bulletin, retrieved from https://archive.org/web/, as archived Oct. 15, 2006, 3 pages.

COMPOSITIONS AND METHODS FOR TREATING ROSACEA AND ACNE

The present application claims the benefit of priority to U.S. Provisional Patent Application No. 62/385,189 filed Sep. 8, 2016; U.S. Provisional Patent Application No. 62/393,545 filed Sep. 12, 2016; U.S. Provisional Patent Application No. 62/444,960 filed Jan. 11, 2017; and U.S. Provisional Patent Application No. 62/550,158 filed Aug. 25, 2017; the entire contents of each are incorporated herein by reference.

BACKGROUND

Rosacea is a chronic acneiform disorder affecting skin and potentially the eye. It is a syndrome of undetermined etiology characterized by both vascular and papulopustular components involving the face and occasionally the neck, scalp, ears and upper trunk. Clinical findings include mid facial erythema, telangiectasis, papules and pustules, and sebaceous gland hypertrophy. Rosacea is characterized by episodic flushing of affected areas, which can be triggered by various factors, such as consumption of alcohol, hot drinks, spicy foods or physical exercise. Facial rosacea is classified/graded in multiple clinical forms: (1) erythematotelangiectatic rosacea which is characterized by (semi-) permanent erythema and/or flushing; (2) papulopustular rosacea, characterized by presence of inflammatory lesions such as papules and pustules; (3) phymatous rosacea characterized by circumscribed permanent swelling/thickening of skin areas, typically the nose; and (4) ocular rosacea characterized by the appearance of redness in eyes and eyelids due to telangiectasias and inflammation, feeling of dryness, irritation, or gritty, foreign body sensations, itching, burning, stinging, and sensitivity to light, eyes being susceptible to infection, or blurry vision.

Rosacea occurs most commonly in adult life, between the ages of 30 and 60 years. It is very common in skin types I-II (according Fitzpatrick) and more common in Caucasians, with a prevalence of up to 5% in the U.S. and in Europe. It is estimated that from 10 to 20 million Americans have the condition.

Topical treatments for rosacea include metronidazole, azelaic acid and brimonidine tartrate. However, approved topical therapies rarely show sufficient clinical efficacy or provide only cosmetic relief for several hours. Mainstays of treatment for rosacea are the oral tetracyclines: doxycycline and minocycline. Low-dose systemic doxycycline (Oracea® resp. Oraycea®) is approved for rosacea whereas systemic minocycline is used in many cases for rosacea off-label. Minocycline is generally regarded as having less photosensitivity than doxycycline. The long-term use of systemic antibiotics is limited by potential liver toxicity, phototoxicity, drug-drug interactions and development of antibacterial resistance. Hence, an efficacious topical tetracycline formulation is highly warranted to close this medical gap.

"Acne" is a general term that describes another very common skin disorder, which afflicts many people. The prevalence of adult acne is about 3% in men and between about 11% and 12% in women. Moderate to severe acne is observed in 14% of acne patients. There are various types of acne recognized in the field, including, for example: acne vulgaris and acne conglobata. Acne vulgaris (cystic acne or simply acne) is generally characterized by areas of skin with seborrhea (scaly red skin), comedones (blackheads and whiteheads), papules (pinheads), pustules (pimples), nodules (large papules) and/or possibly scarring. Acne vulgaris may affect the face, the upper part of the chest, and the back. Severe acne vulgaris is inflammatory, but acne vulgaris can also manifest in non-inflammatory forms. Acne conglobata is a severe form of acne, and may involve many inflamed nodules that are connected under the skin to other nodules. Acne conglobata often affects the neck, chest, arms, and buttocks.

There are typically three levels of acne vulgaris: mild, moderate, and severe. Mild acne vulgaris is characterized by the presence of few to several papules and pustules, but no nodules. Patients with moderate acne typically have several to many papules and pustules, along with a few to several nodules. With severe acne vulgaris, patients typically have numerous or extensive papules and pustules, as well as many nodules.

Acne may also be classified by the type of lesion: comedonal, papulopustular, and nodulocystic. Pustules and cysts are considered inflammatory acne.

Mild to moderate acne is often treated topically, using, e.g., retinoids, benzoyl peroxide and some antibiotics. Topical retinoids are comedolytic and anti-inflammatory. Antibiotics such as tetracycline antibiotics are generally only available orally or by injection. Topical antibiotics are mainly used for their role against P. acnes. Benzoyl peroxide products are also effective against P. acnes. Unfortunately, these medications can lack satisfactory safety and efficacy profiles. In one or more embodiments, there are provided herein new and better topical anti-acne treatments and formulations.

Diagnosis of acne vulgaris may begin with a visual inspection to determine the presence and amount of comedones, papules, pustules, nodules, and other inflammatory lesions. A diagnosis of acne vulgaris may also be confirmed via clinical laboratory tests, for example, measurement of testosterone levels and performing skin lesion cultures.

Systemic antibiotics are generally indicated for moderate or severe acne. The most commonly used systemic antibiotics are tetracycline and their derivatives (e.g., minocycline). These agents have anti-inflammatory properties and they are effective against P. acnes. The more lipophilic antibiotics, such as minocycline and doxycycline, are generally more effective than tetracycline. Greater efficacy may also be due to less P. acnes resistance to minocycline.

Oral tetracycline antibiotics are generally not recommended in the treatment of minor mild acne, primarily because they cause hyper-pigmentation, erythema and dryness. Oral tetracycline therapy may induce hyperpigmentation in many organs, including nails, bone, skin, eyes, thyroid, visceral tissue, oral cavity (teeth, mucosa, alveolar bone), sclerae and heart valves. Skin and oral pigmentation have been reported to occur independently of time or amount of drug administration, whereas other tissue pigmentation has been reported to occur upon prolonged administration. Skin pigmentation includes diffuse pigmentation as well as over sites of scars or injury. Oral tetracyclines should not be used for pregnant women or nursing mothers due to teratogenic effects. Accordingly, there exists a need for topical formulations with tetracyclines which can avoid the side effects observed with oral applications.

For example, SOLODYN®, a commercially available product, is indicated to treat only inflammatory lesions of non-nodular moderate to severe acne vulgaris in patients 12 years of age or older. Adverse side effects from the use of SOLODYN® include, inter alia, diarrhea, dizziness, lightheadedness, and nausea, in addition to allergic reactions, bloody stool, blurred vision, rectal or genital irritation, and red, swollen, blistered, or peeling skin. Because of these side effects, the Food and Drug Administration added oral minocycline to its Adverse Event Reporting System (AERS), a list of medications under investigation by the FDA for potential safety issues.

Thus, a product that requires a shorter treatment period, has no or fewer adverse effects, does not cause or causes less skin irritation, and treats both inflammatory and non-inflammatory lesions would be advantageous and could improve patient compliance. There also exists a need for improved compositions and methods for treating rosacea, as well as acne. Provided herein are compositions and methods to address those needs.

SUMMARY

In one aspect, provided is a method for treating rosacea or acne in a subject in need thereof, the method comprising: administering to said subject a topical composition comprising an effective amount of a tetracycline antibiotic.

In another aspect, provided is a hydrophobic gel or foam composition comprising: a tetracycline antibiotic, wherein said tetracycline antibiotic is present in said gel or foam composition in an amount effective to treat rosacea or acne in a subject.

In an exemplary embodiment, the gel or foam composition provided herein further comprises at least one hydrophobic solvent, at least one viscosity-modifying agent, or a combination thereof. In some embodiments, the composition comprises silicon dioxide ($SiO_2$).

In a particular embodiment, the tetracycline antibiotic is minocycline hydrochloride or doxycycline hyclate, or a combination thereof.

In yet another aspect, provided is a method of manufacturing a gel or foam composition having a tetracycline antibiotic, the method comprising: providing a composition having one or more hydrophobic solvents; heating said composition; adding fatty alcohols, fatty acids, and waxes; cooling said composition; adding $SiO_2$; and adding tetracycline antibiotic.

In a further aspect, provided is a method for treating rosacea or acne in a subject in need thereof, the method comprising: administering to said subject a topical composition comprising an effective amount of a tetracycline antibiotic, wherein said tetracycline antibiotic is minocycline.

In a yet further aspect, provided is a hydrophobic foam or gel composition comprising: about 50% by weight of soybean oil; about 23.6% by weight of coconut oil; about 5% by weight of cyclomethicone; about 2.8 to 4.3% by weight of light mineral oil; about 3.5% by weight of cetostearyl alcohol; about 3% by weight of stearic acid; about 2.5% by weight of myristyl alcohol; about 2% by weight of hydrogenated castor oil; about 2% by weight of beeswax; about 1.5% by weight of stearyl alcohol; about 1.1% by weight of behenyl alcohol; and about 1.5 to 3% by weight of minocycline.

In an additional aspect, provided is a method for treating a rosacea in a subject in need thereof, the method comprising: administering to said subject a hydrophobic foam or gel composition comprising about 50% by weight of soybean oil; about 23.6% by weight of coconut oil; about 5% by weight of cyclomethicone; about 2.8 to 4.3% by weight of light mineral oil; about 3.5% by weight of cetostearyl alcohol; about 3% by weight of stearic acid; about 2.5% by weight of myristyl alcohol; about 2% by weight of hydrogenated castor oil; about 2% by weight of beeswax; about 1.5% by weight of stearyl alcohol; about 1.1% by weight of behenyl alcohol; and about 1.5 to 3% by weight of minocycline.

In an additional aspect, provided is a method for reducing papules and pustules in a subject in need thereof, the method comprising: administering to said subject a topical composition comprising an effective amount of a tetracycline antibiotic to treat, ameliorate, reduce, or cure acne or rosacea.

In an additional aspect, provided is a method for reducing skin lesion in a subject in need thereof, the method comprising: administering to said subject a topical composition comprising an effective amount of a tetracycline antibiotic.

In an additional aspect, provided is a method for reducing skin redness in a subject in need thereof, the method comprising: administering to said subject a topical composition comprising an effective amount of a tetracycline antibiotic.

In an additional aspect, provided is a method for treating erythema in a subject in need thereof, the method comprising: administering to said subject a topical composition comprising an effective amount of a tetracycline antibiotic.

In an additional aspect, provided is a method for treating a rosacea in a subject in need thereof, the method comprising: administering to said subject a placebo topical composition, wherein said composition is free of a tetracycline antibiotic.

In an additional aspect, provided is a method for reducing papules and pustules in a subject in need thereof, the method comprising: administering to said subject a placebo topical composition, wherein said composition is free of a tetracycline antibiotic.

In an additional aspect, provided is a method for reducing skin lesions in a subject in need thereof, the method comprising: administering to said subject a placebo topical composition, wherein said composition is free of a tetracycline antibiotic.

In an additional aspect, provided is a method for reducing skin redness in a subject in need thereof, the method comprising: administering to said subject a placebo topical composition, wherein said composition is free of a tetracycline antibiotic.

In an additional aspect, provided is a method for treating erythema in a subject in need thereof, the method comprising: administering to said subject a placebo topical composition, wherein said composition is free of a tetracycline antibiotic.

Other features and advantages of the compositions and methods will become apparent from the following detailed description examples and figures. It should be understood, however, that the detailed description and the specific examples, while indicating preferred embodiments, are given by way of illustration only, since various changes and modifications within the spirit and scope of the disclosure will become apparent to those skilled in the art from this detailed description.

BRIEF DESCRIPTION OF THE FIGURES

The disclosure will be better understood from a reading of the following detailed description taken in conjunction with the drawings below:

FIG. 1A shows absolute change in papules and pustules, while FIG. 1B shows percent reduction in papules and pustules.

FIG. 2A shows subjects with IGA improvement ≥2 grades and FIG. 2B shows subjects with IGA improvement of at least two grades which resulted in clear (0) to almost clear (1) score.

DETAILED DESCRIPTION

Figure 1:
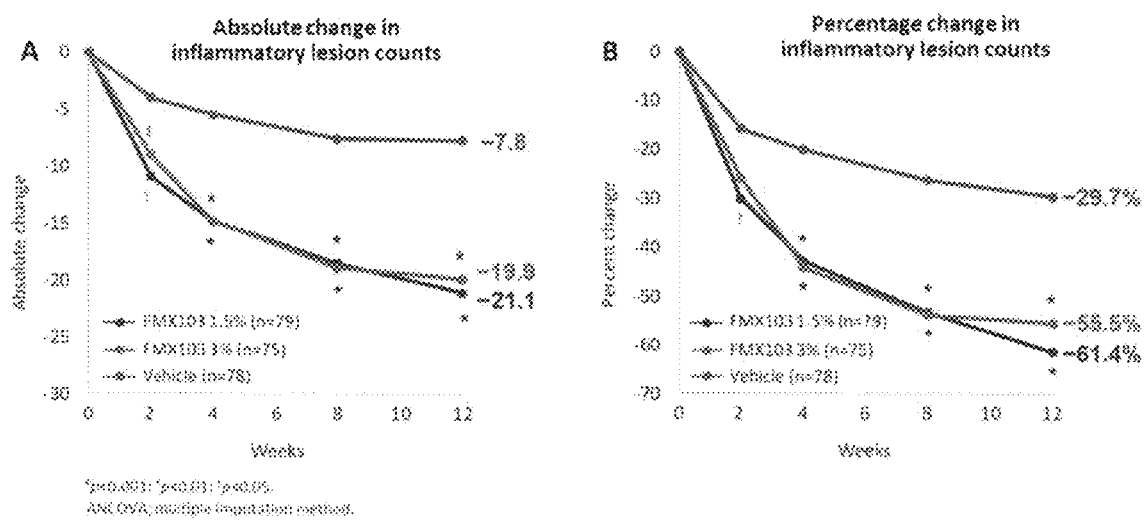
FIG. 1A-FIG. 1B show significant decrease in the number of papules and pustules after treatment with a 1.5% and 3% minocycline foam. Specifically.

Provided herein are compositions and methods for treating rosacea. Specifically, provided herein are gel and foam compositions having a tetracycline antibiotic and uses thereof for treating rosacea and/or acne.

The method provided herein includes administering topically to a surface having the disorder a therapeutic hydrophobic composition comprising a tetracycline antibiotic. In one or more embodiments, the hydrophobic composition comprises a carrier comprising about 60% to about 99% by weight of at least one hydrophobic solvent; at least one viscosity-modifying agent selected from the group consisting of a fatty alcohol, a fatty acid and a wax; and a tetracycline antibiotic. In some embodiments, the composition comprises silicon dioxide ($SiO_2$).

Further provided herein is a method of treating human skin disorders such as rosacea or rosacea related diseases or disorders by topical application of a foam or gel or liquid gel as described herein to a patient in need thereof.

According to one or more embodiments provided herein, the tetracycline is a minocycline or doxycycline, which are semi-synthetic tetracycline antibiotic. In a particular embodiment, the tetracycline is minocycline. The tetracycline drug is usually bacteriostatic in action. It can, among other options, exert its antimicrobial activity by inhibiting protein synthesis. It can also have an antiviral effect. According to one or more embodiments, the minocycline is minocycline hydrochloride (minocycline HCl; hereinafter "MCH"). MCH is a yellow crystalline powder that is sparingly soluble in water, slightly soluble in alcohol and practically insoluble in chloroform and in ether.

Minocycline is known to be highly sensitive to air and light and undergoes rapid degradation. Therefore, storage of foamable formulations in airtight sealed containers under pressure with propellant can contribute to preserving stability subject to selection of compatible canisters and accessories. Likewise, production and/or filling under vacuum in an oxygen free environment can help.

The ingredients of the carrier are selected for their compatibility with tetracycline antibiotics as described. Since it is not sufficient to identify single ingredients that are compatible with tetracycline antibiotics, formulations had to be found in which the ingredients in combination were also compatible with tetracycline antibiotics.

The hydrophobic foamable composition (e.g., foam or gel) provided herein comprises: a) about 60% to about 99% by weight of at least one hydrophobic solvent; b) about 1% to about 22% by weight of at least one viscosity modifying agent; and c) about 0.1% to about 18% of a tetracycline antibiotic (e.g., minocycline HCl or doxycycline).

The hydrophobic foamable composition or gel provided herein comprises: a) about 70% to about 90% by weight of at least one hydrophobic solvent; b) about 10 to about 22% by weight of at least one viscosity modifying agent; and c) about 0.5% to about 8% of a tetracycline antibiotic (e.g., minocycline HCl or doxycycline).

In one or more embodiments, a hydrophobic foamable composition or gel provided herein comprises: a) about 75% to about 90% by weight of at least one hydrophobic solvent; b) about 10 to about 22% by weight of at least one viscosity modifying agent; and c) about 1% to about 4% of a tetracycline antibiotic (e.g., minocycline HCl or doxycycline).

The hydrophobic foamable composition or gel provided herein comprises: a) about 72% to about 88% by weight of at least one hydrophobic solvent; b) about 10 to about 22% by weight of at least one viscosity modifying agent; and c) about 2% to about 6% of a tetracycline antibiotic (e.g., minocycline HCl or doxycycline).

According to one or more embodiments, there are provided substantially surfactant-free oleaginous formulations comprising a tetracycline, such as a minocycline, for use in treatment of a rosacea disease, and/or acne related symptoms, and/or a tetracycline antibiotic responsive rosacea related disorder, and/or a tetracycline antibiotic responsive skin disorder, and/or skin disorder caused by a bacteria, and/or a tetracycline antibiotic responsive disorder, and other superficial infections, including skin infections. In one or more embodiments the tetracycline acts to reduce oxidative stress and/or inflammation in skin pathologies. In one or more embodiments the tetracycline is effective where the condition is accompanied by apoptotic cell death.

In one or more embodiments, the tetracycline is minocycline HCl at a concentration of about 1.5% or about 3%, or any concentration in between.

Definitions

Unless defined otherwise, all technical and scientific terms used herein have the same meaning as is commonly understood by one of ordinary skill in the art to which this disclosure belongs. All ranges disclosed herein include the endpoints. The use of the term "or" shall be construed to mean "and/or" unless the specific context indicates otherwise. All patents, applications, published applications, and other publications are incorporated by reference in their entirety. In the event that there is a plurality of definitions for a term herein, those in this section prevail unless stated otherwise.

All % values are provided on a weight (w/w) basis.

Various carriers and compositions or formulations are described herein. They are often described for use in a method. A reference to or example of a carrier, composition or formulation for use in one method does not in any way limit the carrier, composition or formulation for use just in that method, but it can be for use in any other method or embodiment described herein. The carriers, compositions or formulations described herein are in one or more embodiments provided as carriers, compositions or formulations and are in one or more embodiments provided as a product even where they are described only in relation to their use in a method.

As used herein, the term "about" has its usual meaning in the context of pharmaceutical and cosmetic formulations to allow for reasonable variations in amounts that can achieve the same effect. By the term "about" herein it is meant as indicated above and also that a figure or range of figures can vary in an embodiment plus or minus up to 30%. For example, if an amount of "about 1" is provided, then the amount can be up to 1.3 or from 0.70. In other embodiments, it can reflect a variation of plus or minus 20%, in which case "about 2" can reflect a variation of 1.6 to 2.4. In still further embodiments, it can describe a variation of plus or minus 10%, in which case "about 1" can reflect a variation of 0.9 to 1.1. In still further embodiments, it can describe a variation of plus or minus 5%, in which case "about 5" can reflect a variation of 4.75 to 5.25. In cases where "about X" will lead to a figure of above 100%, the term in one or more embodiments can be read as reflecting up to 100% by weight less the total of the minimum amount of the other ingredients. Likewise, it will be appreciated by one skilled in the art to the extent X is reduced from that upper level the amounts of the other ingredients are increased appropriately. As will be appreciated by one of skill in the art, there is some reasonable flexibility in formulating compositions such that where one or more ingredients are varied, successful formulations can still be made even if an amount falls slightly outside the range. Therefore, to allow for this possibility, amounts are qualified by about. In one or more other embodiments, the figures can be read without the term "about."

As used herein, the terms "composition(s)" and "formulation(s)" can be used interchangeably depending on the context in which they are used as would be appreciated by a person skilled in the art.

The term "room temperature" as used herein, means 20° C. to 25° C. In an embodiment it is 20° C. In an embodiment it is 21° C. In an embodiment it is 22° C. In an embodiment it is 23° C. In an embodiment it is 24° C. In an embodiment it is 25° C.

The term "thixotropic," as used herein, means that the formulation shows a decrease in viscosity upon application of shear force. The structure of the formulation breaks down, leading to a reduction in viscosity. When the formulation is standing without shear force, this decrease in viscosity is recovered over time.

As used herein, the term "gel" means a jelly-like material that can have properties ranging from soft and fluid to hard and tough. Gels can be in a liquid, a semi-liquid, a semi-solid or a solid state. Solid gels are defined as a substantially diluted cross-linked system, which exhibits no flow when in the steady-state. By weight, gels are mostly liquid, yet they behave like semi-solids due to a three-dimensional cross-linked network of a solidifying, gelling or thickening agent within the liquid. It is the crosslinks within the fluid that give a gel its structure (hardness) and contribute to stickiness (tack). Depending on the amounts of gelling agent in a formulation, the gel can be semi-solid with some limited flowability, such that when the semi-solid gel is placed in a tube and is inclined horizontally from a vertical position it will slowly flow from the vertical towards the horizontal or it can be a liquid gel where the amount of gelling agent or gelling effect is lower, such that the gel structure or connections are weaker or loose so that when placed in a tube and tilted from a vertical position to a horizontal position, the gel readily flows and adapts to the horizontal position. The rheological properties of gels at different surface temperatures can influence the release and bioabsorption of drugs therefrom.

The term "liquid gel" refers, inter alia, to a formulation after propellant is added (whereas, prior to adding the propellant, the formulation is a gel), or where the gel is loose or fluid or such that when subjected to gravity, it will pour or become liquid.

The terms "waterless" or "water-free" as used herein, mean that the composition contains no free or unassociated or absorbed water. The terms "substantially water-free" or "substantially waterless" refer to carriers that contain at most incidental or trace amounts of water. As used herein, "low water" means the composition contains about or less than 1% by weight; about or less than 0.9% by weight; about or less than 0.8% by weight; about or less than 0.7% by weight; or about or less than 0.6% by weight. As used herein, "substantially waterless" or "substantially water free" means the composition contains about or less than 0.5% by weight; about or less than 0.4% by weight; about or less than 0.3% by weight; about or less than 0.2% by weight; or about or less than 0.1% by weight. In one or more embodiments, the composition is "essentially water-free," meaning about or less than 0.05% by weight; or about or less than 0.01% water is present in the composition, by weight.

By the term "single phase" it is meant that after addition of propellant to the composition or carrier, the liquid components of the foamable composition or carrier are fully miscible, and the solid components, if any, are either dissolved or homogeneously suspended in the composition so that only one phase is visible.

By the term "substantially a single phase" it is meant that the composition or carrier, after addition of propellant, is primarily or essentially a single phase as explained above, but can also have present a small amount of material which is capable of forming a separate phase amounting to less than about 5% by weight of the composition or carrier after the addition of propellant, or less than about 3% by weight, and/or less than about 1% by weight of the composition.

The term "unstable" as used herein, means a compound, e.g., an active agent, which is oxidized and/or degraded within less than a day, and in some cases, in less than an hour, upon exposure to air, light, skin, or water or a pharmaceutical excipient under ambient conditions.

The term "unstable active agent" as used herein, means an active agent which is oxidized and/or degraded within less than a day, and in some cases, in less than an hour upon exposure to air, light, skin, water, or a pharmaceutical excipient under ambient conditions.

It should be noted that the terms "surfactant," "surface active agent," and "emulsifier" in the context used herein, refer to stand alone compounds used to reduce surface tension between two substances or phases, and which are also capable of stabilizing an emulsion of water and oil. Reduction of surface tension can be significant in foam technology in relation to the ability to create small stable bubbles. "Surfactant" and "emulsifier," as used herein, do not include compounds which do not function effectively as standalone compounds for reducing surface tension between two substances or phases and which are not capable of stabilizing an emulsion of water and oil. For example, a surfactant or emulsifier as provided herein does not include fatty acids, does not include fatty alcohols, and does not include propoxylated lanolin oil derivatives. In the context of the present disclosure, fatty acids and fatty alcohols are defined as foam adjuvants. Similarly, propoxylated lanolin oil derivatives in the context herein are defined as emollients.

"Standard surfactant," "customary surfactant" or "stand alone surfactant" refer to customary non-ionic, ionic, anionic, cationic, zwitterionic, amphoteric and amphiphilic surfactants. Many standard surfactants are derivatives of fatty alcohols or fatty acids, such as ethers or esters formed from such fatty alcohols or fatty acids with hydrophilic moieties, such as polyethylene glycol (PEG). However, a native (non-derivatized) fatty alcohol or fatty acid, as well as waxes are not regarded as a standard surfactant.

The term "co-surfactant" as used herein means a molecule which on its own is not able to form and stabilize satisfactorily an oil-in-water emulsion, but when used in combination with a surfactant as defined herein, the co-surfactant has properties which can allow it to help a surfactant create an emulsion and can boost the stabilizing power or effect of the surfactant. Examples of co-surfactants include fatty alcohols, such as cetyl alcohol, or fatty acids, such as stearic acid. Cetyl alcohol is a waxy hydrophobic substance that can be emulsified with water using a surfactant. Some substances can have more than one function and for example, fatty alcohols can in some formulations act as a co-solvent. In certain circumstances, a co-surfactant can itself be converted into a surfactant or soap by, for example, adding a base, such as, triethanolamine to a fatty acid like stearic acid.

The term "viscosity-modifying agent" in the context of the present disclosure is an agent which, when added to a hydrophobic oil, facilitates the creation of a hydrophobic breakable vehicle in the form of a breakable gel or breakable foam. According to the present disclosure, the viscosity-modifying agent is a "foamer complex," which is also referred as a "foam stabilizer" in this application, comprising a fatty alcohol, a fatty acid and/or a wax. In one or more alternative embodiments the foamer complex is a fatty alcohol and a wax or a fatty acid and a wax. In some embodiments it is a wax. In one or more embodiments the foamer complex or viscosity modifying agent comprises at least one of a fatty alcohol, a wax or a fatty acid. In one or more embodiments the foamer complex or viscosity modifying agent is selected from a group consisting of a fatty alcohol, a wax and a fatty acid. In some embodiments, it is a fatty acid. In some embodiments, it is a fatty alcohol. In some embodiments a fatty alcohol, and/or a fatty acid and/or a wax is an adjuvant. In the context of the present disclosure fatty alcohols, fatty acids and waxes that are compatible with tetracycline antibiotics, and in particular with a minocycline or a doxycycline, are compatible adjuvants.

The term "breakable" refers to a property of a gel or foam wherein the gel or foam is stable upon dispensing from a container, yet breaks and spreads easily upon application of shear or mechanical force, which can be mild, such as a simple rub.

The term "water activity" as used herein represents the hygroscopic nature of a substance, or the tendency of a substance to absorb water from its surroundings. Microorganisms require water to grow and reproduce, and such water requirements are best defined in terms of water activity of the substrate. The water activity of a solution is expressed as Aw=P/Po, where P is the water vapor pressure of the solution and Po is the vapor pressure of pure water at the same temperature. Every microorganism has a limiting Aw, below which it will not grow; e.g., for *Streptococci, Klebsiella* spp, *Escherichia coli, Clostridium perfringens,* and *Pseudomonas* spp, the Aw value is 0.95. *Staphylococcus aureus* is most resistant and can proliferate with an Aw as low as 0.86, and fungi can survive at an Aw of at least 0.7. The identification of a "solvent," as used herein, is not intended to characterize the solubilization capabilities of the solvent for any specific active agent or any other component of the foamable composition. Rather, such information is provided to aid in the identification of materials suitable for use as a component of the foamable composition described herein.

As used herein, the term "preventing" refers to avoiding the onset of a disorder or condition from occurring in a subject that has not yet been diagnosed as having the disorder or condition, but who may be susceptible to it.

As used herein, the term "treatment" refers to inhibiting the disorder or condition, i.e., arresting its development; relieving the disorder or condition, i.e., causing regression of the disorder or condition or reversing the progression of the disorder or condition; or relieving or reducing one or more symptoms of the disorder or condition.

It should be noted that the term "a method of preventing, treating a disease or a disorder" as provided throughout the specification is interchangeable with the term "use of the composition as a medicament for preventing or treating a disease." It should be noted that the term "disease" is used interchangeably with the term "disorder."

It should be noted that the term "substantially free of" an ingredient as provided throughout the specification is intended to mean that the composition comprises less than about 0.5% by weight, e.g., less than about 0.4% by weight, less than about 0.3% by weight, less than about 0.2% by weight, or less than about 0.1% by weight, of an ingredient unless specifically indicated otherwise.

As used herein, the term "essentially free of" an ingredient as provided throughout the specification is intended to mean that the composition comprises less than about 0.05% by weight, less than about 0.01% by weight, less than about 0.001% by weight, or 0% by weight, or insignificant or negligible amounts of the ingredient, unless specifically indicated otherwise.

As used herein, the term "free of" an ingredient as provided throughout the specification is intended to mean that the composition does not comprise any amount of the ingredient, unless specifically indicated otherwise.

The terms "surfactant-free" or "emulsifier-free" or "non-surfactant" refer to compositions which comprise no or negligible levels of surfactants, emulsifiers, or surface active agents. Where a formulation includes insignificant or de minimis amounts of surfactants, emulsifiers, or surface active agents it is considered to be essentially surfactant-free. As used herein, "essentially free" indicates less than about 0.05% by weight, less than about 0.01% by weight, less than about 0.001% by weight, or 0% by weight of a surfactant selected from the group consisting of customary non-ionic, ionic, anionic, cationic, zwitterionic, amphoteric and ampholytic surfactants.

The term "substantially surfactant-free" relates to a composition wherein the ratio between the viscosity-modifying agent and the surfactant is between 10:1 or 5:1; or between 20:1 and 10:1 or between 100:1 and 20:1. In additional embodiments, the term relates to a composition that contains a total of about or less than 0.5% by weight; about or less than 0.4% by weight; or about or less than 0.3% by weight of a surfactant selected from the group consisting of customary non-ionic, ionic, anionic, cationic, zwitterionic, amphoteric and ampholytic surfactants. In some embodiments, the composition comprises about or less than 0.2% by weight of a standard or customary surfactant; about or less than 0.15% by weight; about or less than 0.1% by weight; about or less than 0.05% by weight; or about or less than 0.01% by weight.

By "de minimis" it is meant to be so minor that its effect is to be disregarded.

The terms "hydrophobic gel composition" or "hydrophobic foam composition" or "hydrophobic composition" are intended to mean that the composition has a low solubility in water. In one embodiment, 100 to 1000 parts of water are needed to dissolve or render miscible 1 part of the composition. In another embodiment, 1000 to 10,000 parts of water are needed to dissolve or render miscible 1 part of the composition. In yet another embodiment, more than 10,000 parts of water are needed to dissolve or render miscible 1 part of the composition.

The term "clinical response to treatment", ("clinical success" or "clinical failure") in the context of rosacea treatment is derived from efficacy evaluation endpoints. The term "lesion count" relates to the number of inflammatory lesions (e.g., papules and pustules) present in a designated area of the body (e.g., in case of face, on the forehead, left and right cheeks, nose and chin).

The terms "high rates of clinical response" or "high efficacy" or "substantial decrease" in the context herein can relate to an absolute change in inflammatory lesion count of at least 19 compared to baseline, a reduction of about 45% or more in inflammatory lesions count or to where subjects met a success criterion of "clear" or "almost clear" or to an "improvement of 2 grades from the baseline"; or to where subjects receive an excellent score according to Investigator's Global Improvement Assessment; or to where patients receive a two step drop in Patient's Global Improvement Assessment (IGA) score; or wherein according to any of the aforementioned endpoints a statistically significant reduction or improvement is demonstrated as compared to placebo.

By "regular basis" it is meant a repeated or repeatable interval of time which can be by way of illustration, a part of a day, daily, once daily, twice daily, alternative daily, alternate daily, twice weekly, trice weekly, weekly, fortnightly, monthly or some other repeated or repeatable interval for an appropriate period of time wherein a dose is to be applied. The repeated applications can be determined according to the needs of the subject and the disease or disorder. In some circumstances as little as three repeat doses can be required. In other cases, between 3 and 14, in other cases between 14 and 28, in other cases between 28 and 50, in other cases between 50 and 75, in other cases between 75 and 100, and in other cases, such as where prolonged treatment or a long period of maintenance dosing is needed, as many as one, two, or three hundred repeat doses can be needed.

The term "adverse events" describes any unfavorable or unintended sign, symptom, or disease that appears or worsens in a subject after the subject has commenced using the formulation. Examples of what can be considered an adverse event (AE) include any of the following: A new illness, an exacerbation of a sign or symptom of an underlying condition or of a concomitant illness unrelated to participation in the clinical study, a sign or symptom as an effect of the study drug or comparator drug The common term for such problems is "side effects," and used by patients and physicians.

The term "serious adverse events" describes any adverse effect that: Results in death, is life-threatening (Note: The term "life-threatening" refers to any adverse event that, as it occurs, puts the subject at immediate risk of death. It does not refer to an adverse event that hypothetically might have caused death if it were more severe.), results in hospitalization or prolongation of current hospitalization (not including hospitalization for a pre-existing condition that has not increased in severity or frequency from the subject's underlying medical condition prior to entry into the study), results in persistent or significant disability/incapacity, is a congenital anomaly/birth defect in the offspring of a subject, is an important medical event (Note: Important medical events may not be immediately life-threatening or result in death or hospitalization but may be considered serious when, based upon appropriate medical judgment, they may jeopardize the subject or require medical or surgical intervention to prevent one of the outcomes listed above. Examples of such medical events include allergic bronchospasm requiring intensive treatment in an emergency room or at home; blood dyscrasias or convulsions that do not result in inpatient hospitalization; or development of drug dependency or drug abuse.)

The term "safe" in the context herein means having no or essentially no adverse events (e.g., any unfavorable or unintended sign, symptom, or disease that appears or worsens on the course of treatment).

It should be noted that the term "polyol" as used herein is an organic substance that contains at least two hydroxyl groups in its molecular structure.

The terms "local safety" or "tolerable" or "enhanced tolerability" in the context herein means having no or essentially no skin irritation symptoms such as telangiectasis, burning or stinging, flushing or blushing, or alternatively, when such symptoms arise they are mild and disappear without interrupting treatment. The score for such symptoms is measured by the investigator at baseline, 2, 4, 8, and 12 weeks and is according to a scale of none, mild, moderate and severe. The score represents the subject's condition at the time of evaluation. The score for burning or stinging and flushing or blushing is based on the subject's symptoms reported for the previous three days. These symptoms should not be included as adverse events, unless a symptom is believed to have been related to the study medication or is the reason for discontinuation from the study.

By "essentially no" in the context of tolerability includes insignificant or de minimis occurrences of skin irritation events manifested in symptoms such as telangiectasis, burning or stinging, flushing or blushing, or mild transient events connected with the application of topical tetracyclines or vehicle.

By "essentially no" in the context of safety includes insignificant or de minimis occurrences of systemic or serious adverse events connected with the application of topical tetracyclines or vehicle.

The clinical response was determined at each study visit inter alia by an absolute inflammatory lesion count, by % change in inflammatory lesion count, by Investigator global assessment, by improvement assessment (by the Investigator) and improvement assessment (by the patient). Photographs were also used to assess the clinical improvement. The improvement assessment by the investigator includes scoring rosacea severity based on the number of inflammatory lesions and level of erythema. The improvement assessment by the patient involves measuring the health-related quality of life of patients through Rosacea Quality of Life (RosaQoL), a self-administered questionnaire.

The term clinical failure is defined as insufficient improvement or deterioration (i.e., an increase or no change in the number of lesions).

By "on average," with reference to dosage regimes, it is intended to reflect and/or take into account human nature and that a subject may forget to apply a dose or not strictly adhere to the regime, such that even if a subject forgets a dose or does not strictly adhere to the regime it will still be considered as if the regime has been applied. For example, if a subject misses an occasional dose but does not make it up, or alternatively, if having missed a dose applies a compensatory dose on a different day, it is still counted as having complied with the dosage regime.

Compositions

Gel or foam compositions having tetracycline antibiotic are well-known in the art and fully described in U.S. Patent Application Publication Nos. 2014/0121188 and 2013/0225536, which are herein incorporated by reference in their entirety.

In one or more embodiments there is provided a hydrophobic gel or foam composition comprising a tetracycline antibiotic for use in treating a rosacea in a human subject suffering therefrom comprising topically administering the composition to the human subject in a sufficient amount and for a sufficient time to decrease the number of rosacea lesions.

Tetracycline Antibiotic

Any tetracycline antibiotic known to one of skilled in the art can be used. Examples of a tetracycline antibiotic include, for example, but not limited to tetracycline, oxytetracycline, demeclocycline, doxycycline, lymecycline, meclocycline, methacycline, minocycline, rolitetracycline, chlorotetracycline, and tigecycline.

In a particular example, the tetracycline is a minocycline or doxycycline, which are semi-synthetic tetracycline antibiotic. According to one or more embodiments, the tetracycline is minocycline. The tetracycline drug is usually bacteriostatic in action. It can, amongst other options, exert its antimicrobial activity by inhibiting protein synthesis. It can also have an antiviral effect. According to one or more embodiments, the minocycline is minocycline hydrochloride (minocycline HCl; (hereinafter "MCH")). In some embodiments, MCH is a yellow crystalline powder that is sparingly soluble in water, slightly soluble in alcohol and practically insoluble in chloroform and in ether.

Minocycline and MCH is known to be highly sensitive to air and light and undergoes rapid degradation. Therefore, storage of foamable formulations in airtight sealed containers under pressure with propellant can contribute to preserving stability, subject to selection of compatible canisters and accessories. Likewise, production and/or filing under vacuum in an oxygen free environment can help.

Thus, it was unexpectedly demonstrated that topical minocycline foam offered a safe and effective alternative to topical compositions containing for example, ivermectin, metronidazole, azelaic acid and brimonidine tartrate for the topical treatment of rosacea. The ease of use, with once daily dosing, as well as its broad spectrum of activity, early onset, the low level of adverse events and the rapid reduction in the number of lesions make it an attractive choice and a potentially valuable medication for the treatment of acute bacterial skin infections.

Examples of bacterial infections that can be effectively treated by topical tetracycline antibiotics include, but not limited to, cellulitis, acute lymphangitis, lymphadenitis, erysipelas, cutaneous abscesses, necrotizing subcutaneous infections, staphylococcal scalded skin syndrome, folliculitis, furuncles, hidradenitis suppurativa, carbuncles, paronychial infections, erythrasma, disorders of hair follicles and sebaceous glands, acne, impetigo, rosacea, perioral dermatitis, hypertrichosis (hirsutism), alopecia, including male pattern baldness, alopecia greata, alopecia universalis and alopecia totalis, pseudofolliculitis barbae, and keratinous cyst. For example, rosacea involves papules and pustules, which can be treated with an antibiotic agent, as well as erythema, telangiectasia, and redness, which partially respond to treatment with an antibiotic agent.

In one or more embodiments, the active agent can be a placebo or a cosmetic agent. The foamable composition is suitable for use in the manufacture of a medicament including a placebo or active agent.

In one or more embodiments, the tetracycline antibiotic is hydrophobic.

In one or more embodiments, the Log of the distribution constant of the tetracycline antibiotic at pH 7.0 (buffer/chloroform) is equal to or less than about 0.2.

In one or more embodiments, tetracycline antibiotic forms suitable for use according to the methods and compositions of the present disclosure include, but are not limited to, a free base form, a hydrate form, a salt form, a chelate complex form or a coordination complex form.

In one or more embodiments, the tetracycline antibiotic does not comprise a hydroxyl group at carbons 5, 6, and 7.

In one or more embodiments, the tetracycline antibiotic comprises or is selected from the group consisting of minocycline and doxycycline. In some embodiments, the tetracycline antibiotic is minocycline. In some embodiments, the concentration of minocycline is in a range between about 0.1% to about 10% by weight (e.g., about 0.1% to about 8% by weight, about 0.1% to about 5% by weight, about 0.1% to about 3% by weight, about 0.1% to about 2% by weight, about 0.1% to about 1% by weight, about 0.1% to about 0.75% by weight, about 0.1% to about 0.5% by weight, about 0.1% to about 0.25% by weight, about 0.25% to about 10% by weight, about 0.5% to about 10% by weight, about 0.5% to about 5% by weight, about 0.5% to about 4% by weight, about 0.5% to about 3% by weight, about 1% to about 10% by weight, about 2% to about 10% by weight, about 4% to about 10% by weight, about 6% to about 10% by weight, about 7% to about 10% by weight, about 8% to about 10% by weight, about 0.5% to about 2.0% by weight, about 0.75% to about 1.5% by weight, about 1% to about 3% by weight, about 1% to about 4% by weight, and about 2% to about 6% by weight). In some embodiments, the concentration of minocycline is at least about 0.05% by weight, is at least about 0.1% by weight, at least about 0.5% by weight, at least about 1% by weight, at least about 2% by weight, at least about 4% by weight, at least about 6% by weight, at least about 8% by weight or at least about 10% by weight.

In one or more embodiments, the minocycline is micronized.

In one or more embodiments, the initial dose of tetracycline is about 18%, or about 17.5%, or about 16.5%, or about 15.5%, or about 14.5%, or about 13.5% or about 12.5%, or about 11.5%, or about 10.5% or about 9.5% or about 8.5% or about 7.5% or about 6.5% or about 5.5% or about 4.5% or about 3.5% or about 2.5% or about 1.5% or about 17%, or about 16%, or about 15%, or about 14%, or about 13% or about 12%, or about 11%, or about 10% or about 9% or about 8% or about 7% or about 6% or about 5% or about 4% or about 3% or about 2% or about 1% or about 0.75% or about 0.5% or about 0.25% or about 0.2% by weight of the composition. In one or more embodiments, the maintenance dose of tetracycline is about 7.5% or about 6.5% or about 5.5% or about 4.5% or about 3.5% or about 2.5% or about 1.5%, 7% or about 6% or about 5% or about 4% or about 3% or about 2% or about 1% or about 0.5%, or about 1.9%, or about 1.8% or about 1.7% or about 1.6% or about 1.55 or about 1.4% or about 1.3% or about 1.2% or about 1.1%, or about 0.9% or about 0.8%, or about 0.7%, or about 0.6% or about 0.4% or about 0.35 or about 0.25% or about 0.2% or about 0.15% or about 0.1% by weight of the composition.

According to one or more embodiments, provided are substantially surfactant-free oleaginous formulations comprising a tetracycline, such as a minocycline, for use in treatment of rosacea, and/or rosacea related symptoms, and/or a tetracycline antibiotic responsive rosacea related disorder, and/or a tetracycline antibiotic responsive skin disorder, and/or skin disorder caused by a bacteria, and/or a tetracycline antibiotic responsive disorder, and/or a sebaceous gland disorder. In one or more embodiments the tetracycline is used for the treatment of rosacea. In one or more embodiments the tetracycline is used for the treatment of impetigo. In one or more embodiments the tetracycline is used for the treatment of acne. In one or more embodiments the tetracycline acts to reduce oxidative stress and/or inflammation in skin pathologies. In one or more embodiments the tetracycline is effective where the condition is accompanied by apoptotic cell death.

In one or more embodiments there is provided a hydrophobic gel or foam composition comprising a minocycline antibiotic for use in treating a disorder selected from the group consisting of rosacea, and/or rosacea related symptoms, and/or a tetracycline antibiotic responsive rosacea related disorder, and/or a tetracycline antibiotic responsive skin disorder, and/or skin disorder caused by a bacteria, and/or a tetracycline antibiotic responsive disorder, and/or a sebaceous gland disorder, wherein the hydrophobic gel or foam composition is administered topically at least alternate days or at least once daily for at least two weeks to the skin, wherein the hydrophobic gel or foam composition is waterless and does not comprise a silicone other than cyclomethicone.

In one or more embodiments there is provided a hydrophobic gel or foam composition comprising a minocycline antibiotic for use in treating a disorder selected from the group consisting of rosacea, and/or rosacea related symptoms, and/or a tetracycline antibiotic responsive rosacea related disorder, and/or a tetracycline antibiotic responsive skin disorder, and/or skin disorder caused by a bacteria, and/or a tetracycline antibiotic responsive disorder, and/or a sebaceous gland disorder, wherein the hydrophobic gel or foam composition is administered topically at least alternate days or at least once daily for at least two weeks to the skin, mucosa, or eye, wherein the hydrophobic gel or foam composition is waterless and does not comprise a polyethylene gelling agent or polyethylene homopolymer or polyethylene copolymer or a customary surfactant.

Foam Vehicle

It is postulated, without being bound by any theory, that the use of a hydrophobic oil based foam vehicle contributes to cutaneous bioavailability, including the achievement of therapeutic levels of minocycline in the pilosebaceous unit. Specific targeting of hydrophobic oil based foam vehicle to the pilosebaceous unit is enabled due the hydrophobic nature of the pilosebaceous gland.

Thus, provided in various embodiments is a vehicle for delivering a therapeutically effective amount of active agent to the sebaceous gland or the sebaceous gland area or the pilosebaceous unit comprising: a) about 60% to about 99% by weight of at least one hydrophobic solvent; b) at least one viscosity-modifying agent, wherein said agent is a wax, a fatty alcohol, a fatty acid, or mixtures of any two or more thereof.

Provided herein in various embodiments is a vehicle for delivering a therapeutically effective amount of active agent to the sebaceous gland or the sebaceous gland area or the pilosebaceous unit comprising: a) about 60% to about 99% by weight of at least one hydrophobic solvent; b) at least one viscosity-modifying agent comprising a wax and a fatty alcohol or a fatty acid, or both; wherein the active agent is a tetracycline antibiotic.

Additionally, provided herein in various embodiments is a vehicle for delivering a therapeutically effective amount of active agent to the sebaceous gland or the sebaceous gland area or the pilosebaceous unit comprising: a) about 60% to about 99% by weight of at least one hydrophobic solvent; b) at least one viscosity-modifying agent, wherein said agent is a wax, a fatty alcohol, a fatty acid, or mixtures of any two or more thereof; wherein the active agent is a minocycline.

Hydrophobic Solvent

In certain embodiments, a hydrophobic solvent can be useful. For example, some essential oils can kill microorganisms or can prevent of conditions that involve microbial infection. Additionally, hydrophobic solvents can useful for the treatment of conditions which involve damaged skin, such as psoriasis or atopic dermatitis. The combination of a hydrophobic solvent and a fatty alcohol or fatty acid can be of possible help in conditions characterized, for example, by infection and/or inflammation.

In one or more embodiments, the at least one hydrophobic solvent comprises or is selected from the group consisting of a mineral oil, a hydrocarbon oil, an ester oil, an ester of a dicarboxylic acid, a triglyceride oil, an oil of plant origin, an oil from animal origin, an unsaturated or polyunsaturated oil, a diglyceride, a PPG alkyl ether, an essential oil, a silicone oil, liquid paraffin, an isoparaffin, a polyalphaolefin, a polyolefin, polyisobutylene, a synthetic isoalkane, isohexadecane, isododecane, alkyl benzoate, alkyl octanoate, C12-C15 alkyl benzoate, C12-C15 alkyl octanoate, arachidyl behenate, arachidyl propionate, benzyl laurate, benzyl myristate, benzyl palmitate, bis(octyldodecyl stearoyl)dimer dilinoleate, butyl myristate, butyl stearate, cetearyl ethylhexanoate, cetearyl isononanoate, cetyl acetate, cetyl ethylhexanoate, cetyl lactate, cetyl myristate, cetyl octanoate, cetyl palmitate, cetyl ricinoleate, decyl oleate, diethyleneglycol diethylhexanoate, diethyleneglycol dioctanoate, diethyleneglycol diisononanoate, diethyleneglycol diisononanoate, diethylhexanoate, diethylhexyl adipate, diethylhexyl malate, diethylhexyl succinate, diisopropyl adipate, diisopropyl dimerate, diisopropyl sebacate, diisostearyl dimer dilinoleate, diisostearyl fumerate, dioctyl malate, dioctyl sebacate, dodecyl oleate, ethylhexyl palmitate, ester derivatives of lanolic acid, ethylhexyl cocoate, ethylhexyl ethylhexanoate, ethylhexyl hydroxystearate, ethylhexyl isononanoate, ethylhexyl palmitate, ethylhexyl pelargonate, ethylhexyl stearate, hexadecyl stearate, hexyl laurate, isoamyl laurate, isocetyl behenate, isocetyl lanolate, isocetyl palmitate, isocetyl stearate, isocetyl salicylate, isocetyl stearate, isocetyl stearoyl stearate, isocetearyl octanoate, isodecyl ethylhexanoate, isodecyl isononanoate, isodecyl oleate, isononyl isononanoate, isodecyl oleate, isohexyl decanoate, isononyl octanoate, isopropyl isostearate, isopropyl lanolate, isopropyl laurate, isopropyl myristate, isopropyl palmitate, isopropyl stearate, isostearyl behenate, isostearyl citrate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isostearyl salicylate, isostearyl tartrate, isotridecyl isononanoate, isotridecyl isononanoate, lauryl lactate, myristyl lactate, myristyl myristate, myristyl neopentanoate, myristyl propionate, octyldodecyl myristate, neopentylglycol dicaprate, octyl dodecanol, octyl stearate, octyl palmitate, octyldodecyl behenate, octyldodecyl hydroxystearate, octyldodecyl myristate, octyldodecyl stearoyl stearate, oleyl erucate, oleyl lactate, oleyl oleate, propyl myristate, propylene glycol myristyl ether acetate, propylene glycol dicaprate, propylene glycol dicaprylate, propylene glycol dicaprylate, maleated soybean oil, stearyl caprate, stearyl heptanoate, stearyl propionate, tocopheryl acetate, tocopheryl linoleate, glyceryl oleate, tridecyl ethylhexanoate, tridecyl isononanoate, triisocetyl citrate, alexandria laurel tree oil, avocado oil, apricot stone oil, barley oil, borage seed oil, calendula oil, cannelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrasteatate, poppy oil, propylene glycol ricinoleate, rapeseed oil, rye oil, safflower oil, sesame oil, shea butter, soya oil, soybean oil, sweet almond oil, sunflower oil, sisymbrium oil, syzygium aromaticum oil, tea tree oil, walnut oil, wheat germ glycerides, wheat germ oil, PPG-2 butyl ether, PPG-4 butyl ether, PPG-5 butyl ether, PPG-9 butyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-20 butyl ether, PPG-22 butyl ether, PPG-24 butyl ether, PPG-26 butyl ether, PPG-30 butyl ether, PPG-33 butyl ether, PPG-40 butyl ether, PPG-52 butyl ether, PPG-53 butyl ether, PPG-10 cetyl ether, PPG-28 cetyl ether, PPG-30 cetyl ether, PPG-50 cetyl ether, PPG-30 isocetyl ether, PPG-4 lauryl ether, PPG-7 lauryl ether, PPG-2 methyl ether, PPG-3 methyl ether, PPG-3 myristyl ether, PPG-4 myristyl ether, PPG-10 oleyl ether, PPG-20 oleyl ether, PPG-23 oleyl ether, PPG-30 oleyl ether, PPG-37 oleyl ether, PPG-40 butyl ether, PPG-50 oleyl ether, PPG-11 stearyl ether, herring oil, codliver oil, salmon oil, cyclomethicone, a dimethyl polysiloxane, dimethicone, an epoxy-modified silicone oil, a fatty acid-modified silicone oil, a fluoro group-modified silicone oil, a methylphenylpolysiloxane, phenyl trimethicone and a polyether group-modified silicone oil or mixtures of any two or more thereof. In some embodiments, the hydrophobic solvent comprises or is selected from the group consisting of soybean oil, a coconut oil, a cyclomethicone, a light mineral oil, and mixtures of any two or more thereof. In one or more embodiments the solvent is tested individually for compatibility with a tetracycline antibiotic and is only used if it passes a compatibility test as described below in the Methods.

As contemplated herein, the concentration of the hydrophobic solvent and/or viscosity modifying agent in the composition is selected to provide an Aw value selected from the ranges between or of (1) about 0.8 and about 0.9; (2) about 0.7 and about 0.8; and (3) less than about 0.7. Delivering the formulation in a pressurized package does not allow for humidity to be absorbed by the preparation, and therefore, the water free character of the composition is not altered or compromised.

In one embodiment, no preservative is needed in the formulations provided herein because the formulation is a waterless hydrophobic solvent or oil-based formulation having an Aw (water activity) value of less than 0.9, or less than about 0.8, or less than about 0.7, or less than about 0.6, and/or less than about 0.5, which is below the level of microbial proliferation.

In one or more embodiments, the hydrophobic solvent is at a concentration of about 75% to about 90% by weight. In one or more embodiments, the hydrophobic solvent is at a concentration of at least about 40% by weight, at least about 50% by weight, at least about 60% by weight, at least about 70% by weight, at least about 90% by weight. In some embodiments, the hydrophobic solvent is at a concentration of less than about 90% by weight, less than about 80% by weight, less than about 70% by weight, less than about 60% by weight, less than about 50% by weight.

In some embodiments, the formulation can include a fatty alcohol. Long chain saturated and mono unsaturated fatty alcohols, e.g., stearyl alcohol, erucyl alcohol, arachidyl alcohol and behenyl alcohol (docosanol) have been reported to possess antiviral, anti-infective, ant proliferative and anti-inflammatory properties (see, U.S. Pat. No. 4,874,794). Longer chain fatty alcohols, e.g., tetracosanol, hexacosanol, heptacosanol, octacosanol, triacontanol, etc., are also known for their metabolism modifying properties, and tissue energizing properties.

In one or more embodiments, the fatty alcohol and/or fatty acid have a melting point of at least about 40° C.

In one or more embodiments, the fatty alcohol comprises or is selected from the group consisting of lauryl alcohol, myristyl alcohol, cetyl alcohol, stearyl alcohol, cetostearyl, arachidyl alcohol, behenyl alcohol, tetracosanol, hexacosanol, octacosanol, triacontanol, and tetratriacontanol or mixtures of any two or more thereof. In one or more embodiments, the fatty acid comprises or is selected from the group consisting of dodecanoic acid, tetradecanoic acid, hexadecanoic acid, heptadecanoic acid, octadecanoic acid, eicosanoic acid, docosanoic acid, tetracosanoic acid, hexacosanoic acid, heptacosanoic acid, octacosanoic acid, triacontanoic acid, dotriacontanoic acid, tritriacontanoic acid, tetratriacontanoic acid, and pentatriacontanoic acid or mixtures of any two or more thereof.

In one or more embodiments, the carbon chain of the fatty alcohol or the fatty acid is substituted with a hydroxyl group.

In one or more embodiments, the fatty acid is 12-hydroxy stearic acid.

Viscosity-Modifying Agent

As contemplated herein, the gel is stable and it retains its viscosity upon dispensing from a container, such as a tube, yet, it liquefies and spreads easily upon application of shear force, which can be mild, such as a simple rub. Further, while the gel is oily, it absorbs into the site of application, such as the skin or mucosa membrane, and after minutes the surface does not appear and/or feel significantly oily or greasy.

In some embodiments, formulations comprising a hydrophobic oil and viscosity-modifying agents demonstrated increased viscosity of such oil, and to which when even small amounts of a suspended tetracycline antibiotic were added, a substantial or synergistic increase in the viscosity of the composition was observed.

In one or more embodiments, the viscosity-modifying agent is a wax comprising or selected from the group consisting of a plant wax, carnauba wax, candelilla wax, ouricury wax, sugarcane wax, retamo wax, jojoba oil, an animal waxes, beeswax, a hydrogenated castor oil, a petroleum derived wax, a paraffin wax, polyethylene, and derivatives thereof.

In one or more embodiments, the viscosity-modifying agent is a combination comprising (i) at least one fatty alcohol and at least one fatty acid; or (ii) at least one fatty alcohol and at least one wax; or (iii) at least one fatty acid and at least one wax; or (iv) at least one fatty alcohol, at least one fatty acid, and at least one wax.

In one or more embodiments the at least one viscosity-modifying agent comprises or is selected from the group consisting of a fatty alcohol, a fatty acid and a wax, wherein the fatty alcohols and/or fatty acids have at least 12 carbon atoms in their carbon backbone. In certain embodiments the viscosity modifying agent is a combination of a fatty alcohol and a fatty acid and/or a wax.

In one or more embodiments, the viscosity-modifying agent is at a concentration of about 0.1% to about 22%, about 0.4 to about 18%, about 0.5% to 16%, about 0.6% to 14%, about 0.7% to 13%, about 0.8 to about 12%, about 0.9% to about 11%, about 1% to about 10%, about 10% to about 22% by weight. In one or more embodiments, the viscosity-modifying agent is a fatty alcohol having at least 12 carbon atoms in its carbon backbone. In one or more embodiments, the viscosity-modifying agent is a fatty acid having at least 12 carbon atoms in its carbon backbone.

In one or more embodiments, the viscosity-modifying agent is at a concentration of about 9.5% or about 8.5% or about 7.5% or about 6.5% or about 5.5% or about 4.5% or about 3.5% or about 2.5% or about 1.5%, about 7% or about 6% or about 5% or about 4% or about 3% or about 2% or about 1% or about 0.5%, or about 1.9%, or about 1.8%, or about 1.7%, or about 1.6%, or about 1.55 or about 1.4% or about 1.3% or about 1.2% or about 1.1% or about 0.9% or about 0.8%, or about 0.7%, or about 0.6% or about 0.5% by weight of the composition or less than any of the aforesaid amounts.

Preferably, the fatty alcohol and/or fatty acid and/or wax are solid at ambient temperature. In certain embodiments, the fatty alcohol and/or the fatty acid and/or the wax or the mixture of them have a melting point of more than about 40° C.

Propellant

In one or more embodiments, the composition is a foamable composition, and further comprises a propellant. Any compatible propellant can be used. In one or more embodiments, the propellant is a gas at room temperature under normal pressure and which can be liquefied at increased pressure at room temperature. Examples of propellants include, without limitation, hydrocarbon propellants such as butane, propane, isobutane, dimethyl ether, fluorocarbons such as 1,1,1,2 tetrafluoroethane (Dymel 134a), and 1,1,1, 2,3,3,3 heptafluoropropane (Dymel 227), and mixtures thereof. In one or more embodiments, a hydrocarbon mixture AP-70 (a mixture of about 30% w/w butane, 20% w/w isobutane and 50% w/w propane) is used.

In one or more embodiments, the composition comprises about 0.1% w/w to about 0.3% w/w of fumed (modified) silica. In one or more embodiments, the composition comprises about 1% w/w to about 4% w/w of minocycline hydrochloride or a doxycycline or a tetracycline antibiotic. In one or more embodiments, the composition comprises about 3% w/w to about 15% w/w of propellant based on the weight of the total composition. In one or more embodiments, the composition comprises about 3% w/w to about 25% w/w of propellant based on the weight of the total composition. In one or more embodiments, the composition comprises about 3% w/w to about 35% w/w of propellant based on the weight of the total composition. In one or more embodiments, the composition comprises about 5% w/w to about 30% w/w of propellant based on the weight of the total composition.

Other Ingredients

In certain embodiments, the composition is free of one or more of a petrolatum, surface active agents, protic solvents, certain polar aprotic solvents, isopropyl myristate, polyethylene gelling agents, polyethylene homopolymers, polyethylene copolymers, selenium derivatives and silicone thickening agents; and in certain embodiments, the foamable composition is substantially free of such excipients. In the context herein, the term "substantially-free" relates to a composition that contains a total of less than about 0.4% of a petrolatum, surface active agents, protic solvents, certain polar aprotic solvents, isopropyl myristate, polyethylene gelling agents, polyethylene homopolymers, polyethylene copolymers, selenium derivatives and silicone thickening agents cumulatively. Preferably, the composition comprises less than about 0.2% of two or more or all thereof by weight of petrolatum, surface active agents, protic solvents, certain polar aprotic solvents, isopropyl myristate, polyethylene gelling agents, polyethylene homopolymers, polyethylene copolymers, selenium derivatives and silicone thickening agents cumulatively or, and more preferably less than about 0.1% individually or of two or more or all thereof cumulatively.

In one or more embodiments, the composition is substantially alcohol-free, i.e., free of short chain alcohols having up to 5 carbon atoms in their carbon chain skeleton. In other embodiments, the composition comprises less than about 5% by weight final concentration of short chain alcohols, for example, less than 2% by weight, or less than 1% by weight. In certain embodiments, the composition is free or substantially free of ethanol, propanol, butanol and pentanol.

Surface Active Agents

For clarification, in the context herein whilst the term "standard surfactant" or "customary surfactant" refers herein to customary non-ionic, ionic, anionic, cationic, zwitterionic, amphoteric and amphiphilic surfactants. A fatty alcohol or a fatty acid and certain waxes are not regarded as a standard surfactant. However, in contrast, ethers or esters formed from such fatty alcohols or fatty acids can be regarded as a customary surfactant.

Surfactants of all kinds are undesirable in accordance with the present compositions and methods as (i) they were found to cause degradation of the tetracycline antibiotic; and (ii) they are generally known to possess irritation potential.

Non-limiting examples of classes of non-ionic surfactants that are undesirable according to the present invention include: (i) polyoxyethylene sorbitan esters (polysorbates), such as polysorbate 20, polysorbate 40, polysorbate 60 and polysorbate 80; (ii) sorbitan esters, such as sorbitan monolaurate and sorbitan monooleate; (iii) polyoxyethylene fatty acid esters, such as, PEG-8 stearate, PEG-20 stearate, PEG-40 stearate, PEG-100 stearate, PEG-150 distearate, PEG-8 laurate, PEG-10 laurate, PEG-12 laurate, PEG-20 laurate, PEG-8 oleate, PEG-9 oleate, PEG-10 oleate, PEG-12 oleate, PEG-15 oleate and PEG-20 oleate; (iv) PEG-fatty acid diesters; (v) polyethylene glycol (PEG) ethers of fatty alcohols; (vi) glycerol esters, such as glyceryl monostearate, glyceryl monolaurate, glyceryl monopalmitate and glyceryl monooleate; (vii) PEG-fatty acid mono- and di-ester mixtures; (viii) polyethylene glycol glycerol fatty acid esters; (ix) propylene glycol fatty acid esters; (x) mono- and diglycerides; (xi) sugar esters (mono-, di- and tri-esters of sucrose with fatty acids) and (xii) PEG alkyl phenols.

As disclosed herein, in the context of the compositions and methods provided herein, while fatty alcohols, fatty acids, and certain waxes are somewhat amphiphilic, these substances are not effective as stand-alone surfactants that can stabilize an emulsion, let alone foamable emulsion compositions, because of their very weak emulsifying capacity and further due to their weak foaming capacity on their own.

They are occasionally used in a supporting role as co-emulsifiers, i.e., in combination with a standard surfactant but are commonly used as thickeners and have successfully been used as foam adjuvants to assist customary surfactants to boost foam quality and stability. For the purposes of forming an emulsion they are usually regarded as an oil and thus have a "required" HLB value for the purpose of determining what standard surfactant might be appropriate to use with the oil phase.

Generally, surfactants are known to possess irritation potential. One way to try and reduce or minimize potential irritation and drying of the skin or mucosa due to surfactants and their repeated use, especially when formulations are to be left on the skin or mucosa rather than being washed off, is to use essentially or primarily nonionic surfactants at significant concentrations, although preferably below 5%. The identification of formulations which produce gels and quality breakable foam yet omit customary surfactants from a composition can contribute to improved tolerability of such a composition and can be an important advantage. This is especially so when a formulation is to be applied to a very sensitive target site, and particularly so on a repeated basis.

In certain embodiments, the composition is free of customary surfactants, also known as "surfactant-free," and in certain embodiments, the foamable composition is substantially free of customary surfactants, also known as "substantially surfactant-free".

In certain embodiments, the composition is free or substantially free of an ionic surfactant. In certain embodiments, the composition is free or substantially free of a zwitterionic surfactant. In certain embodiments, the composition is free or substantially free of a non-ionic surfactant.

Protic Solvents

Protic solvents, such as short chain alcohols, glycols and glycerin are incompatible with tetracyclines and therefore are undesirable. In certain embodiments, the composition is free or substantially free of protic solvents.

Aprotic Polar Solvents

It was discovered in PCT Publication No. WO11/039637 that certain polar aprotic solvents are incompatible with tetracycline antibiotics. Thus, aprotic polar solvents, such as dimethyl sulfoxide (DMSO), dimethylformamide (DMF), acetonitrile, acetone, methyl ethyl ketone, 1,4-Dioxane and tetrahydrofuran (THF), N-methylpyrrolidone, pyridine, piperidine, dimethylformamide, N-methyl-2-pyrrolidone and 1-methyl-2-pyrrolidinone) and azone (1-dodecylazacycloheptan-2-one) are undesirable. In certain embodiments, the composition is free or substantially free of aprotic polar solvents.

Silicone Thickening Agents

Silicone thickening agents comprise one or more polysiloxane-derived components. Such polysiloxanes are typically cross-linked and they have rubber-like characteristics, which require their solubilization in an oil, usually a silicone oil. An example of such a silicone thickening agent is ST-Elastomer 10 (Dow Corning), which is a mixture of high molecular weight dimethicone crosspolymer (12%), in cyclopentasiloxane (cyclomethicone, silicone solvent). With reference to bioavailability of an active agent in the skin following topical application, it is conceivable that cross co-polymers will create a non-permeable film which should block skin penetration and therefore, it is undesirable. Further, in the context of a breakable foam, cyclomethicone is known as a defoamer and therefore its presence in high concentrations in the breakable hydrophobic composition is undesirable. In certain embodiments, the composition is free or substantially free of silicone thickening agents other than cyclomethicone.

In one or more other specific embodiments, the drug carrier is formulated substantially free of elastomers. In one or more other specific embodiments, the drug carrier is formulated essentially free of elastomers. In one or more other specific embodiments, the drug carrier is formulated substantially free of silicones. In one or more other specific embodiments, the drug carrier is formulated essentially free of silicones. In one or more other specific embodiments, the drug carrier is formulated with less than about 30% silicones, or less than about 25% silicones, or less than about 20% silicones, or less than about 15% silicones, or less than about 10% silicones, or less than about 7.5% silicones, or less than about 5% silicones or less than about 2% silicones; or less than about 1% silicones; or less than about 0.5% silicones; or about 1% to about 5% silicones; or about 0.5% to about 3% silicones. In one or more other specific embodiments, the drug carrier does not comprise a silicone other than cyclomethicone. In one or more other embodiments, the drug carrier does not comprise one or more volatile silicones. In other embodiments, volatile silicones are present at about 3% or less.

In one or more embodiments, semi-solid hydrophobic oils are a subsidiary component in the composition, for example being present at less than about 45%, at less than about 40%, at less than about 35%, at less than about 30%, at less than about 25%, less than about 20%, less than about 15%, less than about 10%, or less than about 5% by weight of the composition. In one or more alternative embodiments, semi-solid oils are omitted.

Polyols

The identification of a "polyol," as used herein, is an organic substance that contains at least two hydroxyl groups in its molecular structure. In one or more embodiments, the polyol is a diol (a compound that contains two hydroxyl groups in its molecular structure). Examples of diols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol (e.g., 1,3-butanediol and 1,4-butenediol), butynediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2,56-diol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the polyol is a triol (a compound that contains three hydroxyl groups in its molecular structure), such as glycerin, butane-1,2,3-triol, butane-1,2,4-triol and hexane-1,2,6-triol.

In one or more embodiments, the polyol is a saccharide. Exemplary saccharides include, but are not limited to, monosaccharides, disaccharides, oligosaccharides, and sugar alcohols.

A monosaccharide is a simple sugar that cannot be hydrolyzed to smaller units. The empirical formula is $(CH_2O)_n$ and can range in size from trioses (n=3) to heptoses (n=7). Exemplary monosaccharide compounds are ribose, glucose, fructose, and galactose.

Disaccharides are made up of two monosaccharides joined together, such as sucrose, maltose, and/or lactose.

In one or more embodiments, the polyol is a sugar alcohol (also known as a polyol, polyhydric alcohol, or polyalcohol)

or a hydrogenated form of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present disclosure are mannitol, sorbitol, xylitol, maltitol, lactitol. (Maltitol and lactitol are not completely hydrogenated compounds—they are a monosaccharide combined with a polyhydric alcohol.) Mixtures of polyols, including (1) at least one polyol comprises or selected from a diol and a triol; and (2) a saccharide are contemplated within the scope of the present disclosure.

According to some embodiments, the composition is polyol free, i.e., free of polyols.

In other embodiments, the composition is substantially free and comprises less than about 5% final concentration of polyols, preferably less than 2%, more preferably less than 1%; or about 1% to about 5% polyols; or about 0.5% to about 3% polyols. In some embodiments the composition comprises de minimis amounts of polyols. Where a formulation includes insignificant or de minimis amounts of polyols, such as less than 0.05%, the formulation is considered to be essentially free of them.

In an embodiment, the polyol is linked to a hydrophobic moiety. In the context of the present disclosure, a polyol linked to a hydrophobic moiety is still defined as a "polyol" as long as it still contains two or more free hydroxyl groups.

In an embodiment, the polyol is linked to a hydrophilic moiety. In the context of the present disclosure, a polyol linked to a hydrophilic moiety is still defined "polyol" as long as it still contains two or more free hydroxyl groups.

In one or more embodiments, the hydrophobic composition further contains an anti-infective agent, comprises or selected from the group of an antibiotic agent, an antibacterial agent, an antifungal agent, an agent that controls yeast, an antiviral agent, and an antiparasitic agent. In an embodiment, the anti-infective agent comprises a tricyclic antibiotic. Not only can combining the anti-infective effect of a hydrophobic composition, with an anti-infective agent result in a synergistic effect and consequently higher success rate of the treatment but the combination with the viscosity modifying agent achieves a formulation in which the active pharmaceutical ingredient is chemically stable and the formulation is physically stable as demonstrated herein in the Examples. Moreover, the use of hydrophobic based water-free formulation can maximize the antimicrobial and antiviral potentials of the formulations. Delivery topically can be improved by using a hydrophobic carrier with a hydrophobic API. Storage in sealed, light and airtight canisters can assist in preserving the formulations.

In one or more embodiments, the hydrophobic composition is substantially free of at least one or more of surface active agents, protic solvents, polar aprotic solvents, and silicone thickening agents.

In one or more embodiments, the hydrophobic composition is substantially free of at least one or more of surface active agents, polymeric gelling agents, polyols, short chain alcohols, and silicone thickening agents.

In one or more embodiments, the hydrophobic composition contains less than about 0.4% by weight of the composition; or less than about 0.2% by weight of the composition; or less than about 0.1% by weight of the composition of one of or a combination of two, three or all of surface active agents, protic solvents, polar aprotic solvents, and silicone thickening agents.

In one or more embodiments, any composition of the present disclosure can also contain a fragrance. In one or more embodiments, the fragrance is at a concentration of about 0.1% by weight to about 1% by weight.

In one or more embodiments, the composition comprises about 35% w/w to about 65% w/w of soybean oil. In one or more embodiments, the composition comprises about 16.5% w/w to about 30.7% w/w of coconut oil. In one or more embodiments, the composition comprises about 3.5% w/w to about 6.5% w/w of cyclomethicone. In one or more embodiments, the composition comprises about 2% w/w to about 3.7% w/w of light mineral oil.

In one or more embodiments, the composition comprises about 2.5% w/w to about 4.6% w/w of cetostearyl alcohol. In one or more embodiments, the composition comprises about 2% w/w to about 4% w/w of stearic acid. In one or more embodiments, the composition comprises about 1.8% w/w to about 3.3% w/w of myristyl alcohol. In one or more embodiments, the composition comprises about 1% w/w to about 2% w/w of stearyl alcohol. In one or more embodiments, the composition comprises about 0.5% w/w to about 1.5% w/w of behenyl alcohol. In one or more embodiments, the composition comprises about 1% w/w to about 3% w/w of hydrogenated castor oil. In one or more embodiments, the composition comprises about 1% w/w to about 3% w/w of beeswax.

In one or more embodiments, the composition comprises about 48% w/w to about 51% w/w of soybean oil. In one or more embodiments, the composition comprises about 23% w/w to about 24% w/w of coconut oil. In one or more embodiments, the composition comprises about 4% w/w to about 6% w/w of cyclomethicone. In one or more embodiments, the composition comprises about 1% w/w to about 5% w/w of light mineral oil.

In one or more embodiments, the composition comprises about 3% w/w to about 4% w/w of cetostearyl alcohol. In one or more embodiments, the composition comprises about 2% w/w to about 4% w/w of stearic acid. In one or more embodiments, the composition comprises about 2% w/w to about 3% w/w of myristyl alcohol. In one or more embodiments, the composition comprises about 1% w/w to about 2% w/w of stearyl alcohol. In one or more embodiments, the composition comprises about 0.5% w/w to about 1.5% w/w of behenyl alcohol. In one or more embodiments, the composition comprises about 1% w/w to about 3% w/w of hydrogenated castor oil. In one or more embodiments, the composition comprises about 1% w/w to about 3% w/w of beeswax.

In one or more embodiments, the composition comprises about 0.1% w/w to about 0.3% w/w of fumed (modified) silica. In one or more embodiments, the composition comprises about 1% w/w to about 4% w/w of minocycline hydrochloride or a doxycycline or a tetracycline antibiotic. In one or more embodiments, the composition comprises about 3% w/w to about 15% w/w of propellant based on the weight of the total composition.

In one or more embodiments the tetracycline composition further comprises an additional active agent selected from the group consisting of an anti parasitic agent, an azole, an anti-histamine, α1 and α2 adrenergic receptor agonist, a vasoconstrictor and mixtures of any two or more thereof.

In one or more embodiments the tetracycline composition further comprises an additional active agent selected from the group consisting of ivermectine, metronidazole, azelastine, oxymetazoline, brimonidine and mixtures of any two or more thereof.

In one or more embodiments the tetracycline composition further comprises at least one of an additional active selected from an anti parasitic agent, an azole, an anti-histamine, α1 and α2 adrenergic receptor agonist or a vasoconstrictor.

In one or more embodiments the tetracycline composition further comprises at least one of an additional active selected from ivermectine, metronidazole, azelastine, oxymetazoline or brimonidine.

In one or more embodiments the tetracycline composition further comprises at least one of an additional active selected from an anti parasitic agent, an azole, an anti-histamine, α1 and α2 adrenergic receptor agonist or a vasoconstrictor, wherein the composition is configured for the treatment of rosacea.

In one or more embodiments the tetracycline composition further comprises at least one of an additional active selected from ivermectine, metronidazole, azelastine, oxymetazoline or brimonidine, wherein the composition is configured for the treatment of rosacea.

In one or more embodiments the composition comprises an active agent selected from the group consisting of an anti parasitic agent, an azole, an anti-histamine, α1 and α2 adrenergic receptor agonist, a vasoconstrictor and mixtures of any two or more thereof.

In one or more embodiments the composition comprises an active agent selected from the group consisting of ivermectine, metronidazole, azelastine, oxymetazoline, brimonidine and mixtures of any two or more thereof.

In one or more embodiments the composition comprises at least one active agent selected from an anti parasitic agent, an azole, an anti-histamine, α1 and α2 adrenergic receptor agonist and a vasoconstrictor.

In one or more embodiments the composition comprises at least one active agent selected from the group consisting of ivermectine, metronidazole, azelastine, oxymetazoline, brimonidine and mixtures of any two or more thereof.

In one or more embodiments the composition comprises at least one active agent selected from an anti parasitic agent, an azole, an anti-histamine, α1 and α2 adrenergic receptor agonist and a vasoconstrictor, wherein the composition is configured for the treatment of rosacea.

In one or more embodiments the composition comprises at least one active agent selected from ivermectine, metronidazole, azelastine, oxymetazoline and brimonidine, wherein the composition is configured for the treatment of rosacea.

In one or more embodiments the composition is configured to treat a disorder selected from an inflammatory disorders, non inflammatory disorders, atopic dermatitis, acne, dermatitis, impetigo, psoriasis and rosacea.

In one or more embodiments the composition is configured to treat at least one disorder selected from an inflammatory disorder, non inflammatory disorder, atopic dermatitis, acne, dermatitis, impetigo, psoriasis and rosacea.

In one or more embodiments a method for treatment of rosacea, wherein the tetracycline composition comprises an additional agent, wherein the additional agent is selected from tetracycline antibiotic, ivermectin, azelaic acid, azelastine, isotretinoin, metronidazole, brimonidine, oxymetazoline, xylometazolin, sodium sulfacetamide and sulfur, tretinoin, a retinoid, an anti parasitic agent, an azole, an anti-histamine, α1 and α2 adrenergic receptor agonist and a vasoconstrictor.

In another aspect, the ingredients of the carrier can be selected for their compatibility with tetracycline antibiotics as described. In one or more embodiments it was not sufficient to identify single ingredients that were compatible with tetracycline antibiotics but formulations had to be found in which the ingredients in combination were also compatible with tetracycline antibiotics.

In one or embodiments, topical tetracycline treatments can be given with or followed by application of a steroid or a hyaluronic acid or a collagen or a silicone, clindamycin, or metronidazole, or erythromycin, or ivermectin, or azelaic acid, or brimonidine, or sodium sulfacetamide and sulfur, or tretinoin, or a retinoid or mixtures of any two or more thereof, for example to ameliorate or reduce scarring or skin damage effects. In an embodiment treatment with topical tetracycline of dry eyes caused by ocular rosacea could be followed with liquid tears and cleaning of eyelids every day with warm water.

Therapeutic topical compositions must stay on the skin for a sufficient period of time to allow the active agent to be absorbed onto the skin, to perform its activity and to further exert a preventative effect. They should preferably not irritate the skin; and they should be perceived by the patient as pharmaceutically convenient in order to achieve sufficient patient compliance. By "pharmaceutically convenient", it is meant that the skin look and feel to the patient is good, i.e., it must not be too watery or too greasy and it must easily be applied.

A disadvantage of known compositions having an ointment base is greasiness; these compositions are generally considered less usable in the case of facial treatment of rosacea. Another disadvantage is that many known compositions contain surfactants, which can be irritants. It is therefore an advantage of the compositions provided herein that they are breakable gels or foams; and therefore are easy to apply to the skin and also avoid skin irritation that has been associated with compositions containing surfactants Breakable gels, which comprise liquid oils and a thickening agent, are also very convenient for use, as they liquefy on application of mild shear force such as gentle rubbing, and in turn, they readily absorb onto the skin.

Foam is advantageous in the topical treatment of skin diseases, especially in skin afflicted with rosacea, since it is light and easy to apply and collapses and spreads with a minor mechanical force like a simple rub. When dispensed, even in small quantities, drug delivery in the form of foam can also cover a larger surface area of application while also facilitating better product application in areas where conventional topical products cannot be as effective. Foam absorbs rapidly—without the need of repeated rubbing—which is helpful and important for treatment of damaged or irritated skin, sores, and lesions. As the composition is absorbed quickly, this can contribute to a positive treatment effect by the vehicle alone, or when in combination with the active agent, a higher percentage effect by the active agent may be observed.

Thermally stable foam which breaks upon application of mild shear force is extremely advantageous in the topical treatment of skin diseases. It can be applied directly onto skin or hands of the patient without collapsing. The hydrophobic compositions according to the description provided herein facilitate easy application and even distribution of the active agent, thereby improving treatment convenience. This is in contrast to a temperature sensitive foam that collapses immediately on the skin so that it must first be applied onto a cool surface and then quickly applied using fingertips onto the surface, which can impede patient compliance The formulation packaged into an aerosol container is devoid of any contact with air, light, or any other form of contamination (e.g., moisture) as it is a completely sealed system throughout the life of the product. Thus, light and oxidation sensitive active agents can be effectively stabilized in the aerosol system.

It should be noted that hydrophobic compositions disclosed herein can be applied to the target site as a gel or a semi-solid gel or foam. In certain other embodiments, it can be applied as a liquid gel or as a collapsed foam. In one or more embodiments, the composition is thixotropic. In one or more embodiments, the gel formulation subjected to constant shear rate shows a reduction in viscosity with time. In one or more further embodiments, after the material is allowed to rest for a period of time, the viscosity increases again. In one or more embodiments, there is provided prior to adding propellant a solid or semi-solid composition or gel. In one or more embodiments, the composition or gel is a liquid. In one or more embodiments the propellant is miscible with and dilutes the composition.

Upon packaging of the foamable composition in an aerosol container and adding a propellant, a shakable and homogenous foamable composition results, which upon dispensing, forms a breakable foam with good to excellent quality. The resulting foam is pharmaceutically equivalent to the respective gel (prior to adding the propellant), since immediately upon dispensing of the foam the propellant evaporates and the composition, upon collapse, is similar or identical to that of the gel. This is an important pragmatic advantage because many drug development activities, including expensive and lengthy toxicology studies with numerous animals and clinical trials with thousands of patients can be saved by conducting such studies once for either the gel or foam presentation instead of twice (for each presentation).

In one or more embodiments, such a composition is presented as a breakable gel, which breaks down with mild mechanical force.

In one or more embodiments, the hydrophobic composition when packaged in an aerosol container to which is added a liquefied or compressed gas propellant the composition provides upon release from the container a breakable foam of at least good quality that breaks easily upon application of mechanical force.

In one or more embodiments, the composition is a foamable composition that is thermally stable at skin temperature.

In one or more embodiments, when the above composition is filled into an aerosol can or canister and pressurized with a propellant a foamable composition is produced.

In one or more embodiments, a hydrophobic foamable composition (e.g., foam or gel) provided herein comprises: a) about 60% to about 99% by weight of at least one hydrophobic solvent; b) about 1% to about 22% by weight of at least one viscosity modifying agent; and c) about 0.1% to about 18% of a tetracycline antibiotic (e.g., minocycline HCl or doxycycline hyclate).

In one or more embodiments, a hydrophobic foamable composition (e.g., foam or gel) provided herein comprises: a) about 60% to about 99% by weight of at least one hydrophobic solvent or carrier; b) about 1% to about 22% by weight of at least one viscosity modifying agent; c) about 0.1% to about 18% by weight of a tetracycline antibiotic (e.g., minocycline HCl or doxycycline hyclate); and d) an additional active agent.

In one or more embodiments, a hydrophobic foamable composition or gel provided herein comprises: a) about 70% to about 90% by weight of at least one hydrophobic solvent; b) about 10 to about 22% by weight of at least one viscosity modifying agent; and c) about 0.5% to about 8% of a tetracycline antibiotic (e.g., minocycline HCl or doxycycline hyclate).

In one or more embodiments, a hydrophobic foamable composition or gel provided herein comprises: a) about 70% to about 90% by weight of at least one hydrophobic solvent or carrier; b) about 10 to about 22% by weight of at least one viscosity modifying agent; c) about 0.5% to about 8% by weight of a tetracycline antibiotic (e.g., minocycline HCl or doxycycline hyclate); and d) an additional active agent.

In one or more embodiments, a hydrophobic foamable composition or gel provided herein comprises: a) about 75% to about 90% by weight of at least one hydrophobic solvent; b) about 10 to about 22% by weight of at least one viscosity modifying agent; and c) about 0.5% to about 2% of a tetracycline antibiotic (e.g., minocycline HCl or doxycycline hyclate).

In one or more embodiments, a hydrophobic foamable composition or gel provided herein comprises: a) about 75% to about 90% by weight of at least one hydrophobic solvent or carrier; b) about 10 to about 22% by weight of at least one viscosity modifying agent; c) about 0.5% to about 2% by weight of a tetracycline antibiotic (e.g., minocycline HCl or doxycycline hyclate); and d) an additional active agent.

In one or more embodiments, a hydrophobic foamable composition or gel provided herein comprises: a) about 72% to about 88% by weight of at least one hydrophobic solvent; b) about 10 to about 22% by weight of at least one viscosity modifying agent; and c) about 2% to about 6% of a tetracycline antibiotic (e.g., minocycline HCl or doxycycline hyclate).

In one or more embodiments, a hydrophobic foamable composition or gel provided herein comprises: a) about 72% to about 98% by weight of at least one hydrophobic solvent; b) about 1% to about 18% by weight of at least one viscosity modifying agent; and c) about 1% to about 10% of a tetracycline antibiotic (e.g., minocycline HCl or doxycycline hyclate).

In one or more embodiments, a hydrophobic foamable composition or gel provided herein comprises: a) about 72% to about 88% by weight of at least one hydrophobic solvent or carrier; b) about 10 to about 22% by weight of at least one viscosity modifying agent; c) about 2% to about 6% by weight of a tetracycline antibiotic (e.g., minocycline HCl or doxycycline hyclate); and d) an additional active agent.

In one or more embodiments, the hydrophobic gel or foam composition for use in the method comprises: a) about 60% to about 95% by weight of at least one hydrophobic solvent or carrier; b) at least one viscosity-modifying agent selected from the group consisting of a fatty alcohol, a fatty acid, and a wax; c) a therapeutically effective amount of a tetracycline antibiotic; and d) an additional active agent.

In one or more embodiments, there is provided a hydrophobic foam or gel composition comprising: a) about 50% by weight of soybean oil; b) about 23.6% by weight of coconut oil; c) about 5% by weight of cyclomethicone; d) about 2.8% by weight of light mineral oil; e) about 3.5% by weight of cetostearyl alcohol; f) about 3% by weight of stearic acid; g) about 2.5% by weight of myristyl alcohol; about 2% by weight of hydrogenated castor oil; h) about 2% by weight of beeswax; i) about 1.5% by weight of stearyl alcohol; j) about 1.1% by weight of behenyl alcohol; and k) about 3% by weight of minocycline.

In one or more embodiments, there is provided a hydrophobic foam or gel composition comprising: a) about 50% by weight of soybean oil; b) about 23.6% by weight of coconut oil; c) about 5% by weight of cyclomethicone; d)

about 4.3% by weight of light mineral oil; e) about 3.5% by weight of cetostearyl alcohol; f) about 3% by weight of stearic acid; g) about 2.5% by weight of myristyl alcohol; h) about 2% by weight of hydrogenated castor oil; i) about 2% by weight of beeswax; j) about 1.5% by weight of stearyl alcohol; k) about 1.1% by weight of behenyl alcohol; and l) about 1.5% by weight of minocycline.

In one or more embodiments, there is provided a hydrophobic foam or gel composition comprising: a) about 35% to about 65% by weight of soybean oil; b) about 16.5% to about 30.7% by weight of coconut oil; c) about 3.5% to about 6.5% by weight of cyclomethicone; d) about 2% to about 3.7% by weight of light mineral oil; e) about 2.5% to about 4.6% by weight of cetostearyl alcohol; f) about 2.1% to about 4% by weight of stearic acid; g) about 1.8% to about 3.3% by weight of myristyl alcohol; h) about 1.4% to about 2.6% by weight of hydrogenated castor oil; i) about 1.4% to about 2.6% by weight of beeswax; j) about 1% to about 2% by weight of stearyl alcohol; k) about 0.8% to about 1.4% by weight of behenyl alcohol; and l) about 2.1% to about 4% by weight of minocycline.

In one or more embodiments, there is provided a hydrophobic foam or gel composition comprising: a) about 35% to about 65% by weight of soybean oil; b) about 16.5% to about 30.7% by weight of coconut oil; c) about 3.5% to about 6.5% by weight of cyclomethicone; d) about 3% to about 5.6% by weight of light mineral oil; e) about 2.5% to about 4.6% by weight of cetostearyl alcohol; f) about 2.1% to about 4% by weight of stearic acid; g) about 1.8% to about 3.3% by weight of myristyl alcohol; h) about 1.4% to about 2.6% by weight of hydrogenated castor oil; i) about 1.4% to about 2.6% by weight of beeswax; j) about 1% to about 2% by weight of stearyl alcohol; k) about 0.8% to about 1.4% by weight of behenyl alcohol; and l) about 1% to about 2% by weight of minocycline.

In one or more embodiments there is provided a method of treatment for reducing skin redness in a subject having a disorder in which one of the etiological factors is skin redness comprising applying a topical composition to an area of skin with the disorder, wherein the topical composition comprises: a) about 50% by weight of soybean oil; b) about 23.6% by weight of coconut oil; c) about 5% by weight of cyclomethicone; d) about 2.8% by weight of light mineral oil; e) about 3.5% by weight of cetostearyl alcohol; f) about 3% by weight of stearic acid; g) about 2.5% by weight of myristyl alcohol; h) about 2% by weight of hydrogenated castor oil; i) about 2% by weight of beeswax; j) about 1.5% by weight of stearyl alcohol; k) about 1.1% by weight of behenyl alcohol; and l) about 3% by weight of minocycline.

In one or more embodiments there is provided a method of treatment for reducing skin redness in a subject having a disorder in which one of the etiological factors is skin redness comprising applying a topical composition to an area of skin with the disorder, wherein the topical composition comprises: a) about 50% by weight of soybean oil; b) about 23.6% by weight of coconut oil; c) about 5% by weight of cyclomethicone; d) about 4.3% by weight of light mineral oil; e) about 3.5% by weight of cetostearyl alcohol; f) about 3% by weight of stearic acid; g) about 2.5% by weight of myristyl alcohol; h) about 2% by weight of hydrogenated castor oil; i) about 2% by weight of beeswax; j) about 1.5% by weight of stearyl alcohol; k) about 1.1% by weight of behenyl alcohol; and l) about 1.5% by weight of minocycline.

In one or more embodiments there is provided a method of treatment for reducing skin redness in a subject having a disorder in which one of the etiological factors is skin redness comprising applying a topical composition to an area of skin with the disorder, wherein the topical composition comprises: a) about 35% to about 65% by weight of soybean oil; b) about 16.5% to about 30.7% by weight of coconut oil; c) about 3.5% to about 6.5% by weight of cyclomethicone; d) about 2% to about 3.7% by weight of light mineral oil; e) about 2.5% to about 4.6% by weight of cetostearyl alcohol; f) about 2.1% to about 4% by weight of stearic acid; g) about 1.8% to about 3.3% by weight of myristyl alcohol; about 1.4% to about 2.6% by weight of hydrogenated castor oil; i) about 1.4% to about 2.6% by weight of beeswax; j) about 1% to about 2% by weight of stearyl alcohol; k) about 0.8% to about 1.4% by weight of behenyl alcohol; and l) about 2.1% to about 4% by weight of minocycline.

In one or more embodiments there is provided a method of treatment for reducing skin redness in a subject having a disorder in which one of the etiological factors is skin redness comprising applying a topical composition to an area of skin with the disorder, wherein the topical composition comprises: a) about 35% to about 65% by weight of soybean oil; b) about 16.5% to about 30.7% by weight of coconut oil; c) about 3.5% to about 6.5% by weight of cyclomethicone; d) about 3% to about 5.6% by weight of light mineral oil; e) about 2.5% to about 4.6% by weight of cetostearyl alcohol; f) about 2.1% to about 4% by weight of stearic acid; g) about 1.8% to about 3.3% by weight of myristyl alcohol; h) about 1.4% to about 2.6% by weight of hydrogenated castor oil; i) about 1.4% to about 2.6% by weight of beeswax; j) about 1% to about 2% by weight of stearyl alcohol; k) about 0.8% to about 1.4% by weight of behenyl alcohol; and l) about 1% to about 2% by weight of minocycline.

In one or more embodiments, the hydrophobic gel or foam composition for use in the methods provided herein comprises: a) about 57.6% to about 87.5% by weight of heavy mineral oil; b) about 3.5% to about 6.5% by weight of light mineral oil; c) about 3.2% to about 5.9% by weight of stearyl alcohol; d) about 1.75% to about 3.25% by weight of stearic acid; e) about 0.8% to about 1.4% by weight of behenyl alcohol; and f) about 3.3% to about 6.1% by weight of minocycline hydrochloride or doxycycline hyclate.

In one or more embodiments, the hydrophobic gel or foam composition for use in the methods provided herein comprises: a) about 65.8% to about 86% by weight of heavy mineral oil; b) about 4% to about 6% by weight of light mineral oil; c) about 3.6% to about 5.4% by weight of stearyl alcohol; d) about 2% to about 3% by weight of stearic acid; e) about 0.9% to about 1.3% by weight of behenyl alcohol; and f) about 3.7% to about 5.6% by weight of minocycline hydrochloride or doxycycline hyclate.

In one or more embodiments, the hydrophobic gel or foam composition for use in the methods provided herein comprises: a) about 74% to about 84% by weight of heavy mineral oil; b) about 4.5% to about 5.5% by weight of light mineral oil; c) about 4.1% to about 5% by weight of stearyl alcohol; d) about 2.3% to about 2.8% by weight of stearic acid; e) about 1% to about 1.2% by weight of behenyl alcohol; and f) about 4.2% to about 5.1% by weight of minocycline hydrochloride or doxycycline hyclate.

In one or more embodiments, the hydrophobic gel or foam composition for use in the methods provided herein comprises: a) about 31.8% to about 59.2% by weight of light mineral oil; b) about 31.5% to about 58.5% by weight of soybean oil; c) about 2.8% to about 5.2% by weight of stearyl alcohol; d) about 0.2% to about 0.8% by weight of behenyl alcohol; and e) about 3.3% to about 6.2% by weight of minocycline hydrochloride or doxycycline hyclate.

In one or more embodiments, the hydrophobic gel or foam composition for use in the methods provided herein comprises: a) about 82.24% by weight of heavy mineral oil; b) about 5% by weight of light mineral oil; c) about 4.5% by weight of stearyl alcohol; d) about 2.5% by weight of stearic acid; e) about 1.1% by weight of behenyl alcohol; and f) about 4.66% by weight of minocycline hydrochloride or doxycycline hyclate. In one or more embodiments, the hydrophobic gel or foam composition for use in the methods provided herein comprises: a) about 62% to about 91.7% by weight of heavy mineral oil, light mineral oil or combinations thereof; b) about 2.6% to about 4.8% by weight of stearyl alcohol; c) about 1.75% to about 3.25% by weight of stearic acid; d) about 0.5% to about 0.9% by weight of behenyl alcohol; e) about 0.14% to about 0.26% by weight of paraffin 51-53; and f) about 3.3% to about 6.1% by weight of minocycline hydrochloride or doxycycline hyclate.

In one or more embodiments, the hydrophobic gel or foam composition for use in the methods provided herein comprises: a) about 70.6% to about 90.6% by weight of heavy mineral oil, light mineral oil or combinations thereof; b) about 3% to about 4.4% by weight of stearyl alcohol; c) about 2% to about 3% by weight of stearic acid; d) about 0.56% to about 0.84% by weight of behenyl alcohol; e) about 0.16% to about 0.24% by weight of paraffin 51-53; and f) about 3.7% to about 5.6% by weight of minocycline hydrochloride or doxycycline hyclate.

In one or more embodiments, the hydrophobic gel or foam composition for use in the methods provided herein comprises: a) about 79.4% to about 89.4% by weight of heavy mineral oil, light mineral oil or combinations thereof; b) about 3.3% to about 4.1% by weight of stearyl alcohol; c) about 2.3% to about 2.8% by weight of stearic acid; d) about 0.63% to about 0.77% by weight of behenyl alcohol; e) about 0.18% to about 0.22% by weight of paraffin 51-53; and f) about 4.2% to about 5.6% by weight of minocycline hydrochloride or doxycycline hyclate.

In one or more embodiments, the hydrophobic gel or foam composition for use in the methods provided herein comprises: a) about 63% to about 98% by weight of heavy mineral oil; b) about 0.1% to about 15% by weight of light mineral oil; c) about 0.5% to about 7% by weight of stearyl alcohol; d) about 0.5% to about 5% by weight of stearic acid; e) about 0.2% to about 2% by weight of behenyl alcohol; and f) about 1% to about 8% by weight of minocycline hydrochloride or doxycycline hyclate.

In one or more embodiments, the hydrophobic gel or foam composition for use in the methods provided herein comprises: a) about 73% to about 98% by weight of heavy mineral oil, light mineral oil or combinations thereof; b) about 0.5% to about 7% by weight of stearyl alcohol; c) about 0.5% to about 5% by weight of stearic acid; d) about 0.2% to about 2% by weight of behenyl alcohol; e) about 0.1% to about 5% by weight of paraffin 51-53; and f) about 1% to about 8% by weight of minocycline hydrochloride or doxycycline hyclate.

In one or more embodiments, the hydrophobic gel or foam composition for use in the methods provided herein comprises: a) about 81.94% by weight of heavy mineral oil; b) about 5% by weight of light mineral oil; c) about 4.5% by weight of stearyl alcohol; d) about 2.5% by weight of stearic acid; e) about 1.1% by weight of behenyl alcohol; f) about 4.66% by weight of minocycline hydrochloride or doxycycline hyclate; and g) about 0.3% by weight of adapalene.

In one or more embodiments, the hydrophobic gel or foam composition for use in the methods provided herein comprises: a) about 82% by weight of heavy mineral oil; b) about 5% by weight of light mineral oil; c) about 4.5% by weight of stearyl alcohol; d) about 2.5% by weight of stearic acid; e) about 1.1% by weight of behenyl alcohol; f) about 4.8% by weight of minocycline hydrochloride or doxycycline hyclate; and g) about 0.1% by weight of adapalene.

In one or more embodiments, the hydrophobic gel or foam composition for use in the methods provided herein comprises: a) about 88.6% by weight of heavy mineral oil; b) about 3.6% by weight of stearyl alcohol; c) about 2.4% by weight of stearic acid; d) about 0.5% by weight of behenyl alcohol; e) about 4.8% by weight of minocycline hydrochloride or doxycycline hyclate; and f) about 0.1% by weight of adapalene.

In one or more embodiments, the hydrophobic gel or foam composition for use in the methods provided herein comprises: a) about 50% by weight of soybean oil; b) about 23.6% by weight of coconut oil; c) about 5% by weight of cyclomethicone; d) about 0.7% by weight of light mineral oil; e) about 3.5% by weight of cetostearyl alcohol; f) about 3% by weight of stearic acid; g) about 2.5% by weight of myristyl alcohol; h) about 2% by weight of hydrogenated castor oil; i) about 2% by weight of beeswax; j) about 1.5% by weight of stearyl alcohol; k) about 1.1% by weight of behenyl alcohol; l) about 4.8% by weight of minocycline hydrochloride or doxycycline hyclate; and m) about 0.3% by weight of adapalene.

In one or more embodiments, the hydrophobic gel or foam composition for use in the methods provided herein comprises: a) about 49% by weight of heavy mineral oil; b) about 39% by weight of light mineral oil; c) about 3.8% by weight of stearyl alcohol; d) about 2.4% by weight of stearic acid; e) about 0.7% by weight of behenyl alcohol; f) about 4.8% by weight of minocycline hydrochloride or doxycycline hyclate; and g) about 0.3% by weight of adapalene.

In one or more embodiments, the hydrophobic gel or foam composition for use in the methods provided herein comprises: a) about 43.4% by weight of heavy mineral oil; b) about 39% by weight of light mineral oil; c) about 4.3% by weight of stearyl alcohol; d) about 2.5% by weight of stearic acid; e) about 5% by weight of cyclomethicone; f) about 0.7% by weight of behenyl alcohol; g) about 4.8% by weight of minocycline hydrochloride or doxycycline hyclate; and h) about 0.3% by weight of adapalene.

In one or more embodiments, the hydrophobic gel or foam composition for use in the methods provided herein comprises: a) about 45.55% by weight of light mineral oil; b) about 45.05% by weight of soybean oil; c) about 4.0% by weight of stearyl alcohol; d) about 0.6% by weight of behenyl alcohol; e) about 4.8% by weight of minocycline hydrochloride or doxycycline hyclate.

In one or more embodiments, the compositions provided or described herein comprise a carrier and a propellant. In one or more embodiments, the carrier comprises or is a hydrophobic gel or foamable composition provided or described herein.

In one or more embodiments, the composition is a gel, paste, lotion, cream, soap, spray, mask, patch, powder, pomade, ointment, oil, foam or mousse. In one or more embodiments, the composition is hydrophobic. In one or more embodiments, the composition comprises hydrophobic oils and waxes. In one or more embodiments, the composition comprises fatty alcohols. In one or more embodiments, the composition comprises hydrophobic oils and fatty alcohols. In one or more embodiments, the composition comprises fatty acids. In one or more embodiments, the composition comprises hydrophobic oils and fatty acids. In one or more embodiments, the composition is surfactant free.

In one or more embodiments, the composition is substantially free of a fatty acid or of a fatty alcohol or of a wax or any two thereof. In one or more embodiments, the composition is essentially free of a fatty acid or of a fatty alcohol or of a wax or any two thereof. In one or more embodiments, the composition is free of a fatty acid or of a fatty alcohol or of a wax or any two thereof.

In one or more embodiments, the hydrophobic composition comprises a gelled oil. In one or more embodiments, the gelled oil is a gelled mineral oil. In one or more embodiments, the gelled mineral oil is a VERSAGEL®. VERSAGELs® are gelled oils or emollients that can come in different product forms including, for example, the VERSAGEL® m, VERSAGEL® p, VERSAGEL® r, and VERSAGEL® s series, and provide various viscosity grades. There are also VERSAGELs® with isohexadecane, or with isododecane, or with hydrogenated polyisobutene, or with isopropylpalmitate. In an embodiment, it is VERSAGEL® 750 m. In an embodiment, it is VERSAGEL® 200 m. In an embodiment, it is VERSAGEL® 500 m. In an embodiment, it is VERSAGEL® 1600 m. VERSAGEL® m contains a mixture of mineral oil plus one or two or more of e.g., Ethylene/Propylene/Styrene Copolymer plus e.g., Butylene/Ethylene/Styrene Copolymer plus e.g., butylated hydroxyl toluene or similar gelling agents. In one or more embodiments, the gelled oil is at a concentration of about 55% to about 85% by weight. In one or more embodiments, the gelled oil is at a concentration of about 60% to about 80% by weight. In one or more embodiments, gelled oil is at a concentration of about 65% to about 75% by weight. In one or more embodiments, the hydrophobic solvent is at a concentration of about 75% to about 90% by weight. In one or more embodiments, the hydrophobic solvent is at a concentration of about 21% to about 39% by weight. In one or more embodiments, the hydrophobic solvent is at a concentration of about 26% to about 34% by weight. In one or more embodiments, the hydrophobic solvent is at a concentration of about 9% to about 24% by weight. In one or more embodiments, the hydrophobic solvent comprises a petrolatum at a concentration of about 9% to about 24% by weight, or about 26% to about 34% by weight or about 21% to about 39% by weight, or about 45% by weight, or about 50% by weight or about 55% by weight or about 60% by weight.

Topical hydrophobic therapeutic breakable gel and foamable compositions comprising tetracycline, including those without surfactants, have been described, for example in U.S. application Ser. Nos. 13/499,501, 13/499,727, 13/499,475, and 13/499,709, U.S. Publication No. 2011/0281827, WO 11/039637, WO 11/039638, WO 11/138678 and WO 2011/064631, all of which are herein incorporated in their entirety by reference. More particularly, any of the active ingredients, carriers, solvents, surfactants, foam adjuvants, fatty acids, fatty alcohols, polymeric agents, penetration enhancers, preservatives, humectants, moisturizers, and other excipients, as well as the propellants and methods listed therein can be applied herein and are incorporated by reference.

Other carriers and compositions are described in: U.S. Publication No. 2005/0232869, published on Oct. 20, 2005, entitled NONSTEROIDAL IMMUNOMODULATING KIT AND COMPOSITION AND USES THEREOF; U.S. Publication No. 2005/0205086, published on Sep. 22, 2005, entitled RETINOID IMMUNOMODULATING KIT AND COMPOSITION AND USES THEREOF; U.S. Publication No. 2006/0018937, published on Jan. 26, 2006, entitled STEROID KIT AND FOAMABLE COMPOSITION AND USES THEREOF; U.S. Publication No. 2005/0271596, published on Dec. 8, 2005, entitled VASOACTIVE KIT AND COMPOSITION AND USES THEREOF; U.S. Publication No. 2006/0269485, published on Nov. 30, 2006, entitled ANTIBIOTIC KIT AND COMPOSITION AND USES THEREOF; U.S. Publication No. 2007/0292355, published on Dec. 20, 2007, entitled ANTI-INFECTION AUGMENTATION OF FOAMABLE COMPOSITIONS AND KIT AND USES THEREOF; U.S. Publication No. 2008/0317679, published on Dec. 25, 2008, entitled FOAMABLE COMPOSITIONS AND KITS COMPRISING ONE OR MORE OF A CHANNEL AGENT, A CHOLINERGIC AGENT, A NITRIC OXIDE DONOR, AND RELATED AGENTS AND THEIR USES; U.S. Publication No. 2008/0044444, published on Feb. 21, 2008, entitled DICARBOXYLIC ACID FOAMABLE VEHICLE AND PHARMACEUTICAL COMPOSITIONS THEREOF; U.S. Publication No. 2008/0069779, published on Mar. 20, 2008, entitled FOAMABLE VEHICLE AND VITAMIN AND FLAVONOID PHARMACEUTICAL COMPOSITIONS THEREOF; U.S. Publication No. 2008/0206159, published on Aug. 28, 2008, entitled COMPOSITIONS WITH MODULATING AGENTS; U.S. Publication No. 2008/0206161, published on Aug. 28, 2008, entitled QUIESCENT FOAMABLE COMPOSITIONS, STEROIDS, KITS AND USES THEREOF; U.S. Publication No. 2008/0260655, published on Oct. 23, 2008, entitled SUBSTANTIALLY NON-AQUEOUS FOAMABLE PETROLATUM BASED PHARMACEUTICAL AND COSMETIC COMPOSITIONS AND THEIR USES; U.S. Publication No. 2011/0268665, published on Nov. 3, 2011, entitled OIL-BASED FOAMABLE CARRIERS AND FORMULATIONS; U.S. Publication No. 2012/0087872, published on Apr. 12, 2012, entitled FOAMABLE VEHICLES AND PHARMACEUTICAL COMPOSITIONS COMPRISING APROTIC POLAR SOLVENTS AND USES THEREOF; U.S. Publication No. 2012/0213709, published on Aug. 23, 2012, entitled NON SURFACTANT HYDRO-ALCOHOLIC FOAMABLE COMPOSITIONS, BREAKABLE FOAMS AND THEIR USES; U.S. Publication No. 2012/0213710, published on Aug. 23, 2012, entitled SURFACE ACTIVE AGENT NON POLYMERIC AGENT HYDRO-ALCOHOLIC FOAMABLE COMPOSITIONS, BREAKABLE FOAMS AND THEIR USES; U.S. Publication No. 2013/0064777, published on Mar. 14, 2013, entitled SURFACTANT-FREE WATER-FREE FOAMABLE COMPOSITIONS, BREAKABLE FOAMS AND GELS AND THEIR USES; U.S. Publication No. 2013/0053353, published on Feb. 28, 2013, entitled COMPOSITIONS, GELS AND FOAMS WITH RHEOLOGY MODULATORS AND USES THEREOF; U.S. Publication No. 2011/0281827, published on Nov. 17, 2011, entitled COMPOSITIONS, GELS AND FOAMS WITH RHEOLOGY MODULATORS AND USES THEREOF; U.S. Publication No. 2013/0028850, published on Jan. 31, 2013, entitled TOPICAL TETRACYCLINE COMPOSITIONS; U.S. Publication No. 2013/0011342, published on Jan. 10, 2013, entitled SURFACTANT-FREE, WATER-FREE, FOAMABLE COMPOSITIONS AND BREAKABLE FOAMS AND THEIR USES; U.S. Publication No. 2013/0225536, published on Aug. 29, 2013, entitled COMPOSITIONS FOR THE IMPROVED TREATMENT OF ACNE AND RELATED DISORDERS; U.S. Publication No. 2014/0121188, published on May 1, 2014, entitled METHODS FOR ACCELERATED RETURN OF SKIN INTEGRITY AND FOR THE TREATMENT OF IMPETIGO; U.S. Publication No. 2015/0164922, published on Jun. 18, 2015, entitled USE OF TETRACYCLINE COMPOSITIONS FOR WOUND TREATMENT AND SKIN RESTORATION, all of which are incorporated herein by reference in their entirety. More particularly, any of the active ingredients, carriers, solvents, surfactants, foam adjuvants, polymeric agents, penetration enhancers, preservatives, humectants, moisturizers, and other excipients, as well as the propellants and methods listed therein can be applied herein and are incorporated by reference.

Manufacture

The present disclosure also provides a method of manufacturing a gel or foam composition having a tetracycline antibiotic, the method comprising: providing a composition having one or more hydrophobic solvents; heating said composition; adding fatty alcohols, fatty acids and waxes; cooling said composition; optionally adding $SiO_2$; and adding a tetracycline antibiotic.

The compositions provided herein are manufactured according to the methods described in the art and as described in Example 1. Gels are usually packaged in a tube but can also be packaged in any other convenient delivery form including for example, bottles with a pump mechanism or canisters such as bag in can devices where propellant is separate from the gel. Foam formulations are usually packed in a container with an outlet valve e.g., aerosol canister. Possible containers and valves are likewise described in the literature as known by those skilled in the art.

According to another aspect, both the minocycline and the foamable compositions containing minocycline can be manufactured under current Good Manufacturing Principles (cGMP) conditions. The foamable composition was provided in aluminum aerosol canisters mounted with valve and actuator. Each canister was filled with 25 g of product and 3 g of propellant. Upon actuation of the canister an aliquot of quality foam was released.

Administration

In one or more embodiments there is provided a method of administering a tetracycline foam composition to a target area such as skin of a patient comprising releasing foam, applying it to the area, and collapsing the foam. In one or embodiments, the foam is applied by spreading. In the course of spreading mechanical shear can cause the foam to collapse. In one or more embodiments, the collapsed foam is not washed off. In one or more embodiments it is absorbed onto the area of skin. In one or more embodiments it avoids skin irritation or an ointment sensation.

In one or more embodiments, there is provided a method of applying a tetracycline gel composition to an area of skin of a patient comprising releasing a gel, applying it to the area, and collapsing or liquefying the gel. In one or more embodiments, the collapsed or liquefied gel is not washed off. In one or more embodiments, the collapsed or liquefied gel is readily absorbed and does not leave an ointment sensation.

In one or more embodiments, there is provided a method for reducing the number of rosacea lesions, by applying topically an effective amount of a tetracycline gel, liquid gel or foam to an afflicted area of a patient in need. In one or more embodiments, the method involves applying a gel, liquid, gel or foam formulation topically to a target surface in need of treatment and breaking the gel or foam over the target site. In one or more embodiments the gel or foam is collapsed and spread by application of a mechanical force, which can be mild or slight such as a simple rub and the active agent is then absorbed. In one or more embodiments the foam or gel is absorbed.

In one or more embodiments, a gel or a liquid gel or a collapsed foam is absorbed within 240 seconds, or within 200 seconds, or within 180 seconds, or within 150 seconds, within 120 seconds, or within 100 seconds, or within 80 seconds, or within 60 seconds, or within 50 seconds, or within 40 seconds, or within 30 seconds, or within 20 seconds, or within 10 seconds, or within 5 seconds, or within 2 seconds or less. The term "absorbed" means that the composition enters onto and into an area of skin, mucosa or eye, often forming a thin coating on the surface.

In one or more embodiments, the method uses an additional step of pre cleaning and drying the lesions and surrounding area before applying the gel, liquid gel or foam.

In one or more embodiments, the method uses a sterile applicator or prior to the steps of administering and/or collapsing and/or spreading, the hands of the person spreading are sterilized in order to avoid cross contamination.

In one or more other embodiments, the method comprises an additional step of applying an active agent to the lesions and surrounding area after the gel, liquid gel or foam has been absorbed, wherein the active agent is a hyaluronic acid or a retinoid or BPO or salicylic acid, or an alpha hydroxy acid, or azelaic acid, or nicotinamide, or a keratolytic agent, or clindamycin, or metronidazole, or doxycycline, or erythromycin, or ivermectin, or brimonidine, or sodium sulfacetamide and sulfur, or tretinoin. In some embodiments, the active agent, such as, for example, a hyaluronic acid, a retinoid, BPO, salicylic acid, an alpha hydroxy acid, azelaic acid, a nicotinamide, a keratolytic agent, clindamycin, metronidazole, erythromycin, ivermectin, brimonidine, sodium sulfacetamide and sulfur, tretinoin, or mixtures of two or more thereof, is applied once daily at least 1 or 2 or 3 or 4 or 5 or 6 or 7 or 8 or 9 or 10 or 11 or 12 hours after the tetracycline antibiotic formulation has been absorbed. In further embodiments, the active agent, such as, for example, a hyaluronic acid or a retinoid or BPO or salicylic acid, or an alpha hydroxy acid, or azelaic acid, or nicotinamide, or a keratolytic, or clindamycin, or metronidazole, or erythromycin, or ivermectin, or brimonidine, or sodium sulfacetamide and sulfur, or tretinoin, is applied after the third day. In yet additional embodiments, the active agent, such as, for example, a hyaluronic acid or a retinoid or BPO or salicylic acid, or an alpha hydroxy acid, or azelaic acid, or nicotinamide, or a keratolytic agent, or clindamycin, or metronidazole, or erythromycin, or ivermectin, or brimonidine, or sodium sulfacetamide and sulfur, or tretinoin, is applied during the maintenance stage. In an alternative embodiment, the active agent, such as, for example, a hyaluronic acid or a retinoid or BPO or salicylic acid, or an alpha hydroxy acid, or azelaic acid, or nicotinamide, or a keratolytic agent, or clindamycin, or metronidazole, or erythromycin, or ivermectin, or brimonidine, or sodium sulfacetamide and sulfur, or tretinoin, is replaced with or supplemented by a steroid.

In an alternative embodiment, the active agent, such as, for example, a hyaluronic acid or a retinoid or BPO or salicylic acid, or an alpha hydroxy acid, or azelaic acid, or nicotinamide, or a keratolytic agent or steroid, or clindamycin, or metronidazole, or erythromycin, or ivermectin, or brimonidine, or sodium sulfacetamide and sulfur, or tretinoin, is replaced with or supplemented by an antibiotic. In an embodiment, the antibiotic, which is in addition to one or more tetracycline antibiotics, is selected from the group consisting of mupirocin, fusidic acid, a penicillin or penicillin derivative, augmentin, an anti staphylococcal penicillin, amoxicillin/clavulanate, a cephalosporin, cephalexin, a macrolide, erythromycin, clindamycin, trimethoprim-sulfamethoxazole penicillin, retapamulin, and mixtures of any two or more thereof. In an embodiment the antibiotic is applied topically. In another embodiment it is applied orally or by injection or by infusion. In another embodiment more than one antibiotic is applied. For example, one is applied topically and another is given orally. The latter can be appropriate for example where there is a systemic as well as a topical bacterial infection.

Frequency

In one or more embodiments there is provided a regime or regimen for treating a patient having one or more of rosacea, and/or rosacea related symptoms, and/or a tetracycline antibiotic responsive rosacea related disorder, and/or a tetracycline antibiotic responsive skin disorder, and/or skin disorder caused by a bacteria, and/or a tetracycline antibiotic responsive disorder, and/or a sebaceous gland disorder, which comprises applying to the afflicted area on a regular basis a hydrophobic gel or foam composition, said composition comprising a therapeutically effective amount of a tetracycline antibiotic.

In one or more embodiments, there is provided a method for treating rosacea, including administering topically, once a day, to a surface having rosacea a composition comprising a tetracycline antibiotic.

In one or more embodiments, there is provided a method for treating rosacea, including administering topically, twice a day, to a surface having rosacea a composition comprising a tetracycline antibiotic.

In one or more embodiments, there is provided a method for treating rosacea, including administering topically, alternate-day or intermittently, to a surface having rosacea a composition comprising a tetracycline antibiotic.

In one or more embodiments, there is provided a method for treating rosacea, including administering topically, gradual reduction to a lower maintenance dose, which can be increased if further outbreaks occur, to a surface having rosacea a composition comprising a tetracycline antibiotic. In one or more embodiments, a maintenance dose can be applied topically, daily, alternate daily, twice weekly or weekly for a month, two months, quarterly, six months or indefinitely. A maintenance dose can include about 0.9%, or about 0.8%, or about 0.7%, or about 0.6%, or about 0.5%, or about 0.4%, or about 0.3%, or about 0.2%, or about 0.1%, or about 0.09%, or about 0.08%, or about 0.07%, or about 0.06%, or about 0.05% by weight of a tetracycline antibiotic. In one or more embodiments, the maintenance dose can be commenced after four weeks of treatment, or after five weeks of treatment, or after six weeks of treatment, or after seven weeks of treatment, or after eight weeks of treatment, or after nine weeks of treatment, or after ten weeks of treatment, or after eleven weeks of treatment, or after twelve weeks of treatment, or after thirteen weeks of treatment, or after fourteen weeks of treatment, or after fifteen weeks of treatment, or after sixteen weeks of treatment.

In one or more embodiments, there is provided a method for treating rosacea, including administering topically, once daily for at least four weeks, to a surface having rosacea a composition comprising a tetracycline antibiotic.

In one or more embodiments, there is provided a method for treating rosacea, including administering topically, once daily up to four weeks, to a surface having rosacea a composition comprising a tetracycline antibiotic.

In one or more embodiments, there is provided a method for treating rosacea, including administering topically, once daily for twelve weeks or less than twelve weeks, to a surface having rosacea a composition comprising a tetracycline antibiotic.

In one or more embodiments, there is provided a method for treating rosacea, including administering topically, once daily for four weeks or less than four weeks, to a surface having rosacea a composition comprising a tetracycline antibiotic.

In one or more embodiments, there is provided a method for treating rosacea, including administering topically, once daily for three weeks or less than three weeks, to a surface having rosacea a composition comprising a tetracycline antibiotic. In one or more embodiments, there is provided a method for treating rosacea, including administering topically, once daily for two weeks or less than two weeks, to a surface having rosacea a composition comprising a tetracycline antibiotic In one or more embodiments, there is provided a method for treating a condition involving inflammation of the skin or mucosa (the disorder), including administering topically, once daily for six weeks or less than six weeks, to a surface having the disorder a gel of foam composition comprising a tetracycline antibiotic.

Application can be, hourly, every twelve hours (e.g., twice daily), once daily, alternate-day or intermittent, according to the condition of the patient. For reasons of compliance, less frequent applications, where possible, are preferable, e.g., daily single applications. In certain cases, where prolonged or long term treatment is required, an initial dose is provided followed by a gradual reduction to a lower maintenance dose, which can be increased if further outbreaks occur.

In one or more embodiments there is provided a hydrophobic gel or foam composition comprising a tetracycline antibiotic for use in treating one or more of rosacea, and/or rosacea related symptoms, and/or a tetracycline antibiotic responsive rosacea related disorder, and/or a tetracycline antibiotic responsive skin disorder, and/or skin disorder caused by a bacteria, and/or a tetracycline antibiotic responsive disorder, and/or a sebaceous gland disorder, including skin infections, wherein the hydrophobic gel or foam composition is administered topically at least alternate days or at least once daily for twelve weeks or less than twelve weeks of treatment.

In one or more embodiments there is provided a hydrophobic gel or foam composition comprising a minocycline antibiotic for use in treating a disorder selected from the group consisting of rosacea, and/or rosacea related symptoms, and/or a tetracycline antibiotic responsive rosacea related disorder, and/or a tetracycline antibiotic responsive skin disorder, and/or skin disorder caused by a bacteria, and/or a tetracycline antibiotic responsive disorder, and/or a sebaceous gland disorder, wherein the hydrophobic gel or foam composition is administered topically at least alternate days or at least once daily for at least six weeks to the skin, wherein the minocycline antibiotic is the sole active ingredient present in the composition. In one or more embodiments there is provided a hydrophobic foam composition or gel comprising a tetracycline antibiotic for use in retarding, arresting, or reversing the progression of one or more of rosacea, and/or rosacea related symptoms, and/or a tetracycline antibiotic responsive rosacea related disorder, and/or a tetracycline antibiotic responsive skin disorder, and/or skin disorder caused by a bacteria, and/or a tetracycline antibiotic responsive disorder, and/or a sebaceous gland disorder, wherein the hydrophobic foam composition or gel is applied topically to the skin at least alternate days or at least once a day for at least six weeks.

In one or more embodiments, the method uses a once daily dosage regime for twelve weeks or less than twelve weeks. In one or more embodiments the twelve-week dosage regime is followed by a once daily maintenance dose for one, two, three, four or more weeks according to the condition and response of the patient. In one or more embodiments, the method uses a once daily dosage regime for six weeks or less than six weeks. In one or more embodiments the six-week dosage regime is followed by a once daily maintenance dose for one, two, three, four or more weeks according to the condition and response of the patient. In one or more embodiments, the method uses a once daily dosage regime of for six weeks or less than six weeks followed by a once weekly maintenance dose for one, two, three, four, five, six, seven, eight, nine, ten, eleven or more weeks according to the condition and response of the patient. In one or more embodiments, the method uses a once daily dosage regime of for three weeks or less than three weeks followed by a once weekly maintenance dose for one, two, three, four, five, six, seven, eight, nine, ten, eleven or more weeks according to the condition and response of the patient. In one or more embodiments, the method uses a once daily dosage regime of for two weeks followed by a daily maintenance dose for one, two, three or more weeks according to the condition and response of the patient. In one or more embodiments the method uses a once daily dosage regime of for twelve weeks wherein the treatment is every alternate week.

Combination Therapy

Several disorders involve a combination of more than one etiological factor; and therefore, the use of more than one active agent is advantageous. For example, psoriasis involves excessive cell proliferation and inadequate cell differentiation as well as inflammation. Atopic dermatitis involves keratinocyte growth abnormality, skin dryness and inflammation. Bacterial, fungal and viral infections involve pathogen colonization at the affected site and inflammation. Hence, in many cases, the inclusion of a combination of active agents in the pharmaceutical composition can be desirable. Thus, in one or more embodiments, the composition includes at least two active agents, in a therapeutically effective concentration.

In one or more embodiments, a combination of any two or more of an antibacterial, an anti-inflammatory, an antifungal, and an antiviral agent is contemplated.

In one or more embodiments, a tetracycline antibiotic is the sole active ingredient present in the composition. In one or more embodiments, a minocycline is the sole active ingredient present in the composition. In one or more embodiments, a doxycycline is the sole active ingredient present in the composition. In one or more embodiments minocycline and doxycycline are used in combination.

In one or more embodiments, a combination of any two or more of a minocycline, retinoids, and benzoyl peroxide is contemplated In one or more embodiments, a combination of any two or more of a tetracycline, retinoids, and benzoyl peroxide is contemplated.

In one or more embodiments, a combination of any two or more of benzoyl peroxide, antibiotics, retinoids, antiseborrheic medications, anti-androgen medications, hormonal treatments, salicylic acid, alpha hydroxy acid, azelaic acid, nicotinamide, and a keratolytic agent is contemplated. In one or more embodiments the tetracycline is combined with adapalene.

Disease Indications

The diseases or disorders treated by the composition provided herein include, for example, rosacea. Rosacea may begin as redness on the central face across the cheeks, nose, or forehead, but can also less commonly affect the neck, chest, ears, and scalp. In some cases, the symptoms can include additional signs, such as, for example, semi-permanent redness, dilation of superficial blood vessels on the face, red domed papules (small bumps) and pustules, red gritty eyes, burning and stinging sensations, and in some advanced cases, a red lobulated nose (rhinophyma), may develop.

Rosacea may affect all ages. Based on the location, rosacea generally has four subtypes, three affecting the skin and the fourth affecting the eyes (ocular rosacea).

There are several subtypes of rosacea including, for example, but not limited to, erythematotelangiectatic rosacea, papulopustular rosacea, phymatous rosacea, ocular rosacea, pyoderma faciale (also known as rosacea fulminans), rosacea conglobata, phymatous rosacea.

For the purposes of this specification, rosacea can include any of the known subtypes, known to one of skilled in the art.

In one embodiment, rosacea is associated with the elevated levels of cathelicidins. In another embodiment, rosacea is associated with the elevated levels of a stratum corneum tryptic enzyme (SCTE). In yet another embodiment, rosacea is associated with parasitic mite, intestinal bacteria, or a combination thereof.

A rosacea related disorder is any disorder which can occur in parallel with rosacea or be a contributing factor to the outbreak of rosacea or can resemble rosacea. Perioral dermatitis is an erythematous, papulopustular facial eruption that resembles rosacea and/or acne but typically starts around the nose. Rosacea (acne rosacea) is a chronic inflammatory disorder characterized by facial flushing, telangiectasias, erythema, papules, pustules, and in severe cases, rhinophyma.

Rosacea related symptoms include, papules, pustules, blackheads, whiteheads or milia, nodules and cysts.

Pyoderma faciale (also called rosacea fulminans) occurs suddenly on the midface of young women. It can be analogous to acne fulminans. The eruption consists of erythematous plaques and pustules.

A number of other skin disorders and diseases can be treated with the composition provided herein such as rosacea, wounds, burns, inflammatory skin dermatoses superficial infections, including skin infections, such as impetigo, antibiotic responsive dermatoses and sebaceous gland disorders. Minocycline can also have skin regenerating and healing properties responsible for restoration of skin integrity. The combination of minocycline together with a hydrophobic solvent and a fatty alcohol or fatty acid can afford a beneficial effect in conditions characterized, for example, by infection and/or inflammation.

Additionally, provided is a method of maintenance therapy, to prevent rosacea recurrence or reduce the severity of the rosacea recurrence, applied to a patient in need which comprises applying to the skin on a regular basis (as defined above) a hydrophobic gel or foam composition comprising a therapeutically effective amount of a tetracycline antibiotic Chemical Stability, Pharmacokinetics, Safety, and Efficacy Chemical Stability The stability of foamable composition containing minocycline was monitored at 5° C., 25° C., 40° C., and 50° C. during and after the clinical trials and satisfactory stability results were obtained (see, e.g., Example 4).

Pharmacokinetics

In some embodiments, the systemic exposure of a Minocycline and/or Doxycylcine foam as disclosed herein (e.g., 1%, 1.5%, 3%, or 4% minocycline or doxycycline by weight) is equal to or lower than that of an orally administered tetracycline (e.g., minocycline or doxycylcine), as evaluated in a PK Study. In some embodiments, the terms "systemic exposure," "systemic absorption," and "absorption" are used interchangeably.

The systemic exposure of an oral tetracycline or tetracycline foam (e.g., Minocycline or Doxycylcine foam) may be determined based on a pharmacokinetic (PK) study as described in the Examples, e.g., Examples 5, 6 and 9. For example, the minocycline or doxycycline foam may be administered to a subject once or multiple times and blood samples are obtained at various time points to determine the level of minocycline or doxycycline in plasma. Various pharmacokinetic parameters can be calculated and used as an indicator of the systemic exposure, and compared to a control or base line (e.g., the level prior to treatment or the level after administration of an oral tetracycline). One or more of the following pharmacokinetic parameters may be used as an indicator of the systemic exposure: $C_{max}$ (maximum plasma concentration), $t_{max}$ (time of maximum measured plasma concentration), $AUC_{0-inf}$ (area under the plasma concentration vs time curve [AUC] from time 0 to infinity), $AUC_{0-tldc}$ (AUC from time 0 to the time of last detectable concentration), $t_{1/2}$ (terminal phase half-life), $C_{24}$ (minocycline concentration 24 hours after topical application of minocycline foam 4%), $AUC_{0-tau}$ (AUC during the 24-hour dosing interval for topical minocycline foam), and bioavailability. At the end of the PK study, the safety of the foam may be evaluated by surveying any treatment-emergent adverse events (TEAEs).

In some embodiments, a $C_{max}$ value is used as an indicator of the systemic exposure of a tetracycline (e.g., minocycline) foam described herein. In some embodiments, an $AUC_{0-inf}$ value is used as an indicator of the systemic exposure of a tetracycline foam described herein. In some embodiments, an $AUC_{0-tldc}$ value is used as an indicator of the systemic exposure of a tetracycline foam described herein. In some embodiments, an $AUC_{0-tau}$ value is used as an indicator of the systemic exposure of a tetracycline foam described herein. In some embodiments, PK measurements are taken at one or more time points following administration of a tetracycline foam described herein, e.g., 1 hour, 6 hours, 12 hours, 18 hours, 24 hours, 36 hours, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more days after administration, or any time period in between. In some embodiments, a tetracycline foam described herein is administered about 1, 2, 3, 4, 5, 6, 7, 8, 9, 10, 11, 12, 13, 14, or more days after a single dose of an oral tetracycline and PK measurements are taken at one or more time points following administration of the tetracycline foam, e.g., about 1 hour, 6 hours, 12 hours, 18 hours, 24 hours, 36 hours, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more days after administration, or any time period in between.

In some embodiments, a 4% Doxycycline foam pharmacokinetic (PK) study similar to that of a 4% Minocycline foam PK Study is undertaken. In some embodiments, a 1% or 2% or 3% Doxycycline foam PK Study is similar to that of a 1% or 2% or 3%, respectively, Minocycline foam PK Study is undertaken. In some embodiments, a 1% or 2% or 3% Minocycline foam PK Study is similar to that of a 4%, Minocycline foam PK Study. In some embodiments the systemic exposure in a 1% or 2% or 3% Minocycline foam PK Study is lower than that of a 4% Minocycline foam PK Study. In some embodiments, a 1% or 2% or 3% Doxycycline foam PK Study is similar to that of a 4%, Doxycycline foam PK Study. In some embodiments the systemic exposure in a 1% or 2% or 3% Doxycycline foam PK Study is lower than that of a 4% Doxycycline foam PK Study.

In some embodiments, absorption of a foam described herein (e.g., a foam comprising 1-4% tetracycline antibiotic such as doxycycline or minocycline foam or combinations thereof) is low as determined by a PK Study in comparison to a comparable dose of an orally administered tetracycline. In some embodiments, the $C_{max}$ determined on Day 1 after the first dose is about 0.2 ng/mL to about 5 ng/mL. For example, is about 0.2 ng/mL, or about 0.4 ng/mL, or about 0.6 ng/mL, or about 0.8 ng/mL, or about 1 ng/mL, or about 1.2 ng/mL, or about 1.4 ng/mL, or about 1.6 ng/mL, or about 1.8 ng/mL, or about 2 ng/mL, or about 2.2 ng/mL, or about 2.4 ng/mL, or about 2.6 ng/mL, or about 2.8 ng/mL, or about 3 ng/mL, or about 3.2 ng/mL, or about 3.4 ng/mL, or about 3.6 ng/mL, or about 3.8 ng/mL, or about 4 ng/mL, or about 4.2 ng/mL, or about 4.4 ng/mL, or about 4.8 ng/mL, or about 5 ng/mL.

In some embodiments, absorption of a foam described herein (e.g., a foam comprising 1-4% tetracycline antibiotic such as doxycycline or minocycline or combinations thereof) is low as determined by a PK study in comparison to a comparable dose of an orally administered tetracycline. In some embodiments, a $C_{max}$ is identified on Day 16 after the administration of the foam once a day for sixteen consecutive days and is about 0.2 ng/mL to about 12 ng/mL. For example, is about 0.2 ng/mL, or about 0.4 ng/mL, or about 0.6 ng/mL, or about 0.8 ng/mL, or about 1 ng/mL, or about 1.2 ng/mL, or about 1.4 ng/mL, or about 1.6 ng/mL, or about 1.8 ng/mL, or about 2 ng/mL, or about 2.2 ng/mL, or about 2.4 ng/mL, or about 2.6 ng/mL, or about 2.8 ng/mL, or about 3 ng/mL, or about 3.2 ng/mL, or about 3.4 ng/mL, or about 3.6 ng/mL, or about 3.8 ng/mL, or about 4 ng/mL, or about 4.2 ng/mL, or about 4.4 ng/mL, or about 4.8 ng/mL, or about 5 ng/mL, or about 5.2 ng/mL, or about 5.4 ng/mL, or about 5.6 ng/mL, or about 5.8 ng/mL, or about 6 ng/mL, or about 6.2 ng/mL, or about 6.4 ng/mL, or about 6.6 ng/mL, or about 6.8 ng/mL, or about 7 ng/mL, or about 7.2 ng/mL, or about 7.4 ng/mL, or about 7.6 ng/mL, or about 7.8 ng/mL, or about 8 ng/mL, or about 8.2 ng/mL, or about 8.4 ng/mL, or about 8.6 ng/mL, or about 8.8 ng/mL, or about 9 ng/mL, or about 9.2 ng/mL, or about 9.4 ng/mL, or about 9.6 ng/mL, or about 9.8 ng/mL, or about 10 ng/mL, or about 10.2 ng/mL, or about 10.4 ng/mL, or about 10.6 ng/mL, or about 10.8 ng/mL, or about 11 ng/mL, or about 11.2 ng/mL, or about 11.4 ng/mL, or about 11.6 ng/mL, or about 11.8 ng/mL, or about 12 ng/mL.

In some embodiments, absorption of a foam described herein (e.g., a foam comprising 1-4% tetracycline antibiotic such as doxycycline or minocycline or combinations thereof) is low as determined by a PK Study in comparison to a comparable dose of an orally administered tetracycline. In some embodiments, absorption is determined by a PK Study, and a $C_{max}$ is determined on Day 12 after the administration of the foam once a day for twelve consecutive days and is about 0.2 ng/mL to about 5 ng/mL. For example, is about 0.2 ng/mL, or about 0.4 ng/mL, or about 0.6 ng/mL, or about 0.8 ng/mL, or about 1 ng/mL, or about 1.1 ng/mL, or about 1.2 ng/mL, or about 1.4 ng/mL, or about 1.6 ng/mL, or about 1.8 ng/mL, or about 2 ng/mL, or about 2.2 ng/mL, or about 2.4 ng/mL, or about 2.6 ng/mL, or about 2.8 ng/mL, or about 3 ng/mL, or about 3.2 ng/mL, or about 3.4 ng/mL, or about 3.6 ng/mL, or about 3.8 ng/mL, or about 4 ng/mL, or about 4.2 ng/mL, or about 4.4 ng/mL, or about 4.8 ng/mL, or about 5 ng/mL.

In some embodiments, absorption of a foam described herein (e.g., a foam comprising 1-4% tetracycline antibiotic such as doxycycline or minocycline or combinations thereof) is low as determined by a PK Study in comparison to a comparable dose of an orally administered tetracycline. In some embodiments, absorption is determined by a PK Study, and a $C_{max}$ is determined on Day 21 after the administration of the foam once a day for 21 consecutive days and is about 0.2 ng/mL to about 5 ng/mL. For example, is about 0.2 ng/mL, or about 0.4 ng/mL, or about 0.6 ng/mL, or about 0.8 ng/mL, or about 1 ng/mL, or about 1.1 ng/mL, or about 1.2 ng/mL, or about 1.4 ng/mL, or about 1.6 ng/mL, or about 1.8 ng/mL, or about 2 ng/mL, or about 2.2 ng/mL, or about 2.4 ng/mL, or about 2.6 ng/mL, or about 2.8 ng/mL, or about 3 ng/mL, or about 3.2 ng/mL, or about 3.4 ng/mL, or about 3.6 ng/mL, or about 3.8 ng/mL, or about 4 ng/mL, or about 4.2 ng/mL, or about 4.4 ng/mL, or about 4.8 ng/mL, or about 5 ng/mL. In some embodiments, the foam is FMX-101, 4%.

In some embodiments, absorption of a 4% tetracycline antibiotic, e.g., minocycline or doxycycline foam as determined by a PK Study is about 800 times to about 50 times lower than that of a comparable dose of an oral doxycycline. In some embodiments, the 4% tetracycline antibiotic is a composition described herein. In some embodiments, the 4% tetracycline antibiotic is FMX-101, 4%, described herein. In some embodiments, a 4% tetracycline antibiotic foam described herein has about 800 times to about 50 times lower $C_{max}$ and/or AUC values as compared to the $C_{max}$ and/or AUC values of a comparable dose of an oral doxycycline (e.g., an approved dose of Oracea® such as 40 mg). For example, it may be about 800 times lower, or about 750 times lower, or about 700 times lower, or about 650 times lower, or about 600 times lower, or about 550 times lower, or about 500 times lower, or about 450 times lower, or about 400 times lower, or about 350 times lower, or about 300 times lower, or about 250 times lower, or about 200 times lower, or about 150 times lower, or about 100 times lower, or about 50 times lower, than the $C_{max}$ and AUC for the approved dose of the oral extended release doxycycline (Oracea® 40 mg).

In some embodiments, absorption of a 4% tetracycline antibiotic, e.g., minocycline or doxycycline foam as determined by a PK Study is about 800 times to about 50 times lower than that of a comparable dose of an oral minocycline. In some embodiments, the 4% tetracycline antibiotic is a composition described herein. In some embodiments, the 4% tetracycline antibiotic is FMX-101, 4%, described herein. In some embodiments, a 4% tetracycline antibiotic foam described herein has about 800 times to about 25 times lower $C_{max}$ and/or AUC values as compared to the $C_{max}$ and/or AUC values of a comparable dose of an oral minocycline (e.g., an approved dose of SOLODYN® such as 1 mg/kg). For example, it may be about 800 times lower, or about 750 times lower, or about 700 times lower, or about 650 times lower, or about 600 times lower, or about 550 times lower, or about 500 times lower, or about 450 times lower, or about 400 times lower, or about 350 times lower, or about 300 times lower, or about 250 times lower, or about 200 times lower, or about 150 times lower, or about 100 times lower, or about 50 times lower, or about 25 times lower, than the $C_{max}$ and AUC for the approved dose of the oral minocycline (SOLODYN® 1 mg/kg).

In some embodiments, absorption of a 4% foam tetracycline antibiotic, e.g., minocycline or doxycycline foam as determined by a PK Study is about 850 times to about 50 times lower than that of the approved dose of an oral minocycline. In some embodiments, a 4% tetracycline antibiotic foam described herein has about 850 times to about 50 times lower $C_{max}$ and/or AUC values as compared to the $C_{max}$ and/or AUC values of the approved dose of an oral minocycline (e.g., Solodyn® 1 mg/kg). For example, is about 850 times lower, or about 800 times lower, or about 750 times lower, or about 730 times lower or about 700 times lower, or about 650 times lower, or about 600 times lower, or about 550 times lower, or about 500 times lower, or about 450 times lower, or about 400 times lower, or about 350 times lower, or about 300 times lower, or about 250 times lower, or about 200 times lower, or about 150 times lower, or about 100 times lower, or about 50 times lower, than the $C_{max}$ and AUC for the approved dose of the oral extended release minocycline (Solodyn® 1 mg/kg).

In some embodiments, a foam described herein (e.g., a foam comprising 1-4% tetracycline antibiotic such as doxycycline or minocycline or combinations thereof, e.g., FMX-101, 4%) achieves good efficacy comparable to or better than an approved dose of an oral tetracycline (e.g., Oracea® 40 mg or Solodyn® 1 mg/kg) while avoiding systemic adverse events. In some embodiments, the foam exhibits fewer adverse events than a comparable dose of oral tetracycline. In some embodiments, the treatment of rosecea using a composition disclosed herein is superior to a comparable dose of the oral tetracycline while exhibiting fewer adverse events or serious adverse events and/or exhibiting lower systemic exposure as compared to the oral tetracycline. In some embodiments, the treatment of acne using a composition disclosed herein is superior to a comparable dose of an oral tetracycline while exhibiting fewer adverse events and/or exhibiting lower systemic exposure as compared to the oral tetracycline (e.g., Oracea® 40 mg or Solodyn® 1 mg/kg). In some embodiments, the treatment of acne vulgaris using a composition disclosed herein is superior to a comparable dose of the oral tetracycline while exhibiting fewer adverse events and/or exhibiting lower systemic exposure as compared to the oral tetracycline.

In some embodiments, the treatment of rosecea or acne using FMX-101 or FMX-103, as disclosed herein, is superior to a comparable dose of an oral tetracycline while exhibiting fewer adverse events or serious adverse events and/or exhibiting lower systemic exposure as compared to the oral tetracycline. In some embodiments, the treatment of acne using FMX-101, 4% disclosed herein is superior to a comparable dose of the oral tetracycline while exhibiting fewer adverse events and/or exhibiting lower systemic exposure as compared to the oral tetracycline. In some embodiments, the treatment of acne vulgaris using FMX-101, 4% disclosed herein is superior to a comparable dose of the oral tetracycline while exhibiting fewer adverse events and/or exhibiting lower systemic exposure as compared to the oral tetracycline.

Safety

In various embodiments, clinical studies confirm that the once-daily treatment regimen with minocycline foam (1.5% or 3%) is safe even for a prolonged treatment period. During twelve weeks of treatment, no drug-related systemic adverse events or serious adverse events were reported, and the observed occurrences of telangiectasia, burning/stinging, or flushing/blushing resolved before the end of the study. Thus, administration of the minocycline topical foam is efficient, safe, and well-tolerated.

The gel, liquid gel, and foamable compositions disclosed herein meet a long-felt need for a shorter treatment regimen having an earlier onset and a higher percentage reduction in lesions, while maintaining high levels of safety and efficacy.

Thus, provided herein in various embodiments, are methods for treating rosacea or acne, including administering topically, to a surface having the disorder, a composition comprising a tetracycline antibiotic, wherein an enhanced safety and good tolerability of the topical foamable minocycline compositions is demonstrated.

In vitro skin penetration studies (see, e.g., PCT Publication No. WO 11/039637) show that topical administration of minocycline brings appreciable amounts of the drug to its target site of action (the skin), thus possibly avoiding the undesirable high systemic exposure and the negative consequences of the oral dosage route.

The topical compositions provided herein avoid, reduce, minimize or do not cause adverse effects, which are attributed to oral tetracycline antibiotics. Photosensitivity, for example, is a known side effect of oral minocycline. It is manifested as an exaggerated sunburn reaction on areas of the body exposed to direct sunlight or ultraviolet light, resulting in muddy brown skin discoloration. Use of oral minocycline over an extended period of time can also lead to skin pigmentation, e.g., manifested as blue-gray skin and blue-gray staining in areas of scarring and inflammation associated with rosacea. Tooth staining potential of oral minocycline in adult populations has also been acknowledged in recent literature. In contrast, no tooth staining was reported during the period of topical application of 1% or 4% minocycline foam or on follow-up to the study. In one or more embodiments provided herein, the topical minocycline composition avoids tooth staining.

Topical delivery also means that lower doses can be used again, contributing to the elimination or reduction of unwanted side effects. Accordingly, the foamable compositions provided herein can be beneficial for the treatment of a range of skin conditions, including rosacea, wounds, burns, inflammation, superficial infections, antibiotic responsive diseases or dermatoses, skin diseases caused by bacteria, and other skin infections, such as impetigo. Likewise, the foamable compositions provided herein can be beneficial in mucosal infections and in eye infections and inflammatory conditions.

Surprisingly, it has been previously demonstrated by Applicants in U.S. Pat. No. 8,871,184, that minimal to no skin pigmentation was noticed following rubbing of 4% minocycline foam onto the skin when observed after about 30 seconds. It has been surprisingly further discovered that no photosensitivity or skin discoloration was noticed following application of 1% or 4% minocycline foam onto the skin once daily for 12 weeks. Similarly, drug-related pigmentation was not observed.

Thus, the compositions provided herein can have protective properties in the case of UVB-induced sun damage or any other condition associated with sunlight or other light (e.g., laser) exposure. The formulations and methods of treatment provided herein can potentially reduce skin photo damage and photo aging, and more generally reduce oxidative stress and inflammation in skin pathologies which are known to be accompanied by apoptotic cell death.

It is surprisingly shown that therapeutic effects can be achieved with low concentrations of minocycline, such as 1.5%. Thus, it is possible to use lower concentrations of minocycline, thereby reducing toxicity and increasing safety. In some embodiments, the absolute mean lesion count change for the 1.5% and 3% minocycline compositions is about the same. In some embodiments, the percent reduction of lesion count for the 1.5% and 3% minocycline compositions is about the same. In some embodiments, the reduction of IGA score for the 1.5% and 3% minocycline compositions is about the same.

It is now surprisingly shown that topically administering a foam formulation having minocycline at 1.5% or 3% significantly decreases the number of lesions (absolute lesion count and percent change lesion count), and also significantly improves investigator's global assessment (IGA) results (reducing the IGA score by 2 grades and reaching a "clear or "almost clear" rating) in comparison to the vehicle. Further, the difference between the 1.5% and 3% formulations, with respect to decrease in the number of lesions and improvement of IGA score, is not statistically significant. The efficacy of FMX103 in the treatment of rosacea is surprising, as rosacea is a syndrome of undetermined etiology characterized by both vascular and papulopustular components, i.e., it is a chronic inflammatory condition of facial skin affecting both the blood vessels and pilosebaceous unit. Moreover, the observed dose independence of effectiveness in treatment of rosacea is surprising and unexpected in light of dose dependency observed with acne, where 4% minocycline is more effective than 1% minocycline. Also, the effectiveness in the treatment of rosacea is also surprising in view of the lack of bacterial involvement in rosacea, as is the case of acne and impetigo.

It is shown herein that a topically administered foam formulation containing minocycline at 1.5% or 3% is safe and well tolerated. No drug related serious adverse events or systemic adverse events were reported in a clinical study of the formulations. There were only a few treatment-related dermal reactions reported (none in the 1.5% group, three patients in the 3% group and four patients in the vehicle group). These reactions resolved before the end of the study. A total of four subjects discontinued the study due to an adverse event (three patients in the 3% group and one in the vehicle group).

In an embodiment, provided is a hydrophobic gel or foam composition comprising: a tetracycline antibiotic, wherein the tetracycline antibiotic is present in the gel or foam composition in an amount effective to treat rosacea in a subject, which is safe and well-tolerated. In an embodiment, provided is a hydrophobic gel or foam composition comprising: a tetracycline antibiotic, wherein substantially no treatment-related dermal reactions are observed. In an embodiment, provided is a hydrophobic gel or foam composition comprising: a tetracycline antibiotic, wherein no systemic drug-related side effects and no serious adverse reactions are observed. In an embodiment, provided is a hydrophobic gel or foam composition comprising: a tetracycline antibiotic, wherein the tetracycline antibiotic is present in the gel or foam composition at a concentration of 1.5% or 3% to treat rosacea. In an embodiment, provided is a hydrophobic gel or foam composition comprising: a tetracycline antibiotic, wherein the tetracycline is minocycline hydrochloride.

In an embodiment, provided is a hydrophobic gel or foam composition comprising: a tetracycline antibiotic wherein the 1.5% and 3% concentrations are equally effective in reducing the number of papules and pustules, as compared to the placebo vehicle. In another embodiment, provided is a hydrophobic gel or foam composition comprising: a tetracycline antibiotic, wherein the 1.5% dose is more effective the 3% dose in reducing the number of papules and pustules, as compared to the placebo vehicle. In another embodiment, provided is a hydrophobic gel or foam composition comprising: a tetracycline antibiotic, wherein the 3% dose is more effective the 1.5% dose in reducing the number of papules and pustules, as compared to the placebo vehicle. In one or more embodiments the reduction in the papules and pustules is statistically significant as compared to placebo. In one or more embodiments the reduction in the papules and pustules is statistically significant as compared to placebo. In an embodiment, provided is a hydrophobic gel or foam composition comprising: a tetracycline antibiotic, wherein the tetracycline is minocycline hydrochloride.

In an embodiment, provided is a hydrophobic gel or foam composition comprising: a tetracycline antibiotic wherein the 1.5% and 3% concentrations are equally effective in reducing IGA score by two levels, as compared to the placebo vehicle. In another embodiment, provided is a hydrophobic gel or foam composition comprising: a tetracycline antibiotic, wherein the 1.5% dose is more effective that the 3% dose in reducing the IGA score by two levels, as compared to the placebo vehicle. In another embodiment, provided is a hydrophobic gel or foam composition comprising: a tetracycline antibiotic, wherein the 3% dose is more effective the 1.5% dose in reducing the IGA score by two levels, as compared to the placebo vehicle. In one or more embodiments the reduction in IGA score by two levels is statistically significant as compared to placebo. In one or more embodiments the reduction in IGA score by two levels results in clear or almost clear compared to baseline. In an embodiment, provided is a hydrophobic gel or foam composition comprising: a tetracycline antibiotic, wherein said tetracycline is minocycline hydrochloride.

In an embodiment, provided is a hydrophobic gel or foam composition comprising: a tetracycline antibiotic, wherein said tetracycline antibiotic is present in said gel or foam composition in an amount effective to treat moderate-to-severe papulopustular rosacea (IGA score 3-4). In an embodiment, more than half of the tetracycline-treated subjects have severe rosacea at baseline. In an embodiment, there is no statistical significant difference between treatment groups with regard to IGA severity at baseline.

Erythema is redness of the skin or mucous membranes, caused by hyperemia (increased blood flow) in superficial capillaries. It occurs with any skin injury. There are different types of erythema for example erythema nodosum and erythema multiforme. Visible redness of the skin is observed in patients with medium and severe rosacea. In one or more embodiments, there is provided a method of treatment for reducing skin redness in a subject having a disorder in which one of the etiological factors is skin redness comprising applying a topical composition to an area of skin with the disorder, wherein the topical composition comprises a tetracycline antibiotic, for example, minocycline or doxycycline, at the concentration of, for example, about 1.5% to 3%. In some embodiments, the redness is moderate redness. In some embodiments, the redness is severe redness. In some embodiments, the redness is a symptom of Rosacea. In some embodiments, it is a symptom of an infection. In some embodiments, it is a symptom of a bacterial infection. In some embodiments, it is a symptom of a fungal infection. In some embodiments, it is a symptom of a viral infection. In some embodiments, it is a symptom of an allergic reaction. In an embodiment, provided is a hydrophobic gel or foam composition comprising: a tetracycline antibiotic wherein the 1.5% and 3% concentrations are equally effective in reducing the severity of erythema, as compared to the placebo vehicle. In another embodiment, provided is a hydrophobic gel or foam composition comprising: a tetracycline antibiotic, wherein the 1.5% dose is more effective than the 3% dose in reducing in reducing the severity of erythema, as compared to the placebo vehicle. In another embodiment, provided is a hydrophobic gel or foam composition comprising: a tetracycline antibiotic, wherein the 3% dose is more effective than the 1.5% dose in reducing the severity of erythema, as compared to the placebo vehicle. In one or more embodiments, the reduction of erythema severity is statistically significant as compared to placebo. In some embodiments, a foam composition described herein is sufficient to reduce the severity of skin redness or erythema by at least 30%, 35%, 40%, 45%, 50%, 55%, 60%, 65%, 70%, 75%, 80%, or more as compared to the severity of skin redness or erythema before the treatment and/or as compared to a vehicle or oral doxycycline treatment. In an embodiment, provided is a hydrophobic gel or foam composition comprising: a tetracycline antibiotic, wherein the tetracycline is minocycline hydrochloride.

In one or more embodiments there is provided a method for treating rosacea, including administering topically, to a surface having the disorder, a composition comprising a tetracycline antibiotic, wherein essentially no skin irritation such as telangiectasia, burning/stinging, or flushing/blushing, or essentially no adverse events, or no serious adverse events are observed. In one or more embodiments, good tolerability was demonstrated with relatively few reports of skin irritation, such as telangiectasis, burning or stinging, flushing or blushing.

In one or more embodiments there is provided a method for treating rosacea, including administering topically, to a surface having rosacea, a composition comprising a tetracycline antibiotic, wherein an enhanced efficacy of the topical foamable minocycline compositions is demonstrated.

In one or more embodiments there is provided a method for treating rosacea, including administering topically, to a surface having rosacea, a composition comprising a tetracycline antibiotic, wherein better efficacy of the topical foamable minocycline compositions is demonstrated as compared to other topical treatments.

Oral doxycycline administration may cause common side effects, including upset stomach, nausea, diarrhea and mild headache.

Since doxycycline hyclate is a larger molecule compared to minocycline HCl, in some embodiments it can have a reduced penetration and hence the maximum plasma concentrations can be less than those obtained for minocycline HCl.

In some embodiments, doxycycline hyclate penetrates better than minocycline HCl and hence the maximum plasma concentrations can be more than those obtained for minocycline HCl.

In some embodiments, doxycycline hyclate penetration is similar to that of minocycline HCl and hence the maximum plasma concentrations can be similar to those obtained for minocycline HCl.

Efficacy

In one or more embodiments, there is provided an effective method for treating rosacea, as set out herein, to patients with more than twenty inflammatory lesions on the face (papules and/or pustules) and up to 2 nodules, with more than twelve but not more than a nineteen inflammatory lesions on the face and no nodules, and receiving a score of at least Moderate on the Investigator's Global Assessment Scale.

In one or more embodiments, provided herein is an effective method for treating acne using a composition described herein. In one or more embodiments, provided herein is an effective method for treating acne vulgaris using a composition described herein. In some embodiments, the composition is FMX-101. In some embodiments, the composition is FMX-101, 4%.

In one or more embodiments, the methods for treating rosacea, as set out herein, are able to deliver effective amounts of a tetracycline antibiotic into the skin or mucosal surface.

In one or more embodiments, the methods for treating rosacea, as set out herein, are able to deliver effective amounts of a tetracycline antibiotic into and around the hair follicle or the hair follicle area.

In one or more embodiments, the methods for treating rosacea, as set out herein, are able to deliver effective amounts of a tetracycline antibiotic into or around the sebaceous gland or the sebaceous gland area or the pilosebaceous unit.

In one or more embodiments, the methods for treating rosacea, as set out herein, are able to deliver effective amounts of a minocycline, wherein the minocycline composition targets the sebaceous gland or the sebaceous gland area or the pilosebaceous unit.

In one or more embodiments, there is provided a method for treating rosacea, as set out herein, wherein the hydrophobic gel or foam composition targets the hair follicle or the hair follicle area.

In one or more embodiments, there is provided a method for treating rosacea, including administering topically, to a surface having the disorder, a composition comprising a tetracycline antibiotic, wherein a reduction in the number of lesions is observed after twelve weeks or less than twelve weeks of treatment compared to baseline. In one or more embodiments, there is provided a method for treating rosacea, including administering topically, to a surface having the disorder, a composition comprising a tetracycline antibiotic, wherein an improvement in the skin condition is observed after twelve weeks or less than twelve weeks of treatment and wherein an improvement is considered as restoration of visible, normal cutaneous topographic features, indicating the return of skin integrity. In an embodiment the improvement is after two weeks after three weeks, or after four weeks, or after five weeks, or after six weeks or after seven weeks, or after eight weeks, or after nine weeks, or after ten weeks, or after eleven weeks, or after twelve weeks.

In one or more embodiments there is provided a hydrophobic gel or foam composition comprising a therapeutically effective amount of tetracycline antibiotic for use in treating rosacea in a human subject comprising topically administering the composition at least alternate days or at least once daily, wherein a decrease in the number of rosacea papule and pustules is observed after at least twelve weeks of treatment. In an embodiment the decrease in the number of rosacea papule and pustules is after two weeks, after three weeks, or after four weeks, or after five weeks, or after six weeks or after seven weeks, or after eight weeks, or after nine weeks, or after ten weeks, or after eleven weeks, or after twelve weeks.

In one or more embodiments, there is provided a hydrophobic gel or foam composition comprising a therapeutically effective amount of tetracycline antibiotic for use in treating rosacea in a human subject comprising topically administering the composition at least alternate days or at least once daily, wherein a decrease the total number of rosacea lesions is observed after at least three weeks of treatment or after at least two weeks of treatment.

In one or more embodiments, there is provided a hydrophobic gel or foam composition comprising a therapeutically effective amount of tetracycline antibiotic for use in treating rosacea in a human subject comprising topically administering the composition at least alternate days or at least once daily, wherein a decrease the number of inflammatory rosacea lesions is observed after at least three weeks of treatment or after at least two weeks of treatment.

In one or more embodiments, the human subject is 60 or less than 60 years old, is 50 or less than 50 years old, is 40 or less than 40 years old, is 30 or less than 30 years old, or is 25 or less than 25 years old, or is 22 or is less than 22 years old, or is 20 or less than 20 years old, or is 18 or less than 18 years old, or 15 or is less than 15 years old, or is between 8 to 25 years old or is between 9 to 22 years old. In an embodiment the subject is a female. In an embodiment the female is under the age of forty-six and optionally is a pregnant or breastfeeding female. In an embodiment the subject is a male. In an embodiment the subject is a teenager. In another embodiment the subject is a child.

In one or more embodiments, there is provided a method for treating rosacea, including administering topically to a surface having rosacea a composition comprising a tetracycline antibiotic, wherein after twelve weeks of treatment, at least about 40% of the treated rosacea lesions disappear (in other words, a 40% decrease in the number of lesions) so that no further antimicrobial therapy is necessary. In some embodiments, at least about 50%, at least about 60%, at least about 70% or at least about 80% of the treated rosacea lesions disappear. In one or more embodiments, at least about 90% of the treated rosacea lesions disappear.

In other embodiments, a decrease of at least about 60% in the number of rosacea lesions is observed after twelve weeks or less than twelve weeks of treatment.

In one or more embodiments, there is provided a method for treating rosacea, including administering topically to a surface having rosacea a composition comprising a tetracycline antibiotic, wherein after twelve weeks or less than twelve weeks of treatment, at least about 45% of the treated rosacea lesions disappear (in other words, a 45% decrease in the number of lesions) so that no further antimicrobial therapy is necessary. In some embodiments, at least about 50%, at least about 60%, at least about 70% or at least about 80% of the treated rosacea lesions disappear after six week or less than six weeks of treatment. In one or more embodiments, at least about 90% of the treated rosacea lesions disappear after twelve week or less than twelve weeks of treatment.

In one or more embodiments, there is provided a method for treating rosacea, including administering topically, to a surface having rosacea, a composition comprising a tetracycline antibiotic, wherein a percent of total number lesions that disappeared is at least about 30%, at least about 40%, or at least about 50% or at least about 60%, or at least about 70% or at least about 75% or at least about 80% after twelve weeks or less than twelve weeks of treatment.

In one or more embodiments, there is provided a method for treating rosacea, including administering topically, to a surface having rosacea, a composition comprising a tetracycline antibiotic, wherein a percent of total number lesions that disappeared is at least about 50%, or at least about 60%, or at least about 70%, or at least about 80% after four weeks after the end of the treatment.

In one or more embodiments there is provided a method for treating rosacea, including administering topically, to a surface having rosacea, a composition comprising a tetracycline antibiotic, wherein a percent of total number lesions that disappeared at the end of treatment is statistically significant compared to baseline in both 1.5% and 3% dose groups.

In one or more embodiments there is provided a method for treating rosacea, including administering topically, to a surface having rosacea, a composition comprising a tetracycline antibiotic, wherein a percent of total number lesions that disappeared at the end of treatment compared to baseline is statistically significant in both 1.5% and 3% dose groups when compared to placebo.

In one or more embodiments there is provided a method for treating rosacea, including administering topically, to a surface having rosacea, a composition comprising a tetracycline antibiotic, wherein a percent of total number lesions that disappeared at the end of treatment compared to baseline is statistically significant in the 3% dose group when compared to placebo.

In one or more embodiments there is provided a method for treating rosacea, including administering topically, to a surface having rosacea, a composition comprising a tetracycline antibiotic, wherein the baseline severity of rosacea is at least moderate to severe, as judged by the number of rosaceas and investigator's global severity assessment (IGA).

In one or more embodiments there is provided a method for treating rosacea, including administering topically, to a surface having rosacea, a composition comprising a tetracycline antibiotic, wherein the mean number of rosacea papule and pustules at baseline is at least about 30-34 or at least about 34-35.

In one or more embodiments there is provided a method for treating rosacea, including administering topically, to a surface having rosacea, a composition comprising a tetracycline antibiotic, wherein the number of papule and pustules is at least 20 papule and pustules. In other embodiments there is at least one papule and pustules, or at least 5, or at least 10 or at least 15 papule and pustules and in further embodiments there are at least 25, or at least 30 or at least 40 or at least 50 papule and pustules.

In one or more embodiments there is provided a method for treating rosacea, including administering topically, to a surface having rosacea, a composition comprising a tetracycline antibiotic, wherein the rosacea is low to moderate rosacea. In other embodiments the composition can be applied as aforesaid as a method of protecting the skin, for example, by preventing microbial infection or rosacea In one or more embodiments there is provided a method for treating rosacea, including administering topically, to a surface having rosacea, a composition comprising a tetracycline antibiotic, wherein the IGA score as assessed by the investigator at baseline is between 3-4, indicating moderate to severe rosacea at baseline. In other embodiments the composition can be applied to mild rosacea and in still further embodiments it can be applied to very severe rosacea.

In one or more embodiments, there is provided a method for treating rosacea, including administering topically, to a surface having rosacea, a composition comprising a tetracycline antibiotic, wherein the daily application of topical minocycline foam (3% and 1.5%) on facial skin with moderate to severe rosacea results in a significant improvement of the disease, for example, as indicated by the primary and secondary endpoints.

In one or more embodiments there is provided a method for treating rosacea, including administering topically, to a surface having rosacea, a composition comprising a tetracycline antibiotic, wherein there is a clinically and statistically significant reduction in a lesion count, after twelve weeks of treatment in the subjects receiving minocycline foam compared to Placebo.

In one or more embodiments there is provided a method for treating rosacea, including administering topically, to a surface having rosacea, a composition comprising a tetracycline antibiotic, wherein a clinically and statistically significant improvement in the investigator global assessment of rosacea severity is observed after 12 treatment weeks in the subjects receiving minocycline foam compared to Placebo.

In one or more embodiments, there is provided a method for treating rosacea, including administering topically, to a surface having rosacea, a composition comprising a tetracycline antibiotic, wherein a clinically and statistically significant improvement in the investigator global assessment of rosacea severity is observed after 12 treatment weeks in the subjects receiving minocycline foam compared to Placebo, and wherein a clinically significant improvement in the investigator global assessment of rosacea severity comprises improvement by at least two levels.

In one or more embodiments there is provided a method for treating rosacea, including administering topically, to a surface having rosacea, a composition comprising a tetracycline antibiotic, wherein the effect of the minocycline foam is dose dependent, and the effect of 3% minocycline foam is generally greater than 1.5% minocycline foam.

In one or more embodiments there is provided a method for treating rosacea, including administering topically, to a surface having rosacea, a composition comprising a tetracycline antibiotic, wherein the effect of the minocycline foam is dose dependent, and the effect 1.5% minocycline foam is generally greater than 3% minocycline foam.

In one or more embodiments, there is provided a method for treating rosacea, including administering topically, to a surface having rosacea, a composition comprising a tetracycline antibiotic, wherein the effect of the minocycline foam on rosacea is dose independent (in a surprising and unexpected contrast to dose dependency observed with acne), and the effect of 1.5% minocycline foam is similar to 3% minocycline foam.

In one or more embodiments, there is provided a method for treating rosacea, including administering topically, to a surface having rosacea, a composition comprising a tetracycline antibiotic, wherein, a clinically and statistically significant reduction in the number of inflammatory lesions can be seen after 12 weeks of treatment in subjects receiving the 1.5-3%, or about 1.5% or about 3% minocycline foam, as compared to Placebo and/or compared to baseline prior to treatment.

In one or more embodiments there is provided a method for treating rosacea, including administering topically, to a surface having rosacea, a composition comprising a tetracycline antibiotic, wherein, more than a 60% reduction in inflammatory lesion counts can be seen following twelve weeks of treatment in subjects receiving the 1.5-3% minocycline foam compared to Placebo.

In one or more embodiments, there is provided a method for treating rosacea, including administering topically, to a surface having rosacea, a composition comprising a tetracycline antibiotic, wherein, the percent of subjects who had a decrease of more than 40%, 50%, 60%, or 70% in the inflammatory lesions count was statistically significantly higher in the 1.5-3% treatment group compared to Placebo after 6 treatment weeks and onward.

In one or more embodiments there is provided a method for treating rosacea, including administering topically, to a surface having rosacea, a composition comprising a tetracycline antibiotic, wherein, the percent of subjects who had a decrease of more than 50% or 60%, in the inflammatory lesions count was statistically significantly higher in the 1.5-3% treatment group compared to Placebo only at twelve treatment weeks.

In one or more embodiments, there is provided a method for treating rosacea, including administering topically, to a surface having rosacea, a composition comprising a tetracycline antibiotic, wherein according to the investigator's global assessment at 12 weeks, more than 20% of the subjects have "clear" or "almost clear" skin in subjects receiving the 1.5-3% minocycline foam and wherein this change is statistically significant compared to subjects in the Placebo group.

In one or more embodiments, there is provided a method for treating rosacea, including administering topically, to a surface having rosacea, a composition comprising a tetracycline antibiotic, wherein, according to the investigator's global assessment at 12 weeks, the number of the subjects having "severe" or "moderate" rosacea has decreased at least 50% in subjects receiving the 1.5-3% minocycline foam and wherein this change is statistically significant compared to subjects in the Placebo group.

In one or more embodiments, there is provided a method for treating rosacea, including administering topically, to a surface having rosacea, a composition comprising a tetracycline antibiotic, wherein, according to the investigator's global assessment at 12 weeks, the number of the subjects having "severe" or "moderate" rosacea has decreased at least 60% in subjects receiving the 1.5-3% minocycline foam and wherein this change is statistically significant compared to subjects in the Placebo group.

In one or more embodiments, there is provided a method for treating rosacea, including administering topically, to a surface having rosacea, a composition comprising a tetracycline antibiotic, wherein, according to the investigator's global assessment at 12 weeks, the number of the subjects having "severe" or "moderate" rosacea has decreased at least 70% in subjects receiving the 1.5-3% minocycline foam and wherein this change is statistically significant compared to subjects in the Placebo group.

In one or more embodiments, there is provided a method for treating rosacea, including administering topically, to a surface having rosacea, a composition comprising a tetracycline antibiotic, wherein, according to the investigator's global assessment at 12 weeks, the number of the subjects having "severe" rosacea has decreased at least 50% in subjects receiving the 1.5-3% minocycline foam and wherein this change is statistically significant compared to subjects in the Placebo group.

In one or more embodiments, there is provided a method for treating rosacea, including administering topically, to a surface having rosacea, a composition comprising a tetracycline antibiotic, wherein, according to the investigator's global assessment at 12 weeks, the number of the subjects having "severe" rosacea has decreased at least 60% in subjects receiving the 1.5-3% minocycline foam and wherein this change is statistically significant compared to subjects in the Placebo group.

In one or more embodiments, there is provided a method for treating rosacea, including administering topically, to a surface having rosacea, a composition comprising a tetracycline antibiotic, wherein according to the investigator's global assessment at 12 weeks, the number of the subjects having improvement is statistically significantly higher in the 1.5-3% treatment group compared to Placebo after 8 treatment weeks and onward.

In one or more embodiments, there is provided a method for treating rosacea, including administering topically, to a surface having rosacea, a composition comprising a tetracycline antibiotic, wherein according to the investigator's global assessment at 12 weeks, the number of the subjects having improvement by of at least 2 grades is statistically significantly higher in the 1.5-3% treatment group compared to Placebo after 12 treatment weeks and onward.

In one or more embodiments, there is provided a method for treating rosacea, including administering topically, to a surface having rosacea, a composition comprising a tetracycline antibiotic, wherein improvement of at least 2 grades in the investigator's global assessment score is observed in at least 20% of the subjects receiving 1.5-3% minocycline foam and wherein this is statistically more frequent than in subjects receiving Placebo.

In one or more embodiments, there is provided a method for treating rosacea, including administering topically, to a surface having rosacea, a composition comprising a tetracycline antibiotic, wherein improvement of at least 2 grades in the investigator's global assessment score is in at least 15% of the subjects receiving 1.5-3% minocycline foam and wherein this is statistically more frequent than in subjects receiving Placebo.

In one or more embodiments, there is provided a method for treating rosacea, including administering topically, to a surface having rosacea, a composition comprising a tetracycline antibiotic, wherein improvement of at least 3 grades in the investigator's global assessment score is in at least 10% of the subjects receiving 1.5-3% minocycline foam and wherein this is statistically more frequent than in subjects receiving Placebo.

In one or more embodiments, provided is a method for treating rosacea, including administering topically, to a surface having rosacea, a composition comprising a tetracycline antibiotic, wherein according to secondary endpoint relating to rosacea improvement, assessment by the investigator after twelve weeks of treatment indicates improvement in at least 70% of subjects receiving the 1.5-3% minocycline foam, wherein this is statistically significant compared to the Placebo group.

In one or more embodiments, there is provided a method for treating rosacea, including administering topically, to a surface having rosacea, a composition comprising a tetracycline antibiotic, wherein according to secondary endpoint relating to rosacea improvement assessment by the investigator after 12 treatment weeks indicates improvement in at least 60% of subjects in subjects receiving the 1.5-3% minocycline foam and wherein this is statistically significant compared to the Placebo group.

In one or more embodiments there is provided a method for treating rosacea, including administering topically, to a surface having rosacea, a composition comprising a tetracycline antibiotic, wherein at least half the subjects receiving the 1.5-3% minocycline foam evaluated their rosacea as 'much better than prior to study' and wherein this is statistically significant when compared to the Placebo group.

In one or more embodiments there is provided a method for treating rosacea, including administering topically, to a surface having rosacea, a composition comprising a tetracycline antibiotic, wherein the effect was most notably shown on severe rosacea subjects receiving the 1.5-3% minocycline foam.

In one or more embodiments there is provided a method for treating rosacea, including administering topically, to a surface having rosacea, a composition comprising a tetracycline antibiotic, wherein a percent of total number of inflammatory lesions and that disappeared at the end of treatment compared to baseline is higher than placebo in both 1.5% and 3% dose groups.

In one or more embodiments, the placebo formulation has a beneficial effect. In one or more embodiments there is provided a method for treating rosacea, including administering topically, to a surface having rosacea, a placebo composition being a vehicle composition described herein for the delivery of a tetracycline that does not comprise a tetracycline antibiotic, wherein a percent of number of inflammatory lesions that disappeared at the end of treatment compared to baseline is higher than on a surface having rosacea that is untreated. In one embodiment placebo is statistically better than no treatment.

In one or more embodiments there is provided a method for treating rosacea, including administering topically, to a surface having rosacea, a composition comprising a tetracycline antibiotic, wherein a percent of total number of inflammatory lesions that disappeared in the 3% dose group at the end of treatment is significantly statistically higher than that of the 1.5% dose group.

In one or more embodiments there is provided a method for treating rosacea, including administering topically, to a surface having rosacea, a composition comprising a tetracycline antibiotic, wherein a percent of total number of inflammatory lesions that disappeared in the 1.5% dose group at the end of treatment is significantly statistically higher than that of the 3% dose group.

In one or more embodiments there is provided a method for treating rosacea, including administering topically, to a surface having rosacea, a composition comprising a tetracycline antibiotic, wherein a percent of total number of inflammatory lesions that disappeared in the 3% dose group at the end of treatment is significantly statistically higher than that of placebo.

In one or more embodiments there is provided a method for treating rosacea, including administering topically, to a surface having rosacea, a composition comprising a tetracycline antibiotic, wherein a percent of total number of inflammatory lesions that disappeared in the 1.5% dose group at the end of treatment is significantly statistically higher than that of placebo.

In one or more embodiments there is provided a method for treating rosacea, including administering topically, to a surface having rosacea, a composition comprising a tetracycline antibiotic, wherein a percent of total number of inflammatory lesions that disappeared in both 1.5% and 3% dose groups at the end of treatment is statistically significant when compared to placebo.

In one or more embodiments there is provided a method for treating rosacea, including administering topically, to a surface having rosacea, a composition comprising a tetracycline antibiotic, wherein at least about 30%, or at least about 40%, or at least about 50%, or at least about 55%, or at least about 58%, or at least about 60%, or at least about 62%, or at least about 70%, or at least about 75% of total number of inflammatory lesions disappear after twelve weeks after the end of the treatment (F/U). In one or more embodiments these changes at F/U are statistically significant compared to baseline in both 1.5% and 3% dose groups. In one or more embodiments these changes at F/U are statistically significant compared to placebo in both 1.5% and 3% dose groups. In one or more embodiments the number of inflammatory lesions at F/U is the same or similar compared to end of treatment ("EOT") in both 1.5% and 3% dose groups. In one or more embodiments the number of inflammatory lesions at F/U increases compared to EOT. In one or more embodiments there is the number of inflammatory lesions at F/U decreases compared to EOT.

In one or more embodiments, there is provided a method for treating rosacea, including administering topically, to a surface having rosacea, a composition comprising a tetracycline antibiotic, wherein according to the investigator's global assessment of erythema at 12 weeks, more than 15% of the subjects have "clear" or "almost clear" skin in subjects receiving the 1.5-3% minocycline foam and wherein this change is statistically significant compared to subjects in the Placebo group.

In one or more embodiments, there is provided a method for treating rosacea, including administering topically, to a surface having rosacea, a composition comprising a tetracycline antibiotic, wherein according to the investigator's global assessment of erythema at 12 weeks, more than 10% of the subjects have "clear" or "almost clear" skin in subjects receiving the 1.5-3% minocycline foam and wherein this change is statistically significant compared to subjects in the Placebo group.

In one or more embodiments, there is provided a method for treating rosacea, including administering topically, to a surface having rosacea, a composition comprising a tetracycline antibiotic, wherein, according to the investigator's global assessment of erythema at 12 weeks, the number of the subjects having "severe" or "moderate" rosacea has decreased at least 70% in subjects receiving the 1.5-3% minocycline foam and wherein this change is statistically significant compared to subjects in the Placebo group.

In one or more embodiments, there is provided a method for treating rosacea, including administering topically, to a surface having rosacea, a composition comprising a tetracycline antibiotic, wherein, according to the investigator's global assessment of erythema at 12 weeks, the number of the subjects having "severe" or "moderate" rosacea has decreased at least 50% in subjects receiving the 1.5-3% minocycline foam and wherein this change is statistically significant compared to subjects in the Placebo group.

In one or more embodiments, there is provided a method for treating rosacea, including administering topically, to a surface having rosacea, a composition comprising a tetracycline antibiotic, wherein, according to the investigator's global assessment of erythema at 12 weeks, the number of the subjects having "severe" rosacea has decreased at least 70% in subjects receiving the 1.5-3% minocycline foam and wherein this change is statistically significant compared to subjects in the Placebo group.

In one or more embodiments, there is provided a method for treating rosacea, including administering topically, to a surface having rosacea, a composition comprising a tetracycline antibiotic, wherein, according to the investigator's global assessment of erythema at 12 weeks, the number of the subjects having "severe" rosacea has decreased at least 80% in subjects receiving the 1.5-3% minocycline foam and wherein this change is statistically significant compared to subjects in the Placebo group.

In one or more embodiments, there is provided a method for treating rosacea, including administering topically, to a surface having rosacea, a composition comprising a tetracycline antibiotic, wherein according to the investigator's global assessment of erythema at 12 weeks, the number of the subjects having improvement by of at least 2 grades is statistically significantly higher in the 1.5-3% treatment group compared to Placebo after 12 treatment weeks and onward.

In one or more embodiments, there is provided a method for treating rosacea, including administering topically, to a surface having rosacea, a composition comprising a tetracycline antibiotic, wherein according to the investigator's global assessment of erythema at 12 weeks, the number of the subjects having improvement by of at least 2 grades is in at least 10% of the subjects receiving 1.5-3% minocycline foam and wherein this is statistically more frequent than in subjects receiving Placebo.

In one or more embodiments, there is provided a method for treating rosacea, including administering topically, to a surface having rosacea, a composition comprising a tetracycline antibiotic, wherein according to the investigator's global assessment of erythema at 12 weeks, the number of the subjects having improvement by of at least 2 grades is in at least 15% of the subjects receiving 1.5-3% minocycline foam and wherein this is statistically more frequent than in subjects receiving Placebo.

In one or more embodiments, there is provided a method for treating rosacea, including administering topically, to a surface having rosacea, a composition comprising a tetracycline antibiotic, wherein treating said rosacea in said subject results in no adverse event.

In one or more embodiments, there is provided a method for treating rosacea, including administering topically, to a surface having rosacea, a composition comprising a tetracycline antibiotic, wherein at treating said rosacea in said subject results in more than about 30% reduction in lesions, relative to placebo, after about two to twelve weeks of treatment.

In one or more embodiments, there is provided a method for treating rosacea, including administering topically, to a surface having rosacea, a composition comprising a tetracycline antibiotic, wherein treating said rosacea in said subject results about 30-60% reduction in lesions, relative to placebo, after about two to twelve weeks of treatment.

In one or more embodiments, there is provided a method for treating rosacea, including administering topically, to a surface having rosacea, a composition comprising a tetracycline antibiotic, wherein treating said rosacea, in said subject, with said composition having 1.5% or 3% minocycline, results in about 33% reduction in the incidence of erythema, relative to 7% reduction in placebo, after two weeks of treatment.

In one or more embodiments, there is provided a method for treating rosacea, including administering topically, to a surface having rosacea, a composition comprising a tetracycline antibiotic, wherein treating said rosacea, in said subject, with said composition having 1.5% or 3% minocycline, results in a significant reduction in papules and pustules, relative to placebo, after about two to twelve weeks of treatment.

In one or more embodiments, there is provided a method for treating rosacea, including administering topically, to a surface having rosacea, a composition comprising a tetracycline antibiotic, wherein treating said rosacea in said subject results in reduction in the number of lesions ranging from about 10 to about 30, relative to a baseline.

In one or more embodiments, there is provided a method for treating rosacea, including administering topically, to a surface having rosacea, a composition comprising a tetracycline antibiotic, wherein treating said rosacea in said subject results in reduction in the number of lesions of about 10, 15, 20, or 30, relative to a baseline.

In one or more embodiments, there is provided a method for treating rosacea, including administering topically, to a surface having rosacea, a composition comprising a tetracycline antibiotic, wherein treating said rosacea, in said subject, with said composition having 1.5% or 3% minocycline, results reduction in the number of lesions of about 19-22, relative to placebo, after about two to twelve weeks of treatment.

In one or more embodiments, there is provided a method for treating rosacea, including administering topically, to a surface having rosacea, a composition comprising a tetracycline antibiotic, wherein treating said rosacea in said subject results in lesion count ranging from about 10 to about 20.

In one or more embodiments, there is provided a method for treating rosacea, including administering topically, to a surface having rosacea, a composition comprising a tetracycline antibiotic, wherein treating said rosacea in said subject results in lesion count of about 10, 13, 14, 15, 18, or 20.

As with other therapeutic regimens, patient compliance is essential in the effectiveness of prescribed antibiotics. With poor compliance, therapeutic goals are less likely to be achieved, resulting in poorer patient outcomes. Poor compliance is associated with deteriorating skin condition, the need for additional consultations, the emergence of bacterial resistance, extra drugs, additional expenses on cosmeticians and increases in direct and indirect costs of healthcare management.

In general, patients are more compliant with simple and shorter dosing regimens. Both the dosage schedule and the patient's daily routine should be considered when prescribing antibiotics. Topical agents can also be more attractive than oral therapy because they reduce the potential for systemic side effects, typically nausea and diarrhea, which are commonly associated with many systemic antibiotics. They can also help provide a reduction in cross contamination by providing a barrier with antibiotic over the infected area.

In one or more embodiments there is provided a method for treating rosacea, including administering topically, to a surface having rosacea, a composition comprising a tetracycline antibiotic administered at least alternate days or once daily which has a high or improved patient compliance compared with existing treatments.

In one or more embodiments, one or more of the methods provided herein for treating or alleviating rosacea or acne can also be used for treating a disorder including one or more of the following: rosacea related or associated disorder, rosacea-like symptoms, rosacea related symptoms, a tetracycline antibiotic responsive rosacea related disorder, skin disorder caused by a bacteria, and a tetracycline antibiotic responsive sebaceous gland disease.

A multi-center, randomized, double blind, placebo controlled, parallel group, dose finding Phase II clinical study conducted in patients afflicted with papulopustular rosacea is reported in Example 3 below. The study is designed to assess the efficacy, safety and tolerability of foamable composition comprising minocycline at one of two different concentrations (strengths): a lower concentration of minocycline of 1.5% by weight of the formulation and higher concentration of minocycline 3% by weight of the formulation, in comparison with a placebo. The concentrations of minocycline in the composition were selected according to formulation integrity and stability considerations.

In some embodiments similar Phase II clinical studies for additional tetracycline antibiotic formulations such as DOX331, DOX332, DOD-003, MCD-037, MCD-045, MCD-052 MCD-053, MCD-065 and MCD-058 are undertaken.

In some embodiments, Phase II studies in rosacea for other tetracycline antibiotic formulations (such as DOX331, DOX332, DOD-003, MCD-037, MCD-045, MCD-052 MCD-053, MCD-065 and MCD-058) provide similar results to those seen for the FMX103 formulation.

In some embodiments, a Phase II clinical study indicates that other tetracycline antibiotic formulations (such as DOX331, DOX332, DOD-003, MCD-037, MCD-045, MCD-052 MCD-053, MCD-065 and MCD-058) can treat moderate-to-severe rosacea.

In some embodiments, a Phase II clinical study for another tetracycline antibiotic formulation such as DOX331, DOX332, DOD-003, MCD-037, MCD-045, MCD-052 MCD-053, MCD-065 and MCD-058 indicates that such a formulation can reduce papules and pustules in rosacea patients.

In some embodiments, DOX331, DOX332, DOD-003, MCD-037, MCD-045, MCD-052 MCD-053, MCD-065 and MCD-058 can help patients having rosacea. In some embodiments, DOX331, DOX332, DOD-003, MCD-037, MCD-045, MCD-052 MCD-053, MCD-065 and MCD-058 are safe and well tolerated in subjects who have rosacea. In some embodiments there are no drug-related systemic side effects. DOX331, DOX332, DOD-003, MCD-037, MCD-045, MCD-052 MCD-053, MCD-065 and MCD-058 are in some embodiments superior to a vehicle in preventing rosacea. In some embodiments, compliance with DOX331, DOX332, DOD-003, MCD-037, MCD-045, MCD-052 MCD-053, MCD-065 and MCD-058 is high. In some embodiments application with one or more of topical DOX331, DOX332, DOD-003, MCD-037, MCD-045, MCD-052 MCD-053, MCD-065 and MCD-058 can improve patients' quality of life In some embodiments, other tetracycline antibiotic formulations (such as DOX331, DOX332, DOD-003, MCD-037, MCD-045, MCD-052 MCD-053, MCD-065 and MCD-058) are safe and well-tolerated in the subjects having rosacea. In some embodiments no systemic drug-related adverse events are recorded.

The compositions and methods provided herein are described with reference to the following examples, in a non-limiting manner. The following examples exemplify the foamable compositions and methods described herein. The examples are for the purposes of illustration only and are not intended to be limiting. Many variations will suggest themselves and are within the full intended scope.

EXAMPLES

In one or more embodiments, the amounts in the examples should be read with the prefix "about."
As used herein, the term "NM" means not measured.
Exemplary Ingredients Suitable for the Production of Foamable Compositions

| Chemical Name | Function | Commercial Name | Supplier |
| --- | --- | --- | --- |
| Beeswax white | Foam Stabilizer | Beeswax white | STRAHL & PITSCH, Inc. |
| Behenyl alcohol | Foam Stabilizer | Lanette 22 | BASF |
| Cetostearyl alcohol | Foam Stabilizer | Kolliwax ® CSA 50 | BASF |
| Coconut oil | Carrier | Coconut oil | Henry Lamotte |
| Cyclomethicone-5 | Carrier | ST-cyclomethicone-5 | Dow |
| Hydrogenated castor oil | Foam Stabilizer | Kolliwax ® HCO | BASF |
| Light Mineral Oil | Carrier | Pionier 2076P Light Mineral Oil 15 | Hansen & Rosenthal Columbia Petro Chem PVT.LTD. |
| Minocycline HCl | Active agent | Minocycline HCl | Hovione |
| Myristyl alcohol | Foam Stabilizer | Kolliwax ® MA | BASF |
| Propane/Isobutane/Butane (55:18:27) | Propellant | AP-70 | Aeropress |
| Soybean oil | Carrier | Soybean oil | Henry Lamotte |
| Stearic acid | Foam Stabilizer | Kolliwax ® S Fine | BASF |
| Stearyl Alcohol | Foam Stabilizer | Kolliwax ® SA | BASF |

Example 1

General Manufacturing Procedures for a Gel or a Foam

The following procedures were used to produce gel or foam samples, in which only the steps relevant to each formulation were performed depending on the type and nature of ingredients used.

Step 1: Hydrophobic solvents such as mineral oils are mixed at room temperature. Others solvents such as silicones, if present, are added at room temperature under mixing until formulation homogeneity is obtained.

Step 2: The formulation is warmed to 70-80° C. or 80-90° C. and solid compounds such as fatty alcohols, fatty acids and waxes are added and mixed until complete dissolution.

Step 3: The formulation is cooled down to 30-40° C. Silica dioxide ($SiO_2$), if present, and active agents such as tetracyclines are added under mixing until formulation homogeneity is obtained.

Step 4: For gel compositions, the formulation is packaged in suitable containers. For foamable compositions, the formulation is packaged in aerosol canisters which are crimped with a valve, pressurized with propellant and equipped with an actuator suitable for foam dispensing. Optionally, a metered dosage unit can is utilized to achieve delivery of desirable and/or repeatable measured doses of foam.

Step 5: For foamable compositions, pressurizing is carried out using a hydrocarbon gas or gas mixture. Canisters are filled and then warmed for 30 seconds in a warm bath at 50° C. and well shaken immediately thereafter.

Step 6: The canisters or containers are labeled.

Example 2

General Manufacturing Procedures for a Gel or a Foam

The following procedures are used to produce gel or foam samples, in which only the steps relevant to each formulation are performed depending on the type and nature of ingredients used.

Step 1: Hydrophobic solvents and solid compounds such as fatty alcohols, fatty acids and waxes are mixed and heated to a temperature sufficient to achieve complete dissolution.

Step 2: The formulation is cooled down to 35-40° C., sensitive components such as silica dioxide ($SiO_2$), if present, cyclomethicone and sensitive active agents such as tetracyclines are added under mixing until formulation homogeneity is obtained.

Step 3: The formulation is cooled down to room temperature.

Step 4: For gel compositions, the formulation is packaged in suitable containers. For foamable compositions, the formulation is packaged in aerosol canisters which are crimped with a valve, pressurized with propellant and equipped with an actuator suitable for foam dispensing.

Step 5: For foamable compositions, pressurizing is carried out using a hydrocarbon gas or gas mixture. The canisters or containers are labeled.

In one or more embodiments, part of the hydrophobic solvents are added during the cooling process of the formulation (step 2).

In one or more embodiments, one of more of the formulation mixing steps can be done with or without vacuum and in the presence or absence of air, or an inert gas. For example, in an embodiment, one or more steps are done under vacuum, in the absence of air under an inert gas.

In one or more embodiments, likewise packaging in canisters can be done with or without vacuum and in the presence or absence of air, or an inert gas.

Example 3

Clinical Study Phase II (1.5% or 3% Minocycline Foam)

Study Title:
A Randomized, Multicenter, Double-blind, Vehicle-controlled Study to Evaluate the Safety and Efficacy of two Different Doses of a Topical Minocycline Foam Compared to Vehicle in the Treatment of Papulopustular Rosacea.

Study Synopsis:
In this example, topical administration of tetracycline (for example minocycline) is studied and the safety and efficacy of two different doses of minocycline foam compared to vehicle foam are evaluated in the treatment of moderate-to-severe papulopustular rosacea.

Objectives:
The primary objective of the study is to evaluate the efficacy of two different doses of FMX-103 minocycline foam compared to vehicle foam in subjects with moderate-to-severe papulopustular rosacea. The secondary objectives of the study are (a) to determine the relationship between the concentration(s) of topical minocycline foam and treatment response, (b) sensitivity analyses of efficacy of two different doses of FMX-103 minocycline foam compared to vehicle foam in subjects with moderate-to-severe papulopustular rosacea, and (c) to evaluate the safety and tolerability of topical minocycline foam applied daily for 12 weeks.

Study Medication:
Table 2. FMX103 Minocycline (3% and 1.5%) and placebo foamable compositions without silicone dioxide ($SiO_2$), as described in Table 4.

Dosage:

| | |
|---|---|
| Dosage form description | Foam containing minocycline, 1.5% and 3% Vehicle foam (0%) |
| Package description | Canisters, each containing 35gr of the clinical trial supply foam either: vehicle; FMX-103 1.5% minocycline foam; or FMX-103 3% minocycline foam |
| Daily dose | Once daily application of a small amount of study drug (a diameter of a one cent coin/~1.5 cm) onto fingertip to cover the entire face. Estimated maximum is 0.5 gr of the foam containing 7.5 (1.5%) or 15 (3%) mg of minocycline |
| Cumulative maximal dose for dosing (12 weeks) | 630 mg (1.5%) or 1,260 mg (3%) |
| Dispensing | 1 canister containing 35 g of the FMX-103 minocycline formulation, 1.5% or 3% or vehicle dispensed at Visit 2 (Baseline), Visit 4, Visit 5, and optionally at other visits if required. |

Indication:
Papulopustular rosacea.

Design:
A randomized, multicenter, double-blind, vehicle-controlled study assessing 232 male or non-pregnant female subjects aged greater than or equal to 18 years with a clinical diagnosis of moderate-to-severe papulopustular rosacea for at least 6 months, with at least 12 inflammatory facial lesions (i.e., papules/pustules).

Patients:
The study enrolls 210 male or female patients (approximately 70 subjects per arm: control, 1.5% and 3% minocycline) at approximately 14-16 sites in Germany who meet all of the inclusion criteria (Table 1) and none of the exclusion criteria (Table 2).

TABLE 1

| Inclusion criteria |
|---|
| ≥18 years-of-age with moderate-to-severe rosacea (as per IGA) on the proposed facial treatment. area consisting at least 12 facial papules or pustules excluding papule and pustule s involving the eyes and scalp. Diagnosed with rosacea for at least 6 months prior to screening Women of child-bearing potential must have a negative serum pregnancy test and agree to use a highly effective method of contraception. Willing to minimize external factors that might trigger rosacea flare-ups (e.g., spicy foods, thermally hot foods and drinks, hot environments, prolonged sun exposure and extensive alcoholic beverages). Subjects who use make-up must have used the same brands/types of make-up for a minimum period of 14 days prior to study entry and must agree to use the same make-up, brand/type, or frequency of use, throughout the study. Completed and signed an appropriately administered Informed Consent Form (ICF) prior to any study-related procedures. |

TABLE 2

Exclusion Criteria

Pregnancy or breastfeeding.
Any skin condition on the face that would interfere with the diagnosis or assessment of rosacea.
Moderate or severe rhinophyma, dense telangiectasis (score 3, severe), or plaque-like facial edema.
An active nodule on the face >5 mm in diameter.
Excessive facial hair.
History of hypersensitivity or allergy to minocycline, any other tetracycline or any other component of the formulation.
Severe irritation grade for erythema, dryness, scaling, pruritus, stinging/burning, and edema.
Rosacea conglobata or fulminans, corticosteroid-induced rosacea or isolated pustulosis of the chin, facial erythrosis of known origin other than rosacea (e.g., known carcinoid syndrome).
Ocular rosacea (e.g., conjunctivitis, blepharitis, or keratitis)
Use within 6 months prior to baseline of oral retinoids.
Woman of childbearing potential who has used a highly effective method of contraception for less than 3 months prior to baseline.
Use within 1 month prior to baseline of topical retinoids to the face or systemic antibiotics known to have an impact on the severity of papulopustular rosacea or systemic corticosteroids or methoxyflurane.
Use within 2 weeks prior to baseline of: topical corticosteroids, or topical antibiotics in the head and neck area; topical medications for rosacea.
Wax epilation of the face within 2 weeks prior to Baseline and during the study.
use of sauna during the 2 weeks prior to Baseline and during the study.
Bacterial folliculitis.
Alcohol or drug abuse
Excessive or prolonged exposure to weather extremes
Any other clinically significant condition or situation that may interfere with the study evaluations
Uncontrolled/instable relevant arterial hypertension
Participating in another investigational drug study within 30 days prior to Baseline
Previously enrolled in the FX2015-10 study
Prior laser therapy to the facial area within 3 months prior to Baseline.
Prior cosmetic procedures which may affect the efficacy and safety profile within 2 weeks prior to Baseline

Clinical Study Design

Eligible subjects are assigned to 1 of 3 treatments (vehicle, 1.5% and 3% minocycline) at 1:1:1 ratio according to the randomization schedule. Subjects are to apply the study drug topically once daily for 12 weeks as directed. Subjects are advised to use the study drug at approximately the same times each day in the evening. Both the investigator and subject are blinded to the study drug identity.

Subjects return for visits at Weeks, 2, 4, 8, 12, and 16. Efficacy evaluations (Investigator's Global Assessment [IGA] score and inflammatory papule and pustule counts) are performed at Weeks, 2, 4, 8, and 12 during the study, with an additional safety follow-up visit at week 16. Other assessments are performed as described in the Study Flow Chart (Table 3).

The dosing regimen is the same for all treatment groups. All patients receive at Screening Visit a guideline with detailed instructions on how to apply the medication correctly. In addition, patients are asked at each study visit about their medication application to assure a correct use of study medication.

Study drug kits are dispensed at Visit 2 (Baseline), Visit 4 (Week 4), Visit 5 (Week 8), and optionally at other/unscheduled visits if required for continuous dosing.

A small amount of study drug (a diameter of a one-cent coin) should be expressed from the canister onto the thoroughly washed finger tips and then applied topically as a thin layer over all parts of the face.

TABLE 3

Study Flow Chart

| Assessment | Screening | Baseline[a] | Visits | | | Final main protocol Visit[b] | Follow up visit[f] |
|---|---|---|---|---|---|---|---|
| Visit | 1 | 2 | 3 | 4 | 5 | 6 | 7 |
| Week | | | 2 | 4 | 8 | 12 | 16 |
| | | | −3/+5 d | −3/+5 d | −3/+5 d | −3/+5 d | −3/+5 d |
| Informed Consent | X | | | | | | |
| Demographic Data | X | | | | | | |
| Assign subject identification | X | | | | | | |
| Medical/Surgical/Medication History | X | | | | | | |
| Inclusion/Exclusion criteria | X | X | | | | | |
| Physical Exam, height, weight[c] | | X | | | | X | |
| Blood Pressure/heart rate[d] | X | X | X | X | X | X | |
| Blood and urine samples for clinical laboratory tests | X | | | | | X | |
| Urine pregnancy test (females only) | | X | X | X | X | | |
| Serum pregnancy test (females only) | X | | | | | X | |
| Papule and pustule Count | X | X | X | X | X | X | |
| Investigator's Global Assessment | X | X | X | X | X | X | |
| Modified IGA | X | X | X | X | X | X | |
| RosaQoL assessment | | X | | | | X | |
| Randomization | | X | | | | | |
| Photography of face | | X | X | X | X | X | |
| Concomitant Medication | X | X | X | X | X | X | |
| Adverse Events | | X | X | X | X | X | X |
| Local safety assessments | | X | X | X | X | X | |
| Assessments of erythema | X | X | X | X | X | X | |

TABLE 3-continued

Study Flow Chart

| Assessment | Screening | Baseline[a] | Visits | | | Final main protocol Visit[b] | Follow up visit[f] |
|---|---|---|---|---|---|---|---|
| Perform drug accountability | | | X[e] | X | X | X | |
| Collect empty drug canister(s) | | | | X | X | X | |
| Dispense Study Drug | | X | | X | X | | |
| Handout of Patient's Guidelines | X | | | | | | |
| Schedule/Confirm Next Visit | X | X | X | X | X | X | |

[a]Baseline must occur within 6 weeks of screening. Blood results must not show clinically significant abnormalities.
[b]If a subject prematurely withdraws from the study, all evaluations described under Visit 6/Week 12 must be performed.
[c]Height to be measured only at Baseline.
[d]Measure blood pressure and heart rate after the subject has been sitting for at least 5 minutes at rest.
[e]The canister of study drug has to be weighed and given back to the patient.
[f]If patient is unable to come to the visit there should be at least a follow-up phone call.

Efficacy

The efficacy assessments include the lesion counts and IGA at Baseline and Weeks 2, 4, 8, and 12. The primary efficacy endpoint is the absolute change in inflammatory lesion count at Week 12 compared to Baseline. Lesion count is performed by the investigator. The number of papules, pustules and nodules are counted and the numbers recorded. The facial area lesion counts are made for the forehead, left and right cheeks, nose and chin at each visit.

Secondary Efficacy Assessments are performed by the investigator who assesses the global severity of rosacea at Screening, Baseline, Weeks 2, 4, 8, and 12 by grading the severity on a 0-4 scale, with score 0 corresponding to "clear", and score 1 corresponding to "almost clear". Severity Assessment of other Rosacea Criteria will include grading Erythema of the face on a 0-4 scale, patient self-grading of Rosacea quality of life index (RosaQoL), and evaluation of standardized photographs.

Patient Demographics:

Patient demographics can include the individuals with diverse group, gender, height, weight and body mass index (BMI).

Statistical Methodology

All statistical analyses are performed using SAS® software version 9.3 (or higher). Descriptive statistics for qualitative variables (e.g., race) include the number and percentage of subjects with the qualitative response. For quantitative variables (e.g., age), descriptive statistics include the number of subjects with non-missing data, mean, standard deviation, median, and minimum and maximum values. All hypothesis testing is conducted using two-sided tests with $\alpha=0.05$ level of significance. Each minocycline dose group are compared to vehicle, however, the primary comparison is the minocycline 3% treatment group versus the vehicle treatment group.

The Intent-to-treat (ITT) analysis population includes all randomized subjects. The ITT population is primary for all efficacy analyses.

The Per-protocol (PP) population includes all subjects in the ITT population who had at least one post-Baseline assessment, and are without any other major deviations from the protocol that can have an impact on the efficacy assessments and subjects are analyzed as treated. The PP population is secondary for all efficacy analyses.

The Safety population includes all randomized subjects who received at least one application of study medication. Subjects who have no post-Baseline assessments are included in the Safety population unless all dispensed study drug is returned. All safety analyses are performed on the Safety population.

Clinical Response to Treatment Escape Criteria (for Success and Failure):

Success

The primary efficacy endpoint is the absolute change in inflammatory lesion count at Week 12 compared to Baseline.

The secondary efficacy endpoints are, hierarchically: the dichotomized IGA score where success is defined as a two-step drop in score at Week 12 compared to Baseline; the dichotomized IGA score where success is defined as a two-step drop resulting in a 0 or 1 score at Week 12 compared to Baseline; percent change in inflammatory lesion count at Week 12 compared to Baseline; the dichotomized mIGA score where success is defined as a two-step drop resulting in a 0 or 1 score at Week 12 compared to Baseline.

The null hypotheses of the equality of each active treatment mean to the vehicle treatment mean for absolute change from Baseline to Week 12 in the inflammatory lesion count is tested using an Analysis of Covariance (ANCOVA) with treatment as a main effect, investigational site as a blocking factor, and Baseline inflammatory lesion count as a (linear) covariate. Treatment by (pooled) investigational site interaction is tested separately at 0.1 level of significance. The primary comparison is between the 3% minocycline treatment group and vehicle. Secondary comparison is made between the 1.5% minocycline treatment group and vehicle. The assumptions of normality and homogeneity of variance from the ANCOVA model are tested at 0.05 level of significance.

This analysis is performed for the 3% minocycline group versus vehicle and, if significant, is repeated for the 1.5% minocycline group versus vehicle.

Secondary dichotomized endpoints of IGA success rates at Week 12 are tested using Cochran-Mantel-Haenszel (CMH) test (row mean scores) stratified by investigational site. Comparisons of 3% minocycline versus vehicle and 1.5% minocycline versus vehicle are done using only data from the pair of treatments being compared. Continuous endpoints are analyzed using an ANCOVA model with treatment as a main effect, Baseline and (pooled) investigational site as covariates.

Other secondary endpoints are tested in the order listed above, where the 3% minocycline is compared to vehicle, then the 1.5% minocycline is compared to vehicle on the same secondary endpoint.

Sub-group analyses by gender, age (18-30, 31-50, >50), Baseline lesion count (≤34, 35-75). Other cut-off by baseline lesion counts may be explored. Other important demographic and baseline characteristics sub-groups analyses are conducted. Summaries of primary and important secondary endpoints are done by investigational site.

Safety Tolerability and Adverse Events

The safety assessments in this study are standard safety measures in clinical studies, including physical examinations, vital signs (blood pressure, heart rate), local safety assessment scores (telangiectasis, burning/stinging, and flushing/blushing), questioning on Adverse events (AEs) and serious AEs (SAES) (volunteered, observed, and elicited by general questioning), and clinical laboratory test results (serum chemistry, hematology, urinalysis). The severity of each of the following signs/symptoms is measured by an investigator at Baseline and at Weeks 2, 4, 8 and 12: telangiectasis, burning/stinging, and flushing/blushing, all scored on a 1-5 scale. The score for signs is determined by the investigator and must represent the subject's condition at the time of the evaluation. The score for symptoms, burning/stinging and flushing/blushing, should be scored based on the subject's symptoms reported for the previous three days.

A complete relevant medical and surgical history is obtained at Screening Visit, which will include diseases of the head, ears, eyes, nose and throat, respiratory diseases, cardiovascular diseases, gastrointestinal diseases, hepatic diseases, genitourinary diseases, musculoskeletal diseases, endocrine diseases, neurological diseases, psychiatric diseases, skin diseases, allergies, hematological diseases, and other abnormalities.

Other safety evaluation points will include a history of medication usage (including previous use of acne medications and non-medication therapies) and all medication that the subject is currently taking or any change in medication or dosage since the last visit are documented throughout the study.

Safety assessments will include recording adverse events (AEs) reported spontaneously by the subject or observed by the investigator. An Adverse Event (AE) is any unfavorable or unintended sign, symptom, or disease that appears or worsens in a subject after the subject signs the ICF (and/or Assent Form) for a clinical study. AEs are recorded at each visit throughout the study on the appropriate CRF.

In one or more embodiments, similar clinical studies can be conducted for any tetracycline formulations described herein, such as DOX331, DOX332, DOD-003, MCD-037, MCD-045, MCD-052 MCD-053, MCD-065 and MCD-058.

Compositions

The below compositions, for use in the clinical study, are prepared according to the manufacturing procedures detailed in Example 1.

TABLE 4

FMX103 Minocycline (3% and 1.5%) and placebo Foamable compositions without silicone dioxide (SiO$_2$)

| | CAS Number | 3% Minocycline Quantitative Composition (% w/w) | 1.5% Minocycline Quantitative Composition (% w/w) | Placebo Quantitative Composition (% w/w) |
|---|---|---|---|---|
| Minocycline HCl (expressed as minocycline) | 13614987 | 3.00$^a$ | 1.50$^a$ | — |
| Soybean Oil | 8001227 | 50.00 | 50.00 | 50.00 |
| Coconut Oil | 8001318 | 23.60 | 23.60 | 23.60 |
| Light Mineral Oil | 8012951 | 2.14-2.48$^b$ | 3.97-4.14$^b$ | 5.80 |
| Cyclomethicone | 69430246 | 5.00 | 5.00 | 5.00 |
| Cetostearyl Alcohol | 67762270 | 3.50 | 3.50 | 3.50 |
| Stearic Acid | 57114 | 3.00 | 3.00 | 3.00 |
| Myristyl Alcohol | 112721 | 2.50 | 2.50 | 2.50 |
| Hydrogenated Castor Oil | 8001783 | 2.00 | 2.00 | 2.00 |
| White Wax (Beeswax) | 8012893 | 2.00 | 2.00 | 2.00 |
| Stearyl Alcohol | 112925 | 1.50 | 1.50 | 1.50 |
| Docosanol (Behenyl alcohol) | 661198 | 1.10 | 1.10 | 1.10 |
| Total Bulk | | 100.00 | 100.00 | 100.00 |
| AP-70 (butane, isobutane and propane)$^c$ | 106978 | 12.0 | 12.0 | 12.0 |
| butane | 75285 | | | |
| isobutane | 74986 | | | |
| propane | | | | |

$^a$The amount of minocycline hydrochloride is adjusted by the potency of the minocycline hydrochloride.
$^b$The amount of light mineral oil in the formulation is adjusted based on the amount of minocycline hydrochloride. For example, if the potency of minocycline is 100%, then the amount of minocycline hydrochloride is 3% and amount of the mineral oil is 2.8% or then the amount of minocycline hydrochloride is 1.5% and amount of the mineral oil is 4.3%.
$^c$AP-70 (CAS # 6847-86-8) is a mixture of about 27% w/w butane, 18% w/w isobutane and 55% w/w propane.

TABLE 5A

Formulations of 1% Minocycline and 4% Minocycline with SiO$_2$

| | Formulations | |
|---|---|---|
| Ingredients | 244B (FXFM244-1%) (1% Minocycline) % w/w | 244A (FXFM244-4%) (4% Minocycline) % w/w |
| Light Mineral oil | 4.44 | 1.11 |
| Cyclomethicone | 5.00 | 5.00 |
| Coconut oil | 23.60 | 23.60 |
| Soybean oil | 50.00 | 50.00 |
| Hydrogenated castor oil | 2.00 | 2.00 |
| Beeswax | 2.00 | 2.00 |
| Myristyl alcohol | 2.50 | 2.50 |
| Cetostearyl alcohol | 3.50 | 3.50 |
| Stearyl alcohol | 1.50 | 1.50 |
| Behenyl alcohol | 1.10 | 1.10 |
| Fumed Silica (SiO$_2$) | 0.25 | 0.25 |

TABLE 5A-continued

Formulations of 1% Minocycline and 4% Minocycline with SiO$_2$

| | Formulations | |
|---|---|---|
| Ingredients | 244B (FXFM244-1%) (1% Minocycline) % w/w | 244A (FXFM244-4%) (4% Minocycline) % w/w |
| Stearic acid | 3.00 | 3.00 |
| Minocycline HCl (micronized) (90% potency) | 1.11 | 4.44 |
| Total | 100 | 100 |
| Propellant AP-70 | 12.00 | 12.00 |

TABLE 5B

Formulations of 1% Minocycline and 4% Minocycline without SiO$_2$ (FMX-101 Foam).

| Component | FMX-101 (4%) FOAM Quantitative Composition (% w/w) | FMX-101 (1%) FOAM Quantitative Composition (% w/w) |
|---|---|---|
| Minocycline Hydrochloride (micronized) (expressed as minocycline) | 4.00$^a$ | 1.00$^a$ |
| Soybean Oil | 50.00 | 50.00 |
| Coconut Oil | 23.60 | 23.60 |
| Light Mineral Oil | 0.91-1.37$^b$ | 4.58-4.69$^b$ |
| Cyclomethicone | 5.00 | 5.00 |
| Cetostearyl Alcohol | 3.50 | 3.50 |
| Stearic Acid | 3.00 | 3.00 |
| Myristyl Alcohol | 2.50 | 2.50 |
| Hydrogenated Castor Oil | 2.00 | 2.00 |
| White Wax (Beeswax) | 2.00 | 2.00 |
| Stearyl Alcohol | 1.50 | 1.50 |
| Docosanol (behenyl alcohol) | 1.10 | 1.10 |
| Total Bulk | 100 | 100 |
| AP-70 (butane + isobutane + propane)$^c$ | 12.0 | 12.0 |

$^a$The amount of minocycline hydrochloride is adjusted by the potency of the minocycline hydrochloride.
$^b$The amount of light mineral oil in the formulation is adjusted based on the amount of minocycline hydrochloride. For example if the potency of minocycline is 100%, then the amount of minocycline hydrochloride is 4% and amount of the mineral oil is 1.8% or then the amount of minocycline hydrochloride is 1% and amount of the mineral oil is 4.8%.
$^c$AP-70 (CAS # 6847-86-8) is a mixture of about 27% w/w butane, 18% w/w isobutene and 55% w/w propane.

TABLE 5C

Formulation of DOX-244B with SiO$_2$

| Ingredient Name | % W/W |
|---|---|
| Coconut oil | 23.60 |
| Mineral oil light | 4.35 |
| soybean oil | 50.00 |
| stearic acid | 3.00 |
| behenyl alcohol | 1.10 |
| hydrogenated castor oil | 2.00 |
| Beeswax | 2.00 |
| Stearyl alcohol | 1.50 |
| Cetostearyl alcohol | 3.50 |
| Myristyl alcohol | 2.50 |
| Cyclomethicone | 5.00 |
| Silicon dioxide | 0.25 |
| Doxycycline Hyclate (micronized) | 1.20 |

TABLE 5D

Formulation of FDX104 and placebo without SiO$_2$

| Component | FDX-104 4% FOAM Quantitative Composition (% w/w) | FDX-104 Placebo FOAM Quantitative Composition (% w/w) |
|---|---|---|
| Doxycycline hyclate (micronized) (expressed as doxycycline) | 4.00$^a$ | — |
| Soybean Oil | 50.00 | 50.00 |
| Coconut Oil | 23.60 | 23.60 |
| Light Mineral Oil | 0.95-1.21$^b$ | 5.80 |
| Cyclomethicone | 5.00 | 5.00 |
| Cetostearyl Alcohol | 3.50 | 3.50 |
| Stearic Acid | 3.00 | 3.00 |
| Myristyl Alcohol | 2.50 | 2.50 |
| Hydrogenated Castor Oil | 2.00 | 2.00 |
| White Wax (Beeswax) | 2.00 | 2.00 |
| Stearyl Alcohol | 1.50 | 1.50 |
| Docosanol | 1.10 | 1.10 |
| Total Bulk | 100 | 100 |
| AP-70 (butane + isobutane + propane)$^c$ | 12.0 | 12.0 |

$^a$The amount of doxycycline hyclate is adjusted by the potency of the doxycycline hyclate.
$^b$The amount of light mineral oil in the formulation is adjusted based on the amount of doxycycline hyclate. For example if the potency of doxycycline is 100%, then the amount of doxycycline hyclate is 4% and amount of the mineral oil is 1.8%.
$^c$AP-70 (CAS # 6847-86-8) is a mixture of about 27% w/w butane, 18% w/w isobutene and 55% w/w propane.

TABLE 5E

Formulations of DOX331 and DOX332 without SiO$_2$

| | Formulations | |
|---|---|---|
| Ingredient | DOX331 % w/w | DOX332 % w/w |
| Mineral oil, heavy* | 82.24 | 88.24 |
| Mineral oil, light | 5.00 | — |
| Stearyl alcohol | 4.50 | 3.70 |
| Stearic acid | 2.50 | 2.50 |
| Behenyl alcohol | 1.10 | 0.70 |
| Paraffin 51-53 | — | 0.20 |
| doxycycline hyclate (micronized)** | 4.66 | 4.66 |
| Total | 100.00 | 100.00 |
| AP-70 | 12% | 12% |

*The amount of heavy mineral oil in the formulation is adjusted based on the mount of doxycycline hyclate.
**The amount of doxycycline hyclate is adjusted by the potency of the doxycycline hyclate.

TABLE 5F

Formulation of Doxycycline and adapalene without SiO$_2$

| | Formulations DOD-003 |
|---|---|
| Ingredient | % w/w |
| Mineral oil heavy* | 81.94 |
| Mineral oil light | 5 |
| Stearyl alcohol | 4.5 |

TABLE 5F-continued

Formulation of Doxycycline and adapalene without SiO$_2$

| Ingredient | Formulations DOD-003 % w/w |
|---|---|
| Stearic acid | 2.5 |
| Behenyl alcohol | 1.1 |
| Doxycycline hyclate (micronized)** | 4.66 |
| Adapalene | 0.3 |
| Total | 100 |
| AP-70 | 12% |

*The amount of heavy mineral oil in the formulation is adjusted based on the amount of doxycycline hyclate.
**The amount of doxycycline hyclate is adjusted by the potency of the doxycycline hyclate.

TABLE 5G

Formulations of Minocycline and adapalene without SiO$_2$

| Component | MCD-037 | MCD-045 | MCD-052 | MCD-053 | MCD-058 |
|---|---|---|---|---|---|
| Mineral oil "heavy"* | 82.00 | 88.60 | | 49.00 | 43.40 |
| Mineral oil light* | 5.00 | | 0.70 | 39.00 | 39.00 |
| Myristyl alcohol | | | 2.50 | | |
| Cetostearyl alcohol | | | 3.50 | | |
| Stearyl alcohol | 4.50 | 3.60 | 1.50 | 3.80 | 4.30 |
| Stearic acid | 2.50 | 2.40 | 3.00 | 2.40 | 2.50 |
| Cyclomethicone 5 | | | 5.00 | | 5.00 |
| Coconut oil | | | 23.60 | | |
| Soybean oil | | | 50.00 | | |
| Behenyl alcohol | 1.10 | 0.50 | 1.10 | 0.70 | 0.70 |
| Beeswax | | | 2.00 | | |
| Hydrogenated castor oil | | | 2.00 | | |
| MCH (micronized)** | 4.80 | 4.80 | 4.80 | 4.80 | 4.80 |
| Adapalene | 0.10 | 0.10 | 0.30 | 0.30 | 0.30 |
| Total | 100.00 | 100.00 | 100.00 | 100.00 | 100.00 |
| AP-70 | 12% | 12% | 12% | 12% | 12% |

*The amount of heavy mineral oil or light mineral oil in the formulation is adjusted based on the amount of Minocycline hydrochloride.
**The amount of minocycline hydrochloride is adjusted by the potency of the minocycline hydrochloride.

TABLE 5H

Formulation of Minocycline with fatty alcohol without SiO$_2$

| Component | MCD-065 |
|---|---|
| Mineral oil light* | 45.55 |
| Stearyl alcohol | 4.00 |
| Soybean oil | 45.05 |
| Behenyl alcohol | 0.60 |
| MCH (micronized)** | 4.80 |
| Total | 100.00 |
| AP-70 | 12% |
| Foam quality | G |

*The amount of light mineral oil in the formulation is adjusted based on the amount of Minocycline hydrochloride.
**The amount of minocycline hydrochloride is adjusted by the potency of the minocycline hydrochloride.

All inactive ingredients used in the formulation are intended for topical use and listed in the current FDA Inactive Ingredient Database; concentrations used do not exceed the maximum concentrations given in Database.

Example 4

Chemical and Physical Stability

The achievement of a long term stable foamable formulation of tetracycline antibiotics described herein, was a major challenge and required both extensive research and creativity.

The chemical and physical stability results of minocycline HCl (MCH) and doxycycline hyclate ("DOX") in SiO$_2$-containing oleaginous formulations, MCH244 and DOX244, respectively, are described in U.S. application Ser. No. 14/147,376 (U.S. Pub. No. 2014/0121188) and incorporated by reference herein. In an accelerated stability study, samples were stored at 40° C., and the concentrations of minocycline HCl and doxycycline hyclate were determined by UPLC. Stability test for MCH244 results following 2 months, 3 months, 6 months, 9 months, 12 months, 18 months, and 24 months of storage are shown herein below.

The following examples illustrate the chemical stability of minocycline HCl ("MCH") and doxycycline hyclate ("DOX") in oleaginous formulations, as described in Tables 6, 7, and 9-11 below. In an accelerated stability study, samples were stored at 40° C., and the concentrations of minocycline HCl and doxycycline hyclate were determined by UPLC. The stability test results following 2 months, 3 months, 6 months, 9 months, 12 months, and 18 months of storage are shown herein below.

Samples of MCH244 and DOX244 1% and 4% were stored at 25° C. and 40° C. in order to test physical and chemical stability.

Inspection of Formulation in Glass Bottles

The use of pressurized glass bottles enables the inspection of formulations for homogeneity in the presence of propellant. Following 18 months of storage at 25° C. the formulation was found to be re-dispersible, i.e., homogeneous following slight shaking.

Stability Following Storage at 25° C. and 40° C.

Storage at 25° C. and 40° C. for 18 months revealed almost no change in the Minocycline concentration. Test results for chemical stability of minocycline following storage for up to 18 months at 25° C. and 40° C. are summarized in Table 6 and Table 7. There was practically no degradation of 244 1% and 4% minocycline following 18 months at 25° C. and also following 9 months at 40° C. These stability results indicate shelf life of more than two years at ambient temperature. Test results for chemical stability of doxycycline following storage for up to 9 months at 25° C. and 40° C. are summarized in Tables 9-11. There was practically no degradation of doxycycline following 6 months at 25° C. and at 40° C. These stability results likewise indicate a long shelf life of more than two years at ambient temperature. In one or more embodiments, the tetracycline composition has a shelf life of at least 6 months, or at least 9 months, or at least 12 months, or at least 15 months, or at least 18 months, or at least 21 months, or at least 24 months at ambient temperature. In one or more embodiments, the tetracycline composition has a shelf life of at least 6 months, or at least 9 months, or at least 12 months, or at least 15 months, or at least 18 months, or at least 21 months, or at least 24 months at 25° C. In one or more embodiments, the tetracycline composition has a shelf life of at least 1 month, or at least 3 months, or at least 6 months, or at least 9 months, or at least 12 months at 40° C.

TABLE 6

Minocycline content in MC11244 1% (with $SiO_2$) following storage for 18 months at 25° C. and 40° C.

| Temp | \multicolumn{6}{c}{Minocycline content (% w/w)} | | | | | |
|------|-------|-------|-------|-------|-------|-------|
| | T = 0 | 3M | 6M | 9M | 12M | 18M |
| 25° C. | 1.001 | NM | 0.986 | 1.007 | 0.972 | 0.959 |
| 40° C. | 1.001 | 1.002 | 0.983 | 0.965 | NM | NM |

NM = not measured

TABLE 7

Minocycline content in MC11244 4% following storage for 18 months at 25° C. and 40° C. (Lot MCH-244-100825) (with $SiO_2$)

| Temp | Minocycline content (% w/w) | | | | | |
|------|-------|-------|-------|-------|-------|-------|
| | T = 0 | 1M | 3M | 6M | 9M | 12M | 18M |
| 25° C. | 4.049 | NM | NM | 3.993 | 3.991 | 3.886 | 3.701 |
| 40° C. | 4.049 | 3.935 | 3.852 | 4.035 | 3.9137 | NM | NM |

Minocycline Physical Stability:

The results for physical stability following storage at 25° C. and 40° C. for 18 months were as follows:

Foam quality: Conformed to the foam quality specification following storage for 9 months at 40° C.

Odor: Conformed to the specifications and showed no odor following storage at 40° C. for 9 months.

Color: The color of the formulation remained light, slightly changed to grey-yellow following storage at 40° C. for 9 months. No change was observed at 25° C.

Shakeability: Conformed to specifications following storage at 40° C. for 9 months.

Density: No significant change in density was found after storage at 40° C. for 9 months.

Collapse time: No change in foam collapse time (the time for the foam to reach half of its initial height) was found in any of the formulation samples tested after storage for 9 months at 40° C.

Microscopic observations: No significant change in the microscopic appearance was noted following storage at 40° C. for 9 months.

Corrosion and deterioration: The coated aluminum surfaces of the can and valve and the plastic housing of the valve appeared fully intact and showed no signs of corrosion or deterioration. No changes in color or deformation were observed.

Doxycycline DOX-244B Physical and Chemical Stability:

The results for physical stability following storage at 25° C. for 18 months and for 24 months were as follows:

Foam quality: excellent.

Collapse time: At least 180 seconds.

Production: GMP Compliance.

For the purpose of clinical supplies, the production of the compositions was performed according to the principles of current good manufacturing practice (c-GMP). Production conditions were aimed to ensure high quality of the product and to prevent any potential cross contamination. The production site was certified by the Israel Ministry of Health as suitable for GMP production and supply of small clinical batches for Phase I and IIa clinical trials.

The below composition was prepared according to the manufacturing procedures detailed in Example 1.

TABLE 8

Formulation of DOX-244B-111123

| Ingredient Name | % W/W |
|---|---|
| Coconut oil | 23.60 |
| Mineral oil light | 4.35 |
| soybean oil | 50.00 |
| stearic acid | 3.00 |
| behenyl alcohol | 1.10 |
| hydrogenated castor oil | 2.00 |
| Beeswax | 2.00 |
| Stearyl alcohol | 1.50 |
| Cetostearyl alcohol | 3.50 |
| Myristyl alcohol | 2.50 |
| Cyclomethicone | 5.00 |
| Silicon dioxide | 0.25 |
| Doxycycline Hyclate (micronized) | 1.20 |

TABLE 9

Doxycycline content (%) in DOX-244B-111123 PF following storage for 9 months at 5° C., 25° C., 40° C., and 50° C.

| | Doxycycline content (% w/w) | | | | | | | |
|---|---|---|---|---|---|---|---|---|
| | T = 0 | 1M | | 2M | | 3M | | |
| Batch/Sample name | | 5° C. | 25° C. | 50° C. | 25° C. | 50° C. | 25° C. | 40° C. |
| DOX-244-111123 PF | 1.0220 | 1.031 | 1.022 | — | — | — | 1.010 | 1.031 |
| DOX-244-111123 PFF | 1.0800 | 1.098 | 1.080 | 1.060 | — | 1.045 | 1.082 | 1.046 |

| | Doxycycline content (% w/w) | | | | | |
|---|---|---|---|---|---|---|
| | 6M | | 9M | 12M | 18M | 24M |
| Batch/Sample name | 25° C. | 40° C. | 25° C. | 25° C. | 25° C. | 25° C. |
| DOX-244-111123 PF | 1.017 | 1.025 | 1.053 | 0.967 | 0.994 | 1.021 |
| DOX-244-111123 PFF | 1.046 | 1.028 | 1.091 | 1.044 | 1.018 | 1.051 |

TABLE 10

Stability of Doxycycline Foam at 25° C. and 40° C.
%[1] Doxycycline Hyclate in DOX244 foam product

| Months | 40° C. (foam) | 25° C. (foam) |
|---|---|---|
| 0 | 102.2 | 102.2 |
| 1 |  | 102.2 |
| 2 |  |  |
| 3 | 103.1 | 101.0 |
| 6 | 102.5 | 101.7 |
| 9 |  | 105.3 |
| 12 |  | 96.7 |
| 18 |  | 99.4 |
| 24 |  | 102.1 |

[1]The percentages are derived from the PF figures in Table 9. Note 1.2% doxycycline hyclate is equivalent to 1.0176%. doxycycline based on USP

TABLE 11

Degradation of Doxycycline at 5° C., 25° C., 40° C., and 50° C.

| Degradation product w/w | Batch/Sample name | DOX-244B-111123 PF | DOX-244B-111123 PFF |
|---|---|---|---|
| T0 | RRT 0.75 | 0.003 | 0.004 |
|  | RRT 0.85 | 0.010 | 0.011 |
| 1M | 5° C. RRT 0.75 | 0.003 | 0.003 |
|  | 5° C. RRT 0.85 | 0.010 | 0.010 |
|  | 25° C. RRT 0.75 | 0.003 | 0.003 |
|  | 25° C. RRT 0.85 | 0.010 | 0.010 |
|  | 50° C. RRT 0.75 | — | 0.003 |
|  | 50° C. RRT 0.85 | — | 0.01 |
| 2M | 50° C. RRT 0.75 | — | 0.003 |
|  | 50° C. RRT 0.85 | — | 0.009 |
| 3M | 25° C. RRT 0.75 | 0.003 | 0.004 |
|  | 25° C. RRT 0.85 | 0.01 | 0.011 |
|  | 40° C. RRT 0.75 | 0.003 | 0.003 |
|  | 40° C. RRT 0.85 | 0.01 | 0.01 |
| 6M | 25° C. RRT 0.75 | 0.003 | 0.003 |
|  | 25° C. RRT 0.85 | 0.01 | 0.01 |
|  | 40° C. RRT 0.75 | 0.003 | 0.003 |
|  | 40° C. RRT 0.85 | 0.01 | 0.01 |
| 9M | 25° C. RRT 0.75 | 0.003 | 0.003 |
|  | 25° C. RRT 0.85 | 0.009 | 0.01 |
| 12M | 25° C. RRT 0.75 | 0.003 | 0.003 |
|  | 25° C. RRT 0.85 | 0.009 | 0.009 |
| 18M | 25° C. RRT 0.75 | 0.003 | 0.003 |
|  | 25° C. RRT 0.85 | 0.009 | 0.009 |
| 24M | 25° C. RRT 0.75 | 0.003 | 0.003 |
|  | 25° C. RRT 0.85 | 0.009 | 0.009 |

TABLE 12

Appearance and Collapse time of Doxycycline at 25° C. and 40° C.

| Time Points | Appearance (25° C.) Quality | Appearance (40° C.) Quality | Collapse time (25° C.) Collapse time(sec) | Collapse time (25° C.) Time to FG(sec) | Collapse time (40° C.) Collapse time(sec) | Collapse time (40° C.) Time to FG(sec) |
|---|---|---|---|---|---|---|
| T0 | G | — | 100 | 150 | — | — |
| 3M | E | G | 115 | 90 | 165 | 90 |
| 6M | E | G | >180 | 120 | >180 | >180 |
| 9M | E | — | 150 | 120 | — | — |
| 12M | G | — | 105 | 120 | — | — |
| 18M | E | — | >180 | >180 | — | — |
| 24M | E | — | >180 | >180 | — | — |

Doxycycline DOX-330A-140331 (without SiO$_2$) physical and chemical stability:

The results for physical stability following storage at 25° C. for 9 months and for 12 months were as follows:

Foam quality: Excellent.

Collapse time: At least 180 seconds.

Production: GMP Compliance.

For the purpose of clinical supplies, the production of the compositions was performed according to the principles of current good manufacturing practice (c-GMP). Production conditions were aimed to ensure high quality of the product and to prevent any potential cross contamination. The production site was certified by the Israel Ministry of Health as suitable for GMP production and supply of small clinical batches for Phase I and IIa clinical trials.

The below composition was prepared according to the manufacturing procedures detailed in Example 1.

TABLE 13

Formulation of DOX-330A-140331 (FDX104 without SiO$_2$)

| Ingredient Name | % W/W |
|---|---|
| Coconut oil | 23.60 |
| Mineral oil light | 0.90 |
| soybean oil | 50.00 |
| stearic acid | 3.00 |
| behenyl alcohol | 1.10 |
| hydrogenated castor oil | 2.00 |
| Beeswax | 2.00 |
| Stearyl alcohol | 1.50 |
| Cetostearyl alcohol | 3.50 |
| Myristyl alcohol | 2.50 |
| Cyclomethicone | 5.00 |
| Doxycycline Hyclate (micronized) | 4.90 |

TABLE 14

Doxycycline % content in DOX-330A-140331 PF following storage for 12 months at 25° C. and 40° C.

| | T = 0 | 3w | 2M | | 3M | | 6M | 9M | 12M |
|---|---|---|---|---|---|---|---|---|---|
| Batch/Sample name | | 40° C. | 40° C. | 25° C. | 40° C. | 25° C. | 40° C. | 25° C. | 25° C. |
| DOX-330A-140331 PF | 4.032 | 3.984 | 3.981 | 4.086 | 3.942 | 4.086 | 4.088 | 3.993 | 4.032 |

TABLE 15

Stability of Doxycycline Foam Formulation without SiO$_2$ at 25° C. and 40° C.
%[2] Doxycycline Hyclate in DOX330 foam product

| Months | 40° C. (foam) | 25° C. (foam) |
|---|---|---|
| 0 | 100.8 | 100.8 |
| 0.75 | 99.6 | |
| 2 | 99.5 | |
| 3 | 98.6 | 102.2 |
| 6 | 102.2 | 102.2 |
| 9 | | 99.8 |
| 12 | | 100.8 |
| 18 | | |
| 24 | | |

[2]The percentages are derived from the PF figures in Table 14. Note 1.2% doxycycline hyclate is equivalent to 1.0176%. doxycycline based on USP

TABLE 16

Degradation of Doxycycline in Formulation without SiO$_2$ at 25° C. and 40° C.

| Degradation product w/w | Batch/Sample name | DOX-330A-140331 PF |
|---|---|---|
| T0 | RRT 0.85 | — |
| 3w | 40° C. RRT 0.85 | 0.017 |
| 2M | 40° C. RRT 0.85 | 0.014 |
| 3M | 25° C. RRT 0.85 | 0.016 |
| | 40° C. RRT 0.85 | 0.016 |
| 6M | 25° C. RRT 0.85 | 0.017 |
| | 40° C. RRT 0.85 | 0.017 |
| 9M | 25° C. 6-epi (RRT 0.85) | 0.020 |
| 12M | 25° C. 6-epi (RRT 0.85) | 0.0213 |

TABLE 17

Appearance and Collapse time of Doxycycline Foam Formulation without SiO$_2$ at 25° C. and 40° C.

| Time Points | Appearance (25° C.) Quality | Appearance (40° C.) Quality | Collapse time (25° C.) Collapse time(sec) | Collapse time (25° C.) Time to FG(sec) | Collapse time (40° C.) Collapse time(sec) | Collapse time (40° C.) Time to FG(sec) |
|---|---|---|---|---|---|---|
| T0 | E | — | 160 | >180 | — | — |
| 3W | — | E- falls a little | — | — | >180 | >180 |
| 2M | — | E | — | — | >180 | >180 |
| 3M | E | E | >180 | >180 | 180 | >180 |
| 6M | E | E | >180 | >180 | >180 | >180 |
| 9M | E | — | >180 | >180 | — | — |
| 12M | E | — | >180 | >180 | — | — |

Doxycycline physical and chemical stability in formulation without SiO$_2$:

The results for physical stability following storage at 25° C. for 9 months and for 6 months were as follows:

Foam quality: Excellent.

Odor: No odor

Collapse time: At least 120 seconds.

Production: GMP Compliance.

For the purpose of clinical supplies, the production of the compositions was performed according to the principles of current good manufacturing practice (c-GMP). Production conditions were aimed to ensure high quality of the product and to prevent any potential cross contamination. The production site was certified by the Israel Ministry of Health as suitable for GMP production and supply of small clinical batches for Phase I and IIa clinical trials.

The below composition was prepared according to the manufacturing procedures detailed in Example 1.

TABLE 18

Formulation of DOX-330A-140818 PF (FDX104)

| Ingredient Name | % W/W |
|---|---|
| Coconut oil | 23.60 |
| Mineral oil light | 1.13 |
| soybean oil | 50.00 |
| stearic acid | 3.00 |
| behenyl alcohol | 1.10 |
| hydrogenated castor oil | 2.00 |
| Beeswax | 2.00 |
| Stearyl alcohol | 1.50 |
| Cetostearyl alcohol | 3.50 |
| Myristyl alcohol | 2.50 |
| Cyclomethicone | 5.00 |
| Doxycycline Hyclate (micronized) | 4.67 |

TABLE 19

Doxycycline % content in DOX-330A-140818 (FDX104) PF without SiO₂ following storage for 9 months at 25° C. and 40° C.

| | Doxycycline content (% w/w) | | | | | | | |
|---|---|---|---|---|---|---|---|---|
| | T = 0 | 1M | 3M | | 6M | | 9M | 12M | 18M | 24M |
| Batch/Sample name | | 40° C. | 25° C. | 40° C. | 25° C. | 40° C. | 25° C. | 25° C. | 25° C | 25° C. |
| DOX-330A-140818 PF | 3.908 | 3.899 | 3.792 | 3.763 | 3.727 | 3.783 | 3.763 | | | |

TABLE 20

Stability of Doxycycline Foam at 25° C. and 40° C.
%[3] Doxycycline in DOX330 140818

| Months | 40° C. (foam) | 25° C. (foam) |
|---|---|---|
| 0 | 97.7 | 97.7 |
| 1 | 97.5 | |
| 3 | 94.1 | 94.8 |
| 6 | 94.6 | 93.2 |
| 9 | | 94.1 |
| 12 | | |
| 18 | | |
| 24 | | |

[3] The percentages are derived from the PF figures in Table 19. Note 1.2% doxycycline hyclate is equivalent to 1.0176%. doxycycline based on USP

TABLE 21

Degradation of Doxycycline at 25° C. and 40° C.

| Degradation product w/w | Batch/Sample name | DOX330 140818 |
|---|---|---|
| T = 0 | RRT 0.85 (6-epi) | 0.016 |
| 1M | 40° C. RRT 0.85 (6-epi) | 0.017 |
| 3M | 25° C. 6-epi | 0.019 |
| | 40° C. 6-epi | 0.019 |
| 6M | 25° C. 6-epi | 0.019 |
| | 40° C. 6-epi | 0.019 |
| 9M | 25° C. 6-epi | 0.019 |

TABLE 22

Appearance and Collapse time of Doxycycline at 25° C. and 40° C.

| Time Points | Appearance (25° C.) Quality | Appearance (40° C.) Quality | Collapse time (25° C.) Collapse time(sec) | Collapse time (25° C.) Time to FG(sec) | Collapse time (40° C.) Collapse time(sec) | Collapse time (40° C.) Time to FG(sec) |
|---|---|---|---|---|---|---|
| T0 | E | — | 155 | 180 | | |
| 1M | E | — | 90 | >180 | | |
| 3M | E | E | 180 | >180 | 150 | >180 |
| 6M | E | E | 180 | >180 | >180 | >180 |
| 9M | E | — | 120 | >180 | | |

Doxycycline and Adapalene DOD-003 Physical and Chemical Stability:

TABLE 23

Doxycycline % content in DOD-003 following storage for 1 month at 25° C., 40° C. and 60° C.

| | Doxycycline content (% w/w) | | | | | |
|---|---|---|---|---|---|---|
| | T = 0 | | | 1M | | |
| Batch/Sample name | 25° C./40° C. | 60° C. | | 25° C. | 40° C. | 60° C. |
| DOD-003 | 3.850 | 3.880 | | 3.949 | 3.860 | 3.824 |

TABLE 24

Stability of Doxycycline at 25° C., 40° C. and 60° C.
%[4] Doxycycline in DOD-003

| Months | 25° C. (foam) | 40° C. (foam) | 60° C. (Pre foam formulation) |
|---|---|---|---|
| 0 | 96.3 | 96.3 | 97.0 |
| 1 | 98.7 | 96.5 | 95.6 |

[4] The percentages are derived from the figures in Table 23.

TABLE 25

Degradation of Doxycycline at 25° C., 40° C. and 60° C.

| Degradation product w/w | Batch/Sample name | DOD-003 |
|---|---|---|
| T = 0 | 25° C. 6-epi | 0.021 |
| | 40° C. 6-epi | 0.021 |
| | 60° C. 6-epi | 0.022 |
| 1M | 25° C. 6-epi | 0.022 |
| | 40° C. 6-epi | 0.021 |
| | 60° C. 6-epi | 0.021 |

TABLE 26

Appearance, Collapse time and shakeability of Doxycycline at 25° C. and 40° C. in DOD-003

| Time | Appearance | | | Collapse time | | | | | |
|---|---|---|---|---|---|---|---|---|---|
| Pts | 25° C. Quality | 40° C. Quality | 60° C. Quality | 25° C. Collapse time (s) | 25° C. Time to FG (s) | 40° C. Collapse time (s) | 40° C. Time to FG (s) | 60° C. Collapse time (s) | 60° C. Time to FG (s) |
| T0 | E | E | NM | >180 | >180 | >180 | >180 | NM | NM |
| 1M | E | E | NM | >180 | 120 | >180 | 120 | NM | NM |

| Time Points | Shakeability (25° C.) | Shakeability (40° C.) | Shakeability (60° C.) |
|---|---|---|---|
| T0 | 2 | 2 | NM |
| 1M | 0 | 2 | NM |

[4]The percentages are derived from the figures in Table 23.

TABLE 27

Adapalene % content in DOD-003 following storage for 1 month at 25° C., 40° C. and 60° C.

| | Adapalene content (% w/w) | | | | | |
|---|---|---|---|---|---|---|
| Batch/Sample | T = 0 | | 1M | | | |
| name | 25° C./40° C. | 60° C. | 25° C. | 40° C. | 60° C. | |
| DOD-003 | 0.2948 | 0.2948 | 0.3030 | 0.2950 | 0.3076 | |

TABLE 28

Stability of Adapalene at 25° C., 40° C. and 60° C. %[5] Adapalene in DOD-003

| Months | 25° C. (foam) | 40° C. (foam) | 60° C. (Pre foam formulation) |
|---|---|---|---|
| 0 | 98.3 | 98.3 | 98.3 |
| 1 | 101.0 | 98.3 | 102.5 |

[5]The percentages are derived from the FIGURES in Table 27.

Minocycline and Adapalene MCD-037-160320 Physical and Chemical Stability:

TABLE 29

Minocycline % content in MCD-037-160320 following storage for 4 months at 25° C. and 40° C.

| | Minocycline content (% w/w) | | | | | | | | | |
|---|---|---|---|---|---|---|---|---|---|---|
| Batch/Sample | T = 0 | 1M | | 2M | | 3M | | 4M | | |
| name | 25° C./40° C. | 25° C. | 40° C. | 25° C. | 40° C. | 25° C. | 40° C. | 25° C. | 40° C. | |
| MCD-037-160320 | 3.89 | NM | 3.90 | NM | 4.03 | 3.88 | 3.89 | 3.99 | 3.95 | |

TABLE 30

Stability of Minocycline at 25° C. and 40° C. %[6] Minocycline in MCD-037-160320

| Months | 25° C. (foam) | 40° C. (foam) |
|---|---|---|
| 0 | 97.22 | 97.22 |
| 1 | NM | 97.62 |
| 2 | NM | 100.68 |
| 3 | 97.01 | 97.30 |
| 4 | 99.66 | 98.79 |

[6]The percentages are derived from the figures in Table 29.

TABLE 31

Degradation of Minocycline at 25° C. and 40° C.

| Degradation product w/w | Batch/Sample name | MCD-037-160320 |
|---|---|---|
| T = 0 | 25° C. 4-epi | 0.06 |
| | 40° C. 4-epi | 0.06 |
| 1M | 25° C. 4-epi | NM |
| | 40° C. 4-epi | 0.10 |
| 2M | 25° C. 4-epi | NM |
| | 40° C. 4-epi | 0.08 |
| 3M | 25° C. 4-epi | 0.07 |
| | 40° C. 4-epi | 0.09 |
| 4M | 25° C. 4-epi | 0.09 |
| | 40° C. 4-epi | 0.10 |

TABLE 32

Appearance, collapse time, shakeability and homogeneity of Minocycline at 25° C. and 40° C. in MCD-037-160320

| Time Points | Appearance (25° C.) Quality | Appearance (40° C.) Quality | Collapse time (25° C.) Collapse time(sec) | Collapse time (25° C.) Time to FG(sec) | Collapse time (40° C.) Collapse time(sec) | Collapse time (40° C.) Time to FG(sec) |
|---|---|---|---|---|---|---|
| T0 | E | E | >180 | >180 | >180 | >180 |
| 1M | NM | E | NM | NM | >180 | >180 |
| 2M | NM | E | NM | NM | >180 | >180 |
| 3M | E | E | >180 | >180 | >180 | >180 |
| 4M | E | E | >180 | >180 | >180 | >180 |

| Time Points | Shakeability (25° C.) | Shakeability (40° C.) | Homogeneity (25° C.) | Homogeneity (40° C.) |
|---|---|---|---|---|
| T0 | 2 | 2 | Crystals uniformly distributed | Crystals uniformly distributed |
| 1M | NM | 2 | NM | Crystals uniformly distributed |
| 2M | NM | 2 | NM | Crystals uniformly distributed |
| 3M | 2 | 2 | Crystals uniformly distributed | Crystals uniformly distributed |
| 4M | 2 | 2 | Crystals uniformly distributed | Crystals uniformly distributed |

TABLE 33

Adapalene % content in MCD-037-160320 following storage for 4 months at 25° C. and 40° C.

| | Adapalene content (% w/w) | | | | | | | | |
|---|---|---|---|---|---|---|---|---|---|
| | T = 0 | 1M | | 2M | | 3M | | 4M | |
| Batch/Sample name | 25° C./40° C. | 25° C. | 40° C. | 25° C. | 40° C. | 25° C. | 40° C. | 25° C. | 40° C. |
| MCD-037-160320 | 0.09 | NM | 0.10 | NM | 0.10 | 0.10 | 0.10 | 0.0967 | 0.10 |

TABLE 34

Stability of Adapalene at 25° C. and 40° C. %[7] Adapalene in MCD-037-160320

| Months | 25° C. (foam) | 40° C. (foam) |
|---|---|---|
| 0 | 93.9 | 93.9 |
| 1 | NM | 96.9 |
| 2 | NM | 95.7 |
| 3 | 96.4 | 97.4 |
| 4 | 96.7 | 97.10 |

[7]The percentages are derived from the figures in Table 33.

Minocycline and Adapalene MCD-045-160306 Physical and Chemical Stability:

TABLE 35

Minocycline % content in MCD-045-160306 following storage for 3 months at 25° C. and 40° C.

| | Minocycline content (% w/w) | | | | | | |
|---|---|---|---|---|---|---|---|
| | T = 0 | 1M | | 2M | | 3M | |
| Batch/Sample name | 25° C./40° C. | 25° C. | 40° C. | 25° C. | 40° C. | 25° C. | 40° C. |
| MCD-045-160306 | 3.83 | NM | 4.21 | NM | 3.93 | 3.91 | 3.96 |

TABLE 36

Stability of Minocycline at 25° C. and 40° C.
%[8] Minocycline in MCD-045-160306

| Months | 25° C. (foam) | 40° C. (foam) |
|---|---|---|
| 0 | 95.76 | 95.76 |
| 1 | NM | 105.15 |
| 2 | NM | 98.14 |
| 3 | 97.79 | 99.08 |

[8]The percentages are derived from the figures in Table 35.

TABLE 37

Degradation of Minocycline at 25° C. and 40° C.

| Degradation product w/w | Batch/Sample name | MCD-045-160306 |
|---|---|---|
| T = 0 | 25° C. 4-epi | 0.07 |
|  | 40° C. 4-epi | 0.07 |
| 1M | 25° C. 4-epi | NM |
|  | 40° C. 4-epi | 0.11 |
| 2M | 25° C. 4-epi | NM |
|  | 40° C. 4-epi | 0.07 |
| 3M | 25° C. 4-epi | 0.08 |
|  | 40° C. 4-epi | 0.10 |

TABLE 38

Appearance, collapse time, shakeability and homogeneity of Minocycline at 25° C. and 40° C. in MCD-045-160306

| Time Points | Appearance (25° C.) Quality | Appearance (40° C.) Quality | Collapse time (25° C.) Collapse time(sec) | Collapse time (25° C.) Time to FG(sec) | Collapse time (40° C.) Collapse time(sec) | Collapse time (40° C.) Time to FG(sec) |
|---|---|---|---|---|---|---|
| T0 | E | E | >180 | >180 | >180 | >180 |
| 1M | NM | E | NM | NM | >180 | >180 |
| 2M | NM | E | NM | NM | >180 | >180 |
| 3M | E | E | >180 | >180 | >180 | 150 |
| 4M | E | E | >180 | >180 | 140 | 120 |

| Time Points | Shakeability (25° C.) | Shakeability (40° C.) | Homogeneity (25° C.) | Homogeneity (40° C.) |
|---|---|---|---|---|
| T0 | 2 | 2 | Crystals uniformly distributed | Crystals uniformly distributed |
| 1M | NM | 2 | NM | Crystals uniformly distributed |
| 2M | NM | 2 | NM | Crystals uniformly distributed |
| 3M | 2 | 2 | Crystals uniformly distributed | Crystals uniformly distributed |
| 4M | 2 | 2 | Crystals uniformly distributed | Crystals uniformly distributed |

TABLE 39

Adapalene % content in MCD-045-160306 following storage for 3 months at 25° C. and 40° C.

| | Adapalene content (% w/w) | | | | | | |
|---|---|---|---|---|---|---|---|
| | T = 0 | 1M | | 2M | | 3M | |
| Batch/Sample name | 25° C./40° C. | 25° C. | 40° C. | 25° C. | 40° C. | 25° C. | 40° C. |
| MCD-045-160306 | 0.10 | NM | 0.10 | NM | 0.10 | 0.09 | 0.10 |

TABLE 40

Stability of Adapalene at 25° C. and 40° C.
%[9] Adapalene in MCD-045-160306

| Months | 25° C. (foam) | 40° C. (foam) |
|---|---|---|
| 0 | 95.10 | 95.03 |
| 1 | NM | 101.13 |
| 2 | NM | 95.80 |
| 3 | 94.40 | 95.83 |

[9]The percentages are derived from the figures in Table 39.

Minocycline and Adapalene MCD-052-160410 Physical and Chemical Stability:

TABLE 41

Minocycline % content in MCD-052-160410 following storage for 3 months at 25° C. and 40° C.

| | Minocycline content (% w/w) | | | | | | |
|---|---|---|---|---|---|---|---|
| | T = 0 | 1M | | 2M | | 3M | |
| Batch/Sample name | 25° C./40° C. | 25° C. | 40° C. | 25° C. | 40° C. | 25° C. | 40° C. |
| MCD-052-160410 | 3.94 | 3.88 | 3.71 | 3.82 | 3.80 | 3.81 | 3.84 |

TABLE 42

Stability of Minocycline at 25° C. and 40° C.
%[10] Minocycline in MCD-052-160410

| Months | 25° C. (foam) | 40° C. (foam) |
|---|---|---|
| 0 | 98.48 | 98.48 |
| 1 | 97.02 | 92.75 |
| 2 | 95.43 | 95.08 |
| 3 | 95.30 | 96.05 |

[10]The percentages are derived from the FIGURES in Table 41.

TABLE 43

Degradation of Minocycline at 25° C. and 40° C.

| Degradation product w/w | Batch/Sample name | MCD-052-160410 |
|---|---|---|
| T = 0 | 25° C. 4-epi | 0.09 |
| | 40° C. 4-epi | 0.09 |
| 1M | 25° C. 4-epi | 0.07 |
| | 40° C. 4-epi | 0.06 |
| 2M | 25° C. 4-epi | 0.08 |
| | 40° C. 4-epi | 0.08 |
| 3M | 25° C. 4-epi | 0.09 |
| | 40° C. 4-epi | 0.07 |

TABLE 44

Appearance, collapse time, shakeability and homogeneity of Minocycline at 25° C. and 40° C. in MCD-052-160410

| | Appearance | Appearance | Collapse time (25° C.) | | Collapse time (40° C.) | |
|---|---|---|---|---|---|---|
| Time Points | (25° C.) Quality | (40° C.) Quality | Collapse time(sec) | Time to FG(sec) | Collapse time(sec) | Time to FG(sec) |
| T0 | E | E | >180 | >180 | >180 | >180 |
| 1M | E | E | >180 | >180 | >180 | >180 |
| 2M | E | E | >180 | >180 | >180 | >180 |
| 3M | E | E | NM | NM | NM | NM |

TABLE 44-continued

Appearance, collapse time, shakeability and homogeneity of Minocycline at 25° C. and 40° C. in MCD-052-160410

| Time Points | Shakeability (25° C.) | Shakeability (40° C.) | Homogeneity (25° C.) | Homogeneity (40° C.) |
|---|---|---|---|---|
| T0 | 2 | 2 | Crystals uniformly distributed | Crystals uniformly distributed |
| 1M | 2 | 2 | Crystals uniformly distributed | Crystals uniformly distributed |
| 2M | 2 | 2 | Crystals uniformly distributed | Crystals uniformly distributed |
| 3M | 0 | 0 | Crystals uniformly distributed | Crystals uniformly distributed |

TABLE 45

Adapalene % content in MCD-052-160410 following storage for 3 months at 25° C. and 40° C.

| | Adapalene content (% w/w) | | | | | | |
|---|---|---|---|---|---|---|---|
| | T = 0 | 1M | | 2M | | 3M | |
| Batch/Sample name | 25° C./40° C. | 25° C. | 40° C. | 25° C. | 40° C. | 25° C. | 40° C. |
| MCD-052-160410 | 0.29 | 0.29 | 0.29 | 0.30 | 0.30 | 0.30 | 0.29 |

TABLE 46

Stability of Adapalene at 25° C. and 40° C.
%[11] Adapalene in MCD-052-160410

| Months | 25° C. (foam) | 40° C. (foam) |
|---|---|---|
| 0 | 97.31 | 97.31 |
| 1 | 95.50 | 96.74 |
| 2 | 98.69 | 99.00 |
| 3 | 99.16 | 97.78 |

Minocycline and Adapalene MCD-053-160413 Physical and Chemical Stability:

TABLE 47

Minocycline % content in MCD-053-160413 following storage for 3 months at 25° C. and 40° C.

| Batch/Sample name | Minocycline content (% w/w) | | | | | | |
|---|---|---|---|---|---|---|---|
| | T = 0 | 1M | | 2M | | 3M | |
| | 25° C./40° C. | 25° C. | 40° C. | 25° C. | 40° C. | 25° C. | 40° C. |
| MCD-053-160413 | 3.91 | 3.95 | 3.91 | 3.84 | 3.88 | 3.97 | 3.94 |

[11] The percentages are derived from the FIGURES in Table 45.

TABLE 48

Stability of Minocycline at 25° C. and 40° C. %[12] Minocycline in MCD-053-160413

| Months | 25° C. (foam) | 40° C. (foam) |
|---|---|---|
| 0 | 97.79 | 97.79 |
| 1 | 98.64 | 97.69 |
| 2 | 96.03 | 96.98 |
| 3 | 99.32 | 98.43 |

TABLE 49

Degradation of Minocycline at 25° C. and 40° C.

| Degradation product w/w | Batch/Sample name | MCD-053-160413 |
|---|---|---|
| T = 0 | 25° C. 4-epi | 0.07 |
| | 40° C. 4-epi | 0.07 |
| 1M | 25° C. 4-epi | 0.07 |
| | 40° C. 4-epi | 0.08 |
| 2M | 25° C. 4-epi | 0.08 |
| | 40° C. 4-epi | 0.09 |
| 3M | 25° C. 4-epi | 0.11 |
| | 40° C. 4-epi | 0.11 |

[12] The percentages are derived from the FIGURES in Table 47.

TABLE 50

Appearance, collapse time, shakeability and homogeneity of Minocycline at 25° C. and 40° C. in MCD-053-160413

| Time Points | Appearance (25° C.) Quality | Appearance (40° C.) Quality | Collapse time (25° C.) Collapse time (sec) | Collapse time (25° C.) Time to FG (sec) | Collapse time (40° C.) Collapse time (sec) | Collapse time (40° C.) Time to FG (sec) |
|---|---|---|---|---|---|---|
| T0 | E | E | >180 | >180 | >180 | >180 |
| 1M | E | E | >180 | 60 | >180 | >180 |
| 2M | E | E | 175 | 180 | 180 | 180 |

| Time Points | Shakeability (25° C.) | Shakeability (40° C.) | Homogeneity (25° C.) | Homogeneity (40° C.) |
|---|---|---|---|---|
| T0 | 2 | 2 | Crystals uniformly distributed | Crystals uniformly distributed |
| 1M | 2 | 2 | Crystals uniformly distributed | Crystals uniformly distributed |
| 2M | 2 | 2 | Crystals uniformly distributed | Crystals uniformly distributed |

TABLE 51

Adapalene % content in MCD-053-160413 following storage for 3 months at 25° C. and 40° C.

| Batch/Sample name | Adapalene content (% w/w) | | | | | | |
|---|---|---|---|---|---|---|---|
| | T = 0 | 1M | | 2M | | 3M | |
| | 25° C./40° C. | 25° C. | 40° C. | 25° C. | 40° C. | 25° C. | 40° C. |
| MCD-053-160413 | 0.28 | 0.28 | 0.28 | 0.28 | 0.28 | 0.29 | 0.28 |

TABLE 52

Stability of Adapalene at 25° C. and 40° C. %[13] Adapalene in MCD-053-160413

| Months | 25° C. (foam) | 40° C. (foam) |
|---|---|---|
| 0 | 93.41 | 93.41 |
| 1 | 94.66 | 93.42 |
| 2 | 91.80 | 93.78 |
| 3 | 95.44 | 94.07 |

[13] The percentages are derived from the FIGURES in Table 51.

Minocycline and Adapalene MCD-058-160414 Physical and Chemical Stability:

TABLE 53

Minocycline % content in MCD-058-160414 following storage for 3 months at 25° C. and 40° C.

| Batch/Sample name | Minocycline content (% w/w) | | | | | | |
|---|---|---|---|---|---|---|---|
| | T = 0 | 1M | | 2M | | 3M | |
| | 25° C./40° C. | 25° C. | 40° C. | 25° C. | 40° C. | 25° C. | 40° C. |
| MCD-058-160414 | 4.06 | 3.90 | 3.97 | 3.92 | 4.01 | 3.91 | 3.90 |

TABLE 54

Stability of Minocycline at 25° C. and 40° C. %[14] Minocycline in MCD-058-160414

| Months | 25° C. (foam) | 40° C. (foam) |
|---|---|---|
| 0 | 101.61 | 101.61 |
| 1 | 97.58 | 99.20 |
| 2 | 97.88 | 100.36 |
| 3 | 97.76 | 97.50 |

[14] The percentages are derived from the FIGURES in Table 53.

TABLE 55

Degradation of Minocycline at 25° C. and 40° C.

| Degradation product w/w | Batch/Sample name | MCD-058-160414 |
|---|---|---|
| T = 0 | 25° C. 4-epi | 0.09 |
| | 40° C. 4-epi | 0.09 |
| 1M | 25° C. 4-epi | 0.09 |
| | 40° C. 4-epi | 0.10 |
| 2M | 25° C. 4-epi | 0.09 |
| | 40° C. 4-epi | 0.10 |
| 3M | 25° C. 4-epi | 0.12 |
| | 40° C. 4-epi | 0.12 |

TABLE 56

Appearance, Collapse time, shakeability and homogeneity of Minocycline at 25° C. and 40° C. in MCD-058-160414

| Time Points | Appearance (25° C.) Quality | Appearance (40° C.) Quality | Collapse time (25° C.) Collapse time(sec) | Collapse time (25° C.) Time to FG(sec) | Collapse time (40° C.) Collapse time(sec) | Collapse time (40° C.) Time to FG(sec) |
|---|---|---|---|---|---|---|
| T0 | E | E | >180 | 150 | >180 | 150 |
| 1M | E | E | >180 | >180 | >180 | >180 |
| 2M | E | E | >180 | 180 | >180 | 180 |

| Time Points | Shakeability (25° C.) | Shakeability (40° C.) | Homogeneity (25° C.) | Homogeneity (40° C.) |
|---|---|---|---|---|
| T0 | 2 | 2 | Crystals uniformly distributed | Crystals uniformly distributed |
| 1M | 2 | 2 | Crystals uniformly distributed | Crystals uniformly distributed |
| 2M | 2 | 2 | Crystals uniformly distributed | Crystals uniformly distributed |

TABLE 57

Adapalene % content in MCD-058-160414 following storage for 3 months at 25° C. and 40° C.

| | Adapalene content (% w/w) | | | | | | |
|---|---|---|---|---|---|---|---|
| | T = 0 | 1M | | 2M | | 3M | |
| Batch/Sample name | 25° C./40° C. | 25° C. | 40° C. | 25° C. | 40° C. | 25° C. | 40° C. |
| MCD-058-160414 | 0.29 | 0.27 | 0.28 | 0.28 | 0.29 | 0.29 | 0.29 |

TABLE 58

Stability of Adapalene at 25° C. and 40° C.
%[15] Adapalene in MCD-058-160414

| Months | 25° C. (foam) | 40° C. (foam) |
|---|---|---|
| 0 | 95.01 | 95.01 |
| 1 | 91.47 | 94.05 |
| 2 | 93.64 | 95.11 |
| 3 | 95.87 | 95.09 |

[15]The percentages are derived from the FIGURES in Table 57.

Doxycycline DOX331 Physical and Chemical Stability:

TABLE 59

Doxycycline % content in DOX331 following storage for 1 week at 25° C. and 40° C.

| | Doxycycline content (% w/w) | | | |
|---|---|---|---|---|
| | T = 0 | | 1 Week | |
| Batch/Sample name | 25° C. | 40° C. | 25° C. | 40° C. |
| DOX331 | 4.146 | 4.146 | 4.103 | 4.106 |

TABLE 60

Stability of Doxycycline at 25° C. and 40° C.
%[16] Doxycycline in DOX331

| Time | 25° C. | 40° C. |
|---|---|---|
| 0 | 103.7 | 103.7 |
| 1 week | 102.6 | 102.7 |

[16]The percentages are derived from the FIGURES in Table 59.

TABLE 61

Degradation of Doxycycline at 25° C. and 40° C.

| Degradation product w/w | Batch/Sample name | DOX331 |
|---|---|---|
| T = 0 | 25° C. 6-epi | 0.026 |
| | 40° C. 6-epi | 0.026 |
| 1 Week | 25° C. 6-epi | 0.026 |
| | 40° C. 6-epi | 0.025 |

TABLE 62

Appearance, collapse time and shakeability of Doxycycline at 25° C. and 40° C. in DOX331

| Time Points | Appearance (25° C.) Quality | Appearance (40° C.) Quality | Shakeability (25° C.) | Shakeability (40° C.) |
|---|---|---|---|---|
| T0 | E | E | 0 | 0 |
| 1 week | E | E | 1 | 1 |

Doxycycline DOX332 Physical and Chemical Stability:

TABLE 63

Doxycycline % content in DOX332 following storage for 1 week at 25° C. and 40° C.

| Batch/Sample name | Doxycycline content (% w/w) | | | |
|---|---|---|---|---|
| | T = 0 | | 1 Week | |
| | 25° C. | 40° C. | 25° C. | 40° C. |
| DOX332 | 4.074 | 4.074 | 4.124 | 4.169 |

TABLE 64

Stability of Doxycycline at 25° C. and 40° C. %[17] Doxycycline in DOX332

| Time | 25° C. | 40° C. |
|---|---|---|
| 0 | 101.8 | 101.8 |
| 1 week | 103.1 | 104.2 |

TABLE 65

Degradation of Doxycycline at 25° C. and 40° C.

| Degradation product w/w | Batch/Sample name | DOX332 |
|---|---|---|
| T = 0 | 25° C. 6-epi | 0.026 |
| | 40° C. 6-epi | 0.026 |
| 1 Week | 25° C. 6-epi | 0.026 |
| | 40° C. 6-epi | 0.026 |

TABLE 66

Appearance, collapse time and shakeability of Doxycycline at 25° C. and 40° C. in DOX332

| Time Points | Appearance (25° C.) Quality | Appearance (40° C.) Quality | Shakeability (25° C.) | Shakeability (40° C.) |
|---|---|---|---|---|
| T0 | E | E | 1 | 1 |
| 1 week | E | E | 1 | 1 |

[17]The percentages are derived from the figures in Table 63.

Minocycline FMX103 (1.5% Minocycline) Chemical Stability:

TABLE 67

Stability of Minocycline at 25° C., 30° C. and 40° C.

| % Minocycline in FMX103 (1.5% minocycline) Batch: 5042301 | | | | % Minocycline in FMX103 (1.5% minocycline) Batch: 5082401 | | | |
|---|---|---|---|---|---|---|---|
| Months | 25° C. | 30° C. | 40° C. | Months | 25° C. | 30° C. | 40° C. |
| 0 | 92.8-94.6 | 92.8-94.6 | 92.8-94.6 | 0 | 97.8 | 97.8 | 97.8 |
| 1 | NM | 94.8 | 80.2 | 1 | NM | 95.9 | 95.4 |
| 2 | NM | 91.9 | 88.2 | 2 | NM | 94.8 | 92.9 |
| 3 | 92.8 | 91.0 | 87.2/87.3 | 3 | 96.8 | 96.0 | 92.8 |
| 6 | 92.4 | 92.0 | 85.9/85.7 | 6 | 95.9 | 91.2 | 95.9 |
| 9 | 92.4 | 90.5 | NM | 9 | NM | NM | NM |
| 12 | NM | NM | NM | 12 | NM | NM | NM |

TABLE 68

Degradation of Minocycline at 25° C., 30° C. and 40° C.

| Degradation product w/w | Batch/Sample name | FMX103 (1.5% minocycline) Batch: 5042301 | FMX103 (1.5% minocycline) Batch: 5082401 |
|---|---|---|---|
| T = 0 | 25° C. 4-epi | 0.0555 | 0.0465 |
| | 30° C. 4-epi | 0.0555 | 0.0465 |
| | 40° C. 4-epi | 0.0555 | 0.0465 |
| 1M | 25° C. 4-epi | NM | NM |
| | 30° C. 4-epi | 0.06 | 0.042 |
| | 40° C. 4-epi | 0.0495 | 0.048 |
| 2M | 25° C. 4-epi | NM | NM |
| | 30° C. 4-epi | 0.0585 | 0.0585 |
| | 40° C. 4-epi | 0.057 | 0.063 |
| 3M | 25° C. 4-epi | 0.06 | 0.06 |
| | 30° C. 4-epi | 0.0555 | 0.057 |
| | 40° C. 4-epi | 0.054 | 0.051 |
| 6M | 25° C. 4-epi | 0.069 | 0.0525 |
| | 30° C. 4-epi | 0.0615 | 0.0675 |
| | 40° C. 4-epi | 0.0285 | 0.0255 |
| 9M | 25° C. 4-epi | 0.0555 | NM |
| | 30° C. 4-epi | 0.0645 | NM |
| | 40° C. 4-epi | NM | NM |
| 12M | 25° C. 4-epi | NM | NM |
| | 30° C. 4-epi | NM | NM |
| | 40° C. 4-epi | NM | NM |

Minocycline FMX103 (3% Minocycline) Chemical Stability:

TABLE 69

Stability of Minocycline at 25° C. and 30° C.

| % Minocycline in FMX103 (3% minocycline) Batch: 5020901 | | | | % Minocycline in FMX103 (3% minocycline) Batch: 5082601 | | | |
|---|---|---|---|---|---|---|---|
| Months | 25° C. | 30° C. | 40° C. | Months | 25° C. | 30° C. | 40° C. |
| 0 | 96.4 | 96.4 | 96.4 | 0 | 98.8 | 98.8 | 98.8 |
| 1 | NM | 92.9 | 95.0 | 1 | NM | 95.6 | 96.5 |
| 2 | NM | NM | NM | 2 | NM | 94.5 | 96.6 |
| 3 | 94.7 | 93.7 | 92.0 | 3 | 98.2 | 97.9 | 95.5 |
| 6 | 93.2 | 90.6 | 87.5 | 6 | 97.8 | 97.1 | 93.6 |
| 9 | 92.0 | 88.7/91.5 | NM | 9 | NM | NM | NM |
| 12 | 93.4 | 93.5 | NM | 12 | NM | NM | NM |

TABLE 70

Degradation of Minocycline at 25° C., 30° C. and 40° C.

| Degradation product w/w | Batch/Sample name | FMX103 (3% minocycline) Batch: 5020901 | FMX103 (3% minocycline) Batch: 5082601 |
|---|---|---|---|
| T = 0 | 25° C. 4-epi | 0.114 | 0.09 |
|  | 30° C. 4-epi | 0.114 | 0.09 |
|  | 40° C. 4-epi | 0.114 | 0.09 |
| 1M | 25° C. 4-epi | NM | NM |
|  | 30° C. 4-epi | 0.099 | 0.078 |
|  | 40° C. 4-epi | 0.099 | 0.087 |
| 2M | 25° C. 4-epi | NM | NM |
|  | 30° C. 4-epi | NM | 0.105 |
|  | 40° C. 4-epi | NM | 0.12 |
| 3M | 25° C. 4-epi | 0.114 | 0.111 |
|  | 30° C. 4-epi | 0.111 | 0.102 |
|  | 40° C. 4-epi | 0.102 | 0.114 |
| 6M | 25° C. 4-epi | 0.111 | 0.105 |
|  | 30° C. 4-epi | 0.099 | 0.105 |
|  | 40° C. 4-epi | 0.066 | 0.054 |
| 9M | 25° C. 4-epi | 0.114 | NM |
|  | 30° C. 4-epi | 0.114 | NM |
|  | 40° C. 4-epi | NM | NM |
| 12M | 25° C. 4-epi | 0.102 | NM |
|  | 30° C. 4-epi | 0.108 | NM |
|  | 40° C. 4-epi | NM | NM |

Example 5

Clinical Study Phase I (FMX-101 Foam, 4% Minocycline Foam without SiO$_2$) PK Study Under Maximum Use Conditions for 16 Days Study Synopsis In this example, topical administration of tetracycline (for example minocycline) was studied and the pharmacokinetic profile of the drug and its bioavailability was characterized.

Study Title:

An Open-label, Multiple Dose Study to Assess the Pharmacokinetic Profile of Minocycline from FMX-101 Foam (4%) in Male and Female Volunteers.

Objectives:

1. To assess bioavailability of minocycline from FMX-101 minocycline HCl foam, 4%. 2. To characterize the pharmacokinetic profile of minocycline following multiple-dose topical administration of FMX-101 (4%) in healthy volunteers with or without acne.

Study Medication:

FMX-101 minocycline (4%)—approximately 4 gr per application. The composition of FMX-101 Foam (4%) is described in Table 5B above.

Dosage Form:

Foam.

Indication:

Acne vulgaris.

Design:

An open-label, single-center, non-randomized, multiple administrations study in males and females, some of which are with acne. Twelve (12) subjects (at least 4 subjects with acne) enrolled to receive a daily dose of topical FMX-101 minocycline (4%) foam for sixteen consecutive days.

Eligible subjects were admitted to the Clinical Research Center (CRC) in the evening before the first study drug administration (Day 0), and remained in-house for 24 hours after first dosing (Day 1). Throughout this day blood samples for PK were drawn at time points specified below. After receiving the second dose (Day 2) they were released from the CRC.

Subjects then arrived at the CRC on the mornings of Days 3, 5, 7, 8, 9, 10, 11, 12, 14 and 15. They remained under supervision in the CRC, with the application areas uncovered, for 30 min before being released. On Days 3, 7, 9, 11 and 14, blood was drawn for PK (trough) within 10 min before the subjects received the study drug.

On days 4, 6 and 13 the drug was applied at home by the subject according to the Investigator/study staff instructions.

On the evening of Day 15 the subjects were re-admitted to the CRC. On Day 16 they received the last (sixteenth) dose and went through the same procedures as in Day 1. After being released form the CRC they were required to attend three additional ambulatory PK blood sampling (36, 48 and 60 hours post-dose).

PK Evaluation Timing of PK Blood Sampling

Blood samples to determine plasma of minocycline were collected at the following time points:

Day 1: pre-dose (within 90 min before first dosing), 30 min, 1, 2, 4, 8, 12, 16 hours post-dose and Day 2 at 24 hrs post-dose within 10 min before second dosing—a total of 9 samples).

Days 3, 7, 9, 11 and 14: pre-dose (trough) samples, within 10 min before drug application.

Day 16: pre-dose (within 10 min before drug application), 30 min, 1, 2, 4, 8, 12, 16 hours post-dose, Day 17, 24 (±10 min) hours post-dose (before discharge from the CRC) and additional ambulatory PKs at 36 (±15 min), (Day 17), 48 (±30 min) and 60 (±30 min) hours after last drug application (Day 18)—a total of 12 blood samples.

TABLE 71

PK sampling scheme

| Study Day | Time relative to dosing |
|---|---|
| Day 1 | 0 h (Pre-dose) |
|  | 0.5 h |
|  | 1 h |
|  | 2 h |
|  | 4 h |
|  | 8 h |
|  | 12 h |
|  | 16 h |
| Day 2 | Pre-dose (24 h post-dose) |
| Day 3 | Pre-dose (24 h post-dose) |
| Day 7 | Pre-dose (24 h post-dose) |
| Day 9 | Pre-dose (24 h post-dose) |
| Day 11 | Pre-dose (24 h post-dose) |
| Day 14 | Pre-dose (24 h post-dose) |
| Day 16 | 0 h (Pre-dose, 24 h post-dose) |
|  | 0.5 |
|  | 1 |
|  | 2 |
|  | 4 |
|  | 8 |
|  | 12 |
|  | 16 |
| Day 17 | 24 |
|  | 36 |
| Day 18 | 48 |
|  | 60 |

Throughout a period of 18 days a total of 26 samples per subject were drawn for PK.

Calculation of Pharmacokinetic Parameters

PK of minocycline was derived from plasma concentration versus time data. For purposes of calculating PK parameters, concentrations <LLQ were treated as zero. For purposes of tabular presentation and graphing mean profiles, concentration values <LLQ were treated as missing.

The PK parameters assessed included:

$C_{max}$—Maximum plasma concentration achieved (dosing days 1 and 16).

AUCT—The area under the plasma concentration versus time curve in ng*mL/h. The AUC from time zero to the last experimental time point (t*) with a detectable drug concentration equal to or greater than the limit of quantification value was designated AUCT and calculated by the linear trapezoidal rule (dosing days 1 and 16).

All calculated concentration values were electronically transferred. Individual subject PK parameter values were derived by non-compartmental methods by WinNonlin 6.3 within the Phoenix 64 software package. The peak plasma concentration ($C_{max}$) was obtained from experimental observations.

Figure 2:
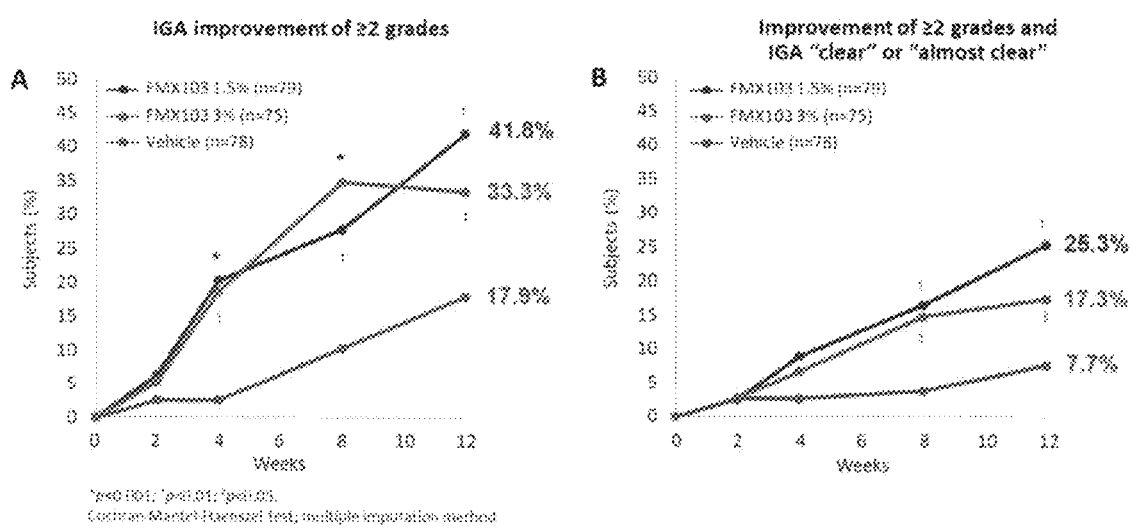
FIG. 2A-FIG. 2B show investigator's global assessment (IGA) results.

FIG. 2 depicts the mean minocycline plasma concentrations from Day 1 to Day 16 for subjects who received FMX-101.

Results:

TABLE 72

FMX101-1 PK parameters PK Non-Compartmental Analysis Summary Statistics (Day 1, Day 16)

| Parameter | Day 1 | Day 16 |
|---|---|---|
| $C_{max}$ [ng/mL] | 2.26 ± 1.60 | 5.04 ± 6.19 |
| $AUC_T$ [ng · h/mL] | 33.83 ± 22.73 | 84.36 ± 48.36 |

Analysis:

In general, the observed minocycline plasma concentrations throughout the study were low and close to the sensitive lower limit of quantification (LLOQ=1.1 ng/mL).

The results of this study showed a very low absorption, with the $C_{max}$ (Day 16)=5 ng/mL, about 500 times lower than the $C_{max}$ and AUC for the labeled dose of the oral extended release minocycline, Solodyn® (100-135 mg, where the actual mg/kg dose corresponds to 1.07-0.99).

Similar PK studies for additional tetracycline antibiotics, such as doxycycline in one or more embodiments may be undertaken. For example, PK studies for doxycycline in formulations such as FDX104, DOX331, DOX332, DOD-003, and minocycline with adapalene MCD-037, MCD-045, MCD-052 MCD-053, MCD-065 and MCD-058.

Doxycycline is generally regarded as non-toxic in short term treatment, as indicated by its oral acute toxicity of LD50=1007 mg/kg (mouse).

Chronic toxicity of doxycycline was evaluated in rats at oral doses up to 500 mg/kg/day for 18 months. Findings revealed no adverse effects on growth, food consumption, or survival.

Example 6

PK Study Results for Tetracycline Formulations

An open-label, single-center, study of the pharmacokinetics of daily applications of tetracycline formulations such as DOX331, DOX332, and DOD-003 doxycycline foam and MCD-037, MCD-045, MCD-052 MCD-053, MCD-065 and MCD-058 minocycline or doxycycline foam, is conducted for 16 consecutive days. Eligible subjects include males or females, 18 to 35 years of age, with or without papulopustular rosacea who are otherwise healthy. At least twelve subjects (preferably 6 male and 6 female), at least 9 of whom have varying degrees of papulopustular rosacea and 3 preferably without papulopustular rosacea, are enrolled to receive daily topical administration of tetracycline formulation, as indicated above. Subjects are admitted to the Clinical Research Center (CRC) in the evening before the first study drug administration (Day 0), and remain in-house for 24 hours after first dosing (Day 1). Throughout this day blood samples (6 mL) for determination of minocycline blood concentrations is drawn as follows:

Day 1: pre-dose (within 60 min before first dosing), 30 min, 1, 2, 4, 8, 12, 16 hours post-dose and Day 2 at 24 hrs post-dose within 10 min before second dosing—a total of 9 samples)

After receiving the second dose (Day 2) subjects are released from the CRC. Subjects then return to the CRC on the mornings of Days 3, 5, 7, 8, 9, 10, 11, 12, 14 and 15 (on Days 4, 6, and 13, subject applied the tetracycline formulation themselves). They remain in the CRC, with the application areas uncovered, for 30 min before being released. On Days 3, 7, 9, 11 and 14, blood is drawn as follows:

Days 3, 7, 9, 11 and 14: pre-dose (trough) samples, within 10 min before drug application On the evening of Day 15 the subjects are re-admitted to the CRC. On Day 16 they receive the last (sixteenth) dose and undergo the same procedures as in Day 1 as follows:

Day 16: pre-dose (within 30 min before drug application), 30 min, 1, 2, 4, 8, 12, 16 hours post-dose After being released from the CRC they are required to attend three additional blood samplings at 36, 48 and 60 hours post-dose as follows:

Day 17: 24 (±10 min) hours post-dose (before discharge from the CRC) and additional ambulatory sample at 36 (±15 min)

Day 18: 48 (±30 min) and 60 (±30 min) hours after last drug application.

Blood samples are analyzed using a validated method with a lower limit of quantification (LLQ) of 1 ng/mL. An End-of Study/Safety Follow-up visit took place on 7-10 days after last dose, which also included a dermatological assessment of response to treatment.

Results: The systemic exposure of a tetracycline foam as disclosed herein is equal to or lower than that of an orally administered tetracycline. There are no serious adverse events (AEs) and no withdrawals due to AEs.

Example 7

Compatibility Study

Procedure: Minocycline hydrochloride ("MCH") was incubated as a suspension with various excipients at 25° C. and 40° C. for maximum of sixty days or to the point where degradation was suspected. The ratio between MCH and the tested excipient is detailed below. Visual inspection was the major criterion for indication of compatibility. The color of intact MCH suspension is pale yellow; and any change of color (e.g., to dark orange, red, green, brown and black) indicates oxidation or degradation.

Hydrophilic solvents were tested for compatibility with MCH at a ratio of MCH:excipient of 1:250. Dimethyl Isosorbide, Glycerin, Ethanol, Propylene glycol, Butylene Glycol, PEG 200, Hexylene Glycol, PEG 400, Dimethyl Sulfoxide and Diethylene glycol monoethyl ether were found to be incompatible with MCH.

Oily emollients and waxes were tested for compatibility with MCH at a ratio of MCH:excipient of 1:250 for oily emollients and 1:50 for waxes. Hydrogenated castor oil, Castor oil, Cocoglycerides, diisopropyl adipate, Mineral oil light, Coconut oil, Beeswax, MCT oil, Cyclomethicone, Isododecane, Cetearyl octanoate, Gelled mineral oil, Isopropyl myristate, PPG 15 stearyl ether, Mineral oil heavy, Octyl dodecanol, White Petrolatum, Petrolatum (Sofmetic), Paraffin 51-53, Paraffin 51-53, Paraffin 58-62, Calendula oil, Shea butter, Grape seed oil, Almond oil, Jojoba oil, Avocado oil, Peanut oil, Wheat germ oil and Hard Fat were found to be compatible with MCH. Pomegranate seed oil was found to be incompatible with MCH. Other than hydrogenated castor oil, beeswax, paraffin and hard fat, the aforesaid items listed are oily emollients.

The compatibility of MCH with hydrophobic surfactant was tested following solubilization of the surfactant in mineral oil (mineral oil was previously shown to be compatible with MCH). Surfactants were tested for compatibility with MCH at a ratio of MCH:excipient of 1:50. PEG 150 distearate, Laureth 4, PEG 40 hydrogenated castor oil, PEG 75 lanolin, Glucam P20 distearate, PEG 100 stearate, Glyceryl monostearate, PEG 40 stearate, Montanov S (Cocoyl Alcohol (and) C12-20 Alkyl Glucoside), Alkyl lactate, Benton gel, SPAN 60, Sorbitan sesquistearate, SPAN 40, SPAN 80, Tween 20, Ceteth 2, Sucrose stearic acid esters D1813, Cetearteh 20, Steareth 2/Steareth 21, Methyl glucose sesquistearate, Oleth 20, PPG 20 methyl glucose ether, Tween 60 were found to be incompatible with MCH. Sucrose stearic acid esters D1803, Sucrose stearic acid esters D1807 and Sucrose stearic acid esters D1811 were found to be compatible with MCH; however, not all of them dissolved in oil (e.g., 1811, 1813).

Foam adjuvants were tested for compatibility with MCH at a ratio of MCH:excipient of 1:50. Isostearyl alcohol, Behenyl alcohol, Stearyl alcohol, Cetyl alcohol, Oleyl alcohol, Myristyl alcohol, Cetostearyl alcohol, Palmitic acid, Stearic acid and Oleic acid were found to be compatible with MCH. Isostearic acid was not compatible with MCH.

Additives were tested for compatibility with MCH at a ratio of MCH:excipient of 1:50. Aerosil and Menthol were found to be compatible with MCH. Titanium dioxide and Ethocel were not compatible with MCH.

Additives were tested for compatibility with MCH. Minimal quantities of water (100 μL) were added to MCH, suspended in excipients that had demonstrated compatibility to examine whether water can enhance oxidation/degradation in the absence or presence of antioxidant. In parallel, antioxidants were added to the MCH suspensions comprising water. Antioxidants were also added to excipients which were found to be non-compatible with MCH. Addition of water caused prompt degradation of MCH. Addition of the antioxidants alpha-tocopherol, BHA/BHT and propyl gallate did not prevent MCH degradation. Compatible excipients became incompatible in the presence of water. Addition of antioxidants did not alter this result.

Doxycycline

A similar compatibility study was conducted for Doxycycline Hyclate and Doxycycline Monohydrate.

The physicochemical properties of these two forms of Doxycycline are similar to those of other tetracycline antibiotics with the exception of differences resulting from the presence of an $H_2O$ molecule in Doxycycline Monohydrate and an $H_2O$ molecule and two HCl molecules for every water molecule in Doxycycline Hyclate.

General properties of Doxycycline Hyclate and Doxycycline Monohydrate:

Doxycycline Hyclate

1. Doxycycline Hyclate is a broad-spectrum antibiotic synthetically derived from oxytetracycline.

2. Doxycycline hyclate is a yellow crystalline powder soluble in water and in solutions of alkali hydroxides and carbonates.

3. Doxycycline hyclate has a high degree of lipid solubility and a low affinity for calcium binding.

Doxycycline Monohydrate

1. Doxycycline monohydrate is a broad-spectrum antibiotic synthetically derived from oxytetracycline.

2. The chemical designation of the light-yellow crystalline powder is alpha-6-deoxy-5-oxytetracycline.

The major degradative pathways for both types of Doxycycline are carbon-4 epimerization and oxidative processes.

Doxycycline is a member of the tetracycline antibiotics group and is commonly used to treat a variety of infections, particularly effective in treating acne condition.

Different compositions of hydrophilic and hydrophobic solvents containing Doxycycline Hyclate (Set I and Set II) and Doxycycline Monohydrate (Set III) were prepared by weighing the antibiotic in a glass vial and shaking overnight with each solvent investigated. Mixtures of Doxycycline salts 1.04% w/w with solid excipients were prepared in a similar way as for Minocycline HCl. The results are presented in Tables 22A-26.

TABLE 73

Doxycycline Hyclate Compatibility Test (Group I)

A.

Mixtures of 1.04% w/w of Doxycycline Hyclate stored at 25° C., 40° C. and 50° C. for two weeks
Ingredients

| Group I | Cyclomethicone | PPG-15 stearyl ether | Octyldodecanol | Mineral oil | Propylene glycol | Glycerol | PEG 200 | PEG 400 | MCT oil | Diisopropyl adipate |
|---|---|---|---|---|---|---|---|---|---|---|
| Visual inspection at T-0 | White liquid and yellow powder sedim. | White liquid and yellow powder sedim. | White liquid and yellow powder sedim. | White liquid and yellow powder sedim. | Light yellow solution | Light yellow solution | Light yellow solution | Light yellow solution | White liquid and yellow powder sedim. | White liquid and yellow powder sedim. |
| Visual inspection after the storage at 25° C. | White liquid and yellow powder sedim. | White liquid and yellow powder sedim. | White liquid and yellow powder sedim. | White liquid and yellow powder sedim. | Light yellow solution | Light yellow solution | Light yellow solution | Light yellow solution | White liquid and yellow powder sedim. | White liquid and yellow powder sedim. |

TABLE 73-continued

Doxycycline Hyclate Compatibility Test (Group I)

| | | | | | | | | | | |
|---|---|---|---|---|---|---|---|---|---|---|
| Visual inspection after the storage at 40° C. | White liquid and yellow powder sedim. | White liquid and yellow powder sedim. | Light orange solution | White liquid and yellow powder sedim. | Yellow solution | brownish Yellow solution | Brown solution | Orange solution | White liquid and yellow powder sedim. | White liquid and yellow powder sedim. |
| Visual inspection after the storage at 50° C. | White liquid and yellow powder sedim. | White liquid and yellow powder sedim. | Orange solution | White liquid and yellow powder sedim. | Brownish orange solution | Light brown solution | Orange solution | Orange solution | White liquid and yellow powder sedim. | White liquid and yellow powder sedim. |
| Compatibility Results after the storage | Compat. no oxidation | Compat. no oxidation | Non compat. no oxidation | Compat. no oxidation | Non compat. oxidation | Non compat. oxidation | Non compat. oxidation | Non compat. oxidation | Compat. no oxidation | Compat no oxidation |

B.

Mixtures of 1.04% w/w of Doxycycline Hyclate stored at 25° C., 40° C. and 50° C. for two weeks
Ingredients

| Group I | Cetearyl octanoate | Hexylene glycol | Butylene glycol | Sorbitan Monolaurate | Dimethyl Isosorbide |
|---|---|---|---|---|---|
| Visual inspection at T-0 | bright yellow solution | bright yellow solution | bright yellow solution | bright yellow mixture | yellow solution |
| Visual inspection after the storage at 25° C. | bright yellow solution | bright yellow solution | bright yellow solution | Brown solution | Yellow solution |
| Visual inspection after the storage at 40° C. | bright yellow solution | light yellow solution | Light orange solution | Brown solution | Brownish orange |
| Visual inspection after the storage at 50° C. | White liquid and yellow powder sedim. | Light yellow liquid and yellow powder sedim. | Light orange solution | Black solution | Orange solution |
| Compatibility Results | Compat. no oxidation | Compat. no oxidation | Non compat. oxidation | Non compat. oxidation | Non compat. Oxidation |

Group II included Doxycycline Hyclate mixed with various vehicles with addition of antioxidants like alpha tocopherol, butylated hydroxytoluene (BHT), and ascorbic acid.

TABLE 74

Doxycycline Hyclate Compatibility Test (Group II)

Mixtures of 1.04% w/w of Doxycycline Hyclate stored at 25° C., 40° C. and 50° C. for two weeks
Ingredients

| Group II | Ethanol 95% | Ethanol 95% and BHT | Ethanol 95%, BHT and ascorbic acid | Propylene glycol, alpha tocopherol and ascorbic acid | PEG 200, alpha tocopherol and ascorbic acid |
|---|---|---|---|---|---|
| Visual inspection at T-0 | bright yellow solution | bright yellow solution | bright yellow solution | bright yellow solution | bright yellow solution |
| Visual inspection after the storage at 25° C. | bright yellow solution | bright yellow solution | Yellow solution | bright yellow solution | Yellow solution |
| Visual inspection after the storage at 40° C. | bright yellow solution | bright yellow solution | Yellow solution | Light orange solution | Orange solution |
| Visual inspection after the storage at 50° C. | bright yellow solution | bright yellow solution | Orange solution | Light orange solution | Brownish orange solution |
| Compatibility Results | compatible. no oxidation | compatible no oxidation | Non compatible. Oxidation | Non compatible. oxidation | non compatible. Oxidation |

TABLE 75

Doxycycline Hyclate Compatibility Test (Group III)

Mixtures of 1.04% w/w of Doxycycline Hyclate stored at 25° C., 40° C. and 50° C. for 3 days
Ingredients

| Group II | Isostearic Acid | Oleyl alcohol | Steareth 20 and Steareth 2 | Hydrogenated Castor Oil | Myristyl alcohol and Stearyl alcohol | PEG 40 Stearate | PEG 100 Stearate | Sorbitan Monostearate | Cocoglycerides |
|---|---|---|---|---|---|---|---|---|---|
| Visual inspection at T-0 | Yellow suspen | Yellow suspen | Yellow suspen | Yellow suspen | Yellow suspen | Yellow suspen | Yellow suspen | Yellow suspen | Yellow suspen |
| Visual inspection after the storage at 25° C. | Yellow suspen | Yellow suspen | Yellow suspen | Yellow suspen | Yellow suspen | Yellow suspen. | Yellow suspen | Yellow suspen | Yellow suspen |
| Visual inspection after the storage at 40° C. | Yellow suspen | Yellow suspen | Brown suspen | Yellow suspen | Yellow suspen | Brown suspen | Yellow suspen | Yellow suspen | Yellow suspen |
| Visual inspection after the storage at 50° C. | Yellow suspen | Yellow suspen | Brown suspen | Yellow suspen | Yellow suspen | Brown suspen | Yellow suspen | Yellow suspen | Light brown powder |
| Compatibility Results | Compat.. no oxidation | Compat. No oxidation | Non compat. Oxidation | Compat. No oxidation | Compat. No oxidation | Non Compat. oxidation | Compat.. No oxidation | Compat. No oxidation | Non Compat. oxidation |

Suspen. - suspension;
compat. - compatible

A similar compatibility test was performed on another form of Doxycycline—Doxycycline Monohydrate. The results are presented in Tables 25A, 25B, and 26.

TABLE 76

Doxycycline Monohydrate Compatibility Test (Group I)

A.

Mixtures of 1.04% w/w of Doxycycline Monohydrate stored at 25° C., 40° C., and 50° C. for two weeks
Ingredients

| Group I | Cyclomethicone | PPG-15 stearyl ether | Octyldodecanol | Mineral oil | Propylene glycol | Glycerol | PEG 200 | PEG 400 | MCT oil | Diisopropyl adipate |
|---|---|---|---|---|---|---|---|---|---|---|
| Visual inspection at T-0 | White liquid and yellow powder sedim. | White liquid and yellow powder sedim. | White liquid and yellow powder sedim. | White liquid and yellow powder sedim. | Light yellow solution | yellow solution | yellow solution | Dark yellow solution | White liquid and yellow powder sedim. | White liquid and yellow powder sedim. |
| Visual inspection after the storage at 25° C. | White liquid and yellow powder sedim. | White liquid and yellow powder sedim. | White liquid and yellow powder sedim. | White liquid and yellow powder sedim. | Orange solution | yellow solution | Yellowish black solution | Yellowish brown solution | White liquid and yellow powder sedim. | White liquid and yellow powder sedim. |
| Visual inspection after the storage at 40° C. | White liquid and yellow powder sedim. | Yellowish orange mixture | orange solution | White liquid and yellow powder sedim. | Black solution | black solution | Black solution | Brown solution | White liquid and yellow powder sedim. | White liquid and yellow powder sedim. |
| Visual inspection after the storage at 50° C. | White liquid and yellow powder sedim. | Yellowish orange mixture | Orange solution | White liquid and yellow powder sedim. | black solution | black solution | Black solution | Black solution | Dirty yellow | Brown mixture |
| Compatibility Results after the storage | Compat. no oxidation | Non compat. oxidation | Non compat. oxidation | Compat. no oxidation | Non compat. oxidation | Non compat. oxidation | Non compat. oxidation | Non compat. oxidation | Non compat. oxidation | Non compat. oxidation |

TABLE 76-continued

Doxycycline Monohydrate Compatibility Test (Group I)

B.

Mixtures of 1.04% w/w of Doxycycline Monohydrate stored at 25° C., 40° C., and 50° C. for two weeks
Ingredients

| Group I | Cetearyl octanoate | Hexylene glycol | Butylene glycol | Sorbitan Monolaurate | Dimethyl Isosorbide |
|---|---|---|---|---|---|
| Visual inspection at T-0 | White liquid and yellow powder sedim. | White liquid and yellow powder sedim. | White liquid and yellow powder sedim. | Brown mixture | yellow solution |
| Visual inspection after the storage at 25° C. | White liquid and yellow powder sedim. | bright yellow solution | Orange solution | orange solution | orange solution |
| Visual inspection after the storage at 40° C. | White liquid and yellow powder sedim. | Brownish black solution | Brownish black solution | Brown solution | orange solution |
| Visual inspection after the storage at 50° C. | White liquid and yellow powder sedim. | Black solution. | black solution | brown solution | Orange solution |
| Compatibility Results | compat. no oxidation | Non compat. oxidation | Non compat. Oxidation | Non compat. oxidation | non compat. Oxidation |

TABLE 77

Doxycycline Monohydrate Compatibility Test (Group II)

Mixtures of 1.04% w/w of Doxycycline Monohydrate stored at 25° C., 40° C., and 50° C. for two weeks
Ingredients

| Group II | Ethanol 95% | Ethanol 95% and BHT | Ethanol 95%, BHT and ascorbic acid | Propylene glycol, alpha tocopherol and ascorbic acid | PEG 200, alpha tocopherol and ascorbic acid |
|---|---|---|---|---|---|
| Visual inspection at T-0 | bright yellow solution | bright yellow solution | bright yellow solution | bright yellow solution | bright yellow solution |
| Visual inspection after the storage at 25° C. | Brown solution | Brown solution | orange solution | Yellowish orange solution | Yellow solution |
| Visual inspection after the storage at 40° C. | Brown solution | Brown solution | Orange solution | Orange solution | Dark yellow solution |
| Visual inspection after the storage at 50° C. | Black solution | Black solution | Black solution | Brownish orange solution | Brown orange solution |
| Compatibility Results | Non compatible. oxidation | Non compatible oxidation | Non compatible. Oxidation | Non compatible. oxidation | non compatible. Oxidation |

Interesting and unexpected phenomena were found during the compatibility studies of Minocycline HCl, Doxycycline Hyclate and Doxycycline Monohydrate:

1. While minocycline displayed intensive oxidation on dissolution in glycerol, the antibiotic surprisingly revealed full compatibility with octyldodecanol, a branched chain fatty alcohol. Both molecules have similar hydroxyl units in their structures.

2. Doxycycline Hyclate and Monohydrate unexpectedly revealed different compatibility with excipients. For example, Doxycycline Hyclate was stable in a mixture with PPG-15 Stearyl Ether. Surprisingly, the Doxycycline Monohydrate was found to be non-compatible with PPG-15 Stearyl Ether during the storage at 40° C. and 50° C. for two weeks.

3. Doxycycline Hyclate was stable in a mixture with ethanol 95% and hexylene glycol. Doxycycline Monohydrate oxidized in similar mixtures.

4. Unexpectedly, addition of strong anti-oxidants like alpha-tocopherol and ascorbic acid did not prevent the oxidation of any of Minocycline HCl, Doxycycline Hyclate and Monohydrate in a waterless medium of propylene glycol and PEG 200.

5. Surprisingly, Doxycycline Hyclate revealed stability in Ethanol 95% following the storage at 40° C. and 50° C. for two weeks although both Minocycline HCl and Doxycycline Monohydrate changed their color from yellow to orange upon dissolution in Ethanol 95%.

6. In conclusion, the following non predictable substances were found to be compatible with Minocycline and Doxycycline:

TABLE 78

Summary of MCH and DOX compatibility studies

Compatibility tested after the storage for up to 3 weeks

| Ingredient | Minocycline HCl | Doxycycline Hyclate | Doxycycline Monohydrate | Comments |
|---|---|---|---|---|
| Cyclomethicone 5 NF | Yes | Yes | Yes | All compatible |
| PPG-15 Stearyl Ether | Yes | Yes | No | |
| Octyldodecanol | Yes | No | No | |
| Mineral Oil | Yes | Yes | Yes | All compatible |
| Propylene Glycol | No | No | No | |
| Glycerol | No | No | No | |
| PEG 200 | No | No | No | |
| PEG 400 | No | No | No | |
| MCT Oil | Yes | Yes | No | |
| Diisopropyl adipate | Yes | Yes | No | |
| Ethanol 95% | No | Yes | No | |
| Isostearic acid | No | Yes | Not tested | |
| Oleyl alcohol | Yes | Yes | Not tested | |
| Steareth 20 (Polyoxyl 20 Stearyl Ether) | No | No | Not tested | |
| Steareth 2 (Polyoxyl 2 Stearyl Ether) | No | No | Not tested | |
| Methyl glycose sesquistearate (MGSS) | No | Not tested | Not tested | |
| Aluminum Starch Octenylsuccinate (ASOS) | Yes | Not tested | Not tested | |
| Cetearyl octanoate | Yes | Yes | Yes | All compatible |
| Hydrogenated Castor Oil | Yes | Yes | Not tested | |
| Stearyl alcohol | Yes | Yes | Not tested | |
| Myristyl alcohol | Yes | Yes | Not tested | |
| Titanium Dioxide | Yes | Not tested | Not tested | |
| PEG 40 stearate | Yes | No | Not tested | |
| PEG 100 Stearate | Yes | Yes | Not tested | |
| Sorbitan Monostearate | Yes | Yes | Not tested | |
| Cocoglycerides | Yes | No | Not tested | |
| Coconut Alcohol | Yes | Not tested | Not tested | |
| Hexylene glycol | No | Yes | No | |
| Butylene glycol | No | No | No | |
| Sorbitan Monolaurate | No | No | No | |
| Dimethyl Isosorbide | No | No | No | |
| Titanium dioxide | Yes | Not tested | Not tested | |
| Methyl glycose sesquistearate (MGSS) | No | Not tested | Not tested | |
| Aluminum Starch Octenylsuccinate (ASOS) | Yes | Not tested | Not tested | |
| Coconut alcohol | Yes | Not tested | Not tested | |

7. As could be seen from Table 76, not all of the ingredients compatible with MCH are compatible with Doxycycline Hyclate or Monohydrate. For example, octyldodecanol is compatible with Minocycline HCl but revealed incompatibility with Doxycycline Hyclate and Monohydrate. Surprisingly, there are discrepancies in the list of ingredients compatible with Doxycycline Hyclate and Doxycycline Monohydrate: for example, PPG-15 Stearyl Ether is compatible with Doxycycline Hyclate and non-compatible with Doxycycline Monohydrate.

8. The data presented herein could be used for selection of active materials from tetracycline family for topical formulations. A list of ingredients that were found to be compatible with MCH and DOX could be applied to other antibiotics from the tetracycline family. The following ingredients are suitable for topical formulations: mineral oil, cyclomethicone, cetearyl octanoate. Few ingredients are compatible with both forms of doxycycline and are also compatible with minocycline.

Example 8

Phase II Study for Papulopustular Rosacea

A double-blind, randomized, placebo-controlled Phase 2 trial has been carried out involving 233 patients who were enrolled in 18 sites throughout Germany. Patients were randomized (1:1:1) to receive high dose FMX103 (3% minocycline foam), low dose FMX103 (1.5% minocycline foam) or vehicle foam once daily (in the evening) over 12 weeks, followed up by a 4-week post-treatment evaluation. However, one subject in the 3% group did not receive treatment and was not included in the intent to treat analysis. The study medication, dosage, inclusion/exclusion criteria, and design generally followed those outlined in Example 3 above, with the inclusion criteria of healthy males or non-pregnant female aged over 18, having at least 12 papules and/or pustules for more than 6 months, and having the Investigator's Global Assessment (IGA) scores moderate to severe. The mean age of the study participants was 52.5 and 63% of the participants were female (see Table 79A and B). The efficacy endpoints were the absolute change in the number of inflammatory facial lesions (papules and pustules (primary endpoint)), improvement of the IGA of severity at 12 weeks compared to baseline (first secondary endpoint), and percent change in inflammatory lesion count at week 12 compared to baseline (second secondary endpoint). IGA score improvement by 2 or more grades and reaching an IGA score of 0 ("clear") or 1 ("almost clear") were considered successful. Safety and tolerability in the treatment of moderate to severe papulopustular rosacea were also evaluated. Safety and efficacy evaluations were performed at week 2, 4, 8, and 12, with an additional safety follow-up visit at week 16.

TABLE 79A

Summary of Analysis Populations by Treatment

|  | Minocycline 1.5% n (%) | Minocycline 3% n (%) | Vehicle n (%) | Overall n (%) |
|---|---|---|---|---|
| Screened | 79 | 76 | 78 | 233 |
| Randomized | 79 | 76 | 78 | 233 |
| Randomized but not treated[a] | 0 | 1 | 0 | 1 |
| Intent-to-Treat Population[b,c] | 79 (100.0) | 75 (98.7) | 78 (100.0) | 232 (99.6) |
| Per-Protocol Population[b,d] | 72 (91.1) | 63 (82.9) | 69 (88.5) | 204 (87.6) |
| Excluded from the Per-Protocol Population[e] | 7 (8.9) | 13 (17.1) | 9 (11.5) | 29 (12.4) |
| Not in ITT population | 0 | 1 (1.3) | 0 | 1 (0.4) |
| Discontinued from the study | 2 (2.5) | 10 (13.2) | 7 (9.0) | 19 (8.2) |
| Had major deviations from protocol | 5 (6.3) | 2 (2.6) | 2 (2.6) | 9 (3.9) |
| Safety Population | 79 (100.0) | 75 (98.7) | 78 (100.0) | 232 (99.6) |

[a]Subject was randomized in error. Baseline inflammatory lesion count was 7, below inclusion criteria of 12. Subject was not dispensed study drug and was not included in the intent-to-treat population. Incomplete baseline assessment was done.
[b]Percentages are based on the number of subjects randomized.
[c]Includes all randomized subjects.
[d]Includes all ITT subjects without any major deviations from the protocol.
[e]Subjects may be excluded for more than one reason.

TABLE 79B

Summary of Demographics and Baseline Characteristics by Treatment - ITT Population

| Parameter | Minocycline 1.5% (N = 79) | Minocycline 3% (N = 75) | Vehicle (N = 78) | Overall (N = 232) |
|---|---|---|---|---|
| Mean Age years (range) | | | | |
| Range | 21-82 | 22-78 | 24-80 | 21-82 |
| Mean (SD) | 51.2 (15.26) | 51.6 (14.15) | 54.8 (14.05) | 52.5 (14.53) |
| Median | 51.0 | 52.0 | 53.5 | 52.0 |
| Age Categories (years), [n (%)] | | | | |
| 18-30 | 13 (16.5) | 7 (9.3) | 5 (6.4) | 25 (10.8) |
| 31-50 | 25 (31.6) | 28 (37.3) | 27 (34.6) | 80 (34.5) |
| >50 | 41 (51.9) | 40 (53.3) | 46 (59.0) | 127 (54.7) |
| Sex, [n (%)] | | | | |
| Male | 26 (32.9) | 24 (32.0) | 37 (47.4) | 87 (37.5) |
| Female | 53 (67.1) | 51 (68.0) | 41 (52.6) | 145 (62.5) |
| Race, [n (%)] | | | | |
| Caucasian | 98.7 | 97.3 | 100.0 | 98.7 |
| Other[a] | 1.3 | 2.7 | 0 | 1.3 |
| Female of Childbearing Potential (Females only), [n (%)] | | | | |
| Yes | 29 (54.7) | 21 (41.2) | 18 (43.9) | 68 (46.9) |
| No | 24 (45.3) | 30 (58.8) | 23 (56.1) | 77 (53.1) |
| IGA of rocasea,[b] % | | | | |
| Moderate (IGA = 3) | 43.0 | 38.7 | 51.3 | 44.4 |
| Severe (IGA = 4) | 57.0 | 61.3 | 48.7 | 55.6 |
| Mean range) total inflammatory lesion count | 34.5 13-125) | 34.1 12-186) | 30.6 12-91) | 33.1 12-186) |

[a]FMX-103 1.5% n = 1 Other; FMX-103 3%:n = 1American Indian or Alaska Native, n = 1 Native Hawaiian or Other Pacific Islander.
[b]IGA grading for rosacea: 0 = clear; 1 = almost clear; 2 = mild; 3 = moderate; 4 = severe.

Study Baseline.

The mean baseline lesion count for all groups ranged from 30.6 to 34.5 and the IGA scores were all moderate (score 3) or severe (score 4), with about 50% to about 60% of the subjects having a severe rating (Table 80A and C). Table 80B summarizes the IGA score system.

TABLE 80A

Summary of Subject Disposition by Treatment - ITT Population

| Completion Status | Minocycline 1.5% (N = 79) n (%) | Minocycline 3% (N = 75) n (%) | Vehicle (N = 78) n (%) | Overall (N = 232) n (%) |
|---|---|---|---|---|
| Treated (at least one treatment) | 79 (100.0) | 75 (100.0) | 78 (100.0) | 232 (100.0) |
| Completed at least 4 weeks of Treatment | 76 (96.2) | 68 (90.7) | 73 (93.6) | 217 (93.5) |
| Completed 12 weeks of Treatment | 74 (93.7) | 60 (80.0) | 67 (85.9) | 201 (86.6) |
| Completed Treatment and Follow-up[a] | 73 (92.4) | 60 (80.0) | 67 (85.9) | 200 (86.2) |
| Discontinued | 2 (2.5) | 10 (13.3) | 7 (9.0) | 19 (8.2) |
| Adverse Event | 0 | 3 (4.0) | 1 (1.3) | 4 (1.7) |
| Abnormal Laboratory Result | 0 | 0 | 0 | 0 |
| Lost to Follow-up | 1 (1.3) | 0 | 0 | 1 (0.4) |
| Subject Request | 1 (1.3) | 6 (8.0) | 3 (3.8) | 10 (4.3) |
| Protocol Deviation | 0 | 1 (1.3) | 1 (1.3) | 2 (0.9) |
| Specific Medical Reasons | 0 | 0 | 0 | 0 |
| Other | 0 | 0 | 2 (2.6) | 2 (0.9) |

[a]Includes subjects who completed 12 weeks of treatment and had the follow-up visit.

TABLE 80B

IGA grading scale for papulopustular rosacea

| Grade | Score | Description |
|---|---|---|
| Clear | 0 | No inflammatory papules or pustules |
| Almost clear | 1 | 1 or 2 inflammatory papules or pustules |
| Mild | 2 | 3 to 11 inflammatory papules or pustules |
| Moderate | 3 | 12 to 19 inflammatory papules or pustules and no nodules |
| Severe | 4 | ≥20 inflammatory papules or pustules, and up to 2 nodules |

IGA = Investigator's Global Assessment.

TABLE 80C

Summary of Baseline Rosacea IGA and Total Inflammatory Lesion Count by Treatment - ITT Population

| Parameter | Minocycline 1.5% (N = 79) | Minocycline 3% (N = 75) | Vehicle (N = 78) | Overall (N = 232) |
|---|---|---|---|---|
| Investigator Global Assessment (IGA) of Rosacea, [n (%)] | | | | |
| Clear | 0 | 0 | 0 | 0 |
| Almost Clear | 0 | 0 | 0 | 0 |
| Mild | 0 | 0 | 0 | 0 |
| Moderate | 34 (43.0) | 29 (38.7) | 40 (51.3) | 103 (44.4) |
| Severe | 45 (57.0) | 46 (61.3) | 38 (48.7) | 129 (55.6) |
| Total Inflammatory Lesion Count | | | | |
| Mean (SD) | 34.5 (20.89) | 34.1 (24.99) | 30.6 (15.48) | 33.1 (20.74) |
| Median | 28.0 | 27.0 | 26.0 | 27.5 |
| Min, Max | 13, 125 | 12, 186 | 12, 91 | 12, 186 |

Results:

232 subjects were randomized and received at least one dose of study drug (ITT population). 201 (86.6%) subjects completed 12 weeks of treatment and the follow-up visit. Statistically significant improvement vs. vehicle in the two most important measurements of efficacy was demonstrated for both FMX-103 doses. At the week 12 time point, designated for the primary end point analysis, both the 1.5% and 3% doses of FMX103 significantly reduced the absolute number of papules and pustules vs. the vehicle (1.5% and 3%, both p<0.001, ANCOVA, intent-to-treat analysis). The mean reduction in inflammatory lesion count (absolute change) of each treatment group vs. its baseline was 21.1 for the 1.5% dose, 19.9 for the 3% dose, and 7.8 for vehicle (FIG. 1A; Table 81A). The corresponding percent reductions were 61.4% and 55.5% for the FMX103 1.5% and 3% groups, respectively, and 29.7% for the vehicle (1.5% and 3%, both p<0.001, ANCOVA, intent-to-treat analysis). (FIG. 1B; Table 81A). A significant reduction in the mean lesion count was observed as early as week 2 for both 1.5% and 3% doses of FMX103 vs. the vehicle (1.5% and 3%, p<0.01, p<0.05 respectively ANCOVA, intent-to-treat analysis). The mean reduction in inflammatory lesion count (absolute change) of each treatment group vs. its baseline was 10.9 for the 1.5% dose, 9 for the 3% dose, and 4 for vehicle. (see FIG. 1A; Table 81B). The corresponding percent reductions were 30% and 26% for the FMX103 1.5% and 3% groups, respectively, and 16% for the vehicle (1.5% p<0.01, ANCOVA, intent-to-treat analysis) (see FIG. 1B; Table 81C).

TABLE 81A

Summary of Percent and Absolute Change from Baseline in Inflammatory Lesion Count at Week 12 by Treatment in the Intent-to-Treat Population (Multiple Imputation Method)

| Parameter | Minocycline 1.5% (N = 79) | Minocycline 3% (N = 75) | Vehicle (N = 78) |
|---|---|---|---|
| Baseline | | | |
| N | 79 | 75 | 78 |
| Mean (SD) | 34.5 (20.89) | 34.1 (24.99) | 30.6 (15.48) |
| Median | 28.0 | 27.0 | 26.0 |
| Min, Max | 13, 125 | 12, 186 | 12, 91 |
| Week 12 | | | |
| N | 79 | 75 | 78 |
| Mean (SD) | 13.4 (13.96) | 14.2 (12.44) | 22.8 (22.21) |
| Median | 9.0 | 12.9 | 16.8 |
| Min, Max | 0, 90 | 0, 57 | 0, 154 |
| Percent Change from Baseline (%) | | | |
| N | 79 | 75 | 78 |
| Mean (SD) | −61.4 (32.29) | −55.5 (31.38) | −29.7 (46.34) |
| Median | −69.6 | −60.9 | −37.8 |
| Min, Max | −100.0, 44.4 | −100.0, 11.2 | −100.0, 165.5 |
| LSMean (SE)[a] | −64.5 (4.55) | −58.5 (4.94) | −32.0 (4.83) |
| P-value[a] | <0.001 | <0.001 | |

TABLE 81A-continued

Summary of Percent and Absolute Change from Baseline in Inflammatory Lesion Count at Week 12 by Treatment in the Intent-to-Treat Population (Multiple Imputation Method)

| Parameter | Minocycline 1.5% (N = 79) | Minocycline 3% (N = 75) | Vehicle (N = 78) |
|---|---|---|---|
| Absolute Change from Baseline | | | |
| N | 79 | 75 | 78 |
| Mean (SD) | −21.1 (17.79) | −19.9 (20.38) | −7.8 (17.37) |
| Median | −17.0 | −14.0 | −8.0 |
| Min, Max | −95, 12 | −129, 2 | −44, 96 |
| LSMean (SE)[a] | −21.2 (1.68) | −20.3 (1.75) | −9.9 (1.80) |
| P-value[a] | <0.001 | <0.001 | |
| Interaction P-value[b]: 0.665 | | | |
| Homogeneity P-value[c]: 0.267 | | | |
| Normality P-value[d]: <0.001 | | | |
| Non-parametric ANCOVA P-value[e] | <0.001 | <0.001 | |

[a]From an analysis of covariance with main effect of treatment and covariates of baseline and pooled site. P-value is the test result for treatment effect versus vehicle.
[b]P-value for treatment by pooled site, based on analysis of covariance on unimputed data with effects of treatment, baseline, and pooled site, and treatment by pooled site interaction.
[c]From Levene's test on unimputed data.
[d]From Shapiro-Wilk test on unimputed data.
[e]From a non-parametric ANCOVA with effects of treatment, baseline, and pooled site.

TABLE 81B

Summary of Absolute Change from Baseline in Inflammatory Lesion Count Visits 2, 4 and 8 by Treatment in the Intent-to-Treat Population (Multiple Imputation Method)

| Visit Parameter | Minocycline 1.5% (N = 79) | Minocycline 3% (N = 75) | Vehicle (N = 78) |
|---|---|---|---|
| Baseline | | | |
| N | 79 | 75 | 78 |
| Mean (SD) | 34.5 (20.89) | 34.1 (24.99) | 30.6 (15.48) |
| Median | 28.0 | 27.0 | 26.0 |
| Min, Max | 13, 125 | 12, 186 | 12, 91 |
| Week 2 | | | |
| N | 79 | 75 | 78 |
| Mean (SD) | 23.6 (15.20) | 25.2 (21.14) | 26.7 (17.83) |
| Median | 21.0 | 19.0 | 23.5 |
| Min, Max | 0, 74 | 2, 152 | 1, 103 |
| Week 2 Change from Baseline | | | |
| N | 79 | 75 | 78 |
| Mean (SD) | −10.9 (14.71) | −9.0 (14.57) | −4.0 (10.95) |
| Median | −8.0 | −7.0 | −4.0 |
| Min, Max | −75, 31 | −82, 24 | −30, 59 |
| LSMean (SE)[a] | −11.2 (1.36) | −9.2 (1.40) | −5.3 (1.37) |
| P-value[a] | 0.002 | 0.038 | |
| Week 4 | | | |
| N | 79 | 75 | 78 |
| Mean (SD) | 19.8 (16.14) | 19.3 (19.72) | 25.1 (16.38) |
| Median | 14.0 | 15.0 | 21.0 |
| Min, Max | 0, 76 | 1, 148 | 0, 81 |
| Week 4 Change from Baseline | | | |
| N | 79 | 75 | 78 |
| Mean (SD) | −14.8 (16.40) | −14.8 (15.00) | −5.5 (9.06) |
| Median | −13.0 | −12.0 | −7.0 |
| Min, Max | −81, 29 | −84, 20 | −22, 23 |
| LSMean (SE)[a] | −14.6 (1.36) | −14.7 (1.42) | −6.6 (1.36) |
| P-value[a] | <0.001 | <0.001 | |

TABLE 81B-continued

Summary of Absolute Change from Baseline in Inflammatory Lesion Count Visits 2, 4 and 8 by Treatment in the Intent-to-Treat Population (Multiple Imputation Method)

| Visit Parameter | Minocycline 1.5% (N = 79) | Minocycline 3% (N = 75) | Vehicle (N = 78) |
|---|---|---|---|
| Week 8 | | | |
| N | 79 | 75 | 78 |
| Mean (SD) | 16.0 (14.51) | 15.2 (15.30) | 23.1 (17.60) |
| Median | 11.2 | 11.0 | 18.5 |
| Min, Max | 0, 79 | 0, 96 | 0, 86 |
| Week 8 Change from Baseline | | | |
| N | 79 | 75 | 78 |
| Mean (SD) | −18.5 (17.71) | −18.9 (17.60) | −7.6 (13.45) |
| Median | −16.0 | −17.0 | −8.4 |
| Min, Max | −85, 29 | −90, 16 | −39, 32 |
| LSMean (SE)[a] | −18.4 (1.46) | −19.0 (1.52) | −9.3 (1.49) |
| P-value[a] | <0.001 | <0.001 | |

[a]From an analysis of covariance with main effect of treatment and covariates of baseline and pooled site. P-value is the test result for treatment effect versus vehicle.

TABLE 81C

Summary of Percent Change from Baseline in Inflammatory Lesion Count Visits 2, 4 and 8 by Treatment in the Intent-to-Treat Population (Multiple Imputation Method)

| Visit Parameter | Minocycline 1.5% (N = 79) | Minocycline 3% (N = 75) | Vehicle (N = 78) |
|---|---|---|---|
| Baseline | | | |
| N | 79 | 75 | 78 |
| Mean (SD) | 34.5 (20.89) | 34.1 (24.99) | 30.6 (15.48) |
| Median | 28.0 | 27.0 | 26.0 |
| Min, Max | 13, 125 | 12, 186 | 12, 91 |
| Week 2 | | | |
| N | 79 | 75 | 78 |
| Mean (SD) | 23.6 (15.20) | 25.2 (21.14) | 26.7 (17.83) |
| Median | 21.0 | 19.0 | 23.5 |
| Min, Max | 0, 74 | 2, 152 | 1, 103 |
| Week 2 Percent Change from Baseline (%) | | | |
| N | 79 | 75 | 78 |
| Mean (SD) | −30.0 (34.05) | −25.9 (31.68) | −15.8 (32.54) |
| Median | −29.6 | −29.2 | −16.7 |
| Min, Max | −100.0, 114.8 | −87.2, 104.3 | −91.7, 134.1 |
| LSMean (SE)[a] | −32.1 (3.83) | −27.5 (3.93) | −17.3 (3.90) |
| P-value[a] | 0.005 | 0.053 | |
| Week 4 | | | |
| N | 79 | 75 | 78 |
| Mean (SD) | 19.8 (16.14) | 19.3 (19.72) | 25.1 (16.38) |
| Median | 14.0 | 15.0 | 21.0 |
| Min, Max | 0, 76 | 1, 148 | 0, 81 |
| Week 4 Percent Change from Baseline (%) | | | |
| N | 79 | 75 | 78 |
| Mean (SD) | −42.9 (37.25) | −44.1 (28.20) | −20.1 (33.68) |
| Median | −46.7 | −46.0 | −19.8 |
| Min, Max | −100.0, 107.4 | −94.4, 32.8 | −100.0, 100.0 |
| LSMean (SE)[a] | −44.5 (3.95) | −45.5 (4.14) | −20.9 (3.97) |
| P-value[a] | <0.001 | <0.001 | |
| Week 8 | | | |
| N | 79 | 75 | 78 |
| Mean (SD) | 16.0 (14.51) | 15.2 (15.30) | 23.1 (17.60) |
| Median | 11.2 | 11.0 | 18.5 |
| Min, Max | 0, 79 | 0, 96 | 0, 86 |

TABLE 81C-continued

Summary of Percent Change from Baseline in Inflammatory Lesion Count Visits 2, 4 and 8 by Treatment in the Intent-to-Treat Population (Multiple Imputation Method)

| Visit Parameter | Minocycline 1.5% (N = 79) | Minocycline 3% (N = 75) | Vehicle (N = 78) |
|---|---|---|---|
| Week 8 Percent Change from Baseline (%) | | | |
| N | 79 | 75 | 78 |
| Mean (SD) | −53.3 (36.17) | −53.8 (34.33) | −26.3 (37.78) |
| Median | −63.6 | −58.1 | −28.3 |
| Min, Max | −100.0, 107.4 | −100.0, 71.4 | −100.0, 69.7 |
| LSMean (SE)$^a$ | −54.9 (4.36) | −55.2 (4.54) | −27.5 (4.41) |
| P-value$^a$ | <0.001 | <0.001 | |

$^a$From an analysis of covariance with main effect of treatment and covariates of baseline and pooled site. P-value is the test result for treatment effect versus vehicle.

Moreover, treatment resulted in significant improvement in IGA scores (FIGS. 2A and 2B; Tables 82A and 82B). Both the 1.5% and 3% doses of FMX-103 were significantly better compared to vehicle in reducing the IGA score by 2 grades and in reaching a "clear" (score=0) or "almost clear" (score=1) rating at Week 12, Both the 1.5% and 3% doses were efficacious and there was no statistically significant difference between the two minocycline doses.

The results indicate that both the 1.5% and 3% doses of FMX-103 were significantly better than the vehicle in improving IGA scores by at least 2 grades at Week 12 (p=0.002 and p=0.032, respectively FIG. 2A, Table 82B). Both active doses of FMX-103 were also significantly better than the vehicle in improving the IGA scores by at least 2 grades and achieving an IGA score of "clear" (score=0) or "almost clear" (score=1) at Week 12 (p=0.001 and p=0.041 for 1.5% and 3% FMX-103, respectively FIG. 2B, Table 82B).

The percent of subjects with improvement of IGA score by 2 grades at Week 12 was 41.8% and 33.3% for the FMX103 1.5% and 3% groups, respectively, and 17.9% for the vehicle (P<0.01 and P<0.05, respectively, Cochran-Mantel-Haenszel test). FIG. 2A; Tables 82A)

The percent of subjects with improvement of IGA score by 2 grades and in reaching a "clear" (score=0) or "almost clear" (score=1) at Week 12 was 25.3% and 17.3% for the FMX103 1.5% and 3% groups, respectively, and 7.7% for the vehicle (P<0.01 and P<0.05, respectively, Cochran-Mantel-Haenszel test FIG. 2B; Tables 82B)

Both the 1.5% and 3% doses of FMX-103 were significantly better compared to vehicle in reducing the IGA score by 2 grades as early as Week 4 (P<0.001 and P<0.01, respectively, Cochran-Mantel-Haenszel test FIG. 2A; Tables 82C). The percent improvement of IGA score by 2 grades at Week 4 was 20.3% and 18.7% for the FMX103 1.5% and 3% groups, respectively, and 2.6% for the vehicle.

Both the 1.5% and 3% doses of FMX-103 were significantly better compared to vehicle in reducing the IGA score by 2 grades resulting in "clear" or "almost clear" as early as Week 8 (P<0.01 and P<0.05, respectively, Cochran-Mantel-Haenszel test FIG. 2B; Table 82D). The percent improvement of IGA score by 2 grades at Week 8 was 16.5% and 14.7% for the FMX103 1.5% and 3% groups, respectively, and 3.8% for the vehicle.

TABLE 82A

Summary of Investigator Global Assessment (IGA) 2-Level Improvement from Baseline to Week 12 by Treatment in the Intent-to-Treat Population (Multiple Imputation Method)

| Parameter | Minocycline 1.5% (N = 79) n (%) | Minocycline 3% (N = 75) n (%) | Vehicle (N = 78) n (%) |
|---|---|---|---|
| Baseline | | | |
| Clear | 0 | 0 | 0 |
| Almost Clear | 0 | 0 | 0 |
| Mild | 0 | 0 | 0 |
| Moderate | 34 (43.0) | 29 (38.7) | 40 (51.3) |
| Severe | 45 (57.0) | 46 (61.3) | 38 (48.7) |
| Week 12 | | | |
| Clear | 7 (8.9) | 2 (2.7) | 1 (1.3) |
| Almost Clear | 13 (16.5) | 11 (14.7) | 5 (6.4) |
| Mild | 29 (36.7) | 26 (34.7) | 25 (32.1) |
| Moderate | 12 (15.2) | 17 (22.7) | 18 (23.1) |
| Severe | 18 (22.8) | 19 (25.3) | 29 (37.2) |
| Severe Cases Change | −60% | −58.7% | −23.7% |
| Change from Baseline | | | |
| Improvement observed | 58 (73) | 53 (70.66) | 35 (45) |
| Improved by 4 Levels | 1 (1.3) | 0 | 0 |
| Improved by 3 Levels | 10 (12.7) | 6 (8.0) | 1 (1.3) |
| Improved by 2 Levels | 22 (27.8) | 19 (25.3) | 13 (16.7) |
| Improved by 1 Level | 25 (31.6) | 28 (37.3) | 21 (26.9) |
| No Improvement | 21 (26.6) | 20 (26.7) | 40 (51.3) |
| Worsened by 1 Level | 0 | 2 (2.7) | 3 (3.8) |
| Worsened by 2 Levels | 0 | 0 | 0 |
| Improved at Least 2 Levels | 33 (41.8) | 25 (33.3) | 14 (17.9) |
| Did Not Improve at Least 2 Levels | 46 (58.2) | 50 (66.7) | 64 (82.1) |
| P-value$^a$ | 0.002 | 0.032 | |

Investigator Global Assessment (IGA) scores are 0-4 (Clear to Severe)
$^a$From a CMH test stratified by pooled site. Only treatment groups being compared included in the analysis.

TABLE 82B

Summary of Investigator Global Assessment (IGA) 2-Level Improvement that Results in Clear or Almost Clear from Baseline to Week 12 by Treatment Intent-to-Treat Population (Multiple Imputation Method)

| Clear or Almost Clear and Improved at Least 2 Levels | Minocycline 1.5% (N = 79) n (%) | Minocycline 3% (N = 75) n (%) | Vehicle (N = 78) n (%) |
|---|---|---|---|
| Yes | 20 (25.3) | 13 (17.3) | 6 (7.7) |
| No | 59 (74.7) | 62 (82.7) | 72 (92.3) |
| P-Value$^a$ | 0.001 | 0.041 | |

Investigator Global Assessment (IGA) scores are 0-4 (Clear to Severe)
$^a$From a CMH test stratified by pooled site. Only treatment groups being compared included in the analysis.

TABLE 82C

Summary of Investigator Global Assessment (IGA) 2-Level Improvement from Baseline Visits 2, 4 and 8 and Treatment in the Intent-to-Treat Population (Multiple Imputation Method)

| Visit Parameter | Minocycline 1.5% (N = 79) n (%) | Minocycline 3% (N = 75) n (%) | Vehicle (N = 78) n (%) |
|---|---|---|---|
| Baseline | | | |
| Clear | 0 | 0 | 0 |
| Almost Clear | 0 | 0 | 0 |
| Mild | 0 | 0 | 0 |
| Moderate | 34 (43.0) | 29 (38.7) | 40 (51.3) |
| Severe | 45 (57.0) | 46 (61.3) | 38 (48.7) |
| Week 2 | | | |
| Clear | 1 (1.3) | 0 | 0 |
| Almost Clear | 1 (1.3) | 2 (2.7) | 2 (2.6) |
| Mild | 19 (24.1) | 15 (20.0) | 12 (15.4) |
| Moderate | 23 (29.1) | 27 (36.0) | 32 (41.0) |
| Severe | 35 (44.3) | 31 (41.3) | 32 (41.0) |
| Week 2 Change from Baseline | | | |
| Improved by 4 Levels | 0 | 0 | 0 |
| Improved by 3 Levels | 1 (1.3) | 0 | 0 |
| Improved by 2 Levels | 4 (5.1) | 4 (5.3) | 2 (2.6) |
| Improved by 1 Level | 25 (31.6) | 28 (37.3) | 19 (24.4) |
| No Improvement | 47 (59.5) | 41 (54.7) | 56 (71.8) |
| Worsened by 1 Level | 2 (2.5) | 2 (2.7) | 1 (1.3) |
| Worsened by 2 Levels | 0 | 0 | 0 |
| Improved at Least 2 Levels | 5 (6.3) | 4 (5.3) | 2 (2.6) |
| Did Not Improve at Least 2 Levels | 74 (93.7) | 71 (94.7) | 76 (97.4) |
| P-Value[a] | 0.239 | 0.363 | |
| Week 4 | | | |
| Clear | 1 (1.3) | 0 | 1 (1.3) |
| Almost Clear | 6 (7.6) | 5 (6.7) | 1 (1.3) |
| Mild | 25 (31.6) | 22 (29.3) | 16 (20.5) |
| Moderate | 21 (26.6) | 23 (30.7) | 27 (34.6) |
| Severe | 26 (32.9) | 25 (33.3) | 33 (42.3) |
| Week 4 Change from Baseline | | | |
| Improved by 4 Levels | 0 | 0 | 0 |
| Improved by 3 Levels | 2 (2.5) | 0 | 1 (1.3) |
| Improved by 2 Levels | 14 (17.7) | 14 (18.7) | 1 (1.3) |
| Improved by 1 Level | 26 (32.9) | 27 (36.0) | 23 (29.5) |
| No Improvement | 36 (45.6) | 33 (44.0) | 51 (65.4) |
| Worsened by 1 Level | 1 (1.3) | 1 (1.3) | 2 (2.6) |
| Worsened by 2 Levels | 0 | 0 | 0 |
| Improved at Least 2 Levels | 16 (20.3) | 14 (18.7) | 2 (2.6) |
| Did Not Improve at Least 2 Levels | 63 (79.7) | 61 (81.3) | 76 (97.4) |
| P-Value[a] | <0.001 | 0.001 | |
| Week 8 | | | |
| Clear | 3 (3.8) | 4 (5.3) | 1 (1.3) |
| Almost Clear | 10 (12.7) | 7 (9.3) | 2 (2.6) |
| Mild | 29 (36.7) | 29 (38.7) | 23 (29.5) |
| Moderate | 15 (19.0) | 16 (21.3) | 21 (26.9) |
| Severe | 22 (27.8) | 19 (25.3) | 31 (39.7) |
| Week 8 Change from Baseline | | | |
| Improved by 4 Levels | 0 | 1 (1.3) | 0 |
| Improved by 3 Levels | 6 (7.6) | 5 (6.7) | 1 (1.3) |
| Improved by 2 Levels | 16 (20.3) | 20 (26.7) | 7 (9.0) |
| Improved by 1 Level | 32 (40.5) | 26 (34.7) | 24 (30.8) |
| No Improvement | 24 (30.4) | 22 (29.3) | 42 (53.8) |
| Worsened by 1 Level | 1 (1.3) | 1 (1.3) | 4 (5.1) |
| Worsened by 2 Levels | 0 | 0 | 0 |
| Improved at Least 2 Levels | 22 (27.8) | 26 (34.7) | 8 (10.3) |
| Did Not Improve at Least 2 Levels | 57 (72.2) | 49 (65.3) | 70 (89.7) |
| P-Value[a] | 0.004 | <0.001 | |

[a] From a CMH test stratified by pooled site. Only treatment groups being compared are included in the analysis. Source: Listing 16.2.10.1

TABLE 82D

Summary of Investigator Global Assessment (IGA) 2-Level Improvement from Baseline that Results in Clear or Almost Clear Visits 2, 4 and 8 and Treatment in the Intent-to-Treat Population (Multiple Imputation Method)

| Visit Clear or Almost Clear and Improved at Least 2 Levels | Minocycline 1.5% (N = 79) n (%) | Minocycline 3% (N = 75) n (%) | Vehicle (N = 78) n (%) |
|---|---|---|---|
| Week 2 | | | |
| Yes | 2 (2.5) | 2 (2.7) | 2 (2.6) |
| No | 77 (97.5) | 73 (97.3) | 76 (97.4) |
| P-Value[a] | >0.999 | 0.933 | |
| Week 4 | | | |
| Yes | 7 (8.9) | 5 (6.7) | 2 (2.6) |
| No | 72 (91.1) | 70 (93.3) | 76 (97.4) |
| P-Value[a] | 0.055 | 0.155 | |
| Week 8 | | | |
| Yes | 13 (16.5) | 11 (14.7) | 3 (3.8) |
| No | 66 (83.5) | 64 (85.3) | 75 (96.2) |
| P-Value[a] | 0.009 | 0.014 | |

[a] From a CMH test stratified by pooled site. Only treatment groups being compared are included in the analysis.

Safety and Tolerability:

Both doses of FMX103 appeared to be generally safe and well-tolerated. There were no serious treatment-related systemic adverse events, and there were only a few subjects overall who reported any treatment-related AEs (2, 4, and 5 in the 1.5%, 3%, and vehicle groups, respectively). Overall, 47% (109/232) of subjects reported ≥1 treatment-emergent AE (TEAE) (Table 83). The most common TEAEs (≥2% of subjects) included nasopharyngitis, urinary tract infection, cystitis, bronchitis (Table 84). 11 (4.7%) subjects reported treatment-related TEAEs, 9 had treatment-related dermal reactions (Tables 83 and Table 85). These reactions resolved before the end of the study. Serious TEAEs were reported in 4 subjects (3 in FMX-103 group and 1 in vehicle group) (Tables 83, and Table 85), however there were no treatment-related systemic TEAEs reported. In the FMX103 1.5% group, two subjects reported serious TEAEs (one had a contusion and one had a cerebral hemorrhage, hemiparesis, and a pulmonary embolism), and in the FMX103 3% group, one subject reported a serious TEAE (hemorrhoids). In the vehicle group, one subject reported a serious TEAE (gastroenteritis). None of these was considered to be treatment-related. A total of 4 subjects discontinued the study due to an adverse event (3 in the 3% group and 1 in the vehicle group (Table 83 and Table 85). All of these discontinued due to dermal-related TEAE skin (one subject in the vehicle group had pruritus and skin burning sensation; three subjects in the FMX103 3% group each had eczema, burning sensation, or worsening of rosacea), and all resolved by the end of the study (Table 83 and Table 85). Treatment appeared to be well tolerated; the severity of local signs and symptoms appeared to be similar between treatment groups.

TABLE 83

Summary of Safety Profile

| Overall Summary of TEAEs, n (%) | Minocycline 1.5% (N = 79) n (%) | Minocycline 3% (N = 75) n (%) | Vehicle (N = 78) n (%) | Overall (N = 232) n (%) |
|---|---|---|---|---|
| Subjects with 1 or more TEAE | 46 (58.2) | 32 (42.7) | 31 (39.7) | 109 (47.0) |
| Subjects with 1 or more treatment-related TEAE$^{ab}$ | 2 (2.5) | 4 (5.3) | 5 (6.4) | 11 (4.7) |
| Treatment-Related Dermal TEAEs$^{c}$ | 1 (1.3) | 4 (5.3) | 5 (6.4) | 10 (4.3) |
| Subjects with 1 or more severe TEAE | 3 (3.8) | 2 (2.7) | 4 (5.1) | 9 (3.9) |
| Subjects with 1 or more TEAE leading to study discontinuation$^{b}$ | 0 | 3 (4.0) | 1 (1.3) | 4 (1.7) |
| Subjects with 1 or more serious TEAE$^{b}$ | 2 (2.5) | 1 (1.3) | 1 (1.3) | 4 (1.7) |

Safety population includes all randomized subjects who applied at least one dose of study drug $^{a}$Includes unassessable, possible, probable, and certainly related adverse events $^{b}$Includes skin and subcutaneous tissue disorders, and general disorders and administration-site conditions (i.e, application-site erythema).

$^{c}$Subjects experiencing ≥1 AEs are counted only once for each AE term.

TABLE 84

Profile of Commmon Treatment-Emergent Adverse Events That Occured in ≥2% of Subjects and Treatmet Related Dermal TEAES

| | Minocycline 1.5% (N = 79) | | Minocycline 3% (N = 75) | | Vehicle (N = 78) | |
|---|---|---|---|---|---|---|
| System Organ Class Preferred Term | Subjects$^{a}$ n (%) | Events n | Subjects$^{a}$ n (%) | Events n | Subjects$^{a}$ n (%) | Events n |
| Any Adverse Event | | | | | | |
| Overall | 26 (32.9) | 32 | 13 (17.3) | 19 | 16 (20.5) | 19 |
| Infections and infestations | | | | | | |
| Nasopharyngitis | 11 (13.9) | 11 | 3 (4.0) | 3 | 9 (11.5) | 9 |
| Urinaiy tract infection | 3 (3.8) | 3 | 2 (2.7) | 2 | 3 (3.8) | 3 |
| Cystitis | 2 (2.5) | 3 | 2 (2.7) | 2 | 0 | 0 |
| Bronchitis | 3 (3.8) | 3 | 0 | 0 | 0 | 0 |
| Urinaiy tract infection bacterial | 2 (2.5) | 2 | 0 | 0 | 0 | 0 |
| Influenza | 0 | 0 | 0 | 0 | 2 (2.6) | 3 |
| Skin and subcutaneous tissue disorders | | | | | | |
| Worsening of rosacea as compared to baseline | 2 (2.5) | 2 | 3 (4.0) | 4 | 0 | 0 |
| Eczema | 2 (2.5) | 2 | 2 (2.7) | 2 | 2 (2.6) | 2 |
| Vascular disorders | | | | | | |
| Hypertension | 2 (2.5) | 2 | 2 (2.7) | 2 | 2 (2.6) | 2 |
| Eye disorders | | | | | | |
| Eczema eyelids | 2 (2.5) | 2 | 0 | 0 | 0 | 0 |
| Gastrointestinal disorders | | | | | | |
| Toothache | 2 (2.5) | 2 | 0 | 0 | 0 | 0 |
| Nervous system disorders | | | | | | |
| Headache | 0 | 0 | 2 (2.7) | 4 | 0 | 0 |

$^{a}$Subjects experiencing one or more adverse events are counted only once for each adverse event term.

TABLE 85

Summary of treatment-related dermal reactions, serious TEAEs, and TEAE leading to study discontinuation

| | FMX-103 1.5% (n = 79) | FMX-103 3% (n = 75) | Vehicle (n = 78) |
|---|---|---|---|
| Subjects with treatment-related TEAEs[a], n (%) | 1 (1.3) | 3 (4.0) | 5 (6.4) |
| Skin and subcutaneous tissue disorders | | | |
| Worsening of rosacea as compared to baseline | 0 | 2 (2.7) | 0 |
| Eczema | 0 | 1 (1.3) | 1 (1.3) |
| Skin exfoliation | 0 | 1 (1.3) | 0 |
| Erythema | 0 | 0 | 1 (1.3) |
| Pruritus | 0 | 0 | 1 (1.3) |
| Scab | 0 | 0 | 1 (1.3) |
| Skin burning sensation | 0 | 0 | 1 (1.3) |
| Spotted redness in treatment area | 1 (1.3) | 0 | 0 |
| Redness after medication application | 0 | 0 | 1 (1.3) |
| Face-burning or stinging | 0 | 1 (1.3) | 0 |
| Eye disorders | | | |
| Eye discharge | 1 (1.3) | 0 | 0 |
| Subjects with ≥1 serious TEAE[a], n (1%) | 2 (2.5) | 1 (1.3) | 1 (1.3) |
| Haemorrhoids | 0 | 1 (1.3) | 0 |
| Contusion | 1 (1.3) | 0 | 0 |
| Cerebral haemorrhage | 1 (1.3) | 0 | 0 |
| Hemiparesis | 1 (1.3) | 0 | 0 |
| Pulmonary embolism | 1 (1.3) | 0 | 0 |
| Gastroenteritis | 0 | 0 | 1 (1.3) |
| Subjects with ≥1 TEAE leading to study discontinuation n (%)[a,b] | 0 | 3 (4.0) | 1 (1.3) |
| Eczema | 0 | 1 (1.3) | 0 |
| Worsening of rosacea as compared to baseline | 0 | 1 (1.3) | 0 |
| Pruritus | 0 | 0 | 1 (1.3) |
| Skin burning sensation | 0 | 0 | 1 (1.3) |
| Face burning or stinging | 0 | 1 (1.3) | 0 |

Safety population includes all randomized subjects who applied at least one dose of study drug.
[a]Subjects experiencing ≥1 AEs are counted only once for each AE term.
[b]Eczema, rosacea, pruritus, face burning or stinging, and skin burning sensation were classed as skin and subcutaneous tissue disorders (TEAE dermal related).

TABLE 86

Summary of Post-Baseline Local Safety Assessments by Treatment Safety Population

| Scale Visit | Minocycline 1.5% (N = 79) n (%) | Minocycline 3% (N = 75) n (%) | Vehicle (N = 78) n (%) |
|---|---|---|---|
| Telangiectasis Week 2 | | | |
| None | 21 (26.6) | 8 (10.7) | 10 (12.8) |
| Mild | 39 (49.4) | 42 (56.0) | 41 (52.6) |
| Moderate | 19 (24.1) | 20 (26.7) | 22 (28.2) |
| Severe | 0 | 1 (1.3) | 2 (2.6) |
| None or Mild | 60 (75.9) | 50 (66.7) | 51 (65.4) |
| Week 4 | | | |
| None | 20 (25.3) | 11 (14.7) | 9 (11.5) |
| Mild | 39 (49.4) | 42 (56.0) | 39 (50.0) |
| Moderate | 20 (25.3) | 14 (18.7) | 24 (30.8) |
| Severe | 0 | 1 (1.3) | 2 (2.6) |
| None or Mild | 59 (74.7) | 53 (70.7) | 48 (61.5) |
| Week 8 | | | |
| None | 20 (25.3) | 13 (17.3) | 11 (14.1) |
| Mild | 38 (48.1) | 37 (49.3) | 32 (41.0) |
| Moderate | 19 (24.1) | 15 (20.0) | 26 (33.3) |
| Severe | 0 | 0 | 2 (2.6) |
| None or Mild | 58 (73.4) | 50 (66.7) | 43 (55.1) |
| Week 12 | | | |
| None | 22 (27.8) | 14 (18.7) | 11 (14.1) |
| Mild | 42 (53.2) | 42 (56.0) | 33 (42.3) |
| Moderate | 14 (17.7) | 16 (21.3) | 31 (39.7) |
| Severe | 0 | 1 (1.3) | 2 (2.6) |
| None or Mild | 64 (81.0) | 56 (74.7) | 44 (56.4) |
| Burning/Stinging Week 2 | | | |
| None | 53 (67.1) | 37 (49.3) | 38 (48.7) |
| Mild | 17 (21.5) | 24 (32.0) | 24 (30.8) |
| Moderate | 8 (10.1) | 8 (10.7) | 11 (14.1) |
| Severe | 1 (1.3) | 2 (2.7) | 2 (2.6) |
| None or Mild | 70 (88.6) | 61 (81.3) | 62 (79.5) |
| Week 4 | | | |
| None | 50 (63.3) | 47 (62.7) | 42 (53.8) |
| Mild | 20 (25.3) | 14 (18.7) | 23 (29.5) |
| Moderate | 7 (8.9) | 7 (9.3) | 9 (11.5) |
| Severe | 2 (2.5) | 0 | 0 |
| None or Mild | 70 (88.6) | 61 (81.3) | 65 (83.3) |
| Week 8 | | | |
| None | 58 (73.4) | 50 (66.7) | 40 (51.3) |
| Mild | 14 (17.7) | 13 (17.3) | 22 (28.2) |
| Moderate | 5 (6.3) | 1 (1.3) | 8 (10.3) |
| Severe | 0 | 1 (1.3) | 1 (1.3) |
| None or Mild | 72 (91.1) | 63 (84.0) | 62 (79.5) |
| Week 12 | | | |
| None | 55 (69.6) | 54 (72.0) | 45 (57.7) |
| Mild | 19 (24.1) | 13 (17.3) | 27 (34.6) |
| Moderate | 4 (5.1) | 5 (6.7) | 5 (6.4) |
| Severe | 0 | 1 (1.3) | 0 |
| None or Mild | 74 (93.7) | 67 (89.3) | 72 (92.3) |
| Flushing/Blushing Week 2 | | | |
| None | 42 (53.2) | 35 (46.7) | 27 (34.6) |
| Mild | 22 (27.8) | 23 (30.7) | 25 (32.1) |
| Moderate | 13 (16.5) | 10 (13.3) | 18 (23.1) |
| Severe | 2 (2.5) | 3 (4.0) | 5 (6.4) |
| None or Mild | 64 (81.0) | 58 (77.3) | 52 (66.7) |
| Week 4 | | | |
| None | 45 (57.0) | 40 (53.3) | 23 (29.5) |
| Mild | 22 (27.8) | 18 (24.0) | 31 (39.7) |
| Moderate | 7 (8.9) | 8 (10.7) | 18 (23.1) |
| Severe | 5 (6.3) | 2 (2.7) | 2 (2.6) |
| None or Mild | 67 (84.8) | 58 (77.3) | 54 (69.2) |
| Week 8 | | | |
| None | 47 (59.5) | 39 (52.0) | 32 (41.0) |
| Mild | 22 (27.8) | 20 (26.7) | 24 (30.8) |
| Moderate | 6 (7.6) | 5 (6.7) | 13 (16.7) |
| Severe | 2 (2.5) | 1 (1.3) | 2 (2.6) |
| None or Mild | 69 (87.3) | 59 (78.7) | 56 (71.8) |
| Week 12 | | | |
| None | 51 (64.6) | 39 (52.0) | 33 (42.3) |
| Mild | 16 (20.3) | 22 (29.3) | 30 (38.5) |
| Moderate | 10 (12.7) | 11 (14.7) | 12 (15.4) |
| Severe | 1 (1.3) | 1 (1.3) | 2 (2.6) |
| None or Mild | 67 (84.8) | 61 (81.3) | 63 (80.8) |

Figure 3:
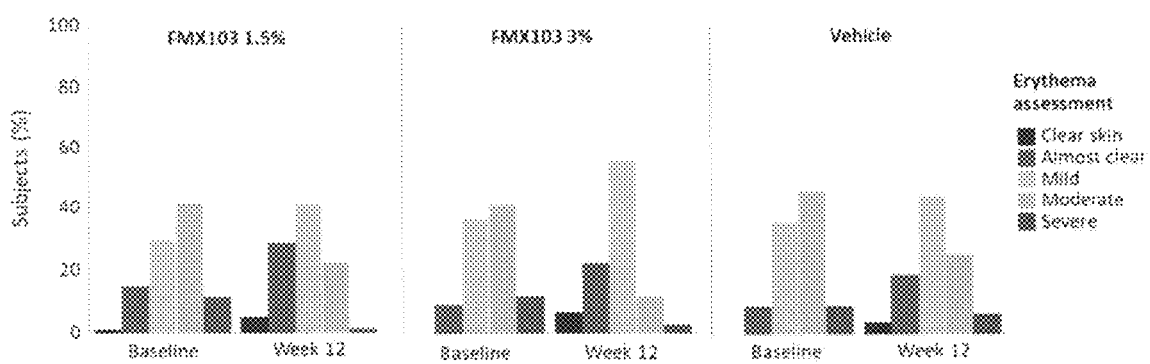
FIG. 3 shows clinical erythema assessment change from the baseline after 12 weeks of treatment.

Clinical Erythema Assessment:

Both FMX103 doses appeared to reduce erythema (Table 87). Following treatment, a decrease in erythema was observed. At 12 weeks, the 1.5% and 3% doses of FMX103 were effective in reducing erythema, compared to the vehicle-treated group (Table 87 and FIG. 3) as opposed to oral Orecea which had no effect on erythema. In particular, the majority of subjects in each treatment group (approximately 53% to 55% in each group) had a clinical erythema assessment of moderate or severe. At Week 12, a larger majority of subjects in the 1.5% and 3% FMX-103 groups (approximately 76% to 85%, respectively) had a clinical erythema assessment of clear to mild vs. approximately 68% of subjects in the vehicle group. Thus, FMX103 advantageously reduced erythema in moderate to severe cases, as well as avoided systemic side effects.

TABLE 87

Summary of Changes from Baseline in Clinical Erythema Assessment by Visit and Treatment Intent-to-Treat Population (Multiple Imputation Method)

| Visit<br>Parameter | Minocycline 1.5%<br>(N = 79)<br>n (%) | Minocycline 3%<br>(N = 75)<br>n (%) | Vehicle<br>(N = 78)<br>n (%) |
|---|---|---|---|
| Week 2 | | | |
| Baseline | | | |
| Clear | 1 (1.3) | 0 | 0 |
| Almost Clear | 12 (15.2) | 7 (9.3) | 7 (9.0) |
| Mild | 24 (30.4) | 28 (37.3) | 28 (35.9) |
| Moderate | 33 (41.8) | 31 (41.3) | 36 (46.2) |
| Severe | 9 (11.4) | 9 (12.0) | 7 (9.0) |
| Post-Baseline | | | |
| Clear | 0 | 2 (2.7) | 0 |
| Almost Clear | 21 (26.6) | 12 (16.0) | 10 (12.8) |
| Mild | 30 (38.0) | 34 (45.3) | 28 (35.9) |
| Moderate | 19 (24.1) | 21 (28.0) | 34 (43.6) |
| Severe | 9 (11.4) | 6 (8.0) | 6 (7.7) |
| Change in Moderate or Severe | | | |
| Erythema Cases* | −33% (42 to 28) | −33% (40 to 27) | −7% (43 to 40) |
| Improved at Least 2 Levels | 1 (1.3) | 5 (6.7) | 0 |
| Did Not Improve at Least 2 Levels | 78 (98.7) | 70 (93.3) | 78 (100.0) |
| Week 4 | | | |
| Baseline | | | |
| Clear | 1 (1.3) | 0 | 0 |
| Almost Clear | 12 (15.2) | 7 (9.3) | 7 (9.0) |
| Mild | 24 (30.4) | 28 (37.3) | 28 (35.9) |
| Moderate | 33 (41.8) | 31 (41.3) | 36 (46.2) |
| Severe | 9 (11.4) | 9 (12.0) | 7 (9.0) |
| Post-Baseline | | | |
| Clear | 3 (3.8) | 2 (2.7) | 1 (1.3) |
| Almost Clear | 22 (27.8) | 18 (24.0) | 12 (15.4) |
| Mild | 25 (31.6) | 39 (52.0) | 29 (37.2) |
| Moderate | 20 (25.3) | 12 (16.0) | 28 (35.9) |
| Severe | 9 (11.4) | 4 (5.3) | 8 (10.3) |
| Change in Moderate or Severe | | | |
| Erythema Cases* | −31% (42 to 29) | −60% (40 to 16) | −16.3% (43 to 36) |
| Improved at Least 2 Levels | 4 (5.1) | 7 (9.3) | 1 (1.3) |
| Did Not Improve at Least 2 Levels | 75 (94.9) | 68 (90.7) | 77 (98.7) |
| Week 8 | | | |
| Baseline | | | |
| Clear | 1 (1.3) | 0 | 0 |
| Almost Clear | 12 (15.2) | 7 (15.2) | 7 (9.0) |
| Mild | 24 (30.4) | 28 (30.4) | 28 (35.9) |
| Moderate | 33 (41.8) | 31 (41.8) | 36 (46.2) |
| Severe | 9 (11.4) | 9 (11.4) | 7 (9.0) |
| Post-Baseline | | | |
| Clear | 5 (6.3) | 1 (1.3) | 4 (5.1) |
| Almost Clear | 23 (29.1) | 21 (28.0) | 10 (12.8) |
| Mild | 29 (36.7) | 39 (52.0) | 33 (42.3) |
| Moderate | 17 (21.5) | 12 (16.0) | 26 (33.3) |
| Severe | 5 (6.3) | 2 (2.7) | 5 (6.4) |
| Change in Moderate or Severe | | | |
| Erythema Cases* | −48% (42 to 22) | −65% (40 to 14) | −28% (43 to 31) |
| Change in Severe Erythema Cases** | −44% (9 to 5) | −78% (9 to 2) | −28.6% (7 to 5) |
| Improved at Least 2 Levels | 12 (15.2) | 12 (16.0) | 6 (7.7) |
| Did Not Improve at Least 2 Levels | 67 (84.8) | 63 (84.0) | 72 (92.3) |

TABLE 87-continued

Summary of Changes from Baseline in Clinical Erythema Assessment by Visit and Treatment Intent-to-Treat Population (Multiple Imputation Method)

| Visit<br>Parameter | Minocycline 1.5%<br>(N = 79)<br>n (%) | Minocycline 3%<br>(N = 75)<br>n (%) | Vehicle<br>(N = 78)<br>n (%) |
|---|---|---|---|
| Week 12 | | | |
| Baseline | | | |
| Clear | 1 (1.3) | 0 | 0 |
| Almost Clear | 12 (15.2) | 7 (9.3) | 7 (9.0) |
| Mild | 24 (30.4) | 28 (37.3) | 28 (35.9) |
| Moderate | 33 (41.8) | 31 (41.3) | 36 (46.2) |
| Severe | 9 (11.4) | 9 (12.0) | 7 (9.0) |
| Post-Baseline | | | |
| Clear | 4 (5.1) | 5 (6.7) | 3 (3.8) |
| Almost Clear | 23 (29.1) | 17 (22.7) | 15 (19.2) |
| Mild | 33 (41.8) | 42 (56.0) | 35 (44.9) |
| Moderate | 18 (22.8) | 9 (12.0) | 20 (25.6) |
| Severe | 1 (1.3) | 2 (2.7) | 5 (6.4) |
| Change in Moderate or Severe | | | |
| Erythema Cases* | −55% (42 to 19) | −73% (40 to 11) | −42% (43 to 25) |
| Change in Severe Erythema Cases** | −89% (9 to 1) | −78% (9 to 2) | −28.6% (7 to 5) |
| Improved at Least 2 Levels | 10 (12.7) | 11 (14.7) | 7 (9.0) |
| Did Not Improve at Least 2 Levels | 69 (87.3) | 64 (85.3) | 71 (91.0) |

*% reduction of moderate to severe cases out of number moderate to severe cases
**% reduction of severe cases out of number severe cases FMX103 vs. Oracea® (Oral Doxycycline 40 mg)[2]

Currently, Oracea® is the drug of choice for treatment of papulopustular rosacea. However, the current Phase 2 trial showed that FMX103 had surprising advantages, since it achieved greater effect despite a shorter treatment period (12 weeks vs. 16 weeks) and despite a higher baseline severity of rosacea (both mean lesion count and IGA severity, see Table 88), while avoiding systemic adverse events associated with oral doxycyline. As shown in Table 88, the results for reduction of absolute mean lesion count of FMX103 (a 21 point reduction for the 1.5% group) and percent change of lesion count (61.4% for the 1.5% group) were all higher than the results observed with Oracea®.

TABLE 88

Summary of clinical trial results for FMX103 and Oracea (literature comparison)

| | FMX103 1.5%<br>Topical Minocycline | | Oracea ® Oral Doxycycline[1, 2]<br>(Week 16) | | | |
|---|---|---|---|---|---|---|
| | (Week 12) | | Study 1 | | Study 2 | |
| | Active | Vehicle | Active | Vehicle | Active | Vehicle |
| Inflammatory Lesions | | | | | | |
| Baseline No. of lesions | 34.5 | 30.6 | 19.5 | 20.3 | 20.5 | 21.2 |
| Mean Absolute Reduction | −21.1 | −7.8 | −11.8 | −5.9 | −9.5 | −4.3 |
| Mean Percent Reduction | 61.4% | −29.7% | — | — | — | — |
| IGA | | | | | | |
| Baseline  Moderate | 43% | 51.3% | 52.8% | 52.4% | 54.2% | 55.6% |
| IGA       Severe | 57% | 48.7% | 40.9% | 39.5% | 33.8% | 39.6% |
| ≥2 IGA Grade Reduction | 41.8% | 17.9% | 45.7% | 25.8% | 22.5% | 16.0% |
| IGA = Clear/Almost Clear | 25.3% | 7.7% | 30.7% | 19.4% | 14.8% | 6.3% |

[1]Source: (1) Oracea Prescribing Information, December 2014; (2) Del Rosso et al, JAAD 56 (2007) 791-802
[2]Literature Comparison: clinical trials are conducted under widely varying conditions, efficacy rates observed in the clinical trials of one drug cannot be directly compared to rates in the clinical trials of another drug. Head-to-head trials with FMX103 were not conducted.

Example 9

Pharmacokinetic Comparison of Once-Daily Topical Minocycline Foam 4% Vs Oral Minocycline for Moderate-to-Severe Acne Objective:

To characterize minocycline pharmacokinetics and relative bioavailability following multiple-dose topical administration of minocycline hydrochloride (HCl) foam 4% (FMX-101 4%) as compared with single-dose oral of minocycline HCl extended-release tablets (Solodyn®) in in both adult and pediatric objects with moderate-to-severe acne.

Methods:

Two Phase I, single-center, nonrandomized, open-label, active-controlled, 2-period, 2-treatment crossover clinical studies were conducted. One study included 30 healthy adults (mean age, 22.6 years; 90% white, and 60% females) and the other included 20 pediatric subjects (mean age, 13.2 years; 65% black or African American, and 55% females) who had moderate-to-severe acne. Subjects were initially assigned to receive a single oral dose of a minocycline HCl extended-release tablet (approximately 1 mg/kg) after an overnight fast of at least 10 hours (Period 1). At 10 days after the oral minocycline dose, topical minocycline foam 4% was applied, once daily for 21 days (Period 2). Each application was approximately 4 g (a maximal-use dose). Serial blood samples were obtained before and after administration of oral minocycline and each topical application of minocycline foam 4% on days 1, 12, and 21. On the day of initial dosing (Day 1), subjects checked into the clinic where they were confined until 1 hour after study drug was administered. Predose clinical assessments were performed and a 1 mL blood sample for PK analysis was obtained before study drug was administered. Pediatric subjects received a 4 g, once-daily topical application of FMX101 4% for 7 days. Blood samples were collected at 3, 12, 16, and 24 hours after application on day 7.

Subjects:

Adults were eligible for this study if they were 18 to 35 years of age; children were eligible for the pediatric study if they were 9 to 16 years and 11 months of age and in good health, as judged on the basis of their medical history and the screening procedures. They were required to have moderate-to-severe facial acne vulgaris as well as acne affecting at least two additional regions of the body (neck, upper chest, upper back, or arms). Body mass index of the subjects was specified to range from 18.5 to 29.9 kg/m$^2$. Use of tobacco and/or nicotine during the 30 days prior to the screening visit was prohibited, and all subjects were required to have a negative test for drug abuse and to be able to fully comply with the study requirements. All subjects provided written, informed consent.

Subjects were excluded if they met any one of the following criteria: female who was pregnant or lactating, or planning a pregnancy; use of medicated cleansers or topical acne treatment within 1 week prior to enrollment, or use of topical retinoids, anti-inflammatories, corticosteroids, or systemic antibiotics or other systemic acne treatments within 4 weeks prior to enrollment, or use of systemic retinoids or corticosteroids within 12 weeks prior to enrollment; any abnormal laboratory values at baseline; any dermatologic condition of the face or facial hair, or any other conditions that, in the opinion of the investigator, could have interfered with the clinical evaluations or the course of the study, or exposed the subject to undue risk.

Sampling:

During Period 1, subjects received a single oral dose of minocycline; blood samples were obtained before dosing and through 96 hours (at 30 minutes and at 1, 1.5, 2, 3, 4, 6, 9, 12, 16, 24, 48, 72, and 96 hours) after administration of oral minocycline. During Period 2, topical minocycline foam 4% was applied daily for 21 days. Blood samples were obtained before dosing and at 2, 4, 8, 12, 16, and 24 hours after the first topical application of minocycline foam 4% (Period 2, day 1). On days 6, 9, 10, 11, and 16, blood samples were obtained at approximately 30 minutes before the scheduled application. On days 12 and 21, blood samples were obtained at 30 minutes before and at 2, 4, 8, 12, 16, and 24 hours after topical application of minocycline foam 4%. Day 21 was the last day of application, at which time all assessments and safety procedures were performed. After the final application, subjects were asked to return for additional blood sampling on days 23, 24, and 25.

Bioanalytical Methods:

Blood samples were collected and centrifuged, and the separated plasma was stored at approximately −70° C. Plasma minocycline concentrations were determined using validated liquid chromatography with a tandem mass spectrometry detection method (Nuvisan GmbH); the limit of detection was 0.270 ng/mL.

Pharmacokinetic Analyses:

Noncompartmental pharmacokinetic parameters for minocycline were calculated for all subjects for each day during Period 1 and on days 1, 12, and 21 for Period 2. Pharmacokinetic parameters included the following: $C_{max}$ (maximum plasma concentration); $t_{max}$ (time of maximum measured plasma concentration); $AUC_{0-inf}$ (area under the plasma concentration vs time curve [AUC] from time 0 to infinity); $AUC_{0-tldc}$ (AUC from time 0 to the time of last detectable concentration); $t_{1/2}$ (terminal phase half-life); $C_{24}$ (minocycline concentration 24 hours after topical application of minocycline foam 4%); and $AUC_{0-tau}$ (AUC during the 24-hour dosing interval for topical minocycline foam 4%).

$AUC_{0-tldc}$ was calculated by the linear trapezoidal method, and $AUC_{0-inf}$ was calculated as the sum of $AUC_{0-tldc}$ plus the ratio of the last measurable plasma concentration to the terminal-phase rate constant; both of these assessments were performed for the oral minocycline dose only. Accumulation ratio was calculated by dividing the $AUC_{0-tau}$ of day 12 or day 21 by the $AUC_{0-tau}$ of day 1 for day 12 and day 21, respectively, where tau is 1 day (24 hours).

Safety Evaluation:

Safety was assessed by the evaluation of reported and observed adverse events (AEs), vital signs (blood pressure, heart rate), clinical laboratory assessments (hematology, chemistry, and urinalysis), and electrocardiograms (ECGs). The number and percentage of subjects were documented for (1) any treatment-emergent AE (TEAE); (2) any treatment-related TEAE (probable, possible); (3) any serious TEAE; (4) any severe TEAE; and (5) any TEAE leading to drug withdrawal. The intensity, duration, and causal relationship to the investigational products were rated for all AEs.

Statistical Analyses:

Descriptive statistics were reported for minocycline concentration data at each sample time and were also calculated for all pharmacokinetic parameters. Actual sample collection times were used for the purpose of calculating pharmacokinetic parameters. All deviations from the scheduled sampling time were reported in the final report as "Sample Time Deviations." No values of kel, $AUC_{0-inf}$, or $t_{1/2}$ were reported for cases that did not exhibit a terminal log-linear phase in the concentration vs time profile. Geometric mean was calculated for $C_{max}$, $AUC_{0-tldc}$, $AUC_{0-inf}$, and $AUC_{0-tau}$, and the harmonic mean was calculated for $t_{1/2}$. Analysis of multiple-dose accumulation, determination of steady state, and other pertinent comparisons of pharmacokinetic parameters across or between doses were performed using the appropriate statistical methods. The 90% confidence intervals (CIs) for the difference between treatment least squares means (LSMs) were calculated for the parameters AUC ($AUC_{0-inf}$, $AUC_{0-tau}$) and $C_{max}$ using log-transformed data. Topical minocycline foam 4% (test treatment) was compared against oral minocycline (reference). The CIs were expressed as a percentage relative to the LSM of the reference treatment.

Results:

In total, 30 subjects were enrolled, and all completed the study as planned. The mean age of the subjects was 22.6 years (range, 18 to 30 years). They were mostly white (90%) and female (60%). All subjects had moderate-to-severe acne at baseline evaluation. Treatment adherence rate was high: only 2 subjects missed a single topical minocycline foam 4% application (on day 3) and only 1 subject missed multiple topical minocycline foam 4% applications (on days 9, 10, and 11).

Figure 4A:
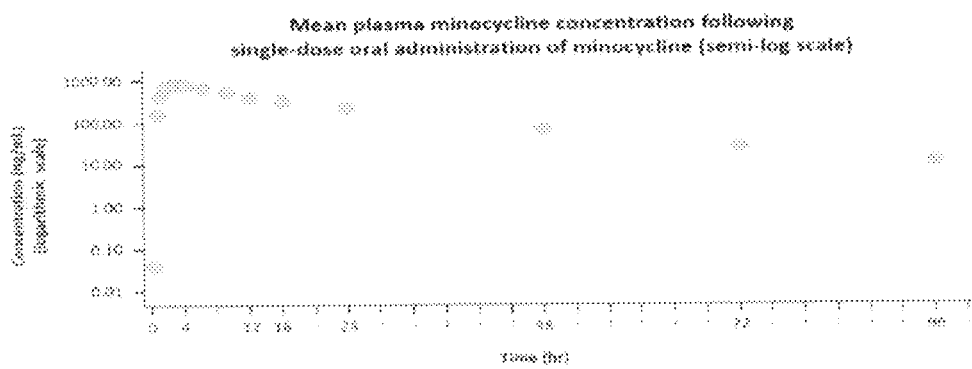
FIG. 4A-FIG. 4B show mean plasma minocycline concentration vs time profiles following a single oral dose of minocycline during Period 1 (FIG. 4A) and topical application of minocycline foam 4% daily for 21 days during Period 2 (FIG. 4B).
Figure 4B:
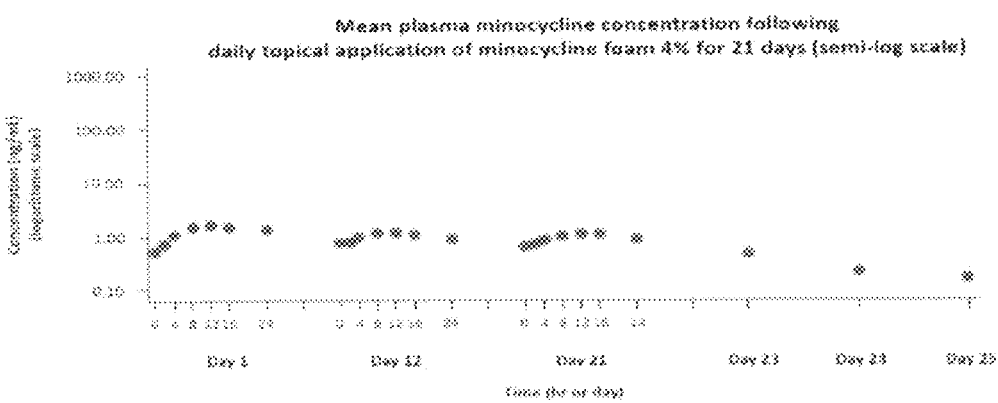
Figure 4C:
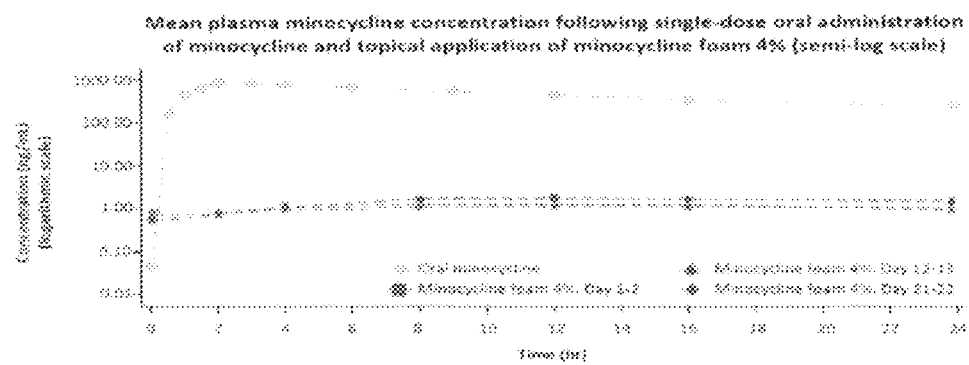
FIG. 4 C shows comparison of mean plasma minocycline concentration over the first 24 hours after oral minocycline dose or topical minocycline foam 4% administration over the 24 hours at day 1, day 12 and day 21. Graphs are shown with semi-log scale.
Figure 5:
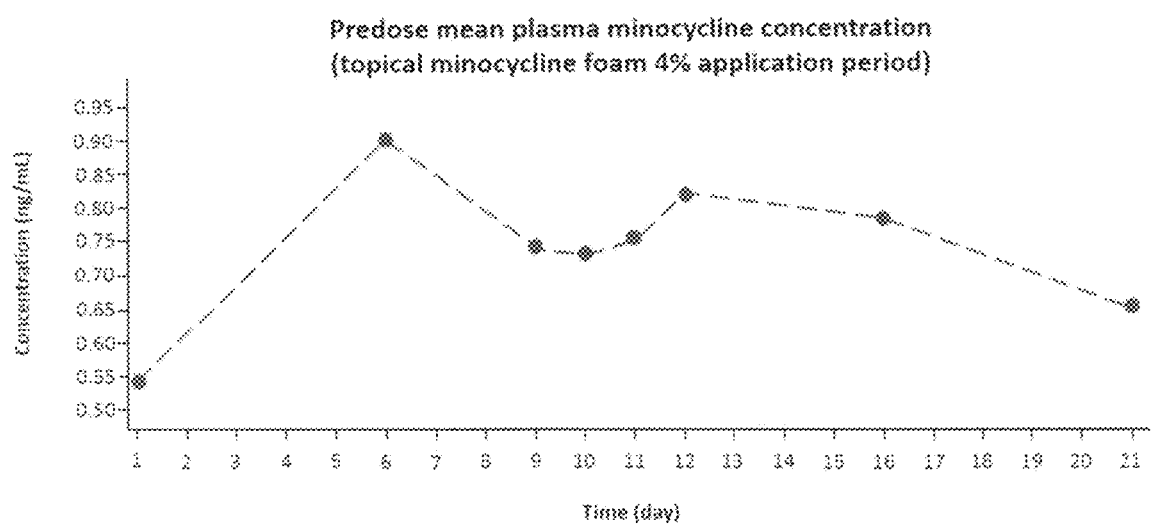
FIG. 5 shows mean plasma minocycline pre-dose concentration-vs-time profile for topical minocycline foam 4% from day 1 through day 21 (linear scale).

After a single oral dose of minocycline, plasma minocycline concentration increased until 3 hours (median $t_{max}$ value), followed by a log-linear decrease over the remainder of the 96-hour sampling period (FIG. 4A). The geometric mean $C_{max}$ was 850.04 ng/mL (Table 89).

foam 4% was low; geometric mean $C_{24}$ values on days 1, 12, and day 21 were 1.192, 0.869, and 0.821 ng/mL, respectively (Table 89). A comparison of the plasma minocycline concentration vs time profiles over the first 24 hours after oral minocycline or topical minocycline foam 4% administration is shown in FIG. 4C. Overall, the plasma minocycline concentration following topical application of minocycline foam 4% was very low; the geometric mean $C_{max}$ values ranged from 1.1 ng/mL to 1.5 ng/mL (Table 89). Steady state for topical application of minocycline foam 4% was achieved by day 6 (FIG. 5). Relative bioavailability of minocycline after topical minocycline foam 4% administration, as compared with oral minocycline, for day 12 and day 21 was 0.126% and 0.131%, respectively, based on $C_{max}$, and it was 0.134% and 0.137%, respectively, based on AUC values (Table 90). Minocycline exposure following daily topical application of minocycline foam 4% was 730 to 765 times lower than that following a single oral dose of ~1

TABLE 89

Summary of PK Parameters (Pharmacokinetic Concentration Population)
Following Single Dose Oral Administration of Solodyn (~1 mg/kg minocycline) and
Topical Application of FMX-101, 4% for 21 days to Acne Patients, Study FX2014-03

| PK Parameter | N | Mean (SD) | Median | Min, Max | CV (%) | Geometric Mean | Harmonic Mean |
|---|---|---|---|---|---|---|---|
| Period 1, Solodyn (~1 mg/kg minocycline) | | | | | | | |
| Day 1-5 | | | | | | | |
| $C_{max}$ (ng/mL) | 30 | 873.367 (220.046) | 801.00 | 603.00, 1620.00 | 25.20 | 850.049 | — |
| $T_{max}$ (h) | 30 | 2.7 (0.81) | 3.0 | 1.5, 4.0 | 30.01 | — | — |
| AUC $_{0\text{-}ddc}$ (ng h/mL) | 30 | 15227.30 (3624.298) | 15363.00 | 9317.00, 25420.00 | 23.80 | 14823.41 | — |
| kel (1/h) | 30 | 0.044 (0.005) | 0.04 | 0.03, 0.05 | 11.52 | — | — |
| AUC$_{0\text{-}inf}$ (ng h/mL) | 30 | 15474.57 (3690.744) | 15553.50 | 9387.00, 25697.00 | 23.85 | 15060.29 | — |
| $T_{1/2}$ (h) | 30 | 16.0 (1.85) | 15.9 | 12.8, 20.1 | 11.59 | — | 15.8 |
| Period 2, FMX-101, 4% (4 g) | | | | | | | |
| Day 1-2 | | | | | | | |
| $C_{max}$ (ng/mL) | 30 | 1.706 (0.823) | 1.50 | 0.68, 3.88 | 48.26 | 1.539 | — |
| $T_{max}$ (h) | 30 | 11.5 (4.01) | 12.0 | 4.0, 23.8 | 35.00 | — | — |
| $C_{24}$ (ng/mL) | 30 | 1.336 (0.667) | 1.13 | 0.53, 3.09 | 49.91 | 1.192 | — |
| AUC$_{0\text{-}tau}$ (ng h/mL)[1] | 30 | 31.75 (14.950) | 28.81 | 10.87, 72.56 | 47.09 | 28.70 | — |
| Day 12-13 | | | | | | | |
| $C_{max}$ (ng/mL) | 29 | 1.325 (0.787) | 1.33 | 0.14, 3.27 | 59.40 | 1.063 | — |
| $T_{max}$ (h) | 29 | 9.4 (5.13) | 8.0 | 0.0, 23.8 | 54.33 | — | — |
| $C_{24}$ (ng/mL) | 29 | 0.919 (0.531) | 0.86 | 0.00, 2.01 | 57.76 | 0.869 | — |
| AUC$_{0\text{-}tau}$ (ng h/mL)[1] | 29 | 24.62 (14.100) | 22.31 | 3.24, 55.69 | 57.26 | 20.06 | — |
| Accumulation Ratio R[2] | 29 | 0.85 (0.552) | 0.76 | 0.00, 2.56 | — | — | — |
| Day 21-25 | | | | | | | |
| $C_{max}$ (ng/mL) | 30 | 1.253 (0.645) | 1.02 | 0.41, 2.73 | 51.52 | 1.109 | — |
| $T_{max}$ (h) | 30 | 12.3 (4.79) | 14.0 | 4.0, 23.8 | 39.05 | — | — |
| kel (1/h) | 14 | 0.018 (0.006) | 0.02 | 0.01, 0.03 | 32.59 | — | — |
| $T_{1/2}$ (h) | 14 | 44.3 (25.39) | 37.8 | 26.7, 125.3 | 57.30 | — | 37.6 |
| $C_{24}$ (ng/mL) | 30 | 0.901 (0.406) | 0.77 | 0.30, 1.89 | 45.11 | 0.821 | — |
| AUC$_{0\text{-}tau}$ (ng h/mL)[1] | 30 | 23.02 (10.798) | 20.45 | 6.28, 46.85 | 46.91 | 20.70 | — |
| Accumulation Ratio R[2] | 30 | 0.79 (0.368) | 0.62 | 0.39, 1.66 | — | — | — |

SD = standard deviation.
CV = coefficient of variation.
Concentrations below the limit of quantitation (LOQ) were reported as zero for the purpose of calculating PK parameters.
[1]AUC$_{0\text{-}tau}$ = AUC during the 24-hour dosing interval.
[2]On Day 12, R = AUC $_{0\text{-}tau}$ Day 12/AUC $_{0\text{-}tau}$ Day 1; On Day 21, R = AUC $_{0\text{-}tau}$ Day 21/AUC $_{0\text{-}tau}$ Day 1.
Source: Table 14.2.2.1.

Following topical application of a 4-g maximal-use dose of minocycline foam 4%, plasma minocycline concentration increased until 8 to 14 hours (median $t_{max}$ value) on days 1, 12, and 21. The change in mean plasma minocycline concentration with time following topical application of minocycline foam 4% is shown in FIG. 4B. The plasma concentration at 24 hours after topical application of minocycline mg/kg minocycline. The daily dosing of topical minocycline foam 4% was associated with a mean (range) accumulation ratio of 0.85 (0.00, 2.56) and 0.79 (0.39, 1.66) at day 12 and day 21, respectively (Table 89). There was no evidence that minocycline had accumulated during the 21 days of topical application of minocycline foam 4%. In pediatric subjects, following topical application of FMX101 4% for 7 days, the overall average plasma concentration of minocycline across all ages was 2.5 ng/mL (relatively constant over the entire sampling interval). See Table 92. Concentrations tend to be higher for younger age groups (9-11 years: 3.5 ng/mL; 12-14 years: 2.5 ng/mL) than for the older age group (15-16 years, 11 months: 1.7 ng/mL). The mean overall maximum observed plasma concentration ($C_{max}$) plasma minocycline concentration 24 hours after FMX101 application ($C_{24}$), and area under the concentration-time curve from time zero (predose) through 24 hours ($AUC_{0-tau}$) were approximately 3.1 ng/mL, 2.5 ng/mL, and 61 ng*h/mL, respectively. See Table 93. $C_{max}$, $C_{24}$, and $AUC_{0-tau}$ tended to be higher in the subjects aged 9 to 11 years and subjects aged 12 to 14 years than the subjects aged 15 years to 16 years 11 months, however the small sample size precludes making any conclusions regarding the effect of age on these PK parameters.

In both studies, FMX101 4% was safe and well-tolerated. There were no drug-related treatment-emergent adverse events (TEAEs), no TEAEs that led to treatment discontinuation, and no serious adverse events. Overall, there was a high rate of subject satisfaction with the use of FMX101, 4%. A majority of subjects reported they were "satisfied" or "very satisfied" with the treatment compared with topical acne therapies used previously. Additionally, the subjects were satisfied with the feel of the foam on the skin.

Safety Evaluation in Adults:

Once-daily application of topical minocycline foam 4% for 21 days was well tolerated. There was minimal systemic absorption and accumulation of minocycline over the 21 days of topical application of minocycline foam 4% as compared with oral minocycline. The most common TEAEs observerd were dysmenorrhea, nasal congestion, and rhinorrhea, all occurring in the topical minocycline foam treatment period (Table 91). In the oral minocycline treatment period, 2 subjects (6.7%) reported a total of 2 TEAEs, while 9 subjects (30%) in the topical minocycline foam 4% treatment period reported a total of 14 TEAEs. There were no TEAEs considered to be related to the study medication. There were also no serious TEAEs, severe TEAEs, or TEAEs that resulted in study medication being withdrawn, as well as no clinically significant laboratory findings in any subjects.

Safety Evaluation in Pediatrics:

Once-daily application of topical minocycline foam 4% for 7 days was safe and well tolerated. There were no TEAEs considered related to study drug. There were no clinically significant laboratory findings in any subject. Adverse events are summarized in Table 94. One subject (5.0%) reported a total of 2 TEAEs (nausea and vomiting). There were no serious TEAEs, no severe TEAEs, and no TEAEs that resulted in study medication being withdrawn. No TEAEs associated with laboratory abnormalities or vital signs were reported. No clinically significant abnormal physical examination findings were reported for any subject.

TABLE 90

Summary of minocycline relative bioavailability with oral minocycline administration and topical application of minocycline foam 4% at days 12 and 21.

| Topical minocycline foam 4% (FMX-101) vs oral minocycline (Solodyn | N | Geometric LSM Ratio (%) (GMR),[a] % (90% CI) |
|---|---|---|
| Day 12 $C_{max}$ | 29 | 0.126 (0.100, 0.159) |
| Day 12 $AUC^b$ | 29 | 0.134 (0.110, 0.163) |
| Day 21 $C_{max}$ | 30 | 0.131 (0.113, 0.151) |
| Day 21 $AUC^c$ | 30 | 0.137 (0.121, 0.156) |

Notes
[a]The 90% confidence intervals for the difference between Test (topical minocycline foam 4%) and Reference (oral minocycline (Solodyn) treatment least squares mean values were calculated using natural logarithm-transformed $C_{max}$ and AUC values.
Geometric LSM ratio (GMR) and the associated 90% CI are back transformed point estimate and the associated 90% CI.
[b]Day 12 $AUC_{0-tau}$ for topical minocycline foam 4% (FMX-101) vs $AUC_{0-inf}$ for oral minocycline (Solodyn).
[c]Day 21 $AUC_{0-tau}$ for topical minocycline foam 4% vs $AUC_{0-inf}$ (FMX-101) for oral minocycline (Solodyn).
Abbreviations:
AUC, area under the curve;
$C_{max}$, maximum plasma concentration;
CI, confidence interval;
$AUC_{0-inf}$, AUC from time 0 to infinity;
$AUC_{0-tau}$, AUC during the 24-hour dosing interval for topical minocycline foam 4%.

TABLE 91

Overall summary of AEs following administration of oral minocycline and topical application of minocycline foam 4% daily for 21 days.

|  | Oral minocycline (N = 30) | Topical minocycline foam 4% (N = 30) |
|---|---|---|
| Subjects with treatment-related[a] TEAE, n (%) | 0 | 0 |
| Subjects with serious TEAE, n (%) | 0 | 0 |
| Subjects with TEAE leading to study discontinuation, n (%) | 0 | 0 |
| Subjects with any TEAE[a], n (%) | 2 (6.7) | 9 (30.0) |
| Dysmenorrhea | 0 | 2 (6.7) |
| Nasal congestion | 0 | 2 (6.7) |
| Rhinorrhea | 0 | 2 (6.7) |
| Asthma | 0 | 1 (3.3) |
| Bronchitis | 0 | 1 (3.3) |
| Cough | 1 (3.3) | 0 |
| Dermatitis contact | 0 | 1 (3.3) |
| Headache | 1 (3.3) | 0 |
| Oropharyngeal pain | 0 | 1 (3.3) |
| Pharyngitis streptococcal | 0 | 1 (3.3) |
| Respiratory tract congestion | 0 | 1 (3.3) |
| Tonsillitis | 0 | 1 (3.3) |

Notes
[a]Subjects with one or more TEAEs that were considered possibly or probably related.
[b]Subjects with one or more TEAEs are only counted once.
Abbreviations:
TEAE, treatment-emergent adverse event.

TABLE 92

Plasma Concentrations of Minocycline in Pediatric Acne Patients Treated with FMX101

| | Mean (SD) Concentrations of Minocycline in Plasma (ng/mL) | | | |
|---|---|---|---|---|
| Day and Time of Sample[1] | Cohort 1 (9 to 11 years) (N = 6) | Cohort 2 (12 to 14 years) (N = 8) | Cohort 3 (15 to 16 years 11 months) (N = 6) | Overall (N = 20) |
| Day 1, Predose | 0.000 (0.0000) | 0.000 (0.0000) | 0.000 (0.0000) | 0.000 (0.0000) |
| Day 7, Predose | 3.700 (4.3614) | 2.111 (2.3463) | 1.870 (1.2783) | 2.515 (2.8473) |

TABLE 92-continued

Plasma Concentrations of Minocycline in Pediatric Acne Patients Treated with FMX101

Mean (SD) Concentrations of Minocycline in Plasma (ng/mL)

| Day and Time of Sample[1] | Cohort 1 (9 to 11 years) (N = 6) | Cohort 2 (12 to 14 years) (N = 8) | Cohort 3 (15 to 16 years 11 months) (N = 6) | Overall (N = 20) |
|---|---|---|---|---|
| Day 7, 3 hours | 3.693 (3.9303) | 2.164 (2.0046) | 1.803 (1.1810) | 2.514 (2.5618) |
| Day 8, 12 hours | 3.972 (3.8346) | 2.233 (1.8408) | 1.775 (0.9688) | 2.617 (2.4961) |
| Day 8, 16 hours | 3.780 (3.7667) | 2.263 (1.9884) | 1.620 (0.9149) | 2.525 (2.4891) |
| Day 8, 24 hours | 3.663 (3.2094) | 2.446 (1.8781) | 1.479 (0.8684) | 2.521 (2.2284) |

Source: Table 14.2.1
Abbreviations: SD = standard deviation
[1]As the Day 7 dose was applied in the evening, some samples were collected on calendar Day 8, but PK parameters calculated from data obtained within approximately 24 hours of the Day 7 dose are referred to as Day 7 parameters in this clinical study report.

TABLE 93

Summary of Pharmacokinetic Parameters of Minocycline in Pediatric Acne Patients Treated with FMX101

Mean (SD) Pharmacokinetic Parameters[1] of Minocycline in Plasma

| Cohort and Age | $C_{max}$ (ng/mL) | $T_{max}$ (h)[2] | $C_{24}$ (ng/mL) | $AUC_{0\text{-}tau}$ (ng * h/mL) |
|---|---|---|---|---|
| Cohort 1 (9 to 11 years) (N = 6) | 4.447 (3.9687) | 12 (0, 24) | 3.663 (3.2094) | 90.861 (90.1626) |
| Cohort 2 (12 to 14 years) (N = 8) | 2.783 (2.1505) | 20 (0, 24) | 2.446 (1.8781) | 54.015 (46.2250) |
| Cohort 3 (15 to 16 years 11 months) (N = 6) | 2.036 (1.1676) | 6 (0, 24) | 1.479 (0.8684) | 40.797 (23.7635) |
| Overall (N = 20) | 3.058 (2.6792) | 12.1 (0, 24) | 2.521 (2.2284) | 61.104 (59.2125) |

Source: Table 14.2.2
Abbreviations:
$AUC_{0\text{-}tau}$ = area under the concentration-time curve (ng/mL * hours) from time zero (predose) through 24 hours;
$C_{24}$ = plasma minocycline concentration 24 hours after FMX101 application;
$C_{max}$ = maximum observed plasma concentration;
SD = standard deviation;
$T_{max}$ = time to maximum measured plasma concentration.
[1]Terminal phase rate constant (kel) and apparent terminal phase half-life ($T_{1/2}$) were not estimable because either there were fewer than 3 values in the terminal phase, the slope was positive, or the $T_{1/2}$ estimate was more than half the range of the terminal phase.
[2]Median (minimum, maximum) shown for $T_{max}$.

TABLE 94

Overall Summary of Adverse Events (Safety Population) Following Topical Application of FMX101, 4% for 7 Days to Pediatric Acne Patients, Study FX2016-21

| | All Subjects (N = 20) |
|---|---|
| Subjects with Any TEAE, N (%) | 1 (5.0) |
| Number of TEAEs | 2 |
| Subjects with Any Treatment-Related TEAE, N (%)[1] | 0 |
| Number of Treatment-Related TEAEs | 0 |
| Subjects with Any Serious TEAE, N (%) | 0 |
| Number of Serious TEAEs | 0 |
| Subjects with Any Severe TEAE, N (%) | 0 |
| Number of Severe TEAEs | 0 |
| Subjects with Any TEAE Leading to Drug Withdrawn, N (%) | 0 |
| Number of TEAEs Leading to Drug Withdrawn | 0 |

Source: Table 14.3.1.1
Abbreviations:
N = number of subjects;
TEAE = treatment-emergent adverse event.
Note:
TEAEs were defined as AEs with an onset date on or after the date of the first dose of study drug or existing events that worsened after the first study drug application during the study.
[1]Treatment-related AEs included possibly and probably related.

This Phase 1 study in adults evaluated the pharmacokinetics and bioavailability of minocycline in multiple-dose, once-daily topical application of minocycline foam 4%, as compared with oral administration of minocycline HCl. The pharmacokinetic results demonstrated minimal systemic absorption and accumulation of minocycline following the maximal-use dose of topical minocycline foam 4% for 21 days, as compared with oral minocycline. Topical minocycline foam 4% was well tolerated in once-daily application in subjects with AV, with no serious or severe AEs or AEs related to study medication or resulting in treatment discontinuation.

Systemic exposure to minocycline with daily topical application of the 4-g dose of minocycline foam 4% for 21 days was 730 to 765 times lower than that following a single, oral, ~1 mg/kg dose of minocycline. There was no evidence of accumulation of minocycline over the 21 days of once-daily topical application of a 4-g maximal-use dose of minocycline foam 4%. The observation of slightly higher mean minocycline values ($C_{max}$) on day 1 than on day 12 or day 21 was probably due to residual minocycline from the oral minocycline dose that had been administered 10 days prior to the start of topical minocycline foam 4% application. Plasma minocycline values were measurable for the majority of subjects before topical minocycline foam 4% application; however, this observation was considered to have no impact on the interpretation of the results.

In this study, all AEs were reported, and vital signs and clinical laboratory assessments, including hematology, chemistry and urinalysis, were monitored. Overall, topical minocycline foam 4% was well tolerated following multiple-dose administration for up to 21 days. The most common TEAEs were dysmenorrhea, nasal congestion, and rhinorrhea. There were no treatment-related AEs, no serious or severe TEAEs, and no serious TEAEs that led to withdrawal from the study.

Common systemic adverse reactions reported in clinical trials with oral minocycline have included headache, fatigue, dizziness, and itch, which were not seen in this study. There were also no reported cases of autoimmune conditions, such as drug-induced lupus-like syndrome, nor of skin and hypersensitivity reactions that have been associated with oral minocycline. There were no findings of clinically significant abnormalities of laboratory values or vital signs, or abnormalities in ECGs or physical examinations in any subjects. Acne severity did not worsen in subjects after 21 days of using topical minocycline foam 4%.

CONCLUSION: In both adult and pediatric subjects, the plasma concentration of minocycline was low after topical application of FMX101 4%. No significant systemic exposure to minocycline was observed with once-daily topical application of FMX101 4% for 21 days in adults and 7 days in pediatric subjects. FMX101 4% appears to be a well-tolerated treatment option for both pediatric and adult subjects with moderate-to-severe acne.

Without being bound by any theory, the improved patient satisfaction with the use of FMX101, 4%, may correlate at least in part with the lower blood exposure of the minocycline after application of the FMX101, 4% formulation versus oral administration of SOLODYN®. Additionally, the lower blood exposure of the minocycline in patients treated with FMX101, 4% may correlate with a lower incidence of treatment-related adverse events.

Example 10

Changes in RosaQoL Index Score at Week 12 from Baseline

Figure 6:
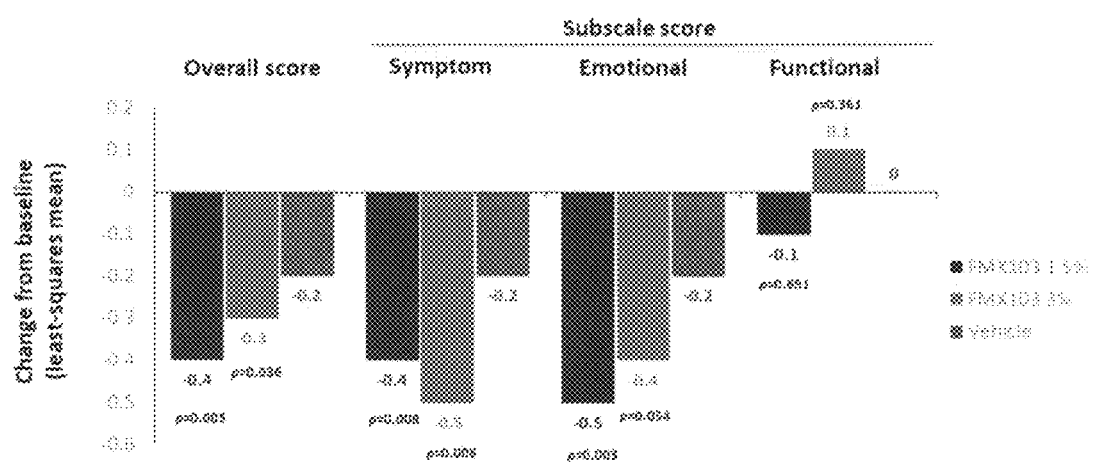
FIG. 6 shows changes in RosaQoL (Rosacea Quality of Life) index score at Week 12 of treatment with two doses of FMX103 (1.5% and 3%) and vehicle foam as compared to baseline (prior to treatment).

RosaQoL (Rosacea Quality of Life) index scores, measuring the impact of rosacea treatment on health-related quality of life, indicated that both doses of FMX103 were significantly better than the vehicle foam in improving the RosaQoL overall score from baseline at Week 12 (p=0.003 and p=0.036, respectively) (FIG. 6). Significant improvement at Week 12 was demonstrated in the symptom subscale scores for both doses of FMX103 and in the emotional subscale scores for FMX103 1.5%, as compared to vehicle foam. Post hoc analyses of global questions to assess patient-reported outcomes showed a similar trend. For the question, "How do you rate your rosacea over the past 4 weeks?", approximately 52 percent and 54 percent of the FMX103 1.5% and 3% groups, respectively, answered "good" to "excellent," as compared to approximately 20 percent of subjects in the vehicle foam group at Week 12 (both p<0.001). Approximately 75 percent in both treatment groups also reported "better" to the comparative question, "How is your rosacea compared to the last time you filled out this survey?", while approximately 42 percent of subjects in the vehicle group at Week 12 answered "better" to the same question (both p<0.001).

Compliance with study drug dosing was high, with rates of 97.5, 94.7, and 98.7 percent in the FMX103 1.5%, FMX103 3%, and vehicle foam groups, respectively. The number of grams of study drug used per day was also similar among treatment groups: 0.36, 0.38, and 0.39 g for FMX103 1.5%, FMX103 3%, and vehicle, respectively.

Having described preferred embodiments of the compositions and methods with reference to the accompanying drawings, it is to be understood that the compositions and methods provided herein are not limited to the precise embodiments, and that various changes and modifications can be effected therein by those skilled in the art without departing from the scope or spirit of the disclosure as defined in the appended claims.

What is claimed is:

1. A method for treating acne vulgaris in a subject in need thereof, comprising topically administering to the subject a therapeutically effective amount of a breakable foam obtained from a foamable composition once daily for at least seven consecutive days, wherein the foamable composition comprises:
  (a) a hydrophobic vehicle comprising:
    (i) about 70% to about 90% by weight of a hydrophobic solvent comprising:
      about 50% w/w of soybean oil;
      about 16.5% w/w to about 30.7% w/w of coconut oil;
      about 3.5% w/w to about 6.5% w/w of cyclomethicone; and
      about 1% w/w to about 6% w/w of light mineral oil; and
    (ii) about 10% to about 22% by weight of a foamer complex comprising:
      about 3.5% w/w of cetostearyl alcohol;
      about 2% w/w to about 4% w/w of stearic acid;
      about 1.8% w/w to about 3.3% w/w of myristyl alcohol;
      about 1% w/w to about 3% w/w of hydrogenated castor oil;
      about 1% w/w to about 3% w/w of beeswax;
      about 1% w/w to about 2% w/w of stearyl alcohol; and
      about 0.5% w/w to about 1.5% w/w of behenyl alcohol;
    (iii) minocycline in an amount ranging from about 1% w/w to about 4% w/w; and
  (b) a propellant in an amount ranging from about 3% to about 25% w/w; and wherein the foamable composition does not comprises silicon dioxide (SiO$_2$), wherein seven days of topical treatment with the breakable foam at the therapeutically effective amount results in a maximum concentration of minocycline in plasma from the subject of about 2 ng/mL, as measured during a 24 hour period following the last topical administration, and wherein the subject is between 15 years old and 16 years and 11 months old.

2. The method of claim 1, wherein seven days of topical treatment with the therapeutically effective amount results in a concentration of minocycline in plasma from the subjects of about 1.4 ng/mL to about 3.7 ng/mL, as measured 24 hours after the last topical administration.

3. The method of claim 1, wherein the area under a concentration-time curve of the amount of the minocycline in the plasma of the subjects is determined during a 24 hour period following the last topical administration.

4. The method of claim 3, wherein the area under the concentration-time curve of the minocycline in the plasma is about 40.8 ng/mL*hour.

\* \* \* \* \*

UNITED STATES PATENT AND TRADEMARK OFFICE
CERTIFICATE OF CORRECTION

PATENT NO.          : 10,398,641 B2
APPLICATION NO.     : 15/699692
DATED               : September 3, 2019
INVENTOR(S)         : Dov Tamarkin et al.

Page 1 of 1

It is certified that error appears in the above-identified patent and that said Letters Patent is hereby corrected as shown below:

In the Claims

Claim 2, Column 137, Line 14, "of about 1.4 ng/mL to about 3.7 ng/mL," should read --of about 1.4 ng/mL,--.

Signed and Sealed this
First Day of October, 2019

Andrei Iancu
*Director of the United States Patent and Trademark Office*